US012751203B2

(12) United States Patent
Dai et al.

(10) Patent No.: US 12,751,203 B2
(45) Date of Patent: Sep. 29, 2026

(54) HETEROCYCLIC ARYLAMINE COMPOUND, ORGANIC ELECTROLUMINESCENT DEVICE AND DISPLAY PANEL

(71) Applicants: Wuhan Tianma Microelectronics Co., Ltd., Wuhan (CN); Wuhan Tianma Microelectronics Co., Ltd. Shanghai Branch, Shanghai (CN)

(72) Inventors: Wenpeng Dai, Wuhan (CN); Wei Gao, Wuhan (CN); Lu Zhai, Wuhan (CN); Tingting Lu, Wuhan (CN); Yi Liu, Wuhan (CN)

(73) Assignees: Wuhan Tianma Microelectronics Co., Ltd., Wuhan (CN); Wuhan Tianma Microelectronics Co., Ltd. Shanghai Branch, Shanghai (CN)

( * ) Notice: Subject to any disclaimer, the term of this patent is extended or adjusted under 35 U.S.C. 154(b) by 997 days.

(21) Appl. No.: 17/981,563

(22) Filed: Nov. 7, 2022

(65) Prior Publication Data

US 2023/0127291 A1 Apr. 27, 2023

(30) Foreign Application Priority Data

Jun. 30, 2022 (CN) ......................... 202210772873.9

(51) Int. Cl.

| | |
|---|---|
| ***H10K 85/60*** | (2023.01) |
| ***C07D 491/048*** | (2006.01) |
| ***C07D 519/00*** | (2006.01) |
| ***H10K 50/844*** | (2023.01) |
| ***H10K 50/858*** | (2023.01) |

(52) U.S. Cl.
CPC ....... *H10K 85/636* (2023.02); *C07D 491/048* (2013.01); *C07D 519/00* (2013.01); *H10K 50/844* (2023.02); *H10K 50/858* (2023.02); *H10K 85/633* (2023.02); *H10K 85/626* (2023.02); *H10K 85/657* (2023.02)

(58) Field of Classification Search
CPC ..................................................... H10K 85/636
See application file for complete search history.

(56) References Cited

FOREIGN PATENT DOCUMENTS

| | | | | | |
|---|---|---|---|---|---|
| CN | 108658980 | A | * | 10/2018 | ........... H10K 85/633 |
| CN | 111635410 | A | * | 9/2020 | ........... C07D 487/08 |
| CN | 114106001 | A | | 3/2022 | |
| CN | 116745298 | A | | 9/2023 | |
| JP | 2019073486 | A | | 5/2019 | |

(Continued)

OTHER PUBLICATIONS

Machine-generated English-language translation of WO-2021261851-A1.*

*Primary Examiner* — Vu A Nguyen
(74) *Attorney, Agent, or Firm* — KDW FIRM PLLC

(57) ABSTRACT

Provided are a heterocyclic arylamine compound, an organic electroluminescent device and a display panel. The heterocyclic arylamine compound has a structure represented by Formula I. The structure of the heterocyclic arylamine compound is designed so that the heterocyclic arylamine compound has relatively high molecular polarizability, relatively high refractive index and relatively high crystallinity and may be used as a material of a capping layer to prepare a top-emitting OLED device, and the prepared OLED device has relatively high current efficiency and long lifetime.

10 Claims, 1 Drawing Sheet

(56) References Cited

FOREIGN PATENT DOCUMENTS

| | | | | | |
|---|---|---|---|---|---|
| KR | 20210133331 | A | * | 11/2021 | ......... H10K 85/6576 |
| KR | 20210142561 | A | * | 11/2021 | |
| WO | WO-2021020799 | A1 | * | 2/2021 | ........... H10K 85/649 |
| WO | 2021177616 | A1 | | 9/2021 | |
| WO | WO-2021261851 | A1 | * | 12/2021 | ........... C07D 263/58 |

* cited by examiner

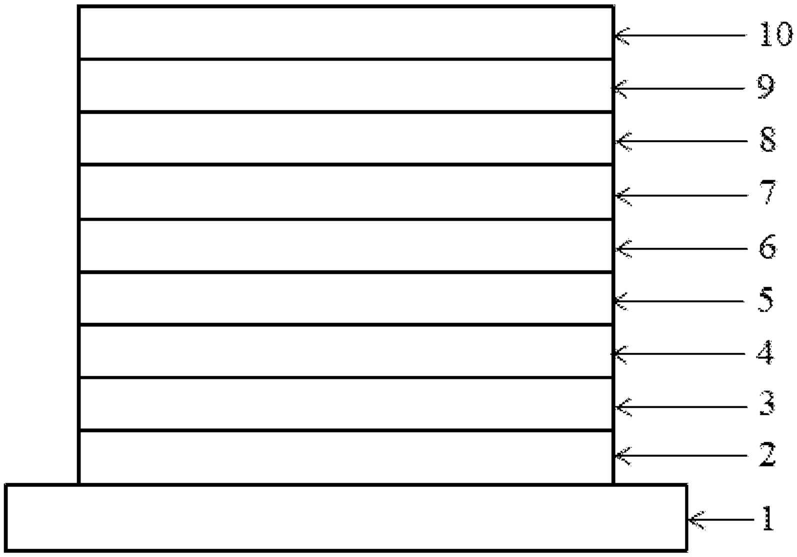
10
9
8
7
6
5
4
3
2
1

HETEROCYCLIC ARYLAMINE COMPOUND, ORGANIC ELECTROLUMINESCENT DEVICE AND DISPLAY PANEL

CROSS-REFERENCE TO RELATED APPLICATION(S)

This application claims priority to Chinese Patent Application No. 202210772873.9 filed Jun. 30, 2022, the disclosure of which is incorporated herein by reference in its entirety.

TECHNICAL FIELD

The present disclosure belongs to the technical field of organic electroluminescent materials, and specifically, relates to a heterocyclic arylamine compound, an organic electroluminescent device and a display panel.

BACKGROUND

An organic light-emitting diode (OLED), also referred to as an organic electroluminescent device, may be classified into a bottom-emitting OLED display and a top-emitting OLED display according to a direction of light emitted by an organic light-emitting layer. In the bottom-emitting OLED (BEOLED) display, light is emitted toward a substrate, a reflective electrode is formed on the organic light-emitting layer, and a transparent electrode is formed under the organic light-emitting layer, that is, a transparent anode made of indium tin oxide (ITO) (or indium zinc oxide (IZO)) is grown on a glass substrate through sputtering, and light emitted by an interior of the device is exited after successively passing through ITO (or IZO) and the glass substrate. For a display screen manufactured in this manner, a driver circuit and a display region are both manufactured on the glass, resulting in a display region with a relatively reduced area and a display screen with a reduced aperture ratio. Moreover, if the OLED display is an active-matrix OLED display, a formed thin-film transistor does not transmit light, resulting in a reduced light-emitting area. In the top-emitting OLED display, a transparent electrode is formed on the organic light-emitting layer, and a reflective electrode is formed under the organic light-emitting layer. Therefore, light is emitted toward an opposite direction to a substrate, thereby increasing a light transmission area and improving the brightness. Since a display screen made of the top-emitting device also has advantages such as a high resolution and a high information content, the top-emitting organic electroluminescent device has attracted more and more attention in recent two years and become a research hotspot.

CN103579521A discloses a top-emitting organic electroluminescent device and a manufacturing method thereof. A covering layer is plated on a cathode layer of the top-emitting organic electroluminescent device, where the covering layer is an organic material having a refractive index greater than 1.8 and an energy gap Eg greater than 3.0 eV within a wavelength range of 450-650 nm. The refractive index of the covering layer disclosed in this technical solution is relatively low, which cannot meet gradually increasing technical requirements.

After decades of development, the OLED has gained considerable progress. The OLED has an internal quantum efficiency of approximately 100% and an external quantum efficiency of only about 20%. Most light is confined inside a light-emitting device due to factors such as a loss of a substrate mode, a surface plasmon loss and a waveguide effect, resulting in a loss of a large amount of energy. Moreover, the refractive index of the material of the organic electroluminescent device prepared in the related art cannot meet market requirements, and a light extraction effect is not good enough. Since a difference in refractive index measured in respective wavelength regions of blue, green and red is relatively large, all light in each blue, green and red light-emitting device cannot have high light extraction efficiency at the same time.

In the top-emitting device, an organic covering layer, also referred to as a capping layer (CPL), is deposited by means of evaporation on a translucent metal electrode so that an optical interference distance is adjusted, the reflection of external light is suppressed, and the extinction caused by the movement of surface plasmon is suppressed, thereby improving light extraction efficiency and light-emitting efficiency. Therefore, how to provide an organic covering layer material having relatively high refractive index to meet the market requirements has become an urgent technical problem to be solved.

SUMMARY

To develop more types of organic covering layer materials having better performance, a first aspect of the present disclosure is to provide a heterocyclic arylamine compound. The heterocyclic arylamine compound has a structure represented by Formula I:

Formula I

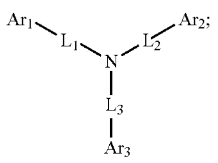

wherein $Ar_1$ has a structure represented by Formula II:

Formula II

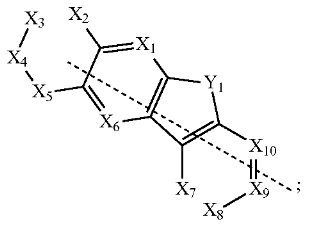

wherein $X_1$ to $X_{10}$ are each independently selected from N or C—R', wherein R' is selected from any one of H, D (deuterium), halogen or cyano.

$Y_1$ is selected from O or S;

$L_1$ to $L_3$ are each independently selected from any one of a single bond, substituted or unsubstituted C6 to C18 arylene, or substituted or unsubstituted C3 to C18 heteroarylene; when $L_1$ to $L_3$ are each independently selected from a single bond, it means that corresponding $Ar_1$, $Ar_2$ and $Ar_3$ are each independently and directly joined to an N atom;

the substituted substituents in $L_1$ to $L_3$ are each independently selected from at least one of D (deuterium), halogen or cyano (—CN);

$Ar_2$ and $Ar_3$ are each independently selected from any one of substituted or unsubstituted C6 to C30 aryl, or substituted or unsubstituted C3 to C30 heteroaryl;

the substituted substituents in $Ar_2$ and $Ar_3$ are each independently selected from at least one of D (deuterium), halogen, cyano or $C_1$ to $C_5$ alkyl; and $Ar_1$, $Ar_2$ and $Ar_3$ include at least one nitrogen atom.

In the present disclosure, the halogen includes fluorine, chlorine, bromine or iodine.

In the present disclosure, C6 to C18 may be C6, C10, C12, C18 or the like.

C3 to C18 may be C3, C5, C6, C10, C12, C18 or the like.

C6 to C30 may be C6, C8, C10, C12, C13, C14, C15, C16, C18, C20, C22, C24, C26, C28 or the like.

C3 to C30 may be C4, C5, C6, C8, C10, C12, C13, C14, C15, C16, C18, C20, C22, C24, C26, C28 or the like.

C1 to C5 may be C1, C2, C3, C4 or C5.

According to a Lorentz-Lorenz equation, a refractive index is proportional to a polarizability and inversely proportional to a molecular volume. The greater the polarizability, the greater the refractive index of the material. The smaller the molecular volume, the greater the refractive index of the material. In the related art, to increase the density of molecules and achieve high thermal stability, a molecular structure is designed to be large and loose so that molecules cannot be tightly packed, resulting in too many molecular gel holes when a capping layer is prepared by means of evaporation, poor tightness of coverage and a low refractive index.

A horizontal dipole orientation of the structure of the heterocyclic arylamine compound provided in the present disclosure is conducive to the stacking arrangement of molecules, which can improve the refractive index. Furthermore, in terms of molecular crystallinity and thin film stability, a molecular mass should not be too large. Therefore, the structure of the heterocyclic arylamine compound is designed in the present disclosure so that the heterocyclic arylamine compound has a suitable weight average molecular weight, further improving the stability of the capping layer. Therefore, with the heterocyclic arylamine compound provided in the present disclosure as a material of the capping layer, a prepared organic electroluminescent device has relatively high light removal efficiency and current efficiency and can effectively block water and oxygen in an external environment, thereby protecting a display panel from being eroded by water and oxygen.

A second aspect of the present disclosure is to provide an organic electroluminescent device. The organic electroluminescent device includes an anode, an organic thin-film layer and a cathode which are stacked in sequence and a capping layer located on a side of the cathode facing away from the anode, where a material of the capping layer includes at least one of the heterocyclic arylamine compounds each according to the first aspect.

A third aspect of the present disclosure is to provide a display panel. The display panel includes the organic electroluminescent device according to the second aspect.

BRIEF DESCRIPTION OF DRAWINGS

The Figure is a structure diagram of an organic electroluminescent device according to the present disclosure.

REFERENCE LIST

1 substrate
2 anode
3 hole injection layer
4 first hole transport layer
5 second hole transport layer
6 light-emitting layer
7 electron transport layer
8 electron injection layer
9 cathode
10 capping layer

DETAILED DESCRIPTION

Technical solutions of the present disclosure are further described below through examples. It is to be understood by those skilled in the art that the examples described below are used for a better understanding of the present disclosure and are not to be construed as specific limitations to the present disclosure.

A first aspect of the present disclosure is to provide a heterocyclic arylamine compound. The heterocyclic arylamine compound has a structure represented by Formula I:

Formula I

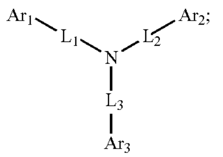

wherein, $Ar_1$ has a structure represented by Formula II:

Formula II

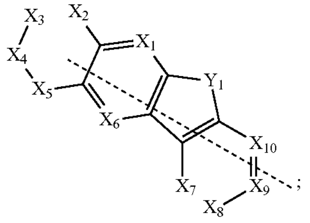

wherein $X_1$ to $X_{10}$ are each independently selected from N or C—R', wherein R' is selected from any one of H, D (deuterium), halogen or cyano;

$Y_1$ is selected from O or S;

$L_1$ to $L_3$ are each independently selected from any one of a single bond, substituted or unsubstituted C6 to C18 arylene, or substituted or unsubstituted C3 to C18 heteroarylene;

the substituted substituents in $L_1$ to $L_3$ are each independently selected from at least one of D (deuterium), halogen or cyano (—CN);

$Ar_2$ and $Ar_3$ are each independently selected from any one of substituted or unsubstituted C6 to C30 aryl, or substituted or unsubstituted C3 to C30 heteroaryl;

the substituted substituents in $Ar_2$ and $Ar_3$ are each independently selected from at least one of D (deuterium), halogen, cyano or C1 to C5 alkyl; and $Ar_1$, $Ar_2$ and $Ar_3$ include at least one nitrogen atom.

According to a Lorentz-Lorenz equation, a refractive index is proportional to a polarizability and inversely proportional to a molecular volume. The greater the polarizability, the greater the refractive index of the material. The smaller the molecular volume, the greater the refractive index of the material. In the related art, to increase the density of molecules and achieve high thermal stability, a molecular structure is designed to be large and loose so that molecules cannot be tightly packed, resulting in too many molecular gel holes when a capping layer is prepared by means of evaporation, poor tightness of coverage and a low refractive index.

A horizontal dipole orientation of the structure of the heterocyclic arylamine compound provided in the present disclosure is conducive to the stacking arrangement of molecules, which can improve the refractive index. Furthermore, in terms of molecular crystallinity and thin film stability, a molecular mass should not be too large. Therefore, the structure of the heterocyclic arylamine compound is designed in the present disclosure so that the heterocyclic arylamine compound has a suitable weight average molecular weight, further improving the stability of the capping layer. Therefore, with the heterocyclic arylamine compound provided in the present disclosure as a material of the capping layer, a prepared organic electroluminescent device has relatively high light removal efficiency and luminescence efficiency and can effectively block water and oxygen in an external environment, thereby protecting a display panel from being eroded by water and oxygen.

In the present disclosure, the halogen includes fluorine, chlorine, bromine or iodine.

In the present disclosure, $L_1$ to $L_3$ are each independently selected from any one of a single bond, substituted or unsubstituted C6 to C18 arylene or substituted or unsubstituted C3 to C18 heteroarylene.

In an embodiment, $L_1$ in Formula I is selected from a single bond, and $Ar_1$ is directly joined to a nitrogen atom.

In an embodiment, $L_2$ in Formula I is selected from a single bond, and $Ar_2$ is directly joined to a nitrogen atom.

In an embodiment, $L_3$ in Formula I is selected from a single bond, and $Ar_3$ is directly joined to a nitrogen atom.

C6 to C18 may be C6, C10, C12, C18 or the like.

C3 to C18 may be C3, C5, C6, C10, C12, C18 or the like.

In the present disclosure, $Ar_2$ and $Ar_3$ are each independently selected from any one of substituted or unsubstituted C6 to C30 aryl, or substituted or unsubstituted C3 to C30 heteroaryl.

C6 to C30 may each independently be C6, C8, C10, C12, C13, C14, C15, C16, C18, C20, C22, C24, C26, C28 or the like.

C3 to C30 may each independently be C4, C5, C6, C8, C10, C12, C13, C14, C15, C16, C18, C20, C22, C24, C26, C28 or the like.

In the present disclosure, the substituted substituents in $Ar_2$ and $Ar_3$ are each independently selected from at least one of D, halogen, cyano or C1 to C5 alkyl (which may be, for example, methyl, ethyl, propyl, butyl or pentyl).

In an embodiment, $Ar_1$ is selected from any one of the following groups, or any one of the following groups substituted with a substituent:

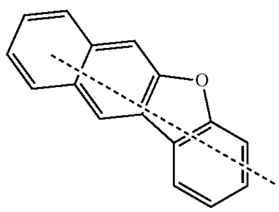
,

-continued

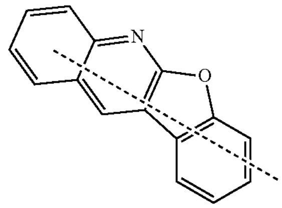
,

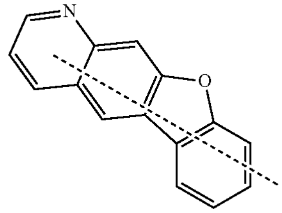
,

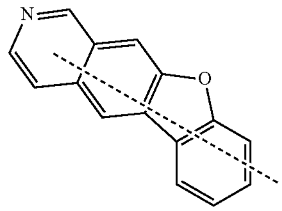
,

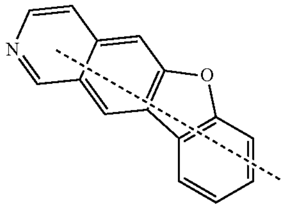
,

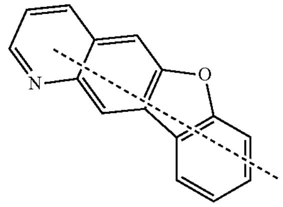
,

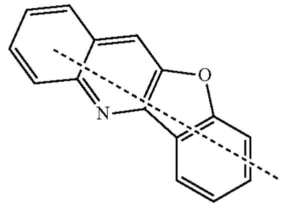
,

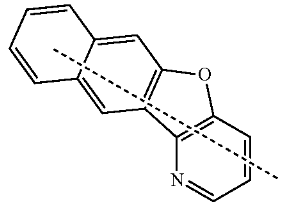
,

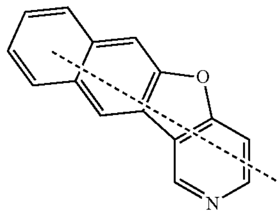
,

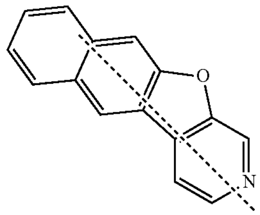
,

-continued
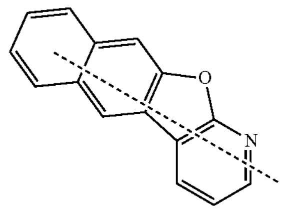
,
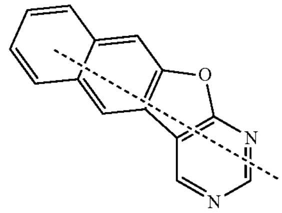
,
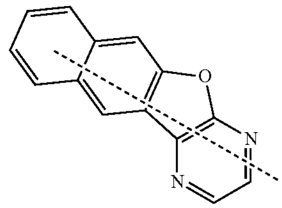
,
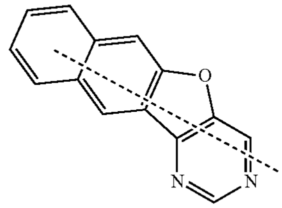
,
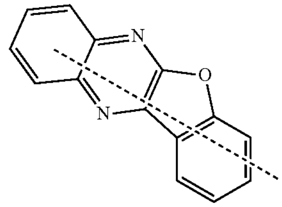
,
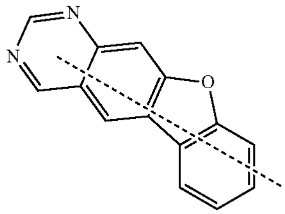
,
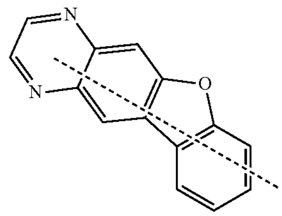
,
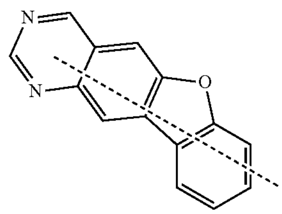
,
-continued
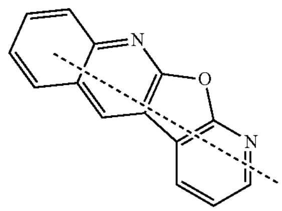
,
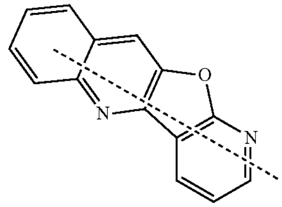
,
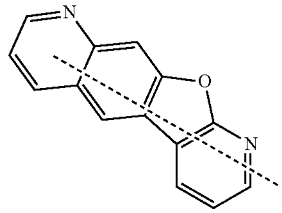
,
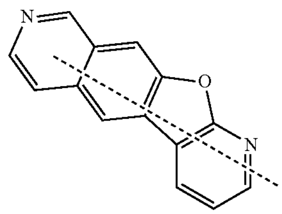
,
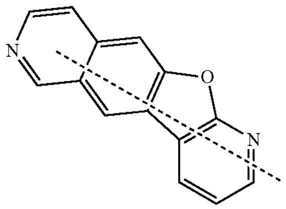
,
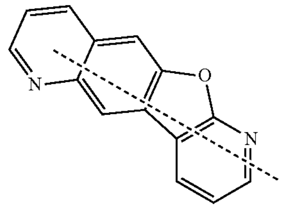
,
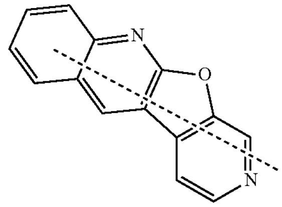
,
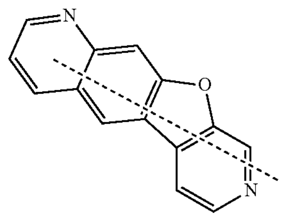
, -continued
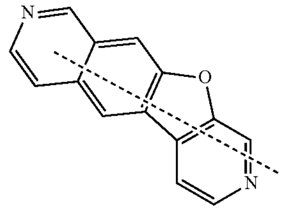
,
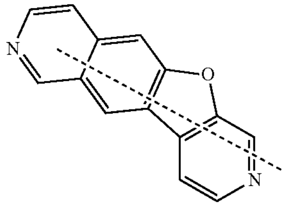
,
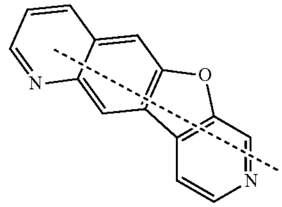
,
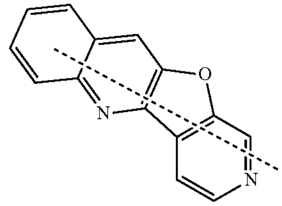
,
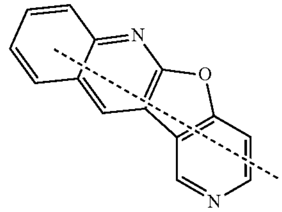
,
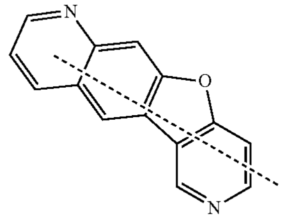
,
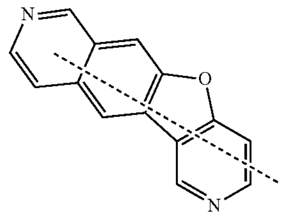
,
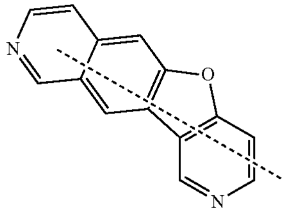
,
-continued
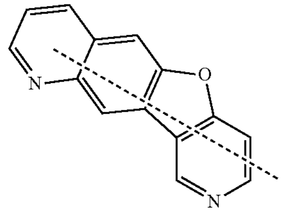
,
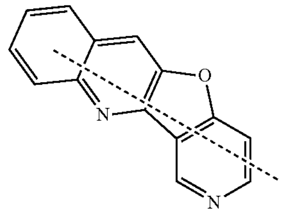
,
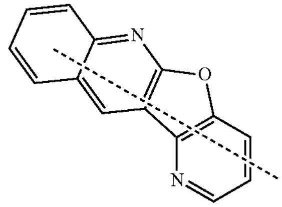
,
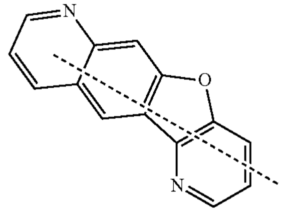
,
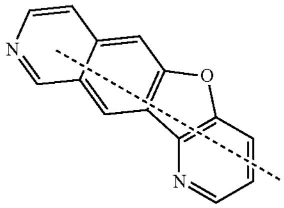
,
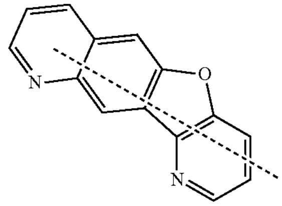
,
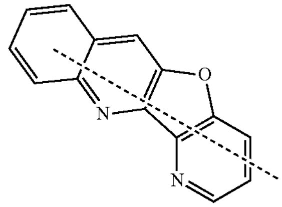
,
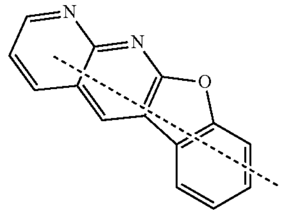
, -continued
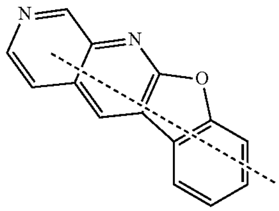,
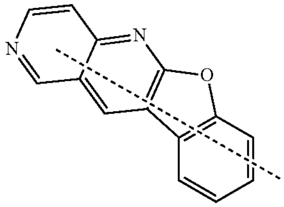,
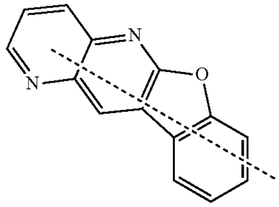,
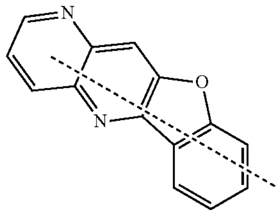,
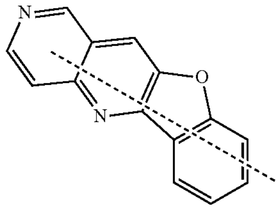,
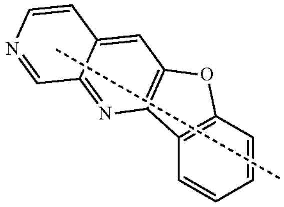,
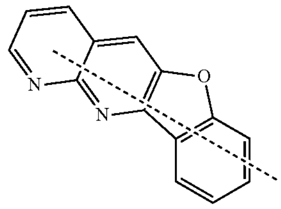,
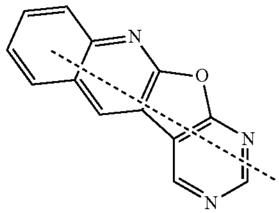,
-continued
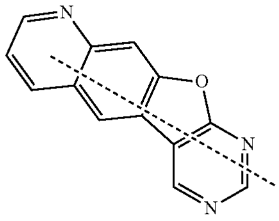,
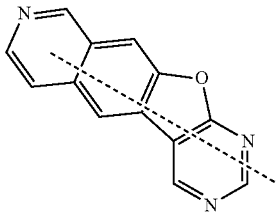,
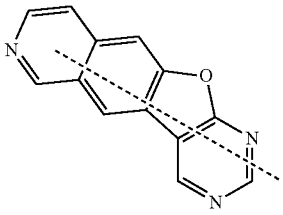,
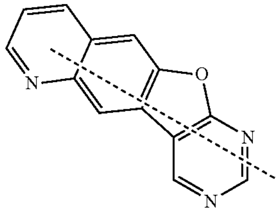,
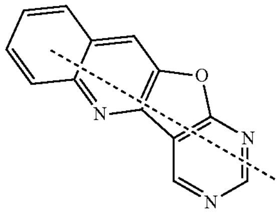,
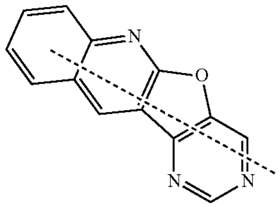,
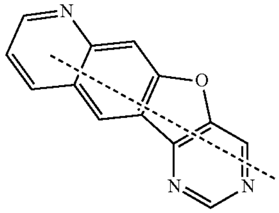,
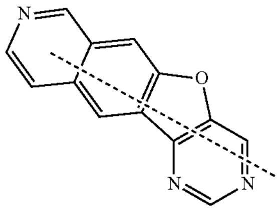, -continued
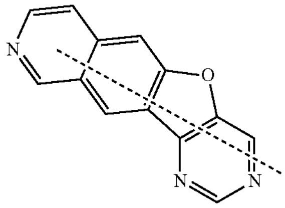
,
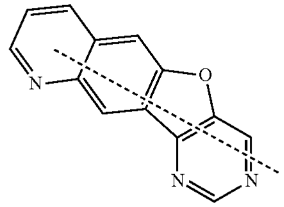
,
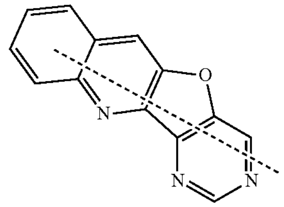
,
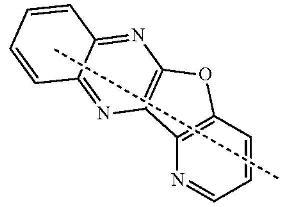
,
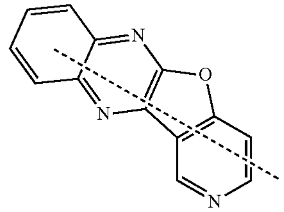
,
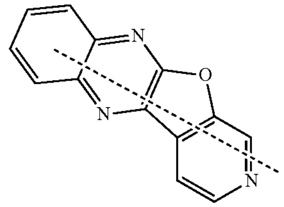
,
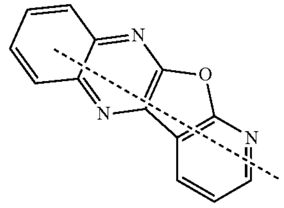
,
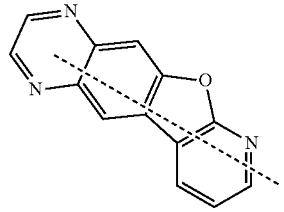
,
-continued
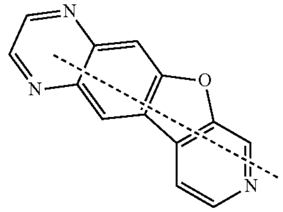
,
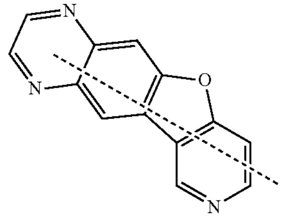
,
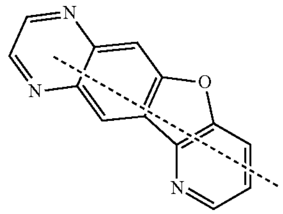
,
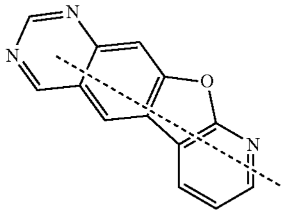
,
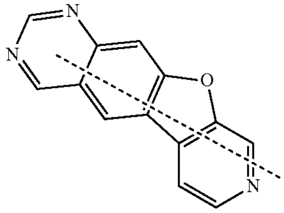
,
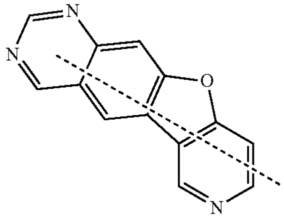
,
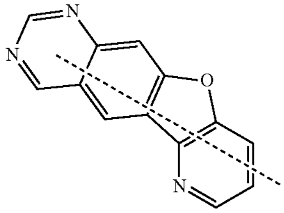
,
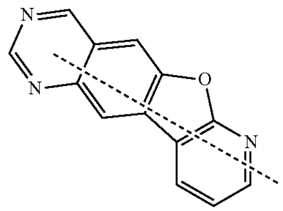
, -continued
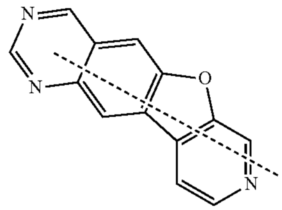
,
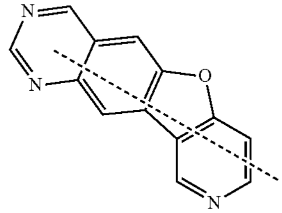
,
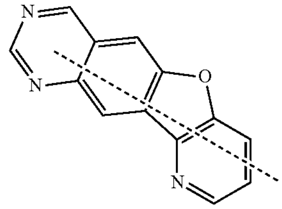
,
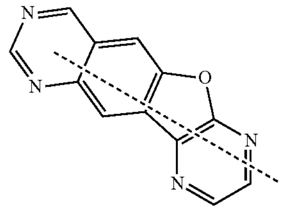
,
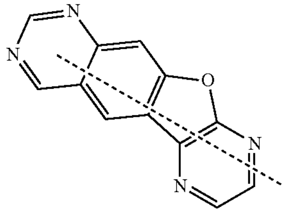
,
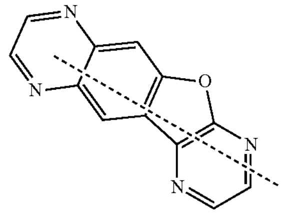
,
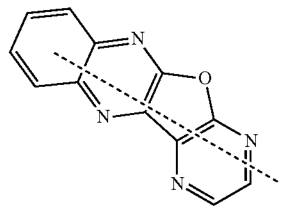
,
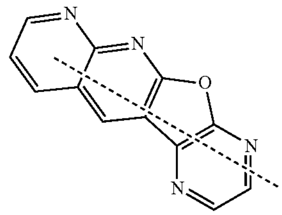
,
-continued
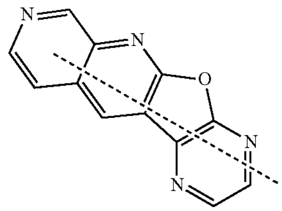
,
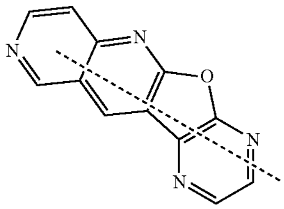
,
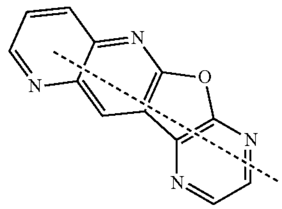
,
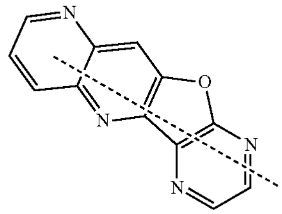
,
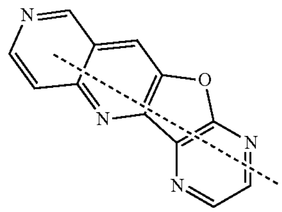
,
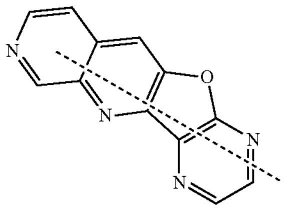
,
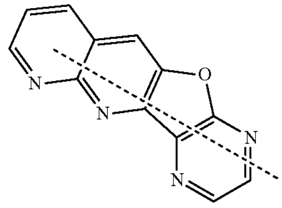
,
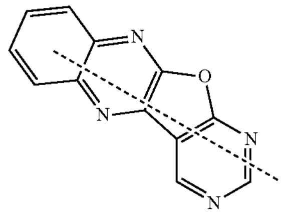
, -continued
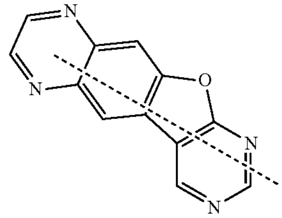
,
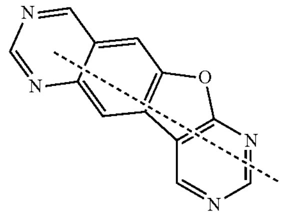
,
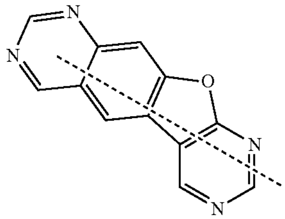
,
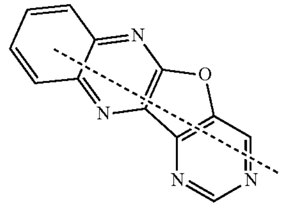
,
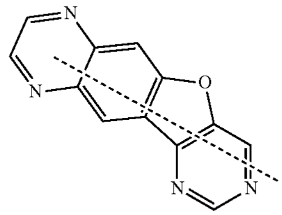
,
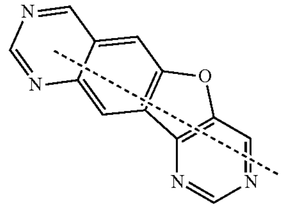
,
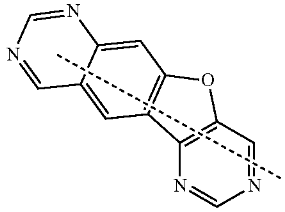
,
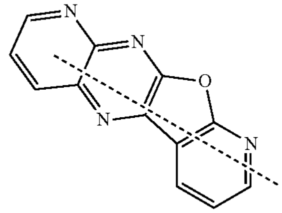
,
-continued
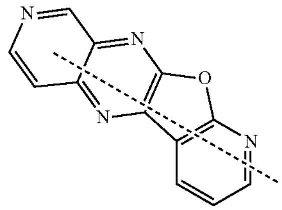
,
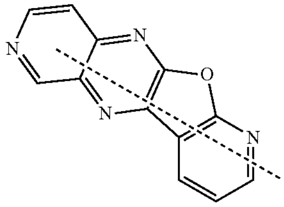
,
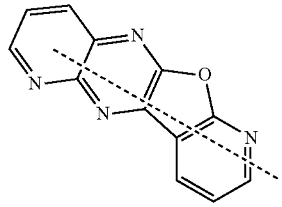
,
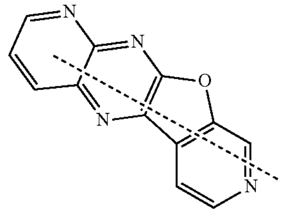
,
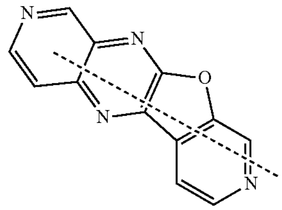
,
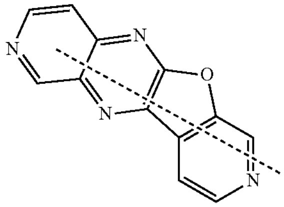
,
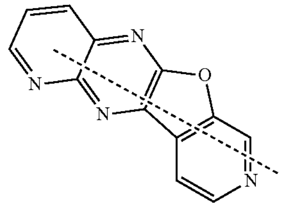
,
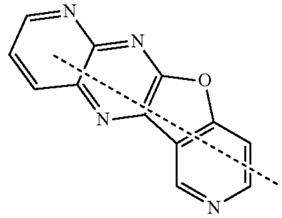
, -continued
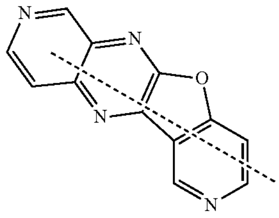
,
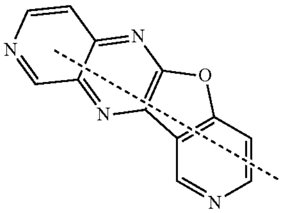
,
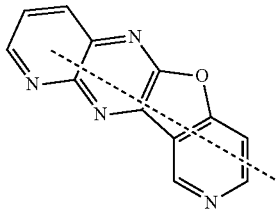
,
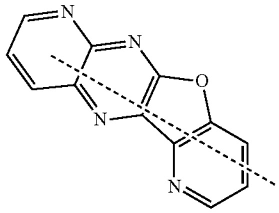
,
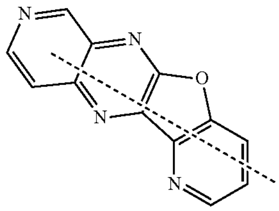
,
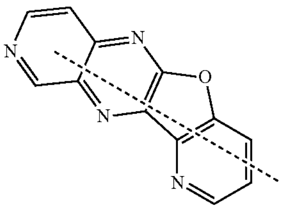
,
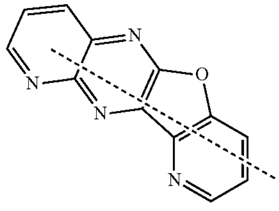
,
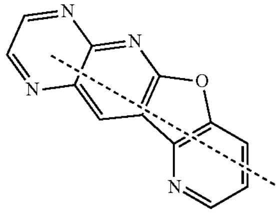
,
-continued
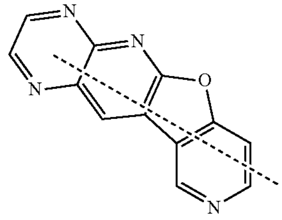
,
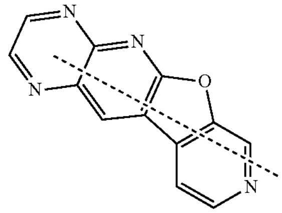
,
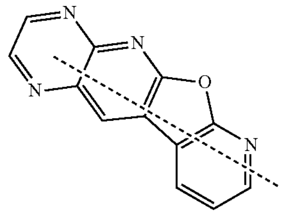
,
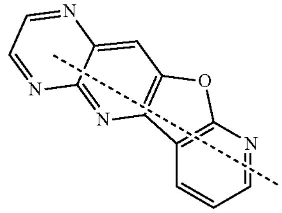
,
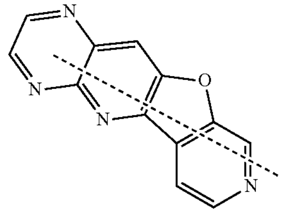
,
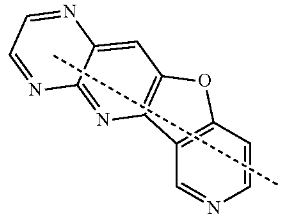
,
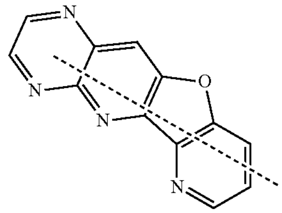
,
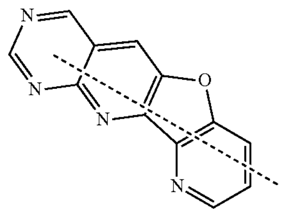
, -continued
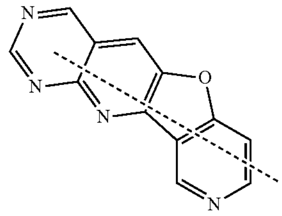
,
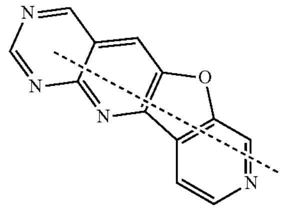
,
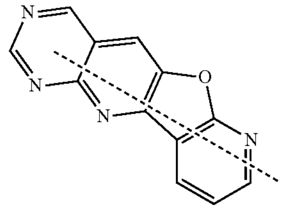
,
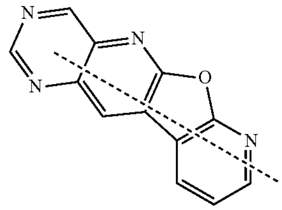
,
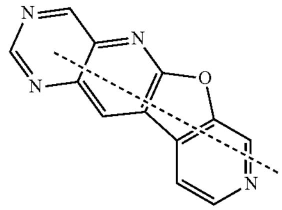
,
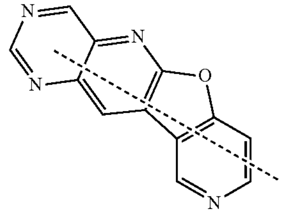
,
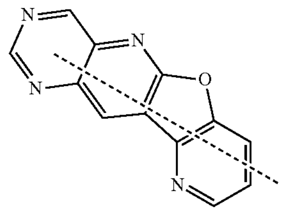
,
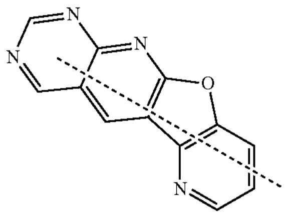
,
-continued
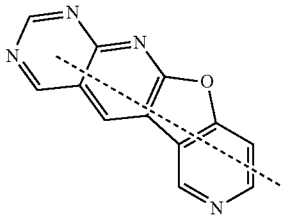
,
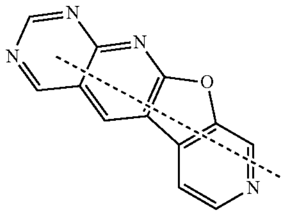
,
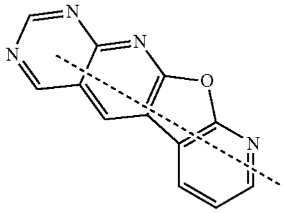
,
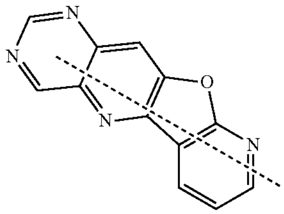
,
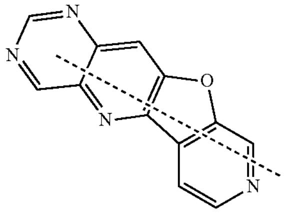
,
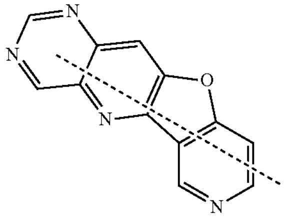
,
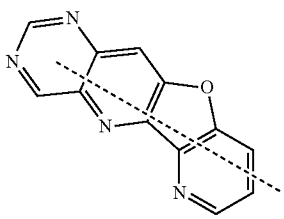
,
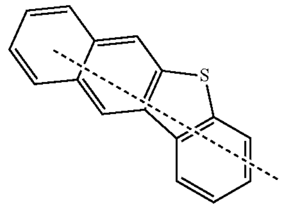
, -continued
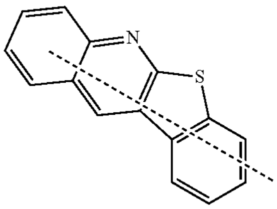,
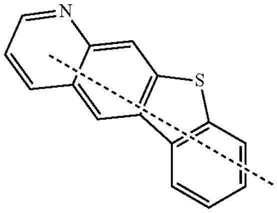,
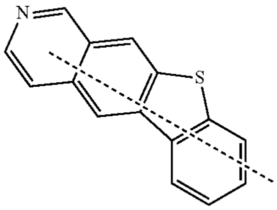,
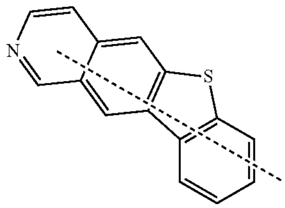,
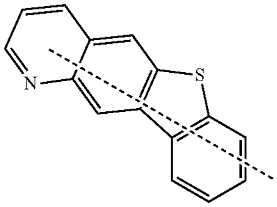,
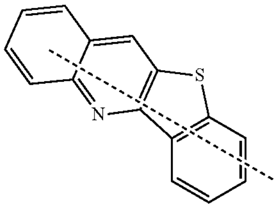,
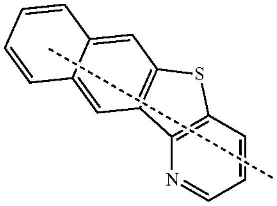,
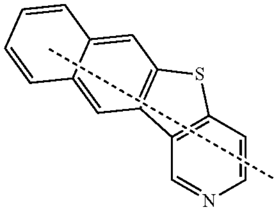,
-continued
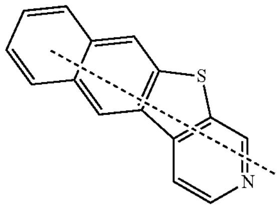,
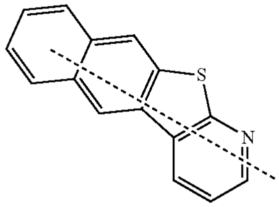,
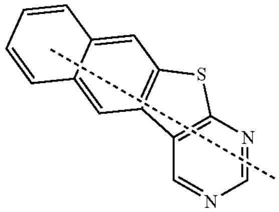,
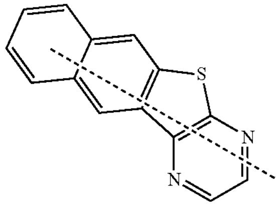,
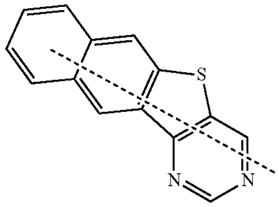,
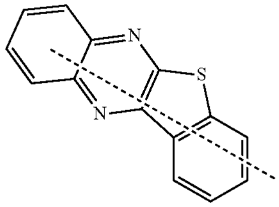,
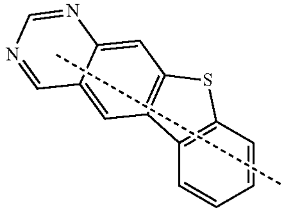,
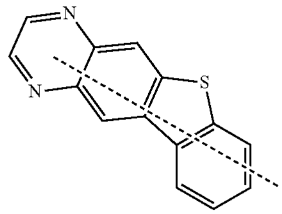, -continued
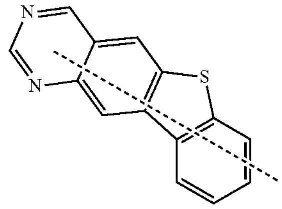
,
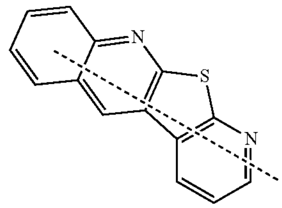
,
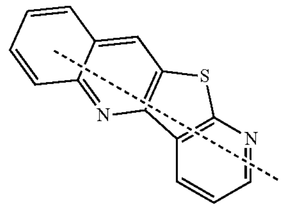
,
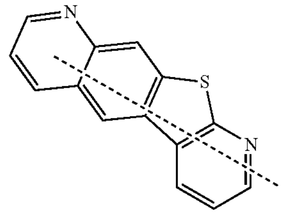
,
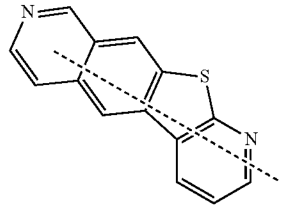
,
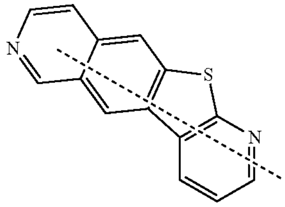
,
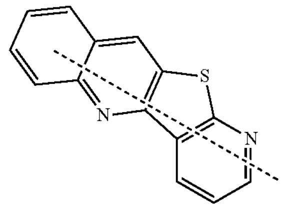
,
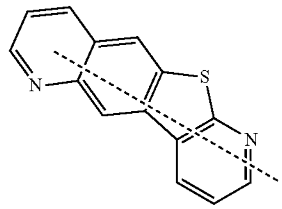
,
-continued
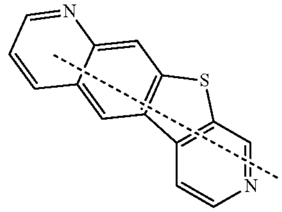
,
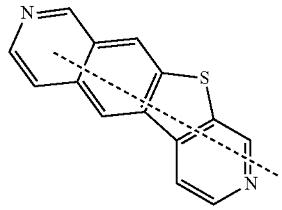
,
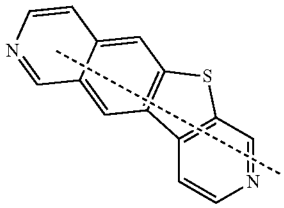
,
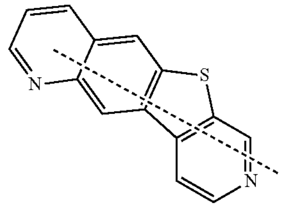
,
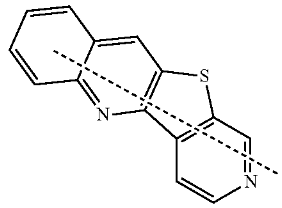
,
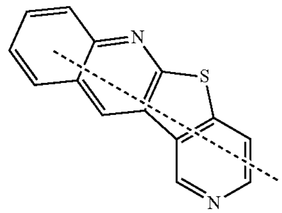
,
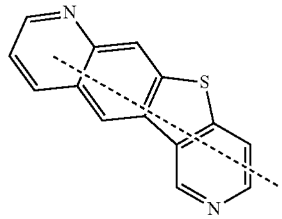
,
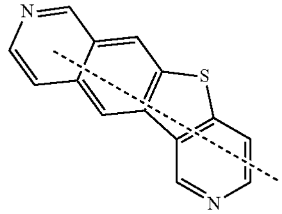
, -continued
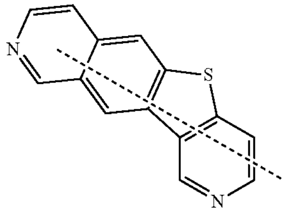
,
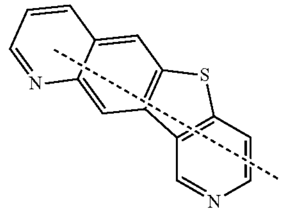
,
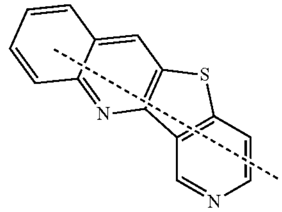
,
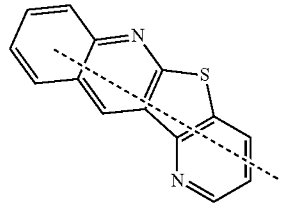
,
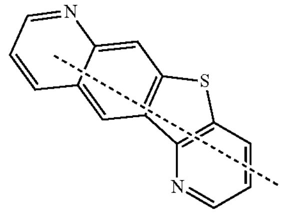
,
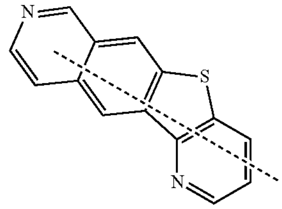
,
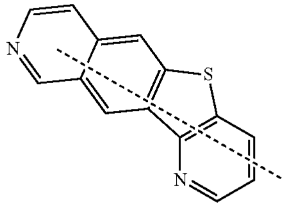
,
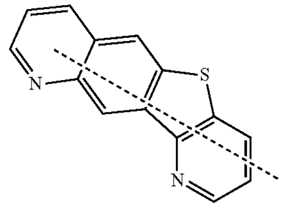
,
-continued
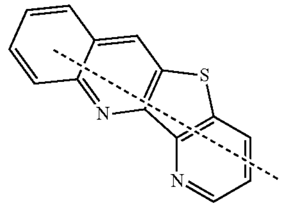
,
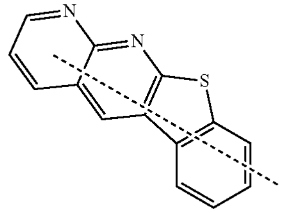
,
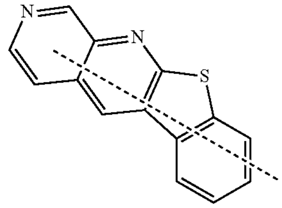
,
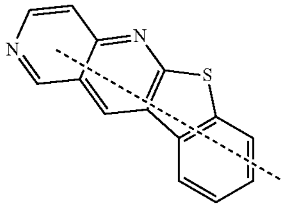
,
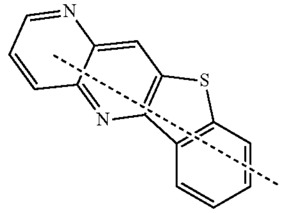
,
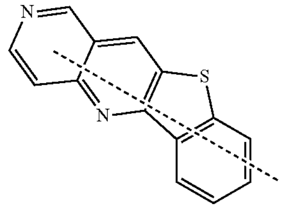
,
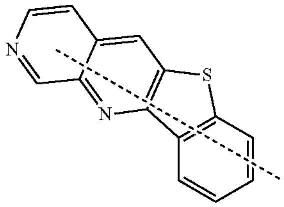
,
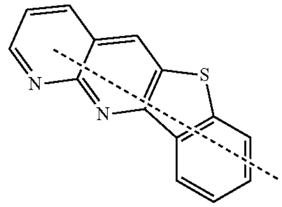
, -continued
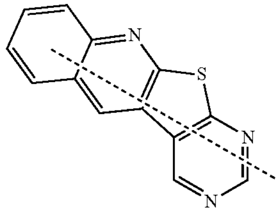
,
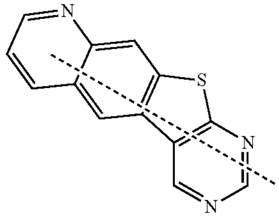
,
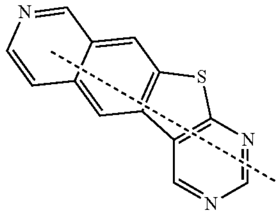
,
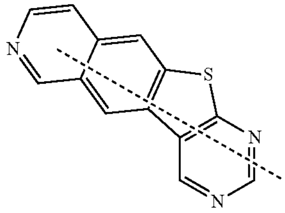
,
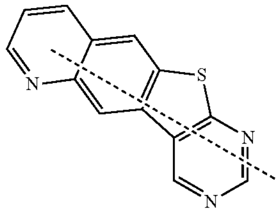
,
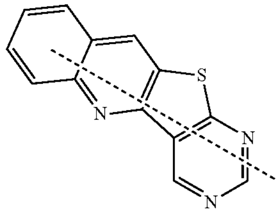
,
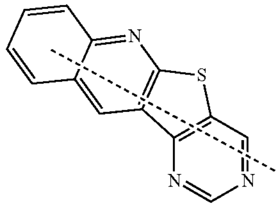
,
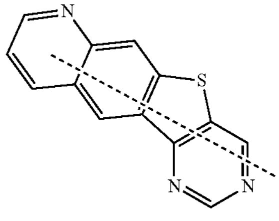
,
-continued
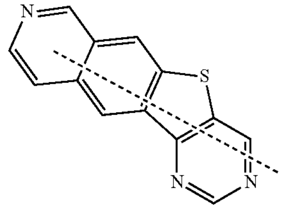
,
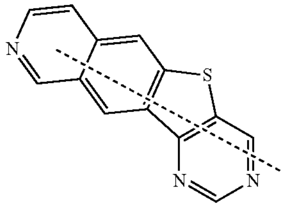
,
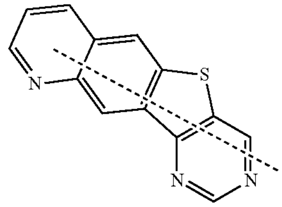
,
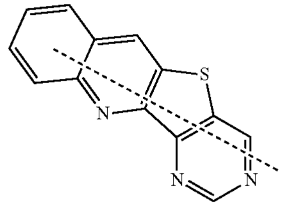
,
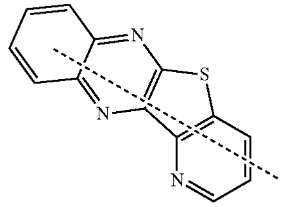
,
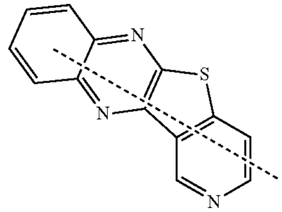
,
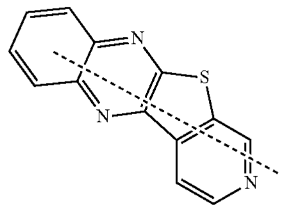
,
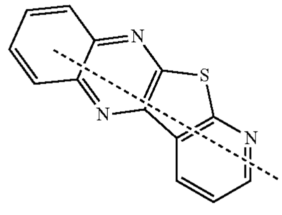
, -continued
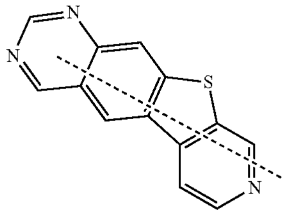
,
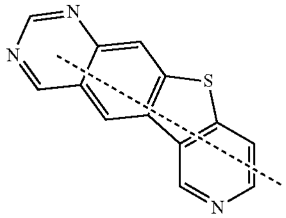
,
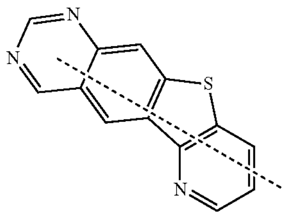
,
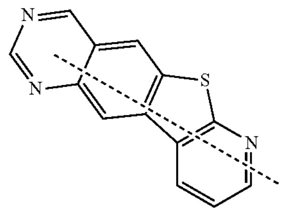
,
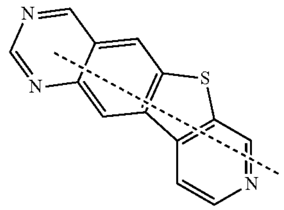
,
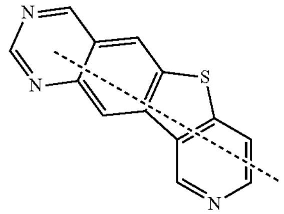
,
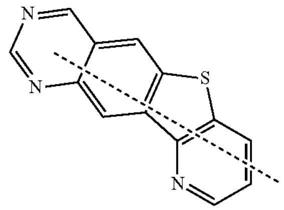
,
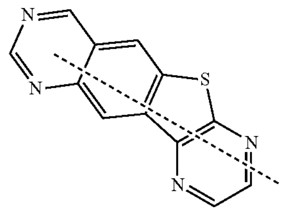
,
-continued
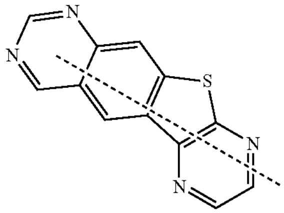
,
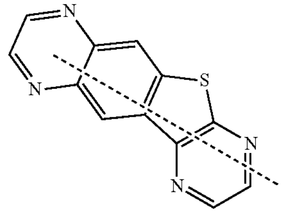
,
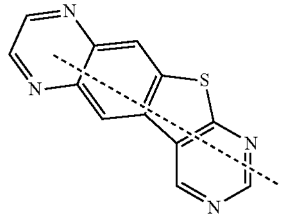
,
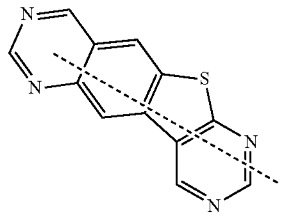
,
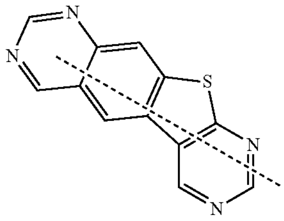
,
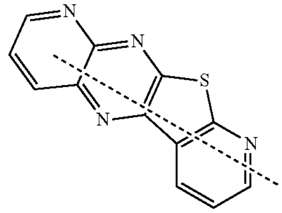
,
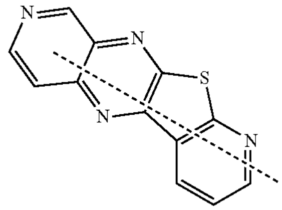
,
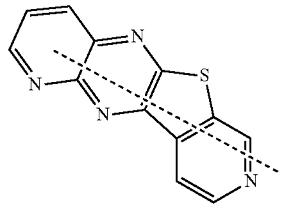
, -continued
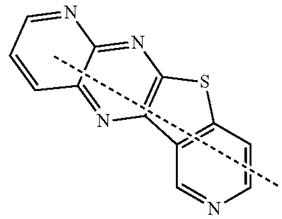,
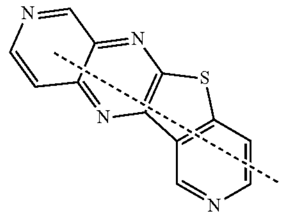,
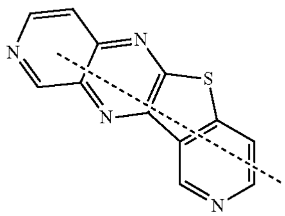,
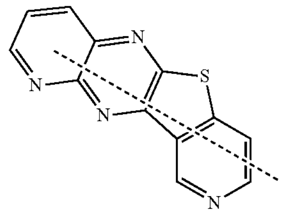,
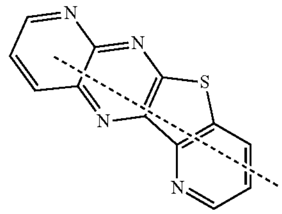,
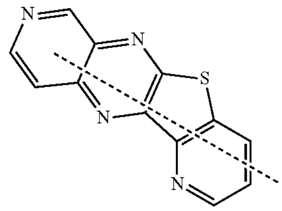,
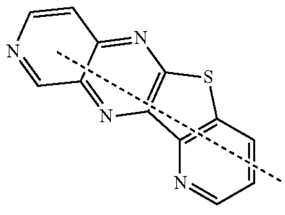,
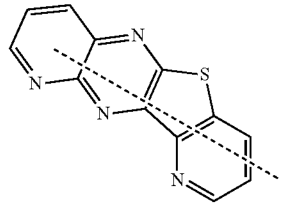,
-continued
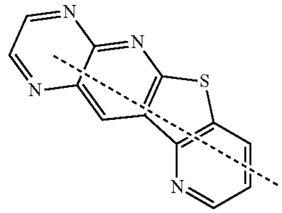,
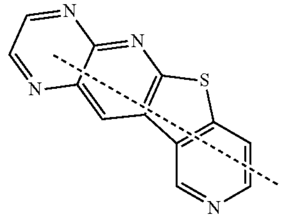,
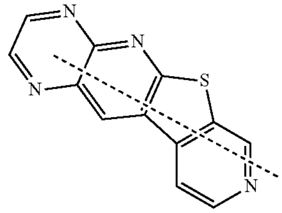,
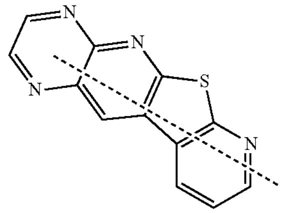,
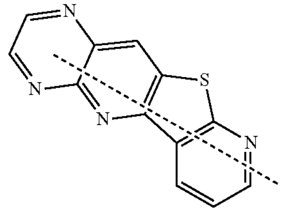,
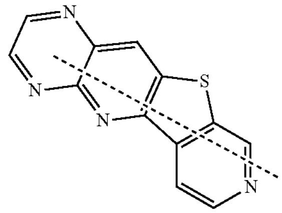,
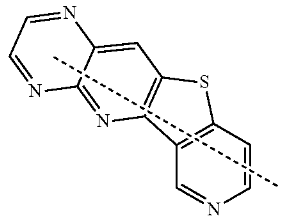,
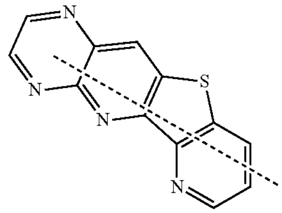, -continued
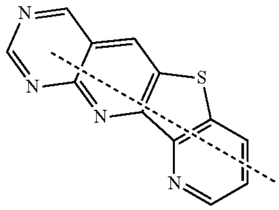
,
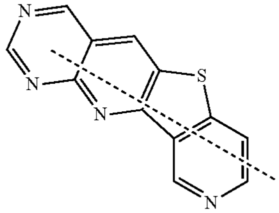
,
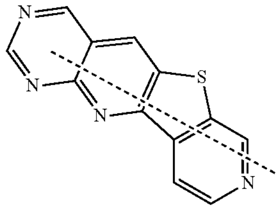
,
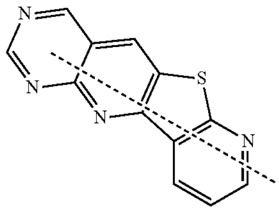
,
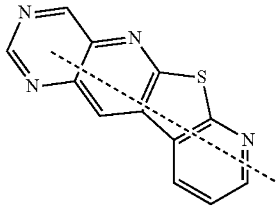
,
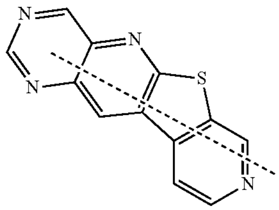
,
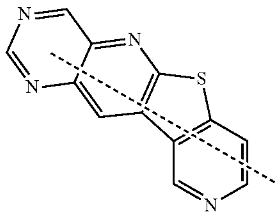
,
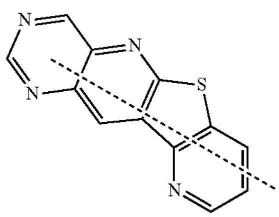
,
-continued
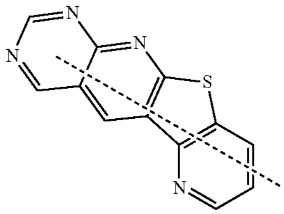
,
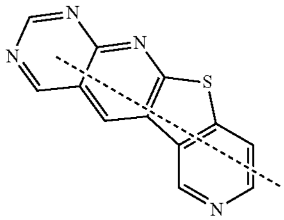
,
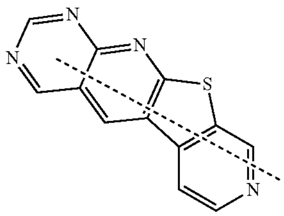
,
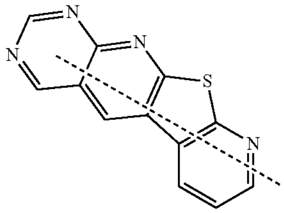
,
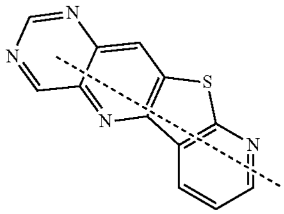
,
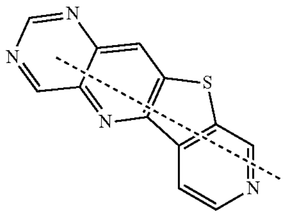
,
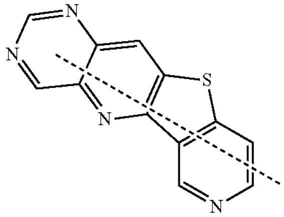
, or
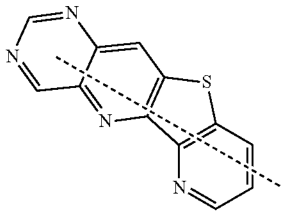
;

wherein, the dashed line represents a linkage site of the group;

the substituent is selected from D (deuterium), halogen (fluorine, chlorine, bromine or iodine) or cyano (—CN).

In an embodiment, $Ar_1$ is selected from any one of the following groups, or any one of the following groups substituted with a substituent:

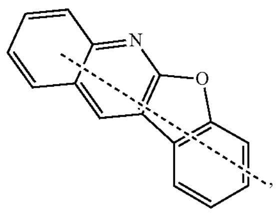
,
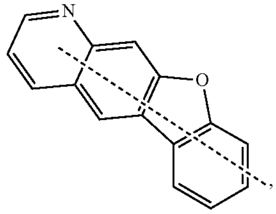
,
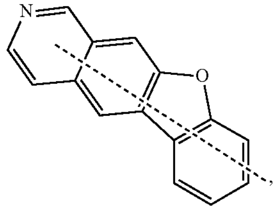
,
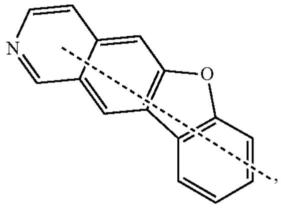
,
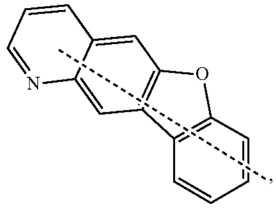
,
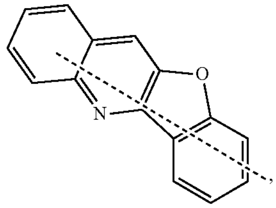
,
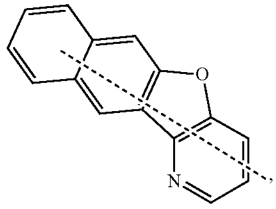
,
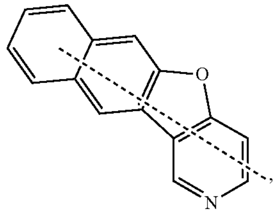
,
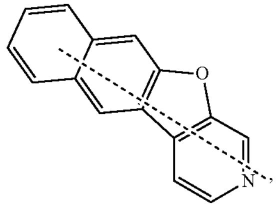
,
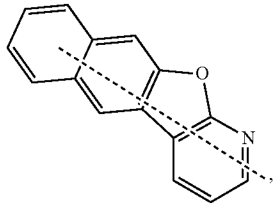
,
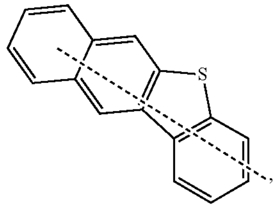
,
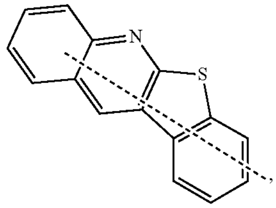
,
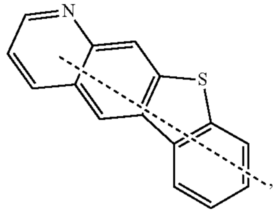
,
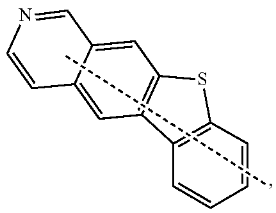
, -continued

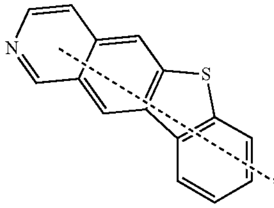
,
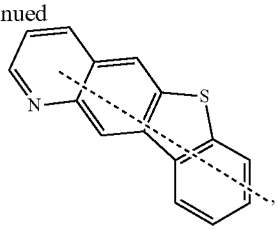
,
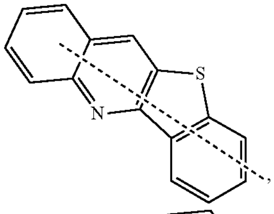
,
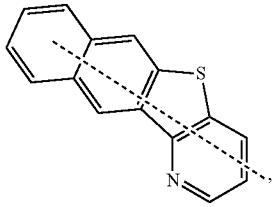
,
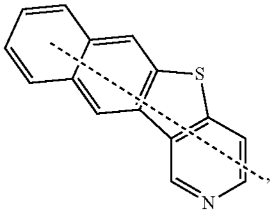
,
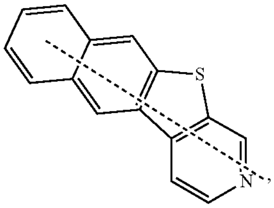
, or
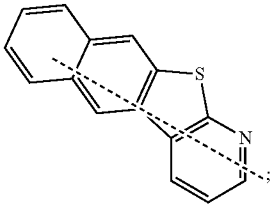
;

wherein, the dashed line represents a linkage site of the group;

the substituent is selected from D (deuterium), halogen (fluorine, chlorine, bromine or iodine) or cyano (—CN).

In an embodiment, C6 to C18 arylene is selected from any one of phenylene, naphthylene, anthrylene or phenanthrylene.

In an embodiment, C3 to C18 heteroarylene is selected from any one of furanylene, thienylene, pyrrolylene, pyridylene, pyranylene, pyrimidinylene, pyrazinylene, pyridazinylene, triazinylene, naphthylene, quinolylene, quinoxalinylene, isoquinolylene or quinazolinylene.

In an embodiment, $L_1$ to $L_3$ are each independently selected from a single bond, substituted or unsubstituted phenylene or substituted or unsubstituted naphthylene;

the substituted substituents in phenylene and naphthylene are each independently selected from at least one of D (deuterium), halogen (fluorine, chlorine, bromine or iodine) or cyano (—CN).

In an embodiment, C6 to C30 aryl is selected from any one of phenyl, naphthyl, anthryl, phenanthryl, pyrenyl, perylenyl, benzophenanthryl, benzopyrenyl or benzoanthryl.

In an embodiment, C3 to C30 heteroaryl is selected from any one of furanyl, thienyl, pyrrolyl, pyridyl, pyranyl, pyrimidinyl, pyrazinyl, pyridazinyl, triazinyl, naphthyl, quinolyl, quinoxalinyl, isoquinolyl, quinazolinyl, acridinyl, carbazolyl, indolyl, benzofuranyl, benzothienyl, dibenzofuranyl, dibenzothienyl, 2-N-heterodibenzofuran or 2-N-heterodibenzothiophene.

In an embodiment, Are and Ara are each independently selected from any one of the following groups:

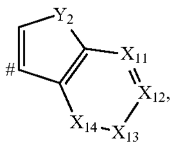
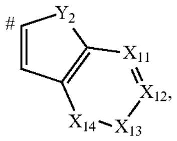
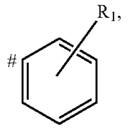
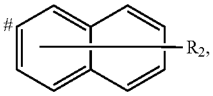
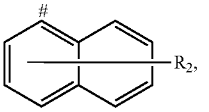
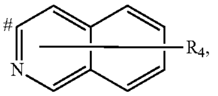
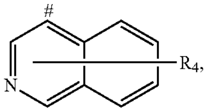
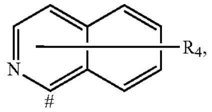
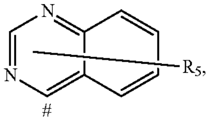
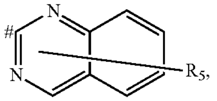
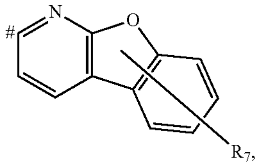
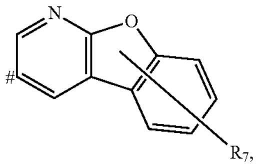
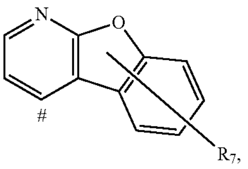
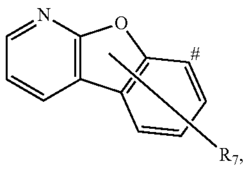
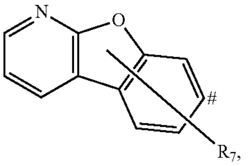
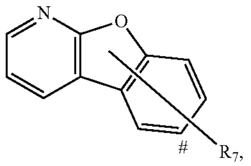
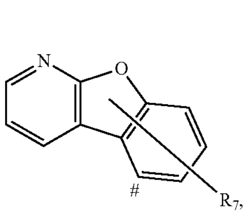
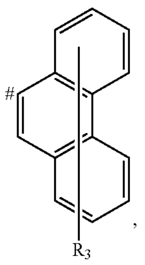

-continued

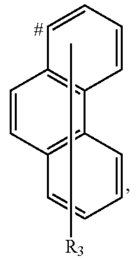
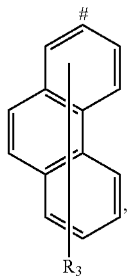
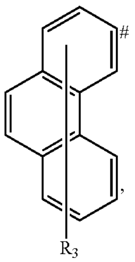
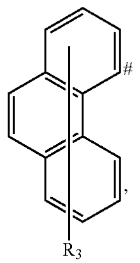
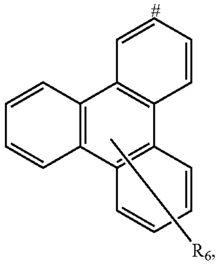
or
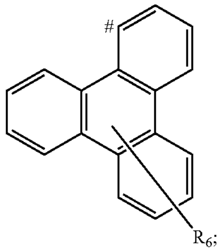

wherein, "#" represents a linkage site of the group;

$X_{11}$, $X_{12}$, $X_{13}$ and $X_{14}$ are each independently selected from N or C—R;

$Y_2$ is selected from N, O or S; and

R, $R_1$, $R_2$, $R_3$, $R_4$, $R_5$, $R_6$ and $R_7$ are each independently selected from H, D (deuterium), halogen (fluorine, chlorine, bromine or iodine) or cyano (—CN).

In an embodiment, the heterocyclic arylamine compound is selected from any one of the following compounds:

-continued
P001
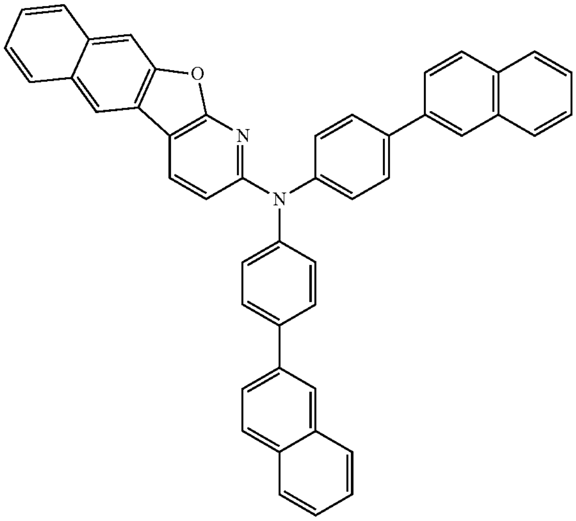
P002
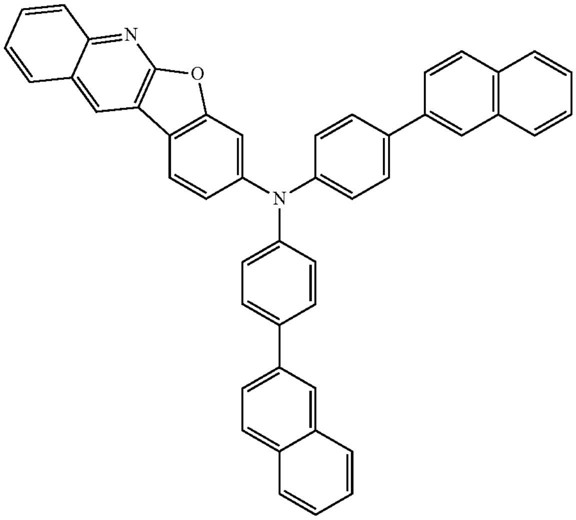
P003
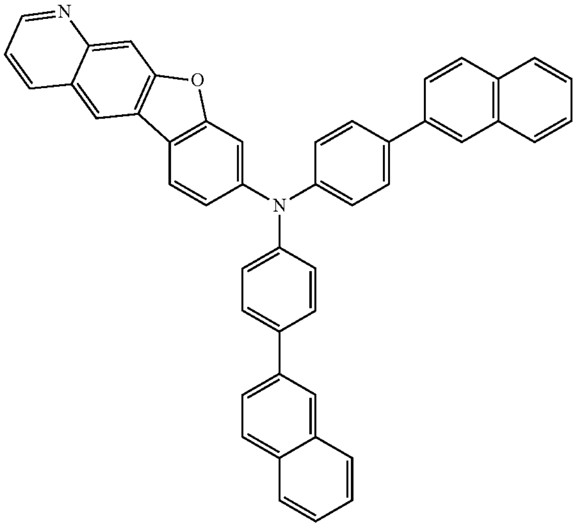
P004
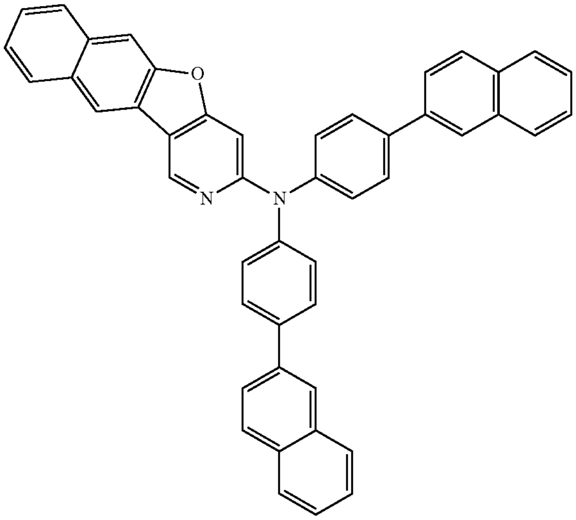
P005
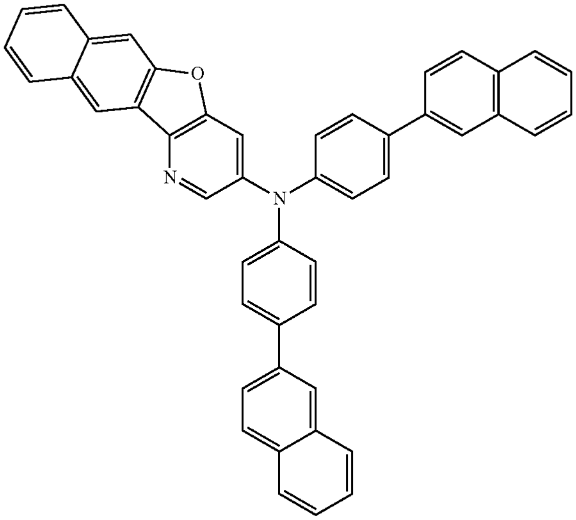
P006
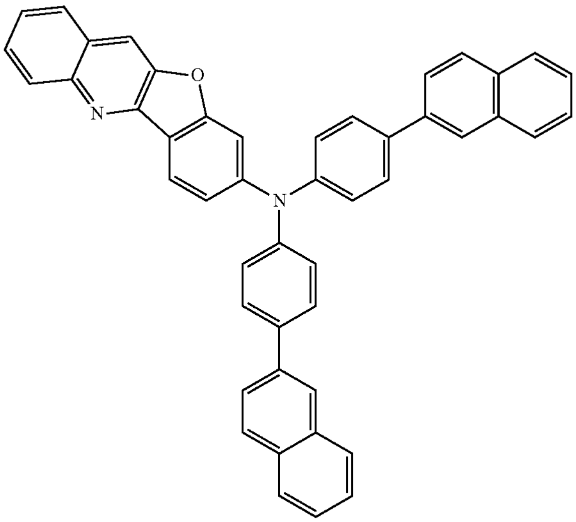

-continued
P007
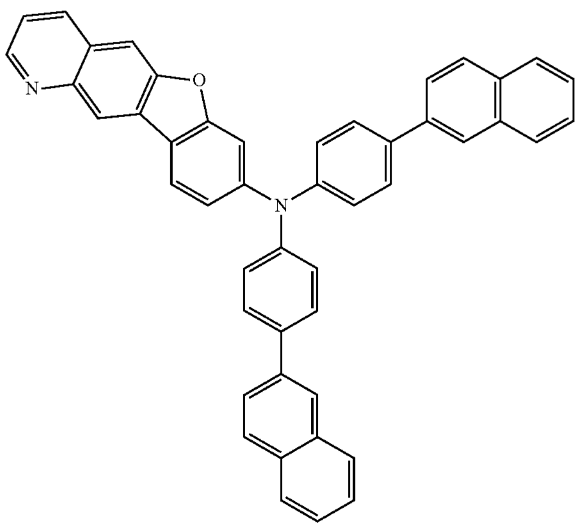
P008
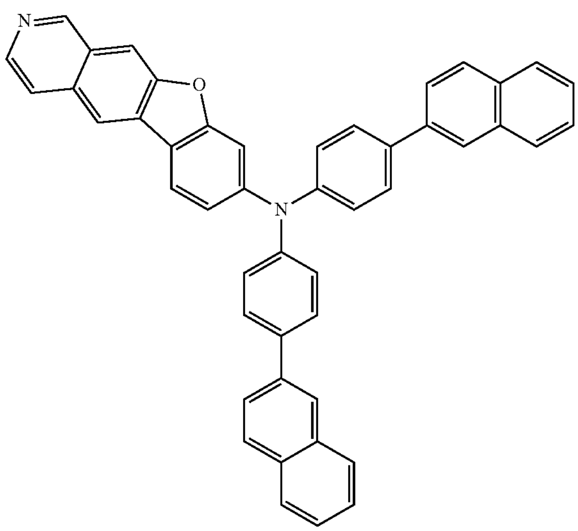
P009
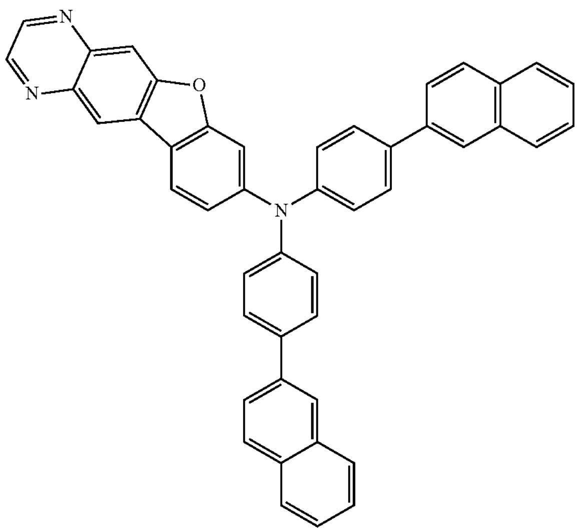
-continued
P010
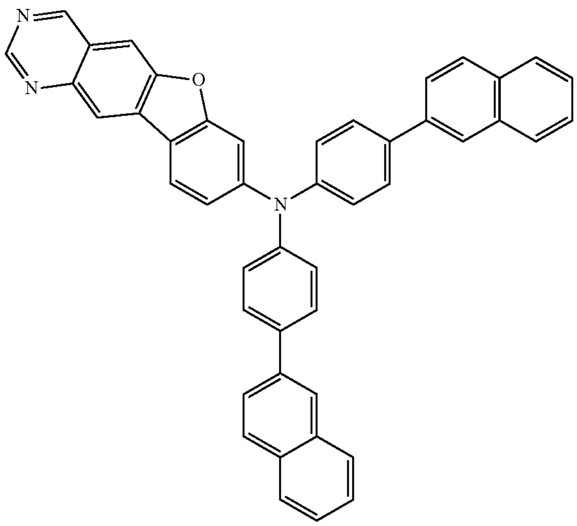
P011
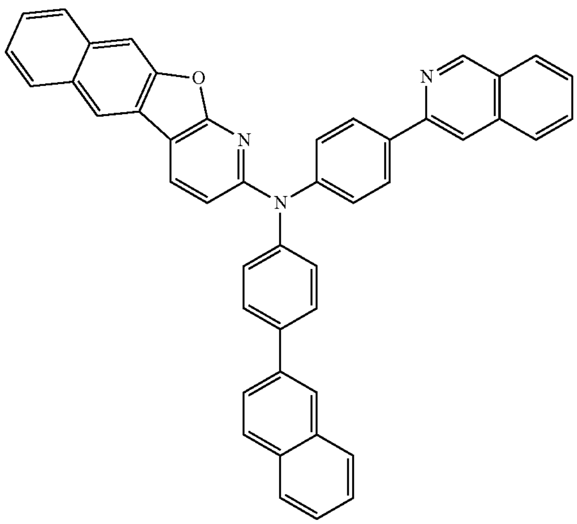
P012
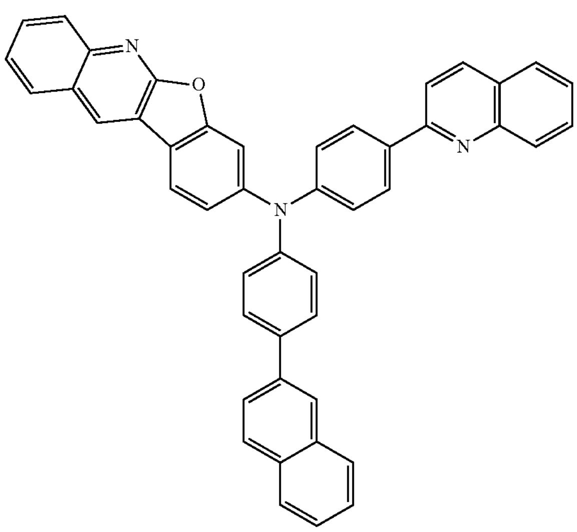

-continued
P013
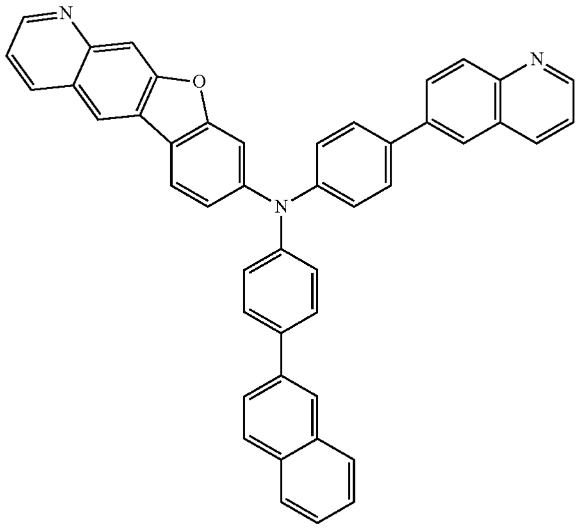
P014
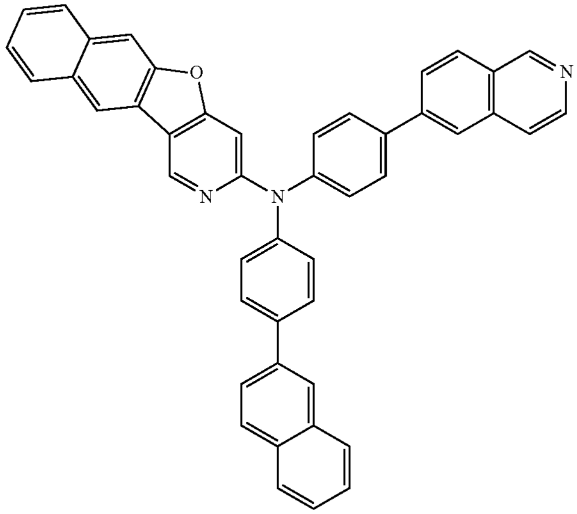
P015
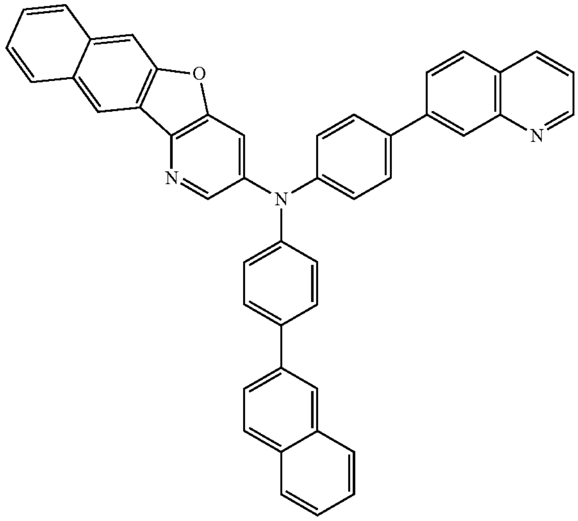
-continued
P016
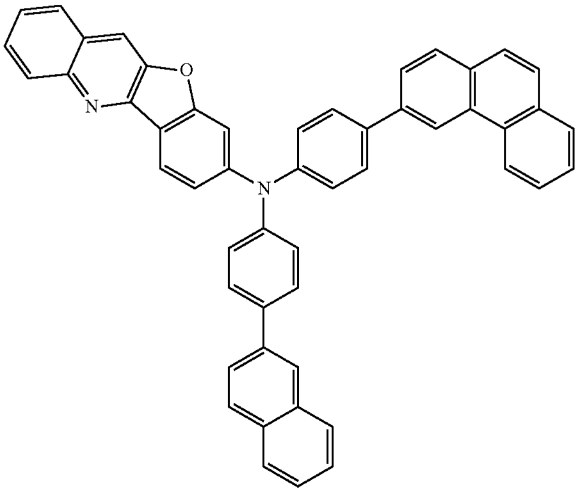
P017
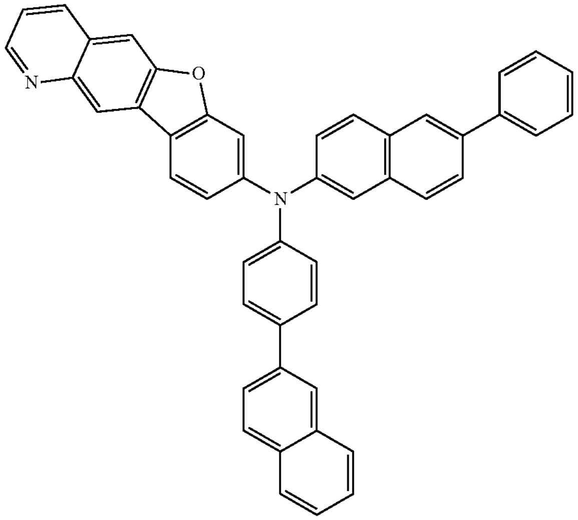
P018
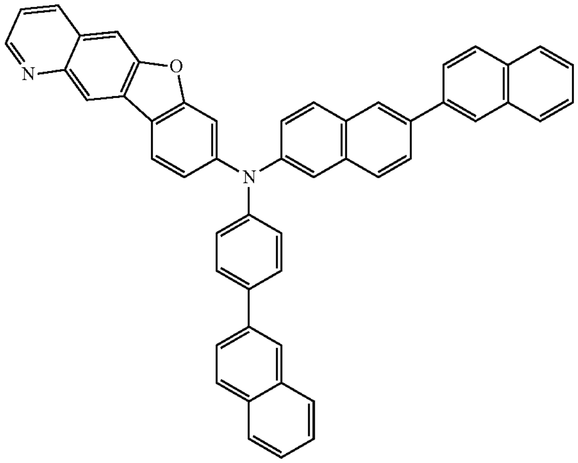

P019
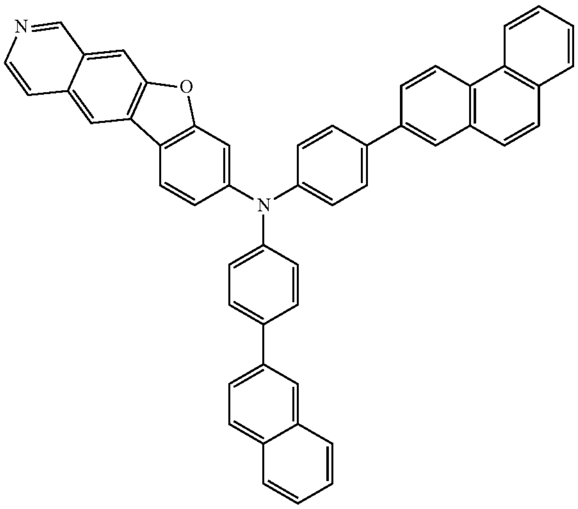
P020
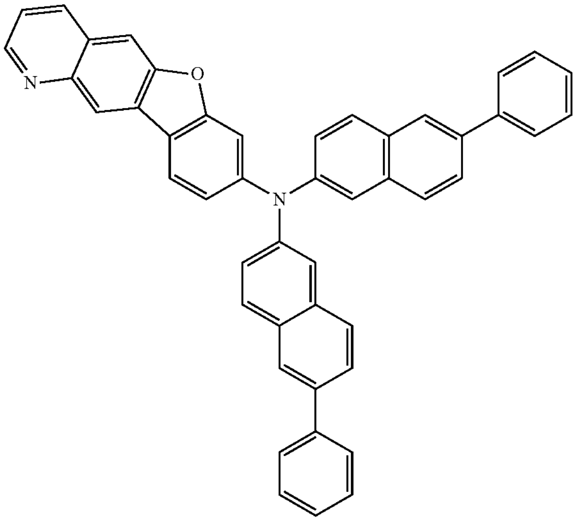
P021
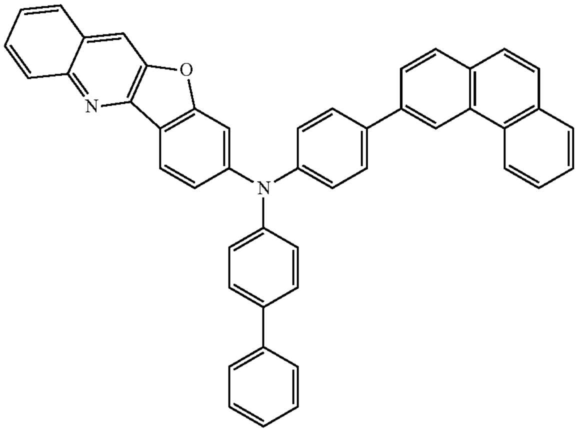
P022
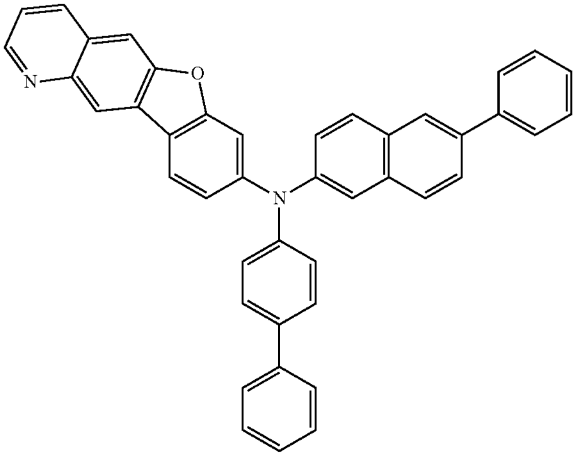
P023
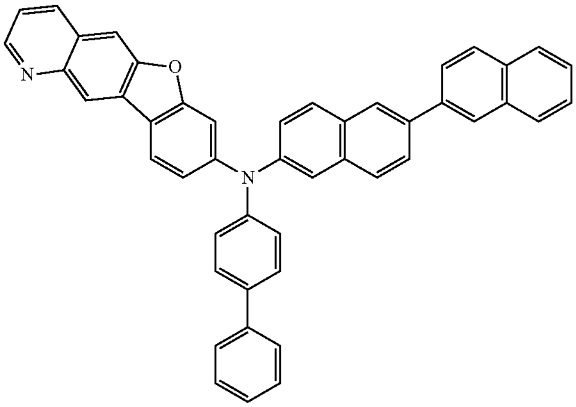
P024
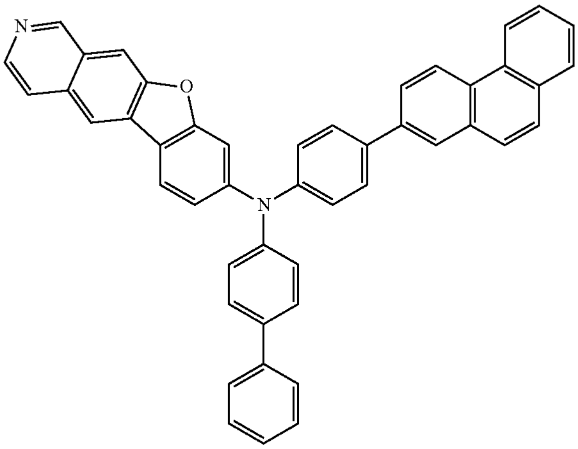

-continued
P025
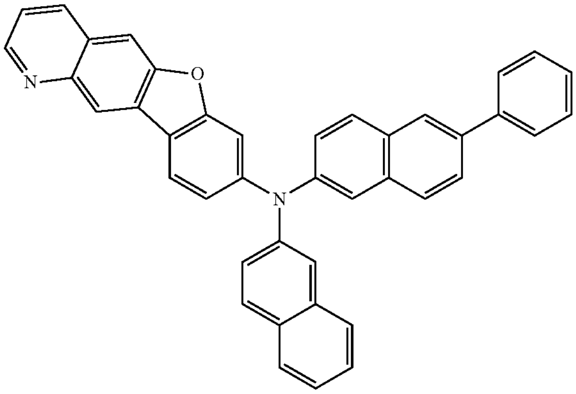
P026
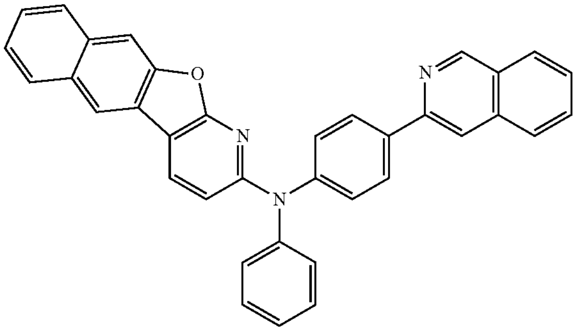
P027
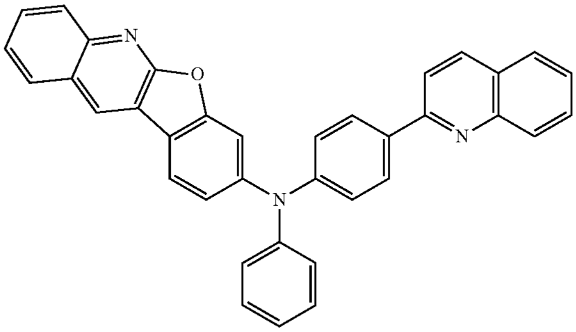
P028
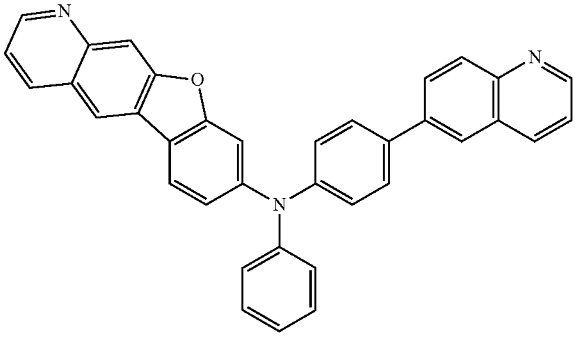
-continued
P029
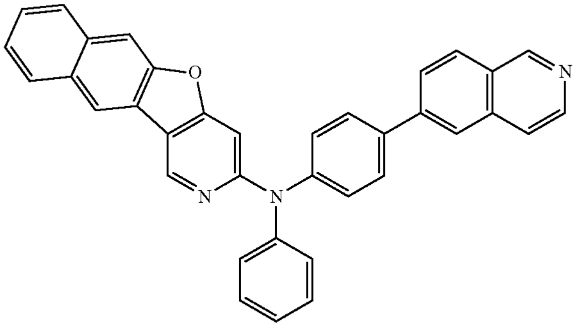
P030
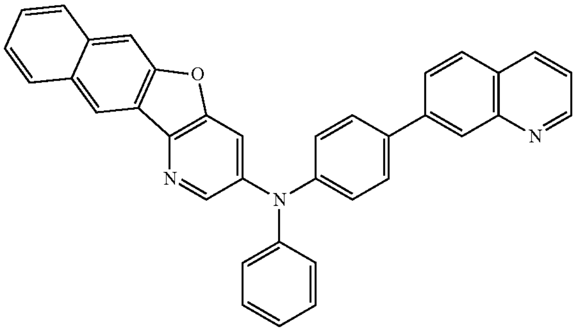
P031
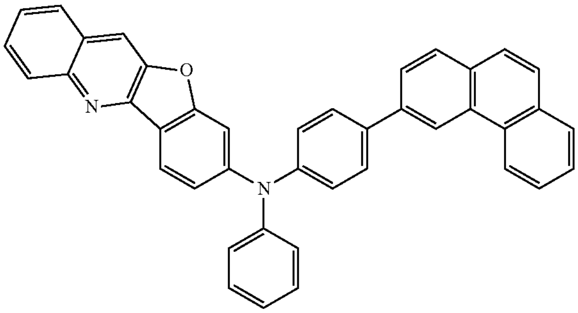
P032
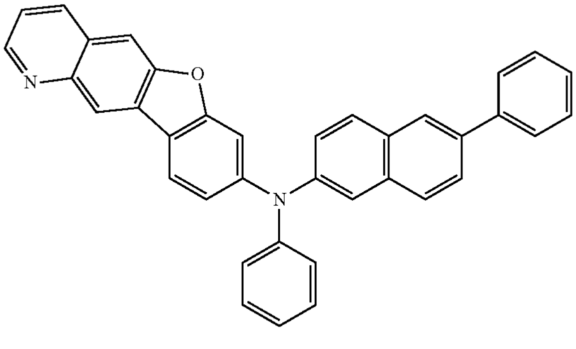

-continued
P033
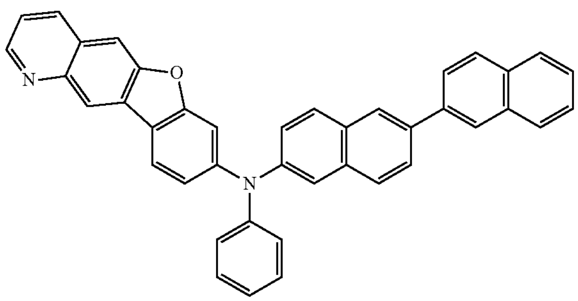
P034
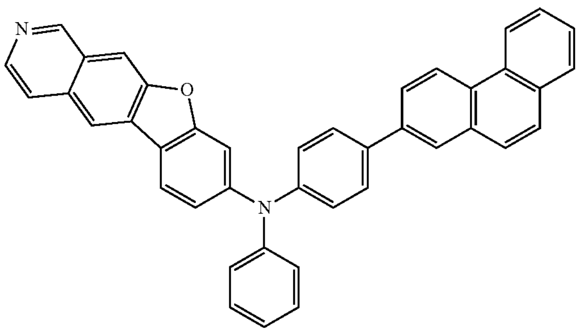
P035
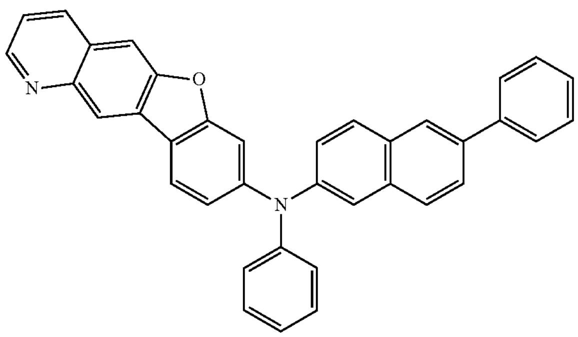
P036
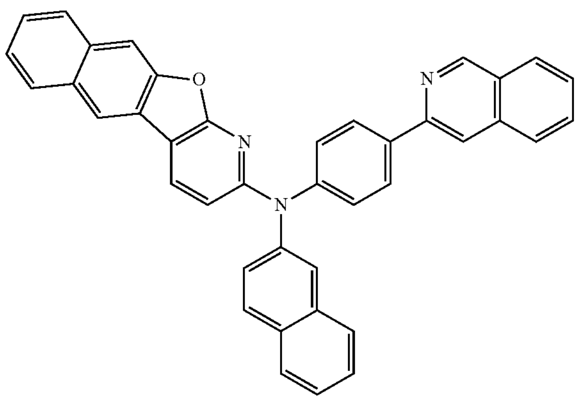
-continued
P037
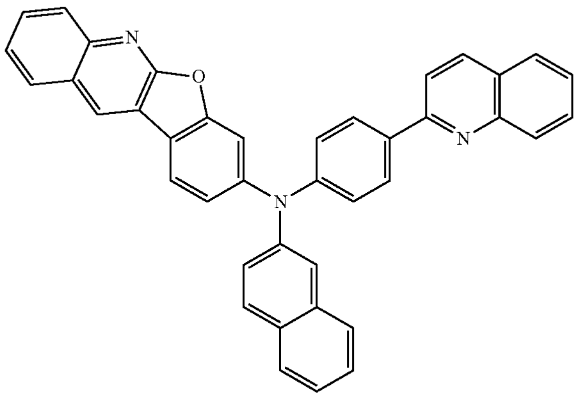
P038
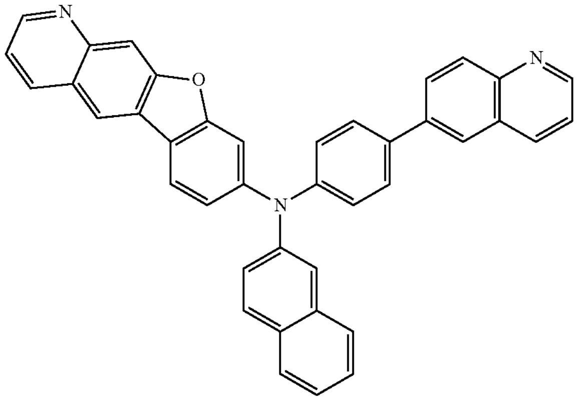
P039
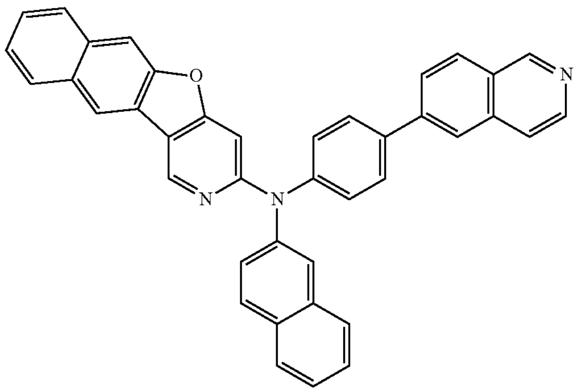

-continued
P040
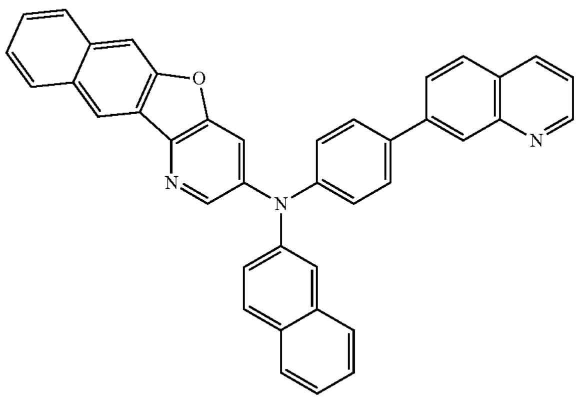
P045
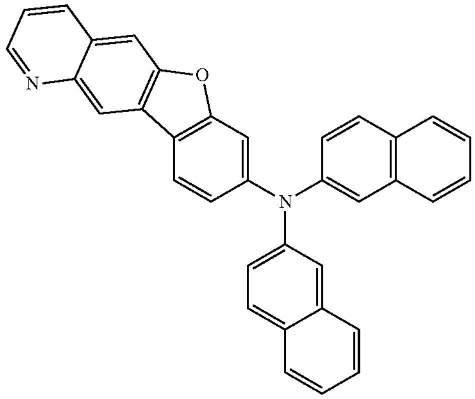
P046
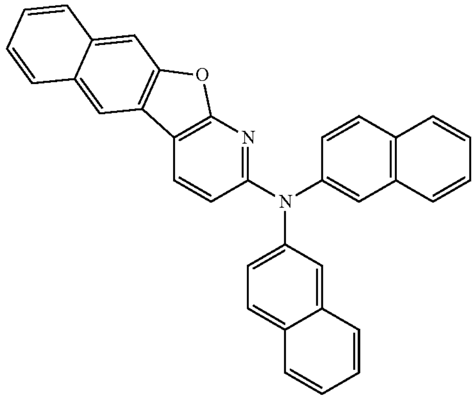
P047
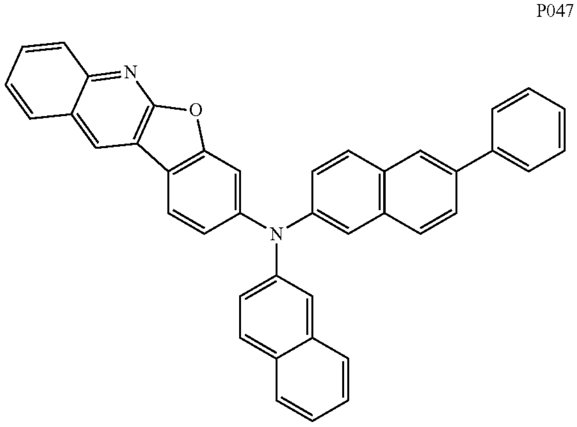
-continued
P048
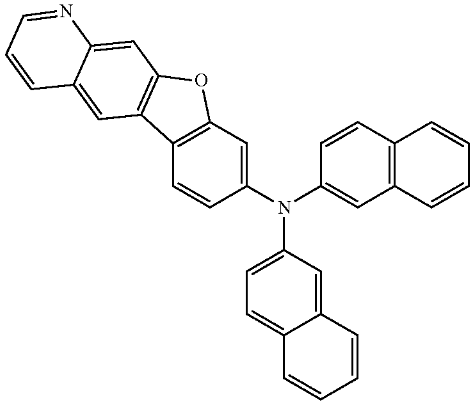
P049
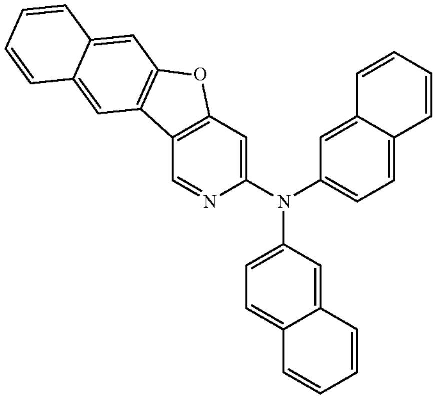
P050
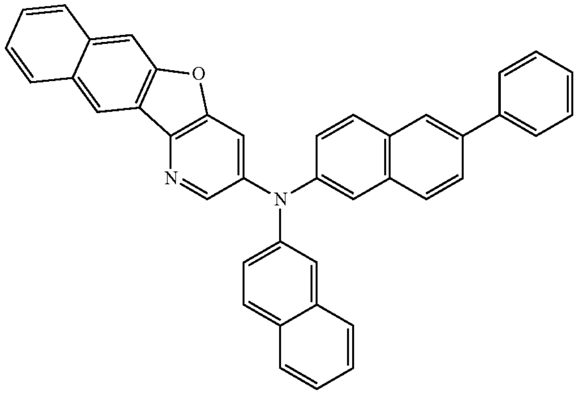
P051
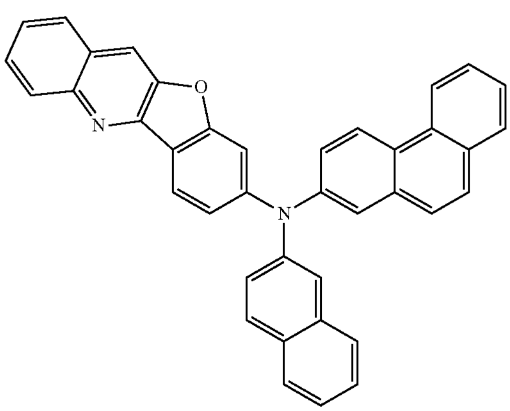

-continued
P052
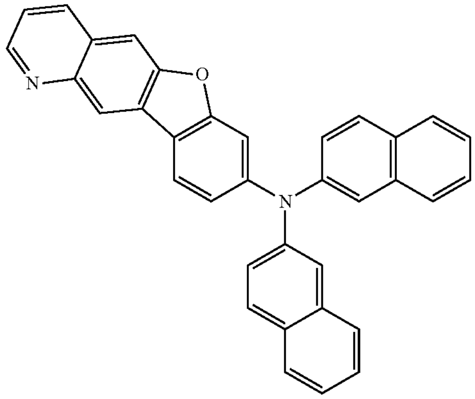
P053
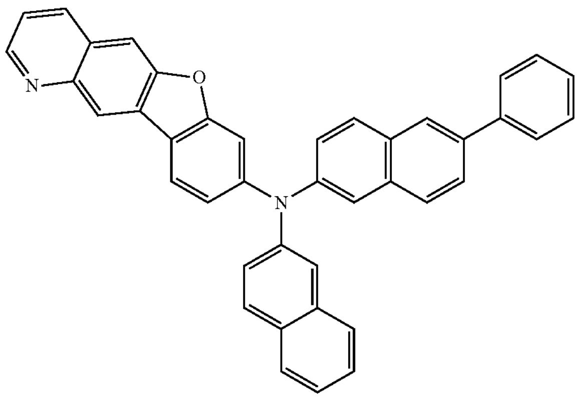
P054
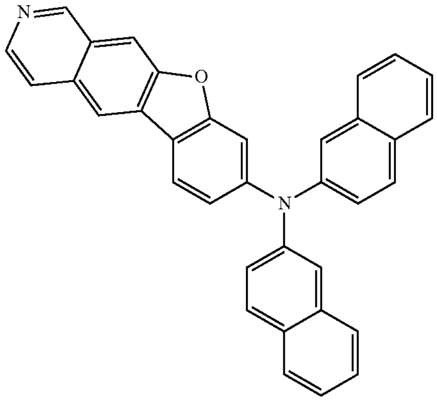
P055
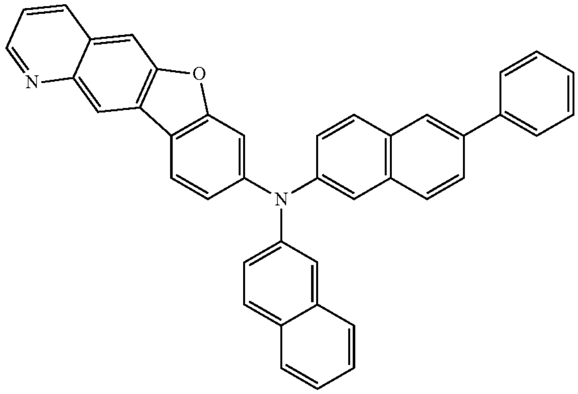
-continued
P056
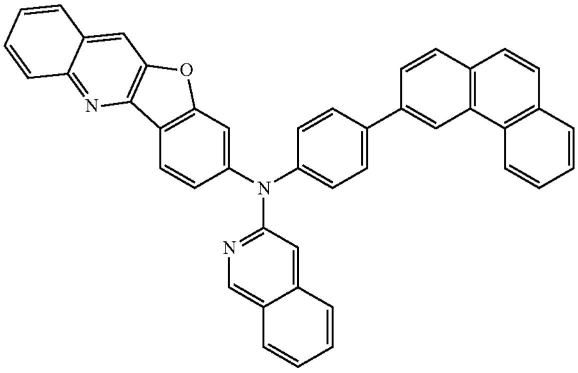
P057
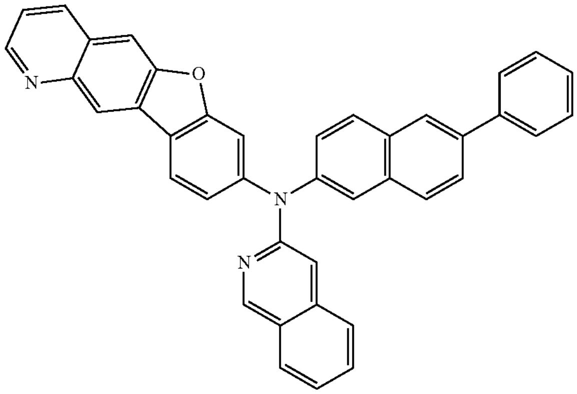
P058
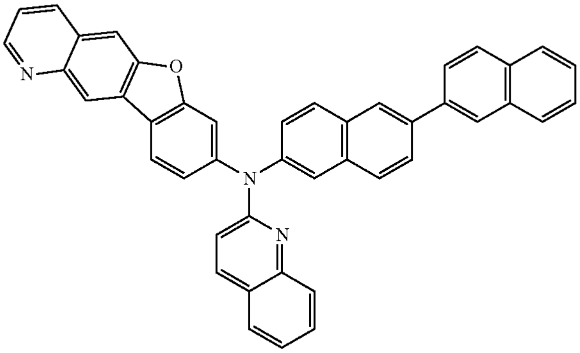
P059
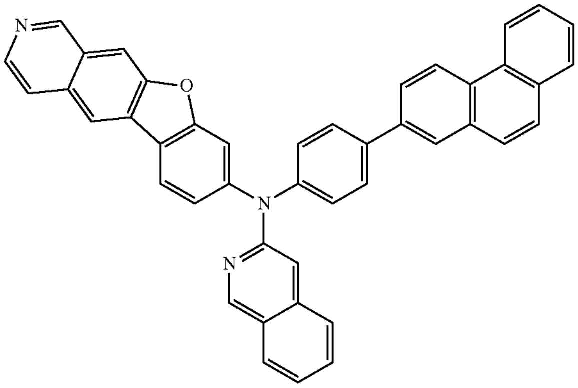

-continued
P060
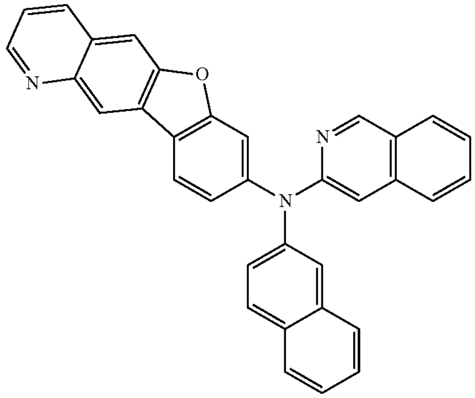
P061
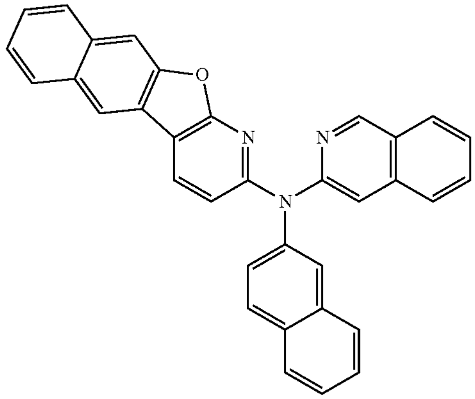
P062
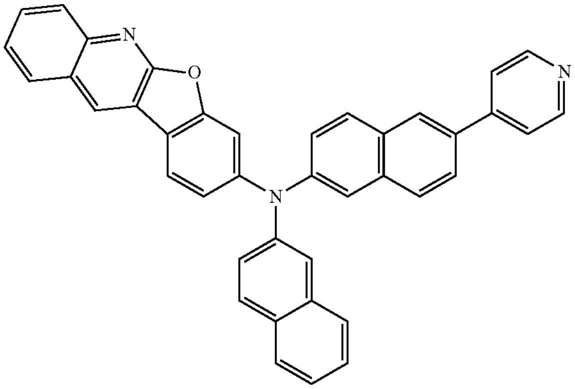
P063
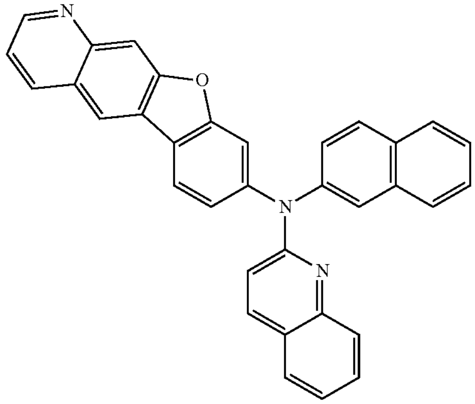
-continued
P064
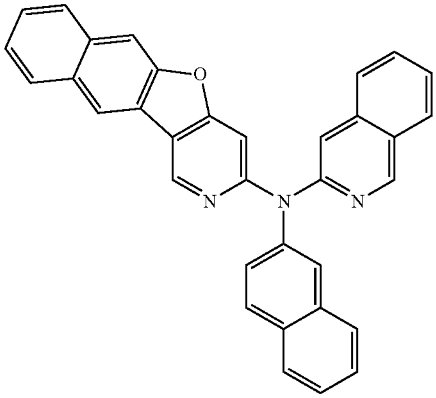
P065
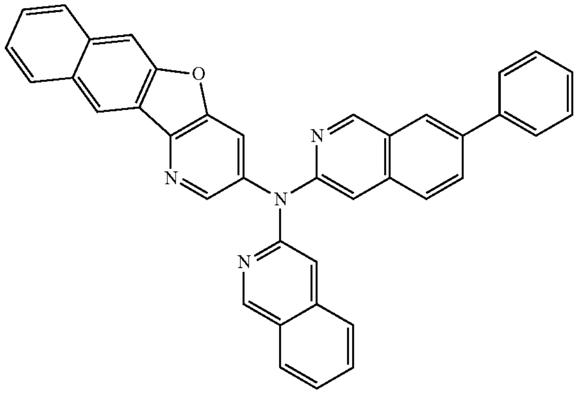
P066
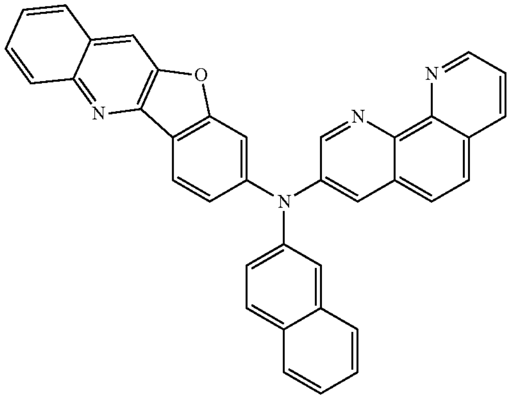
P067
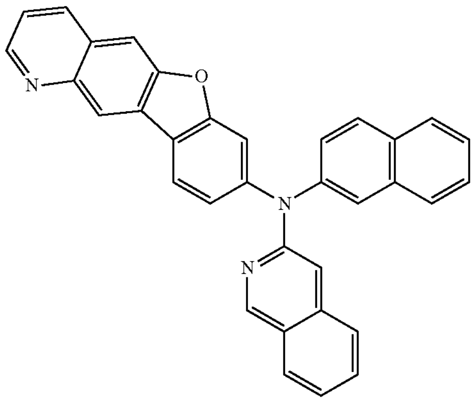

-continued
P068
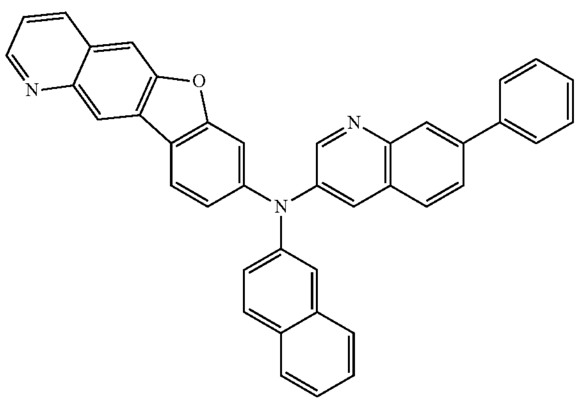
P069
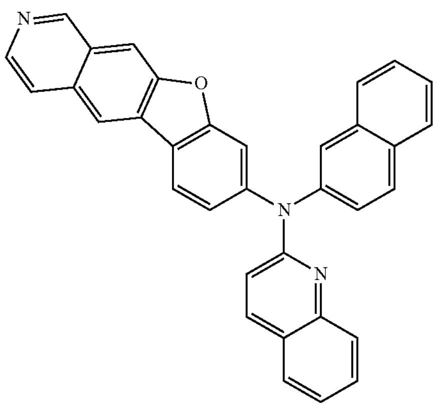
P070
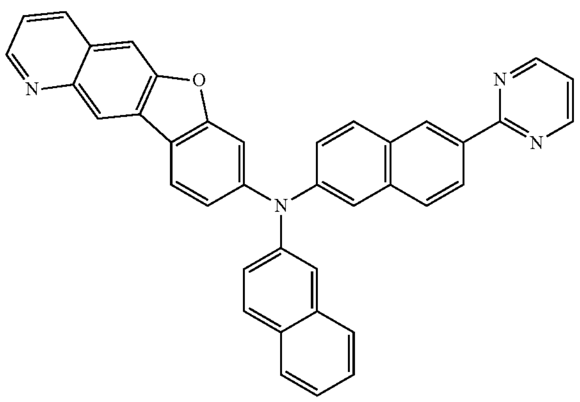
-continued
P071
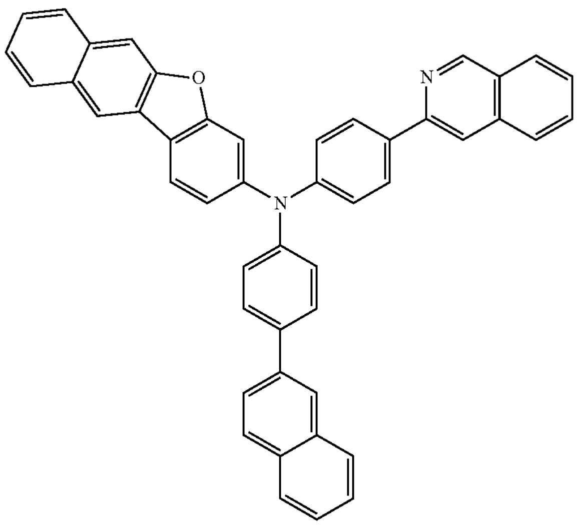
P072
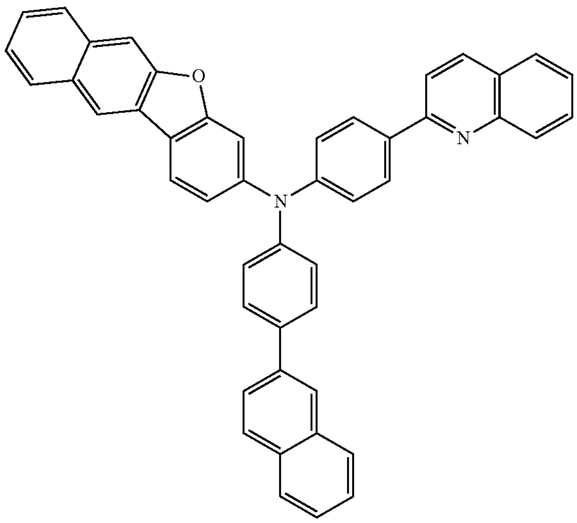
P073
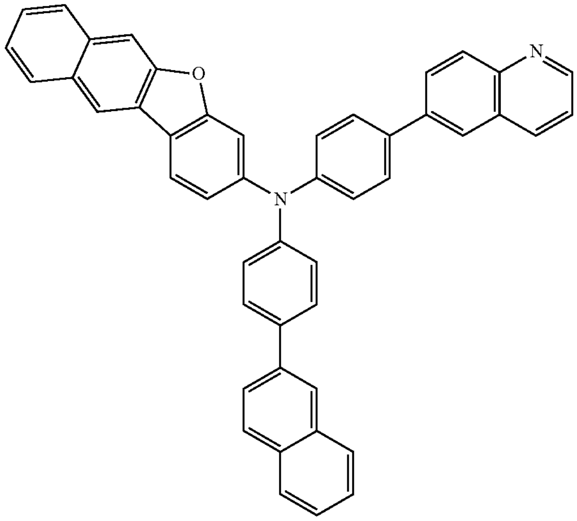

-continued
P074
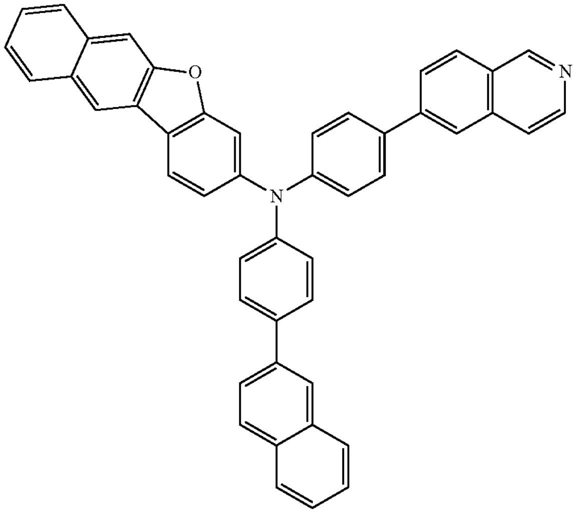
P075
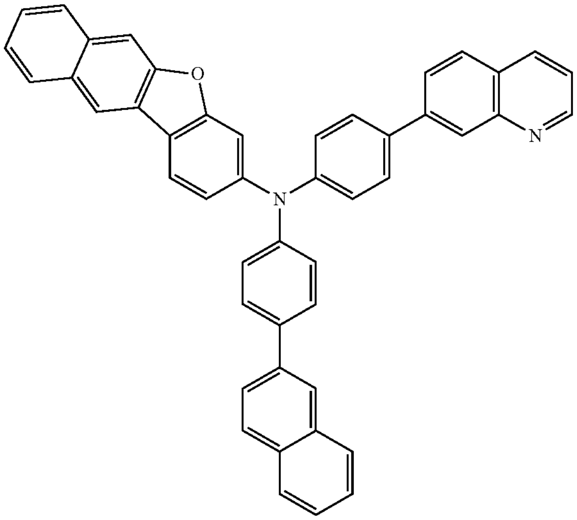
P076
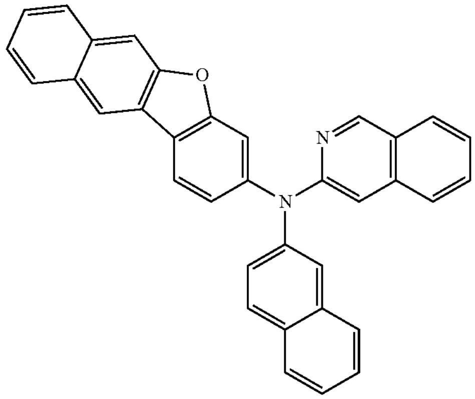
-continued
P077
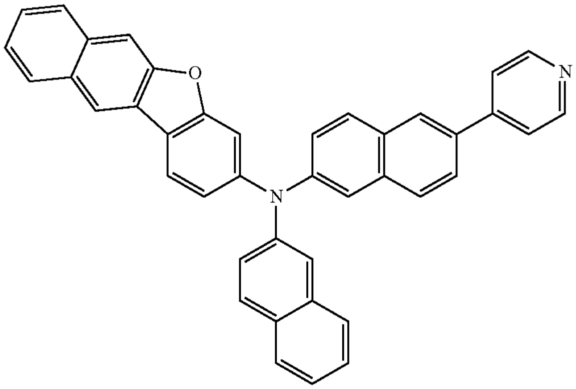
P078
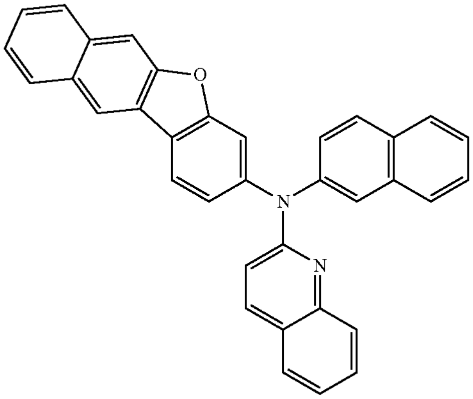
P079
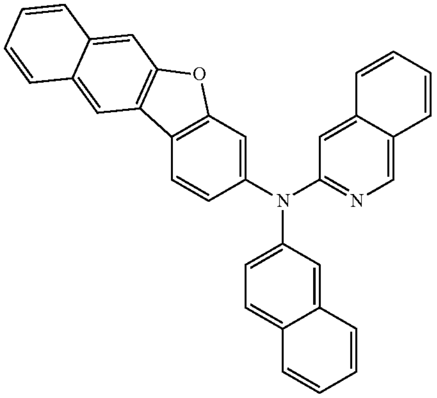
P080
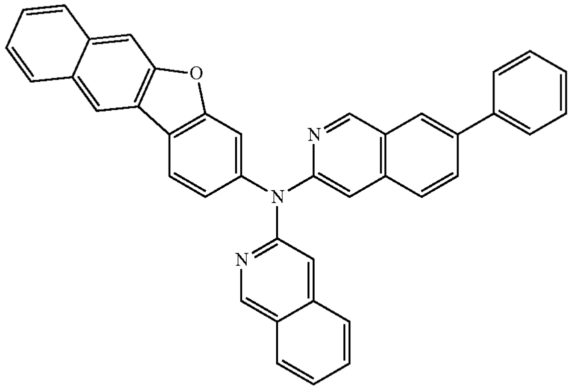

-continued
P081
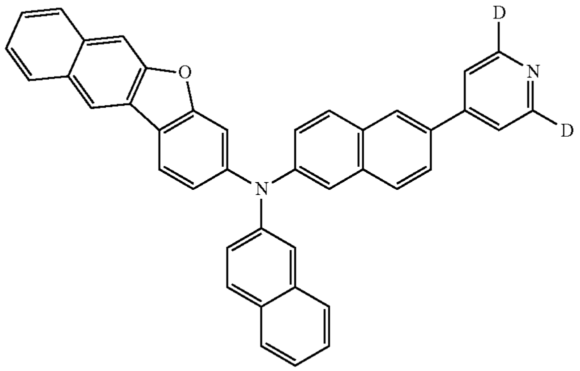
P082
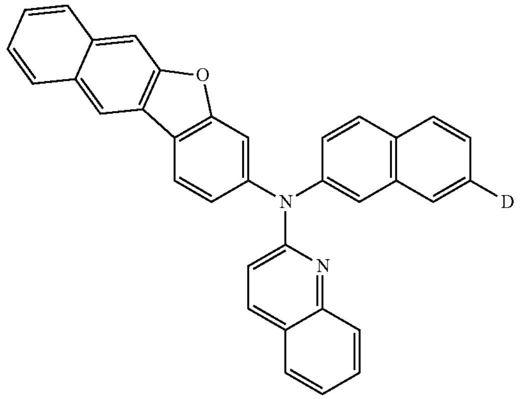
P083
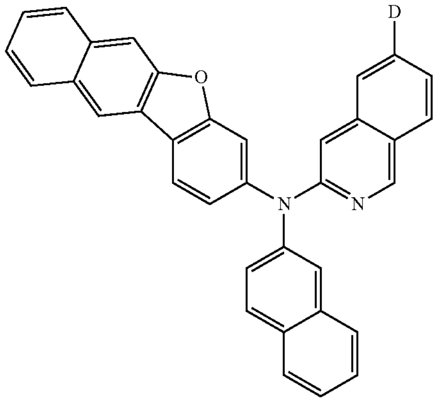
P084
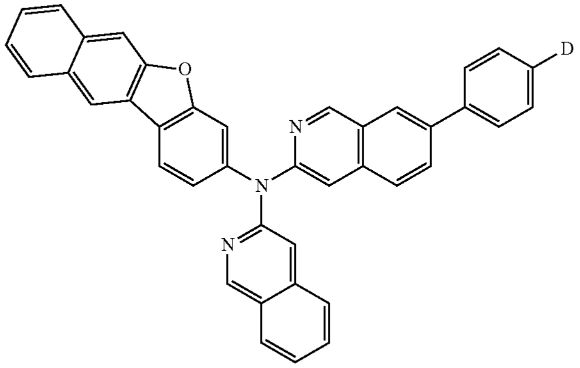
-continued
P085
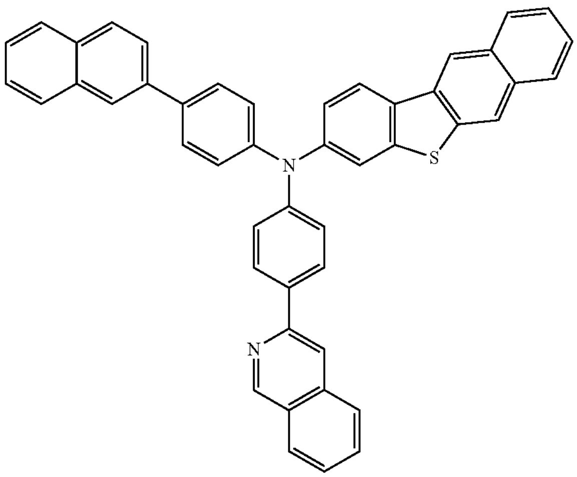
P086
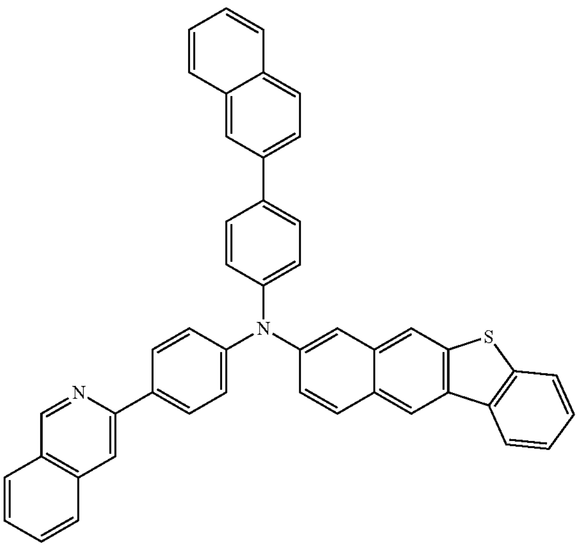
P087
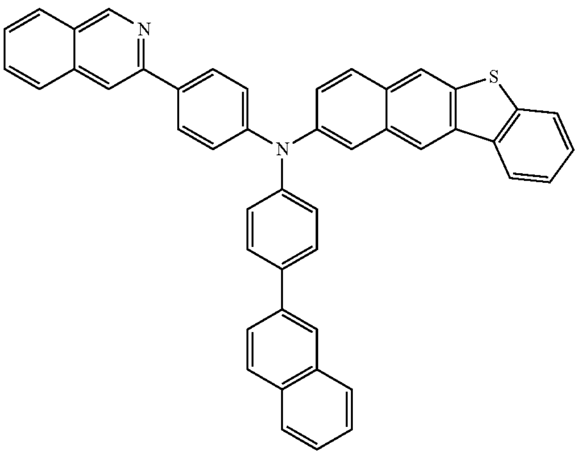

-continued
P088
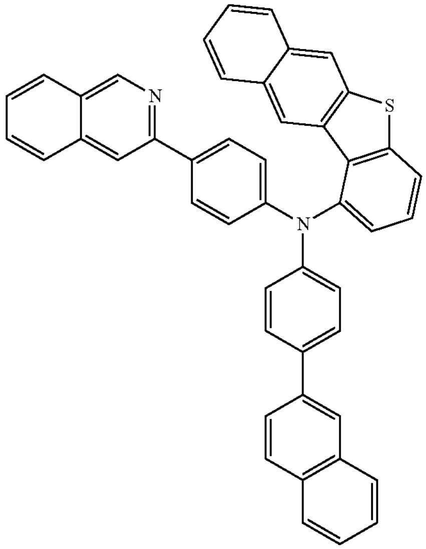
P089
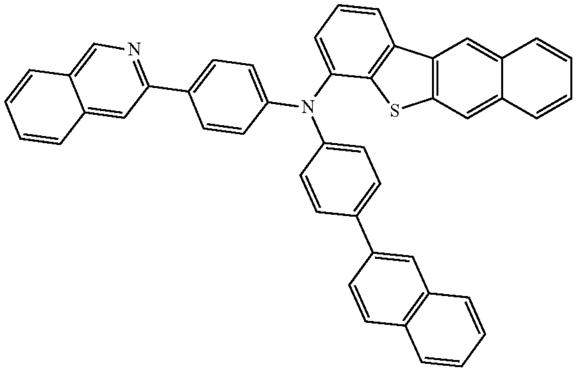
P090
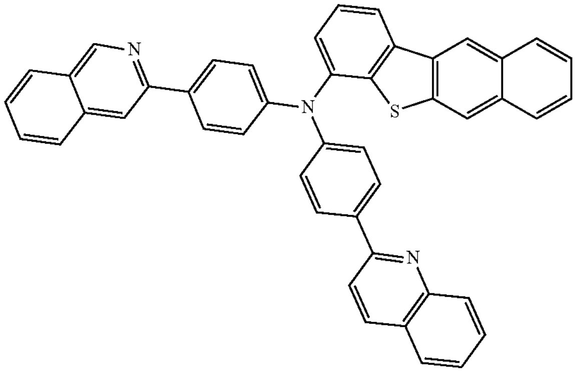
-continued
P091
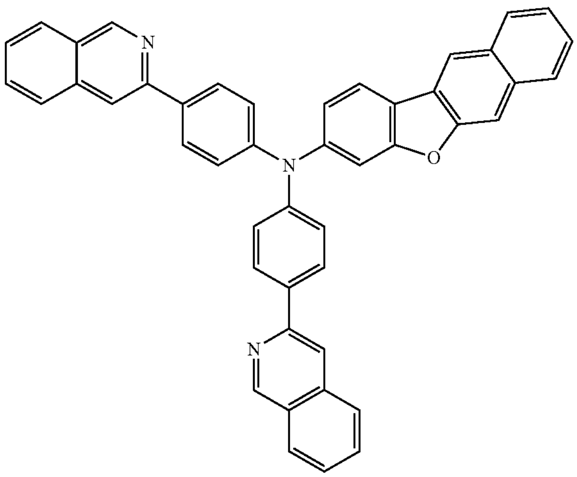
P092
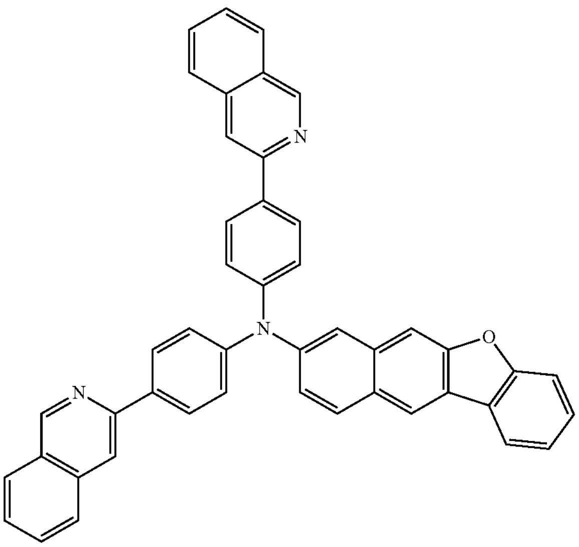
P093
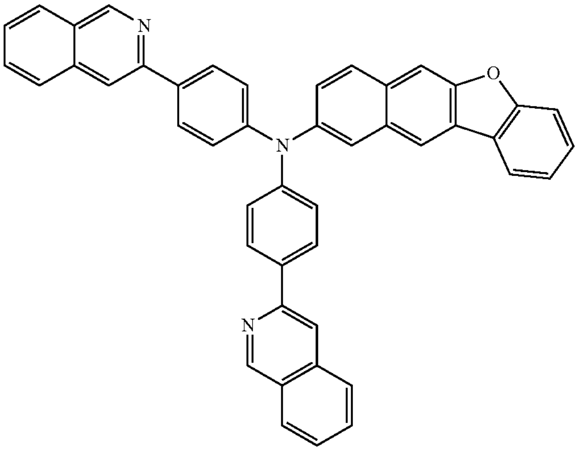

-continued
P094
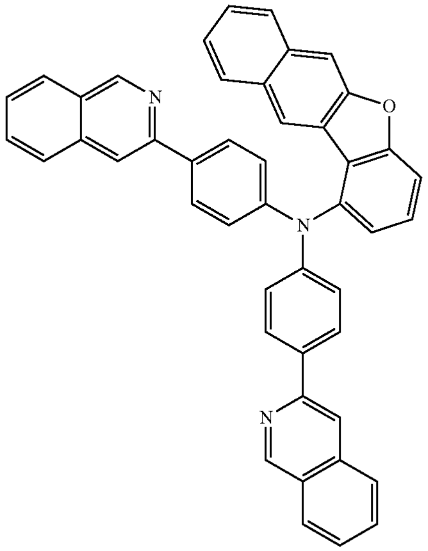
P095
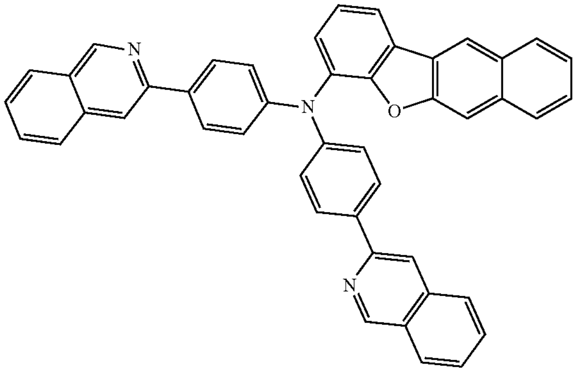
P096
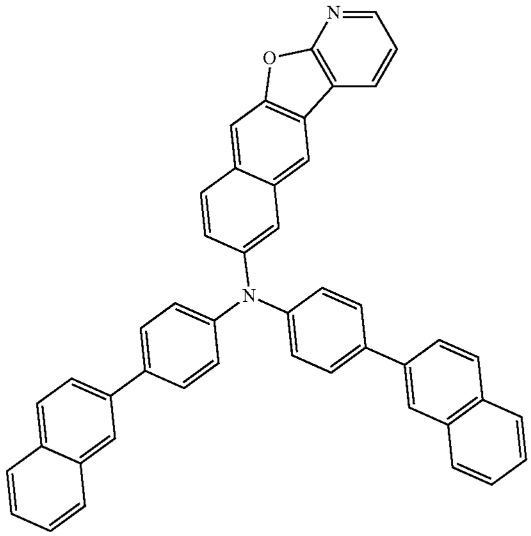
-continued
P097
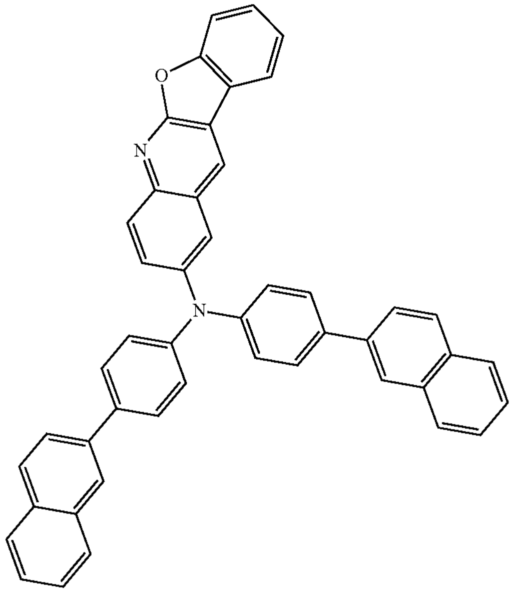
P098
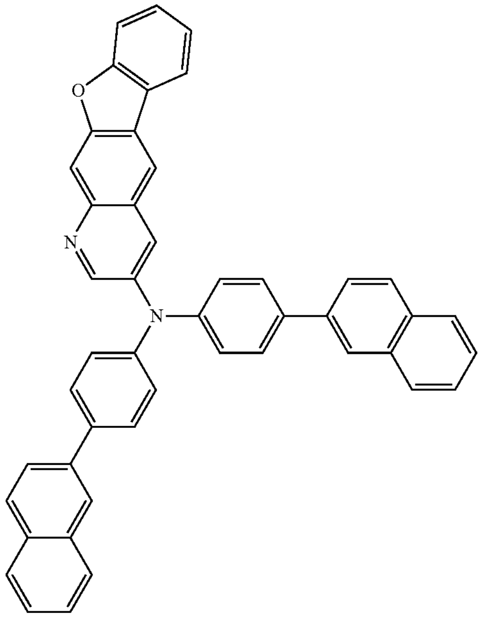

-continued
P099
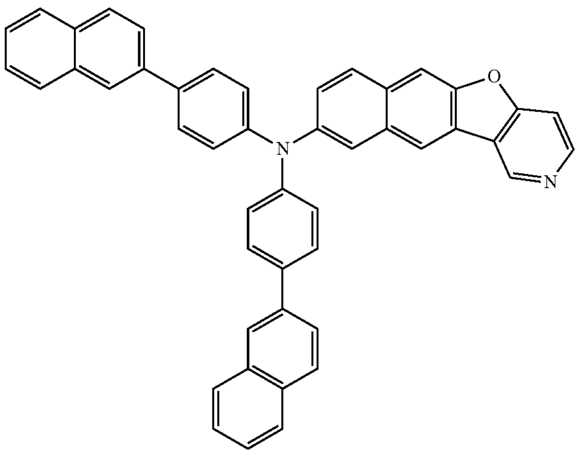
P100
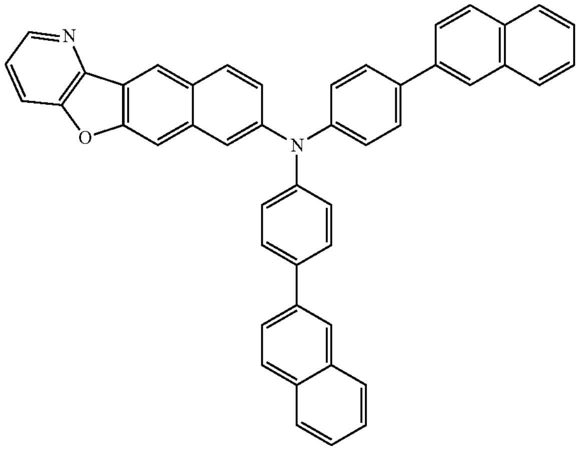
P101
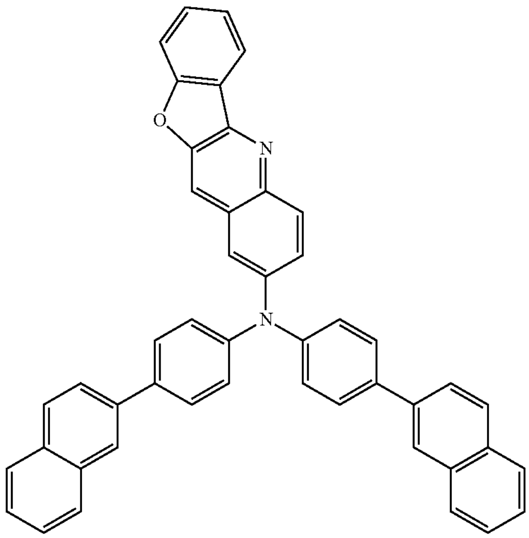
-continued
P102
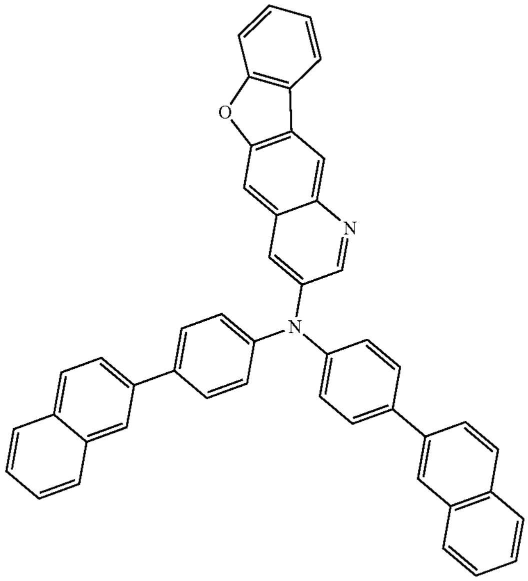
P103
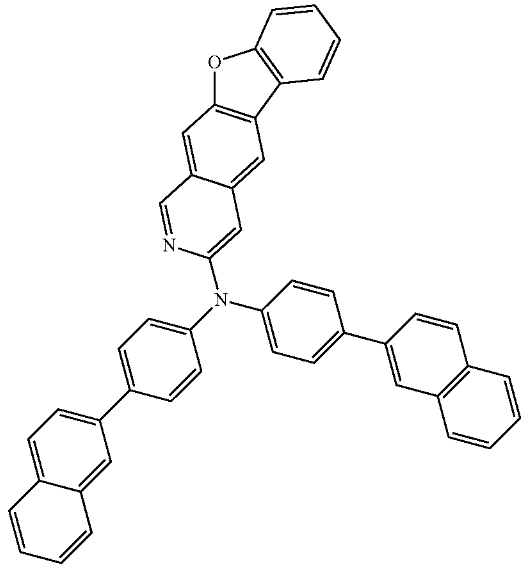

-continued
P104
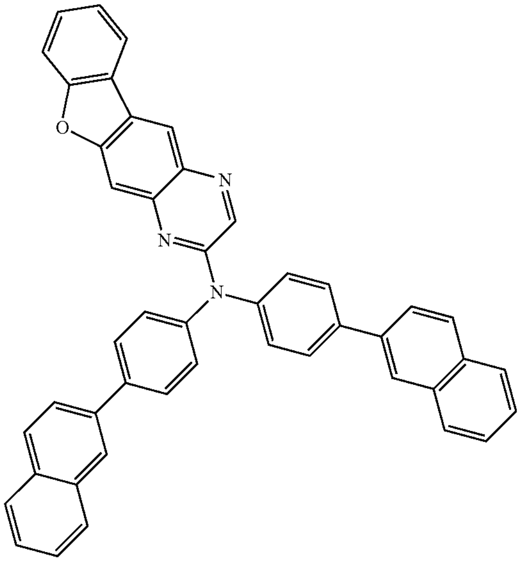
P105
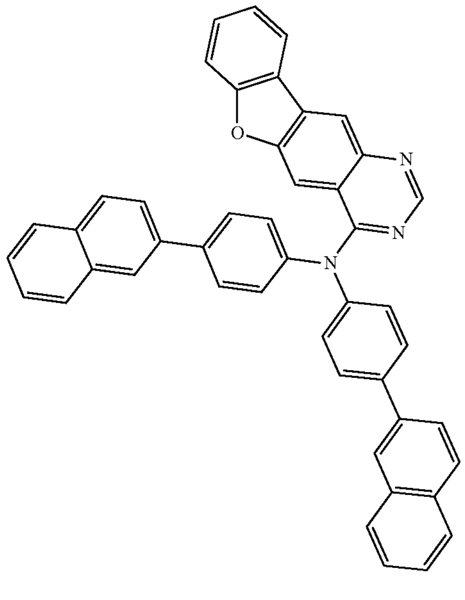
-continued
P106
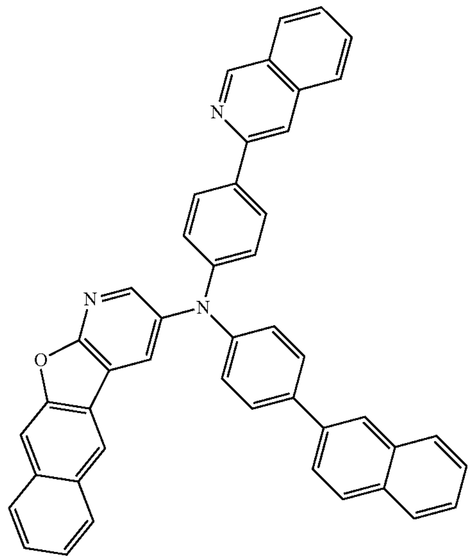
P107
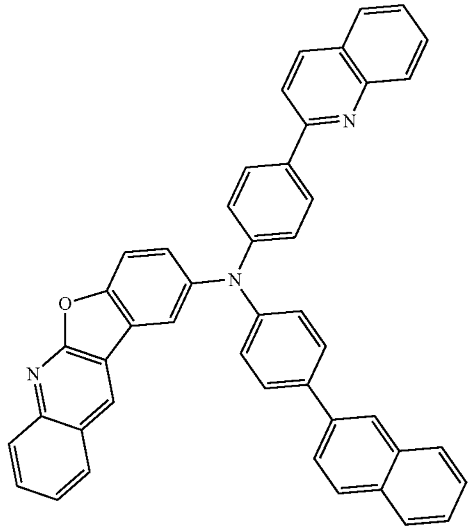
P108
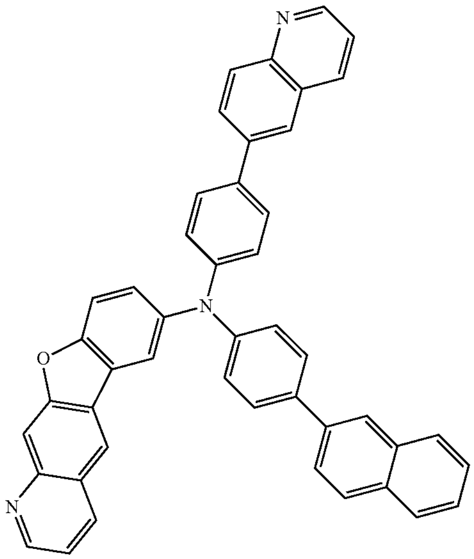

-continued
P109
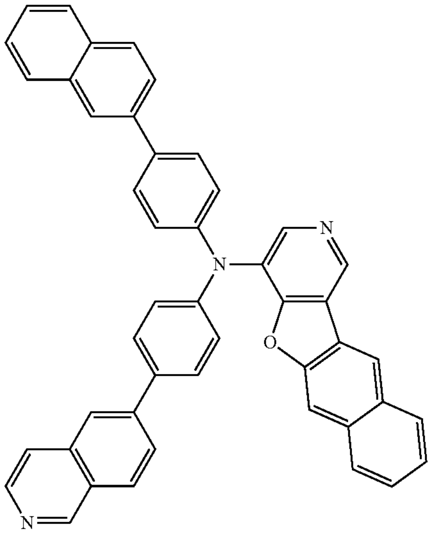
P110
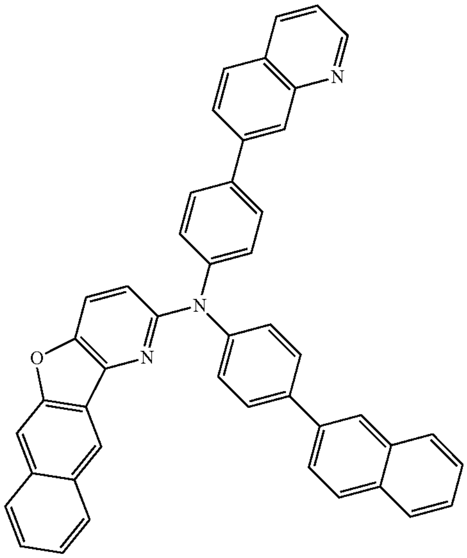
P111
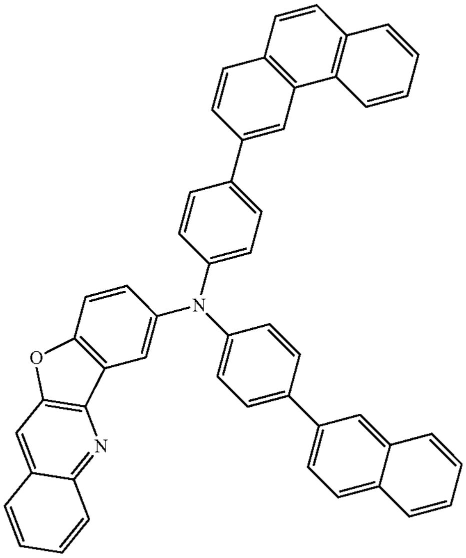
-continued
P112
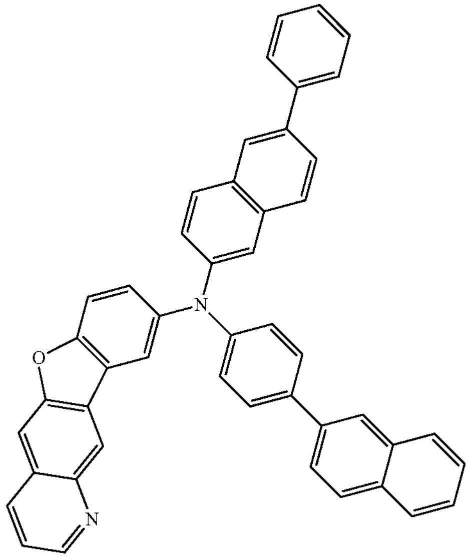
P113
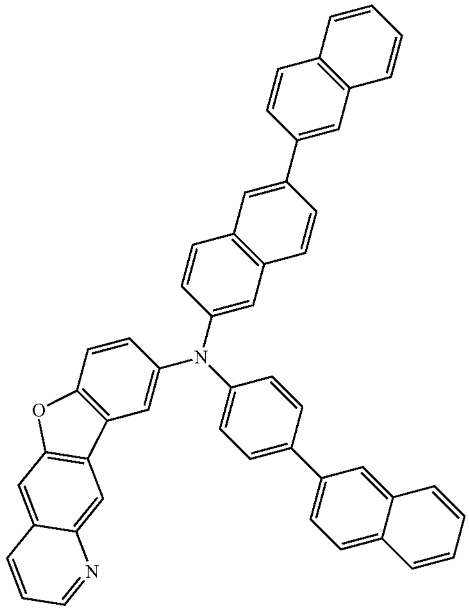

-continued
P114
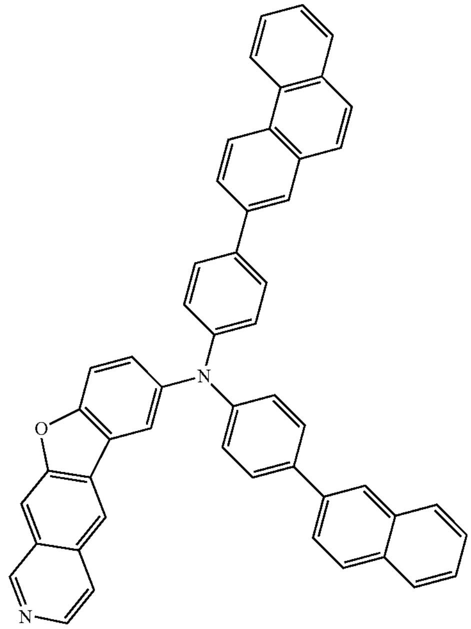
P115
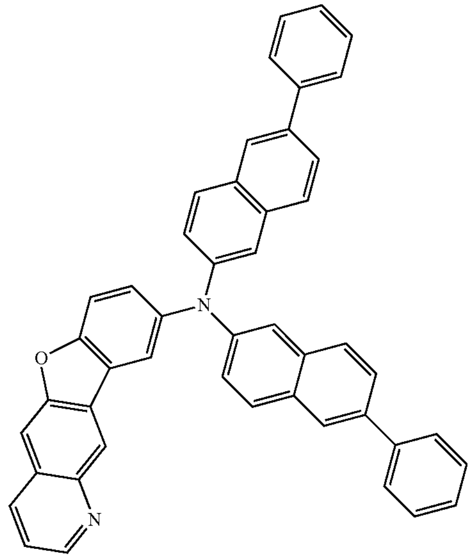
-continued
P116
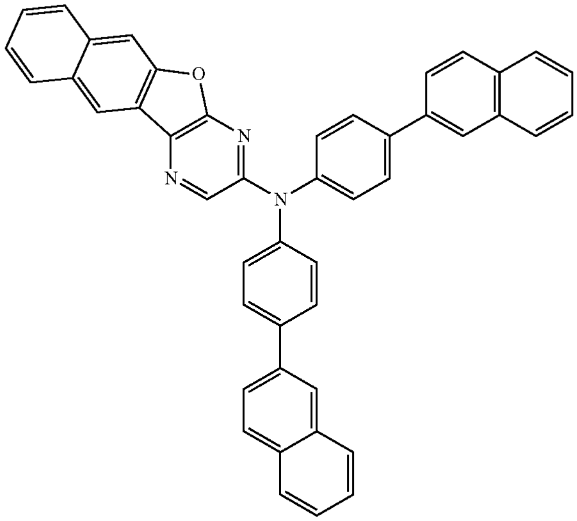
P117
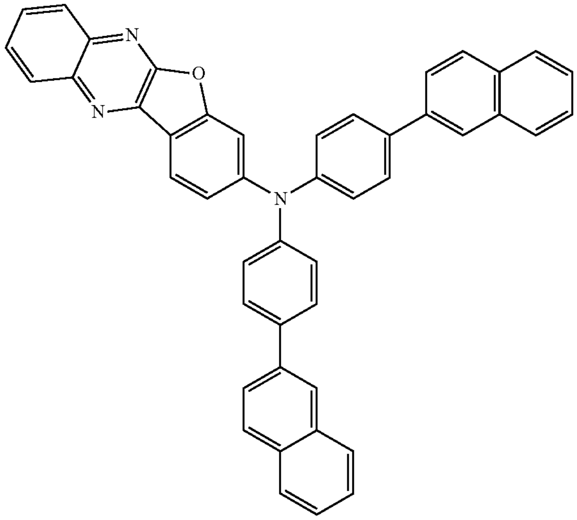
P118
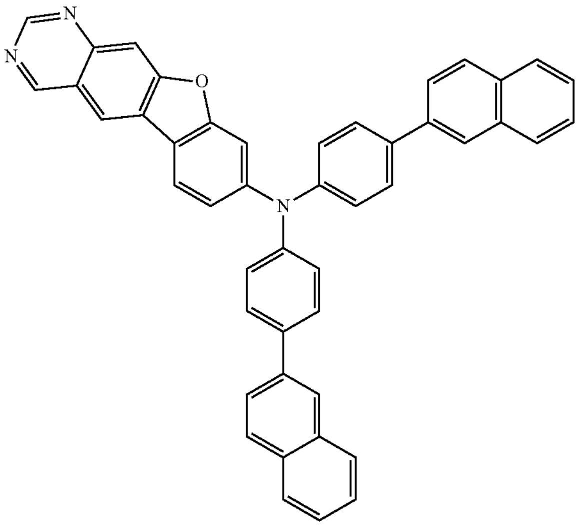

-continued
P119
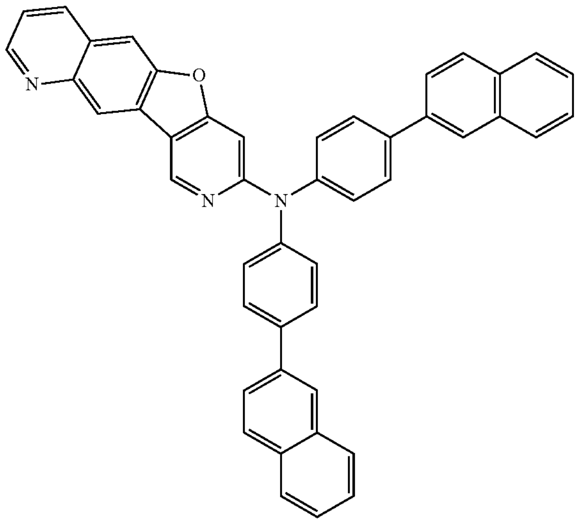
P120
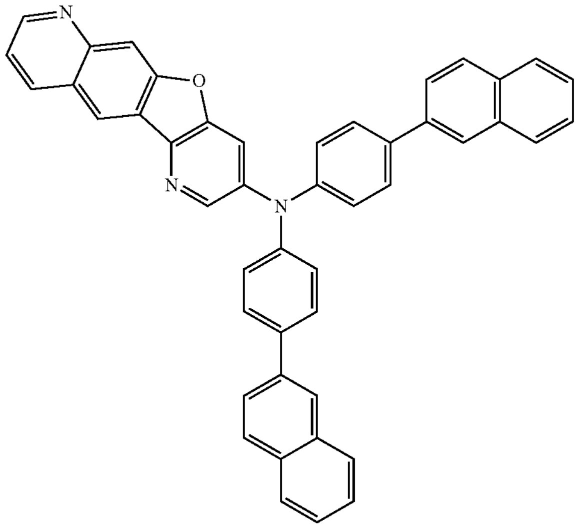
P121
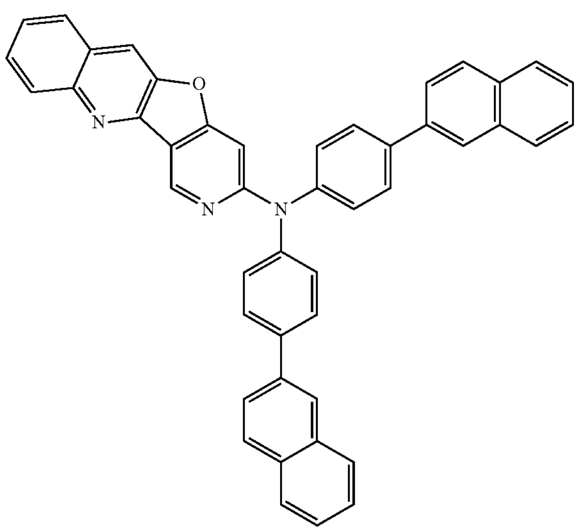
-continued
P122
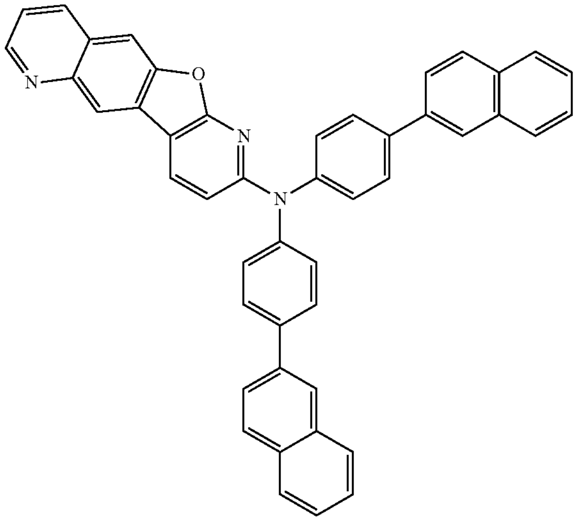
P123
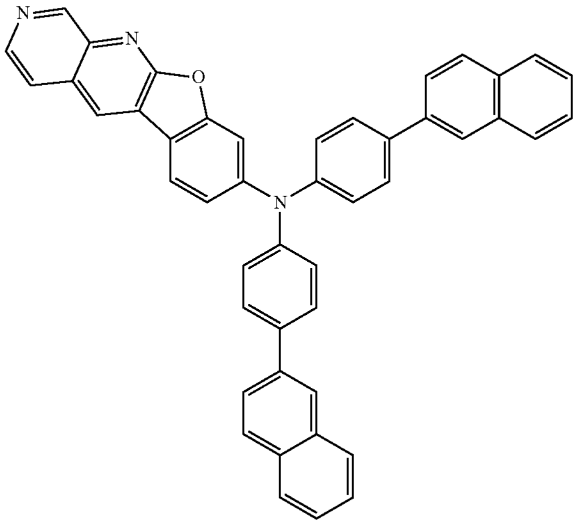
P124
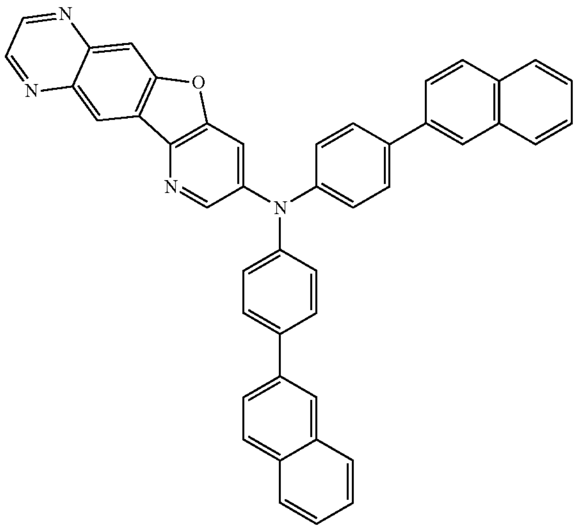

-continued
P125
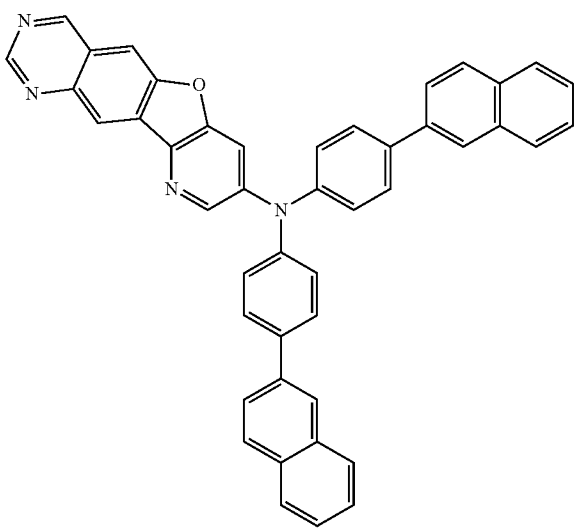
P126
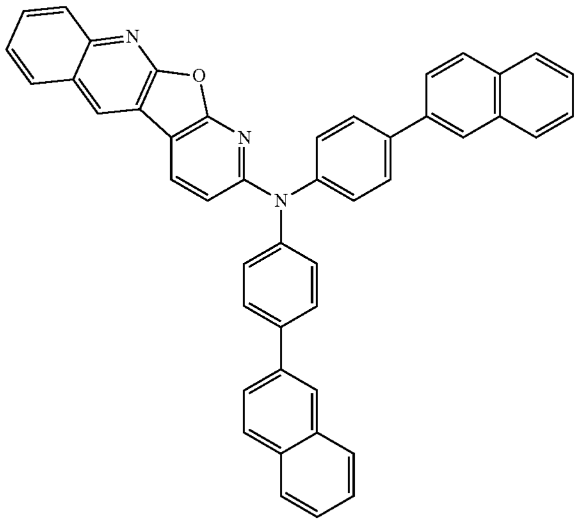
P127
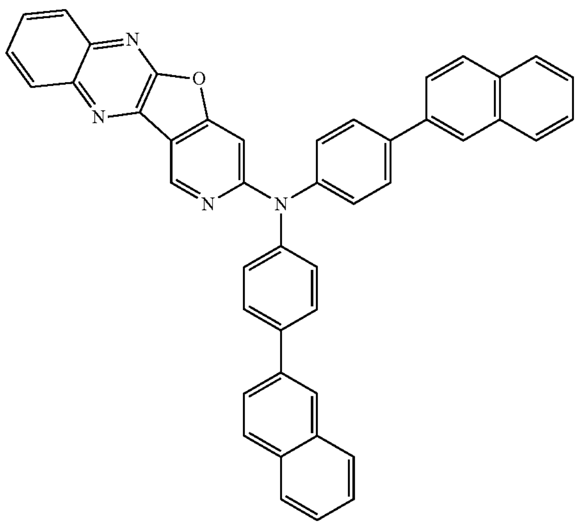
-continued
P128
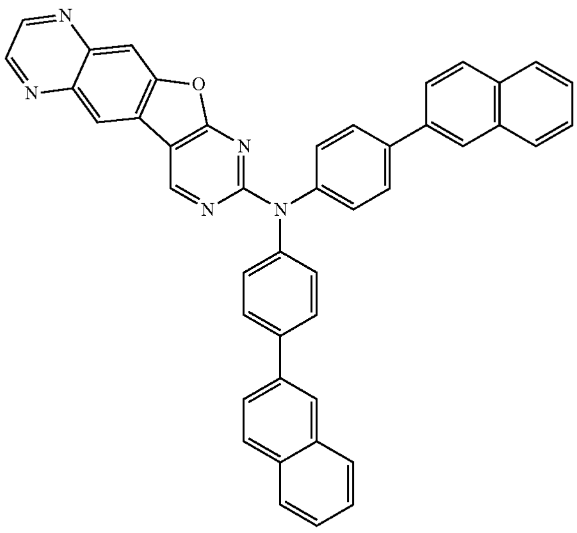
P129
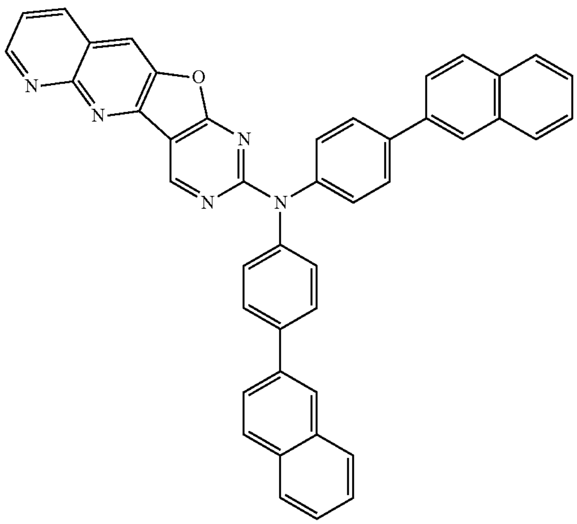
P130
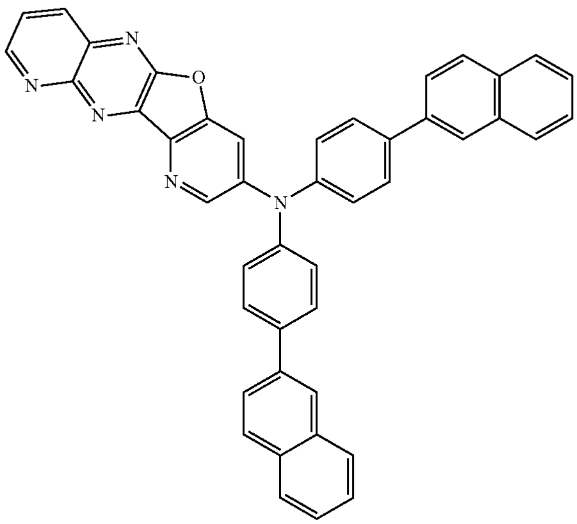

-continued
P131
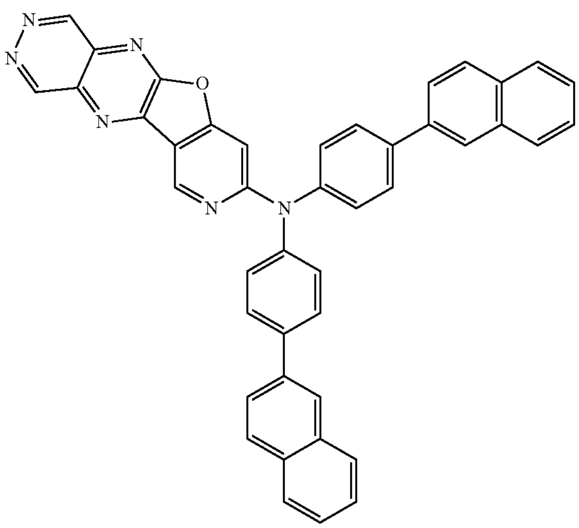
P132
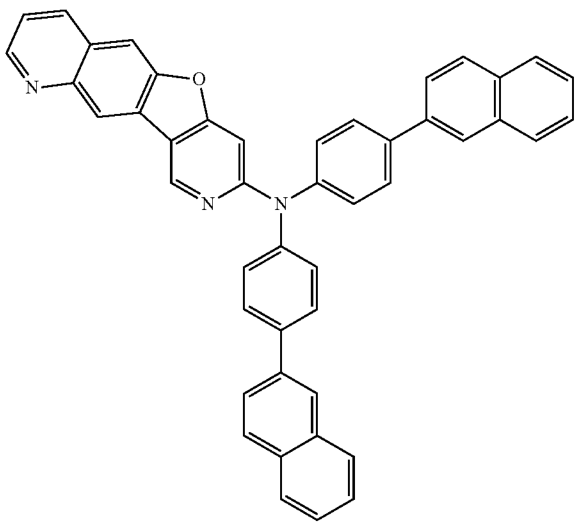
P133
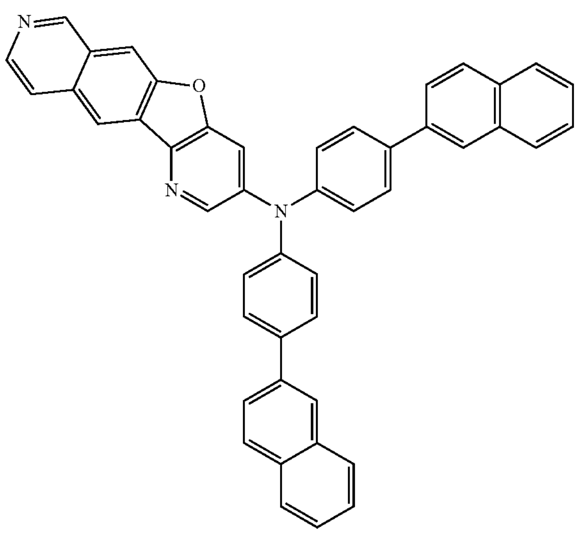
-continued
P134
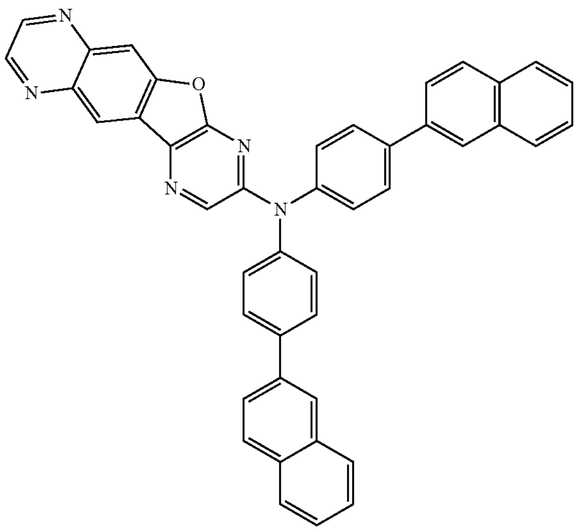
P135
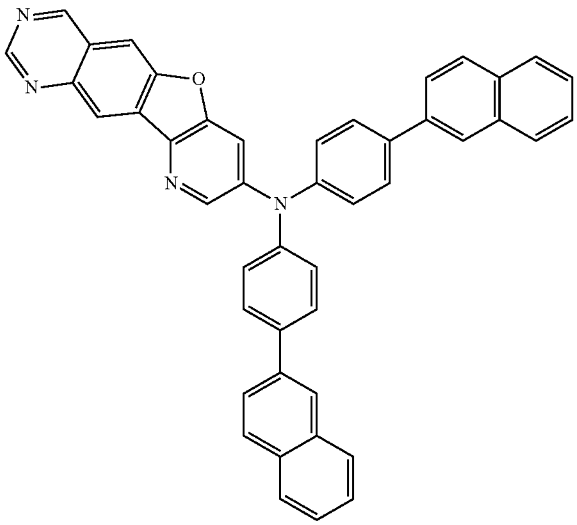
P136
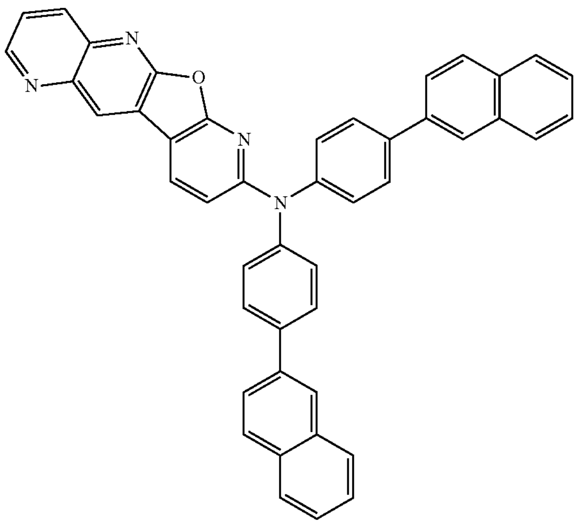

-continued
P137
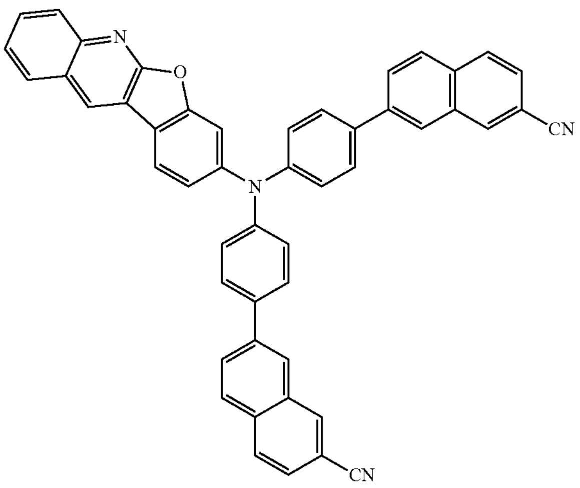
P138
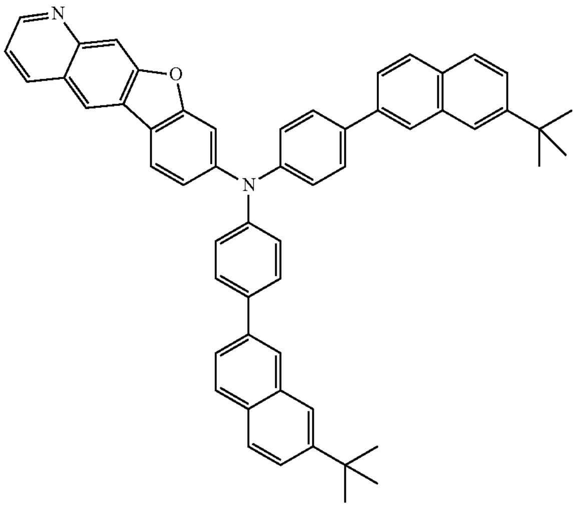
P139
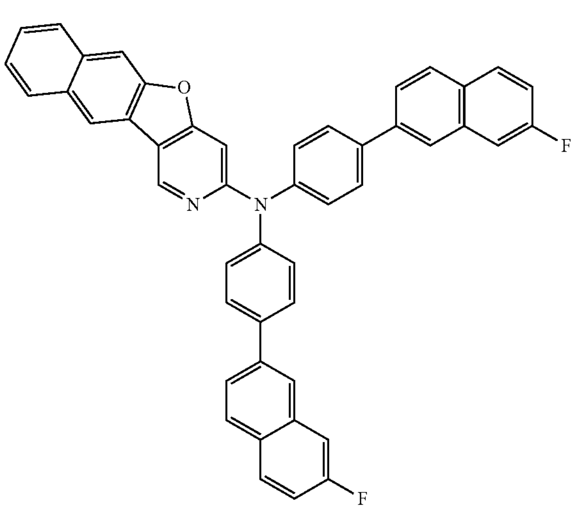
-continued
P140
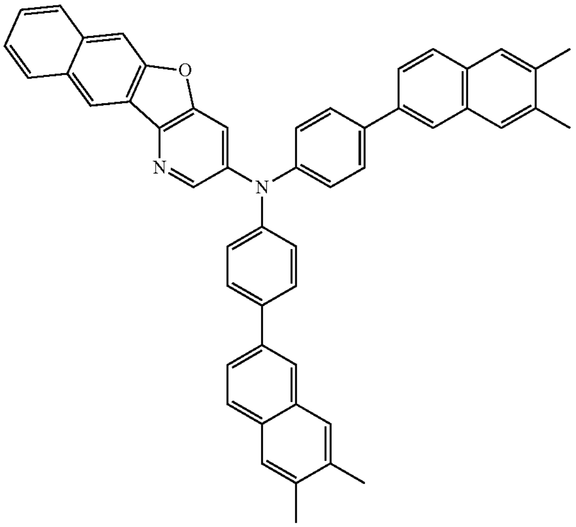
P141
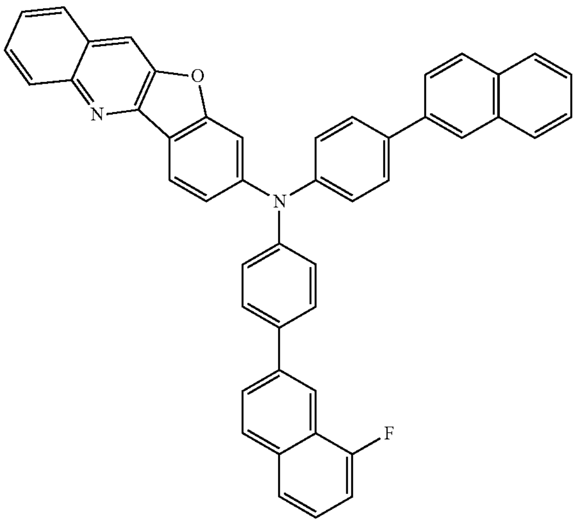
P142
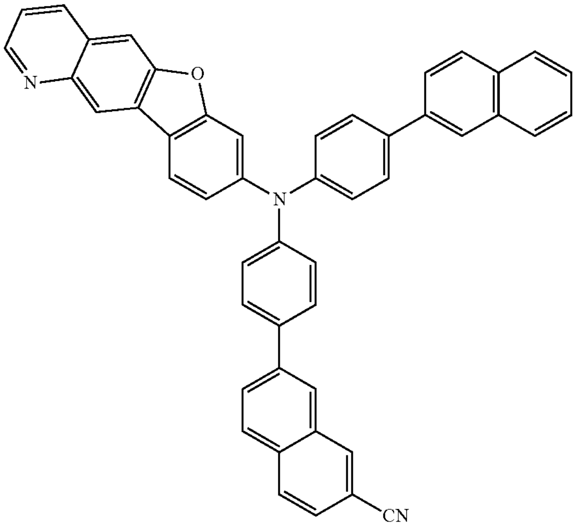

-continued
P143
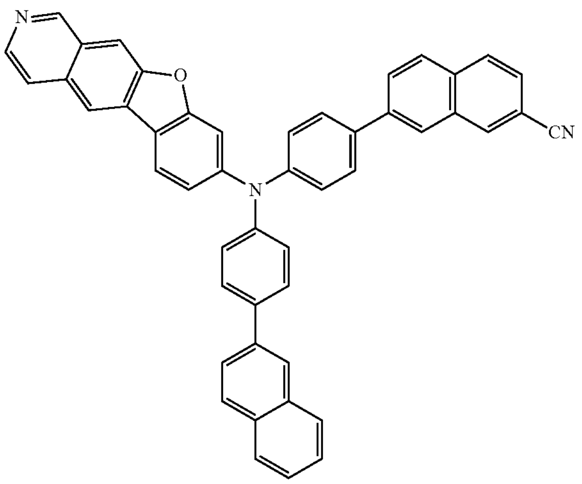
P144
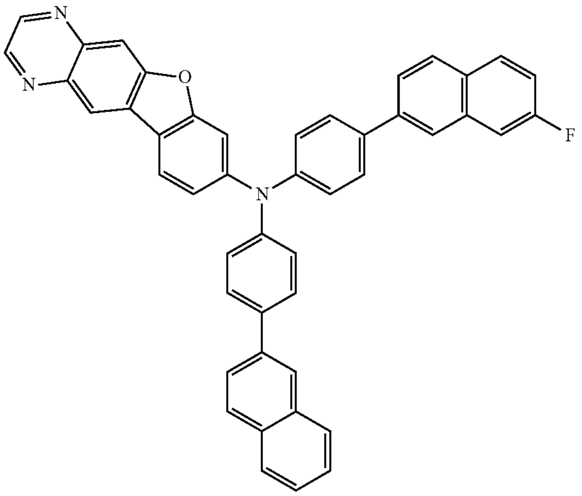
P145
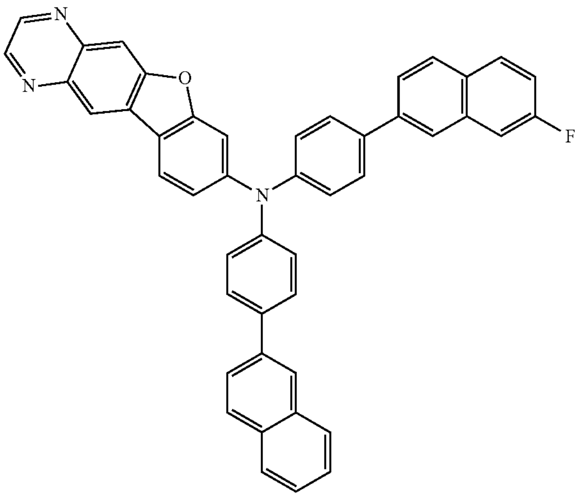
-continued
P146
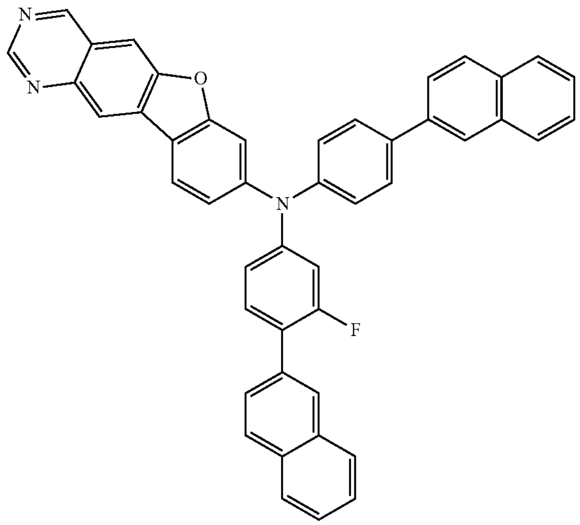
P147
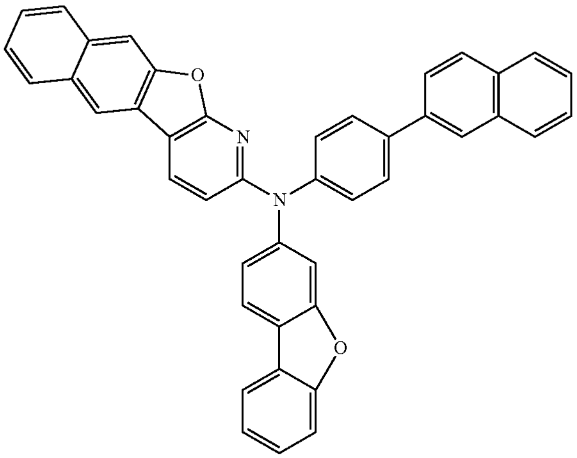
P148
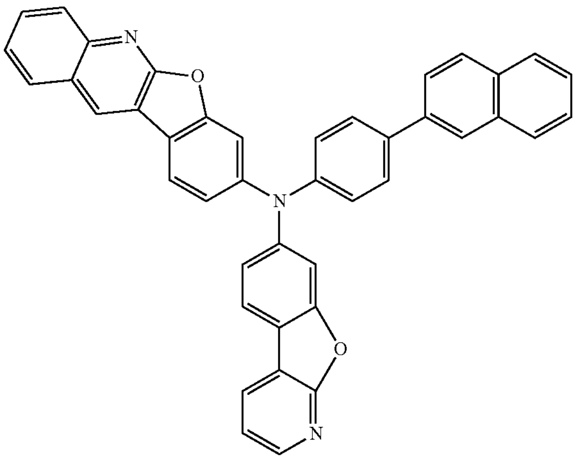

-continued
P149
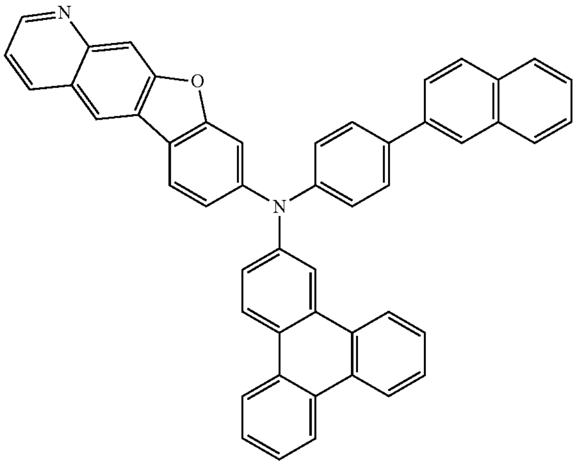
P150
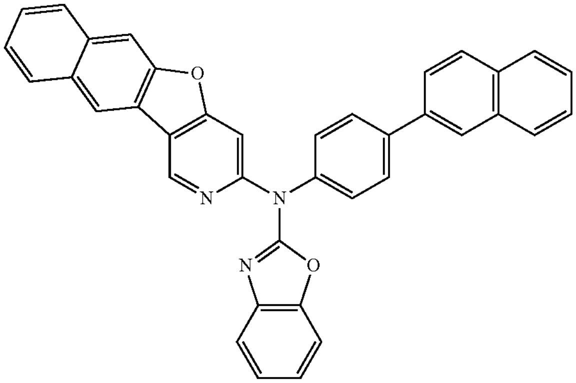
P151
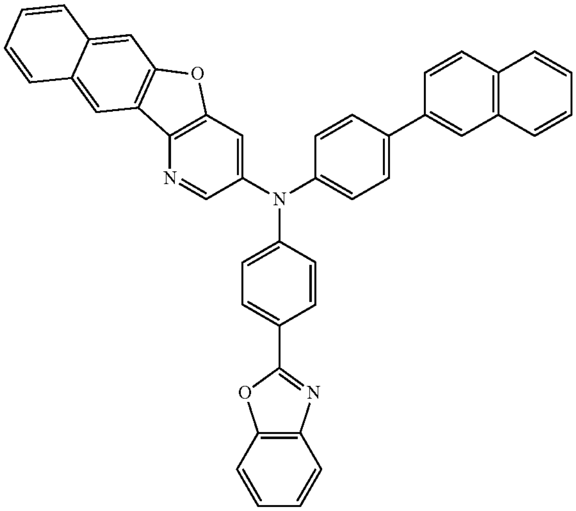
-continued
P152
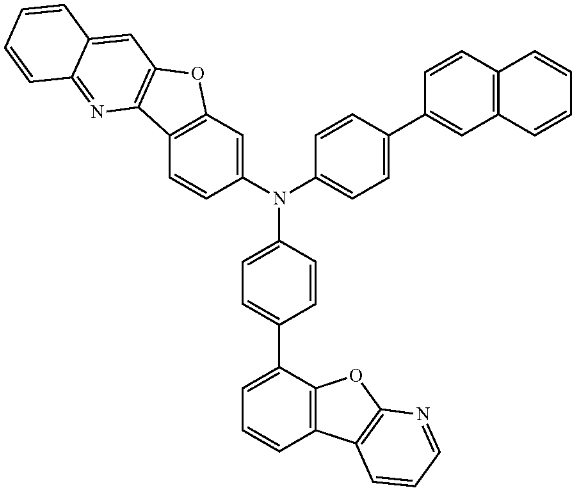
P153
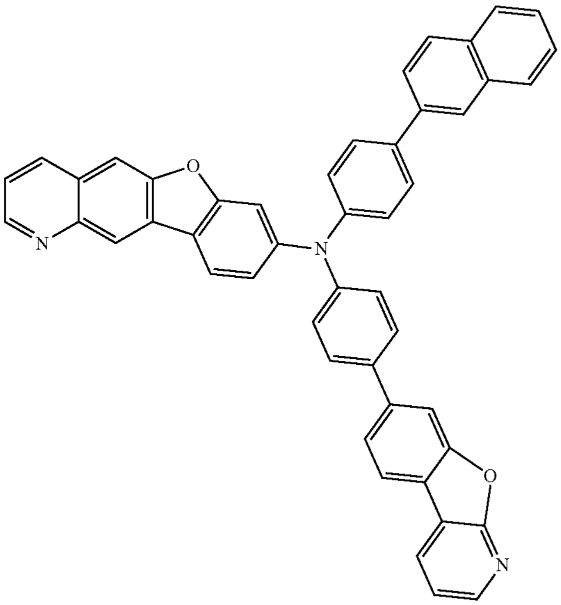

-continued
P154
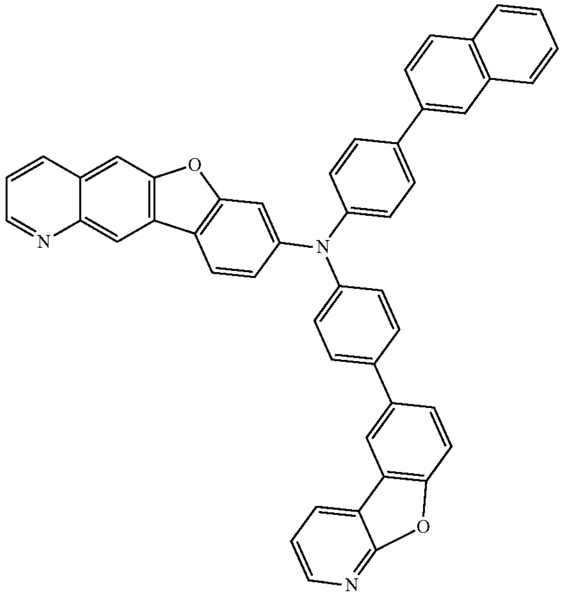
P155
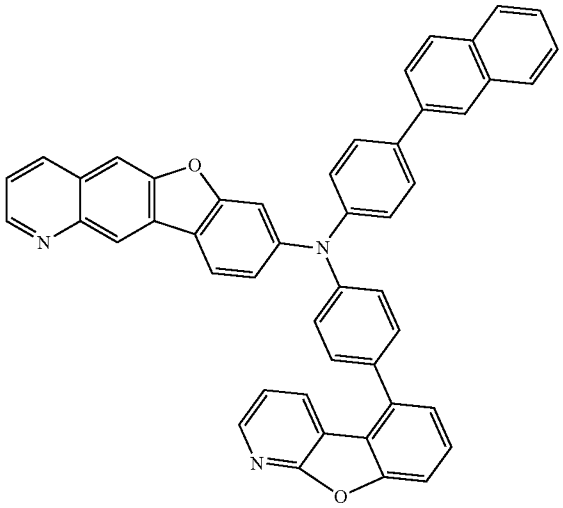
-continued
P156
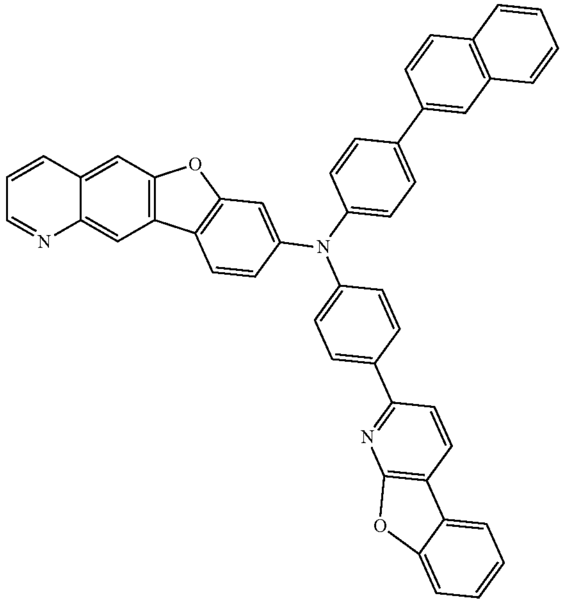
P157
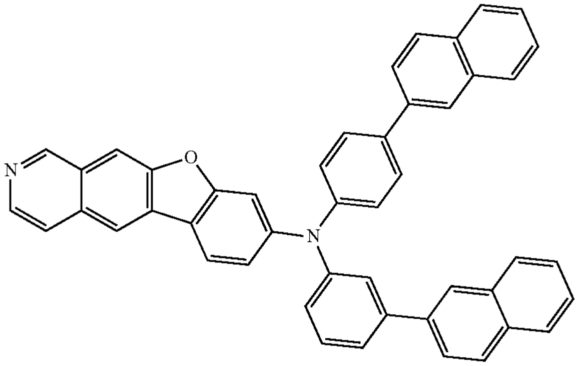
P158
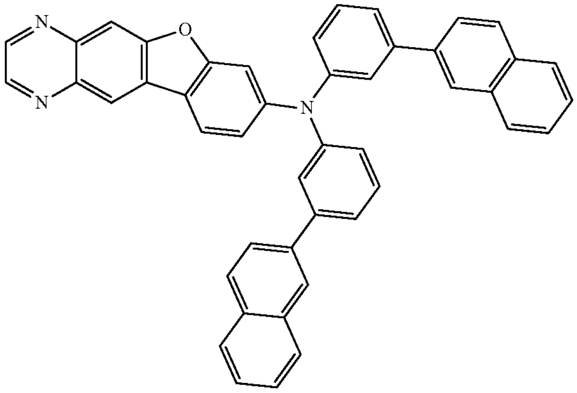

-continued
P159
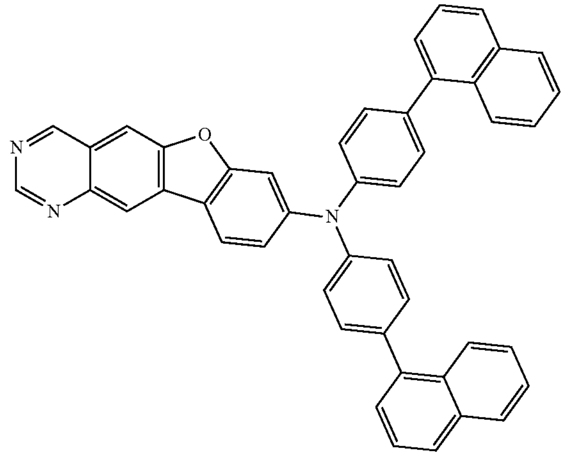
P160
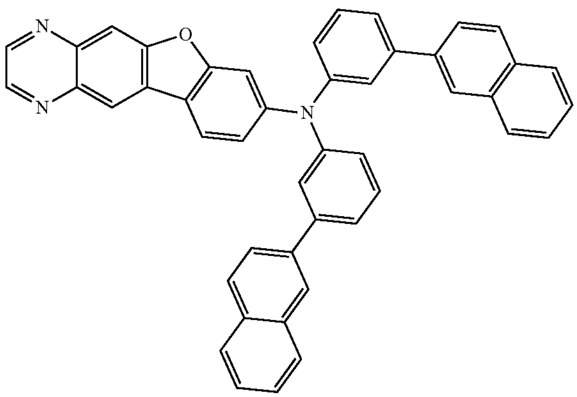
P161
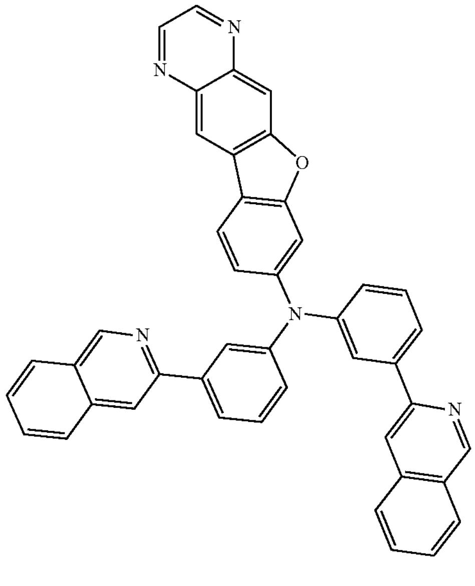
-continued
P162
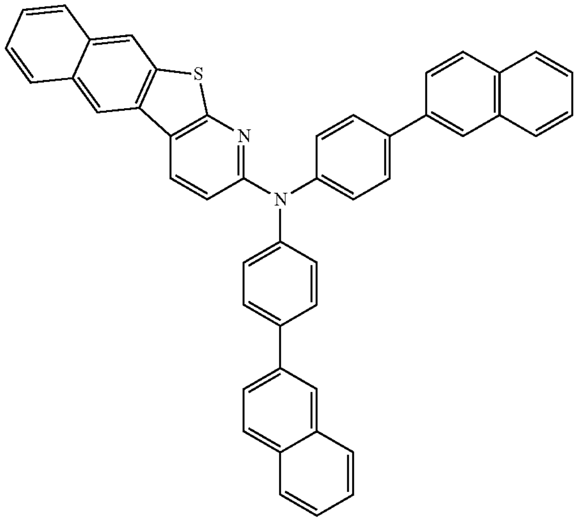
P163
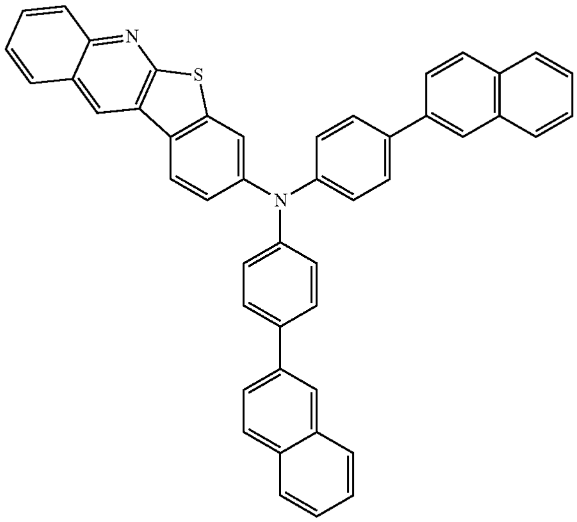
P164
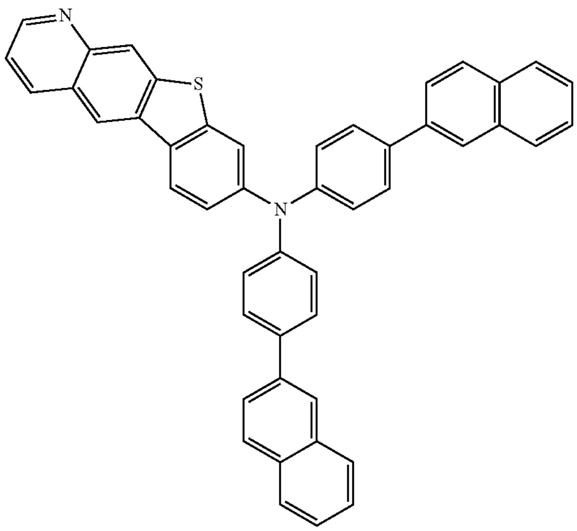

-continued
P165
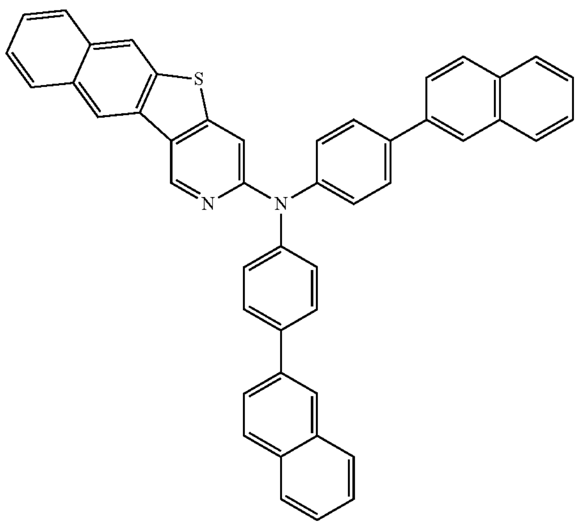
P166
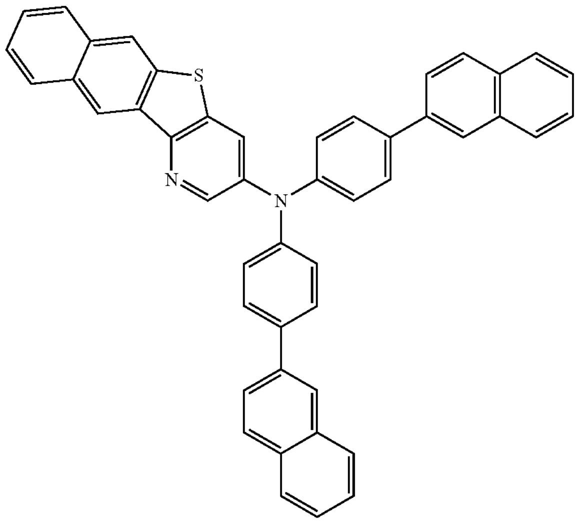
P167
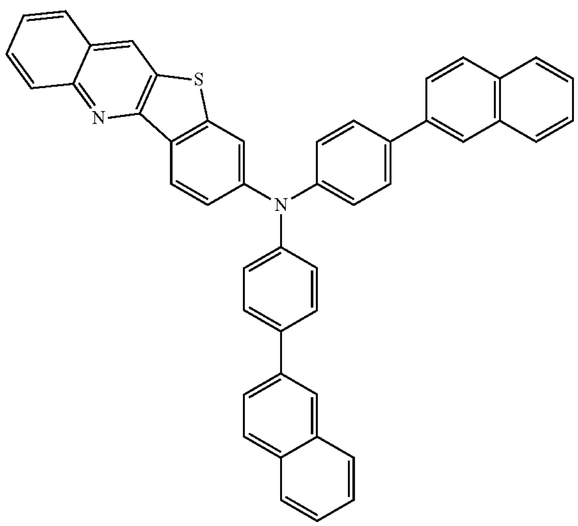
-continued
P168
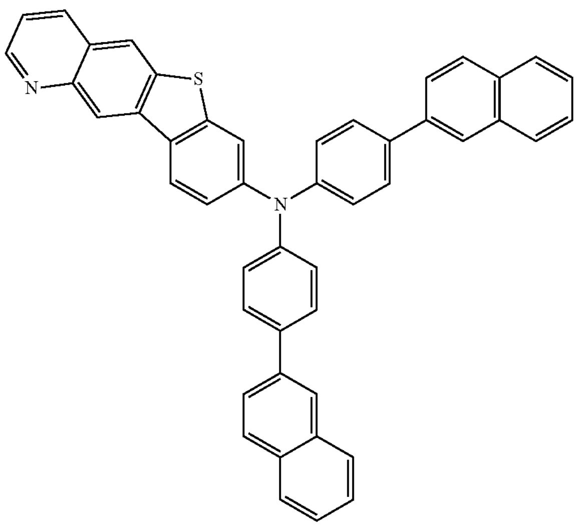
P169
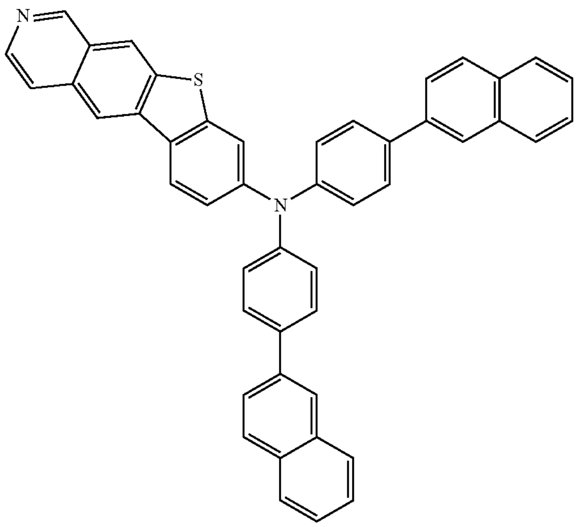
P170
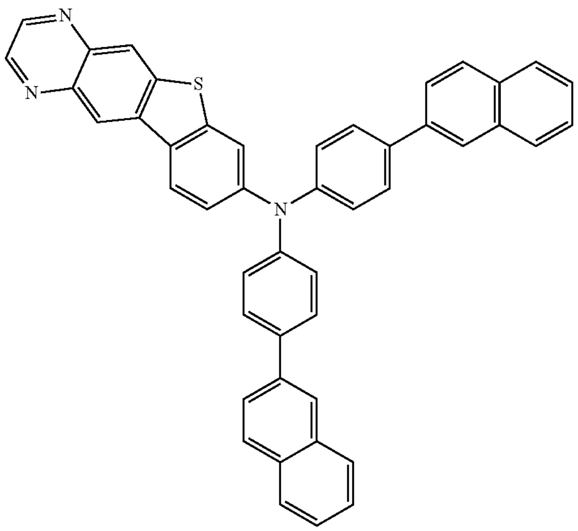

-continued
P171
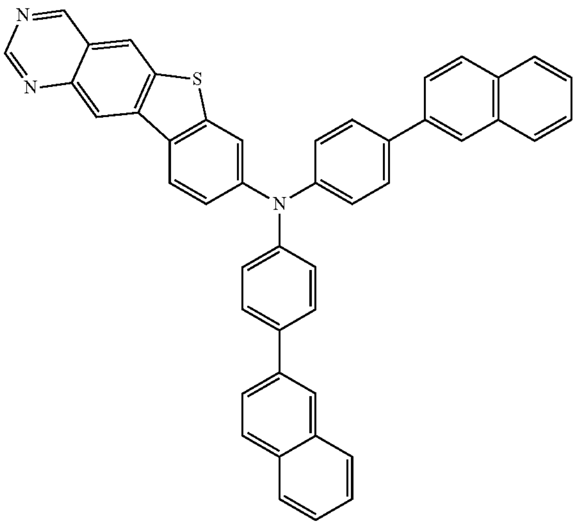
P172
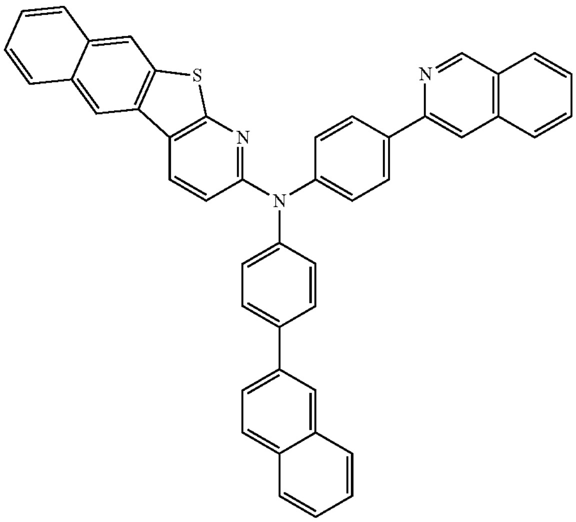
P173
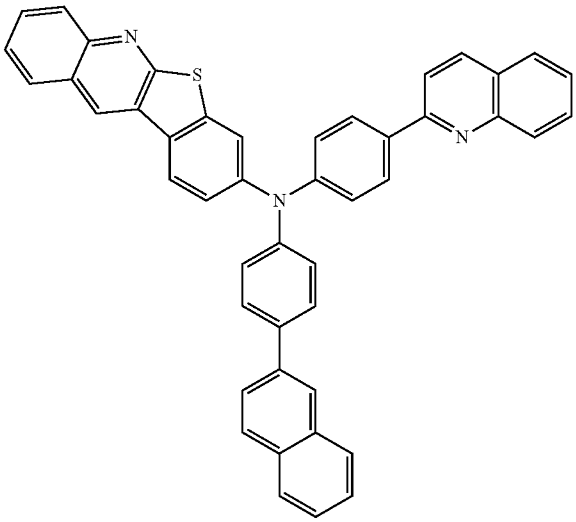
-continued
P174
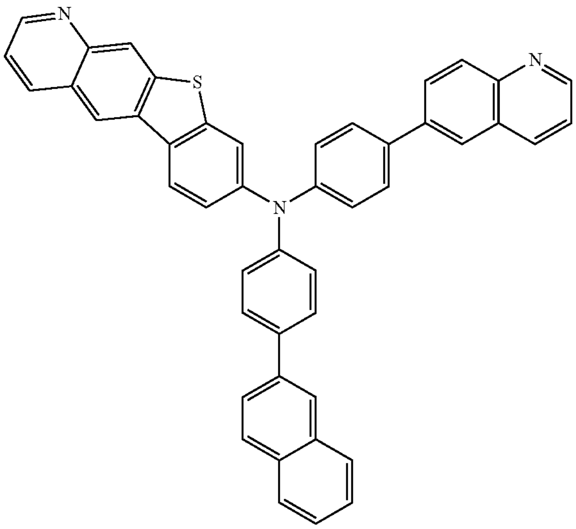
P175
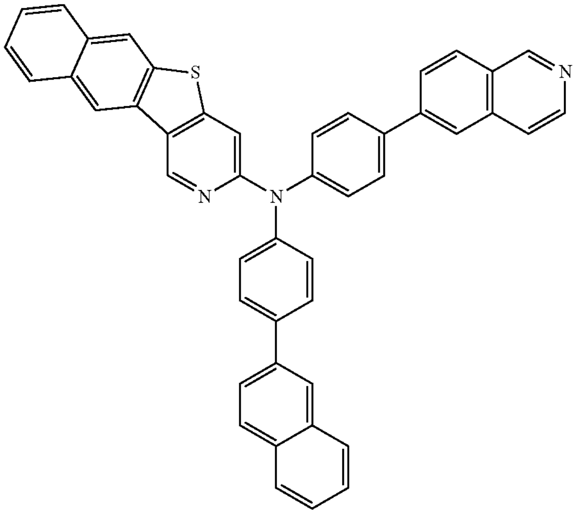
P176
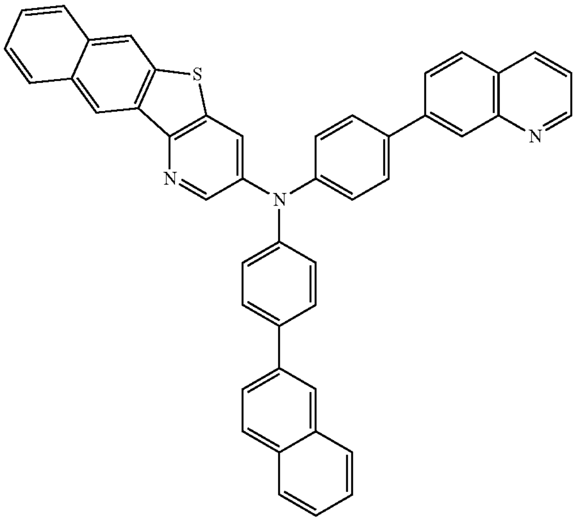

-continued
P177
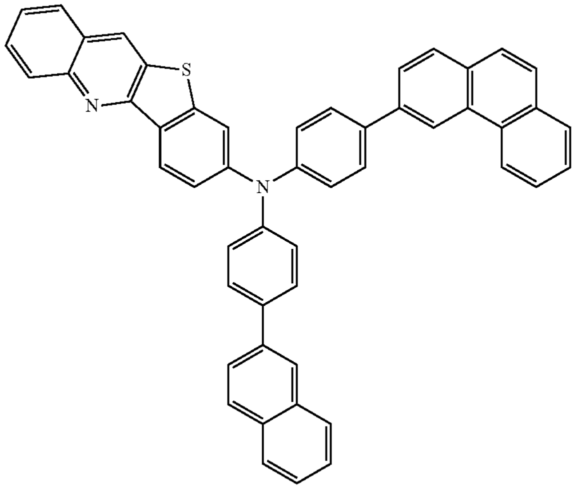
P178
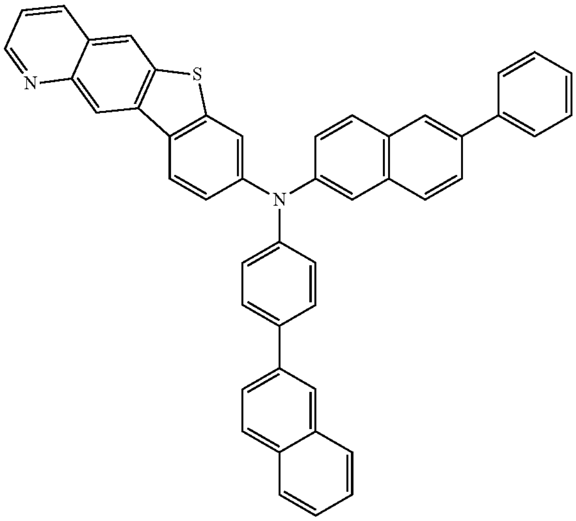
P179
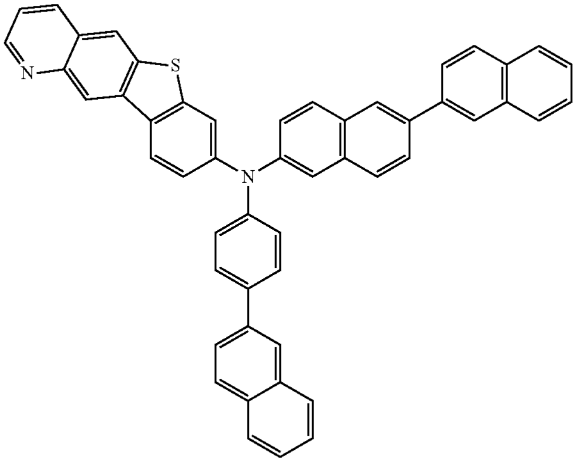
-continued
P180
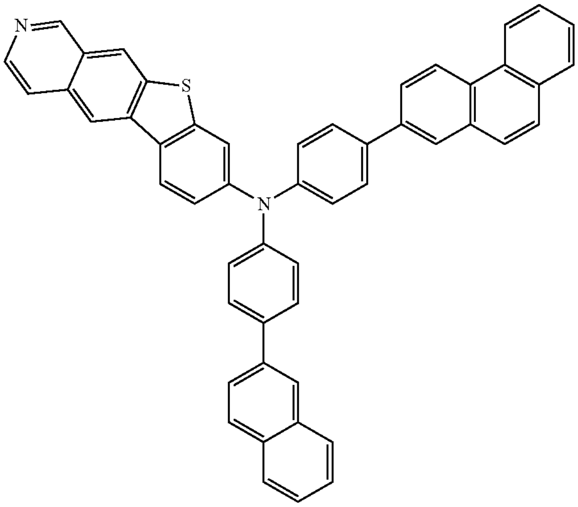
P181
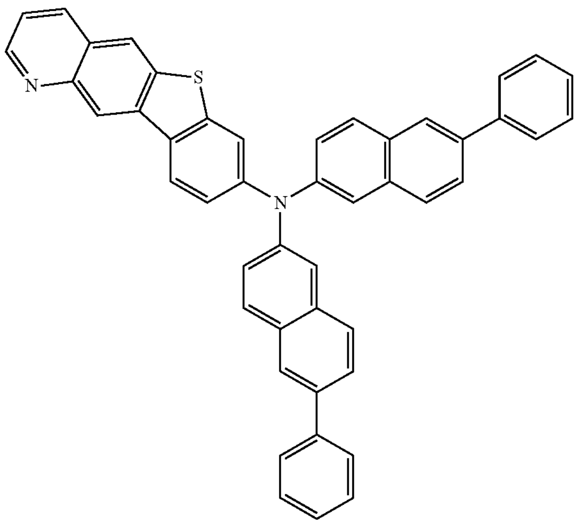
P182
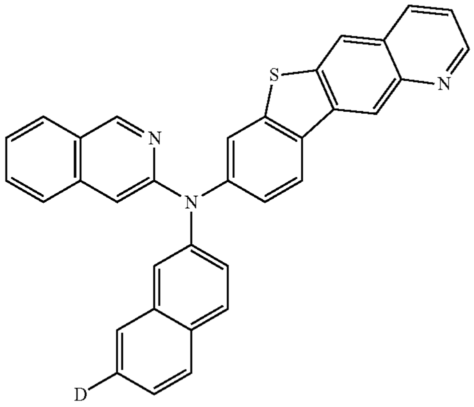

-continued
P183
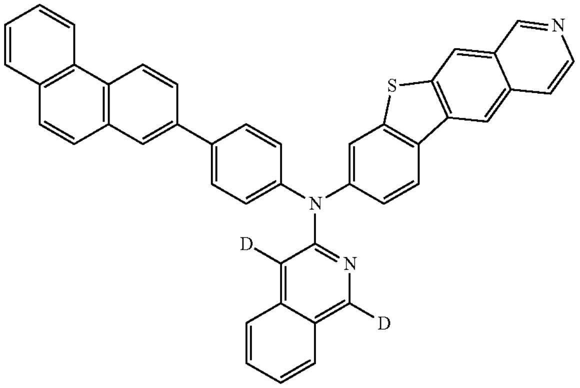
P184
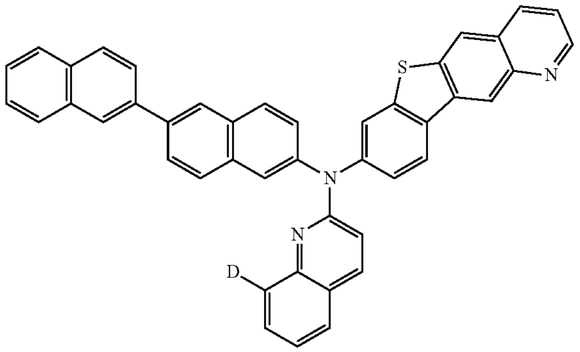
P185
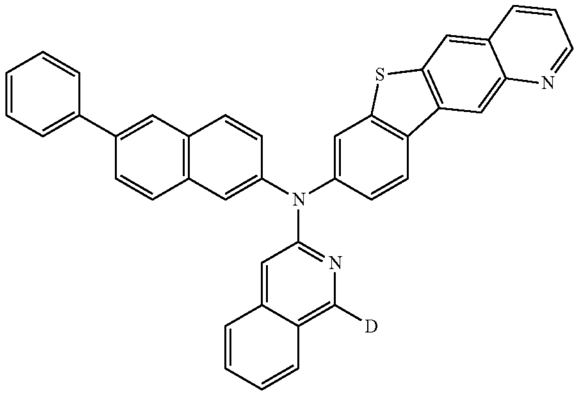
P186
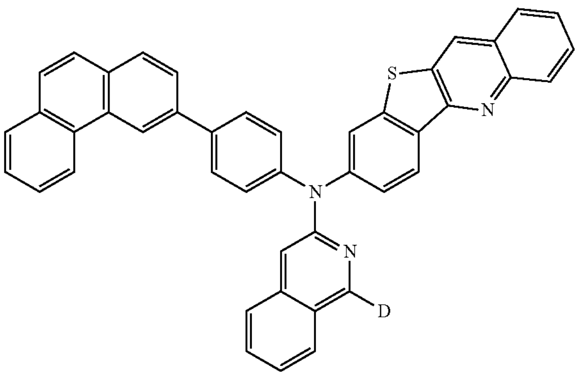
-continued
P187
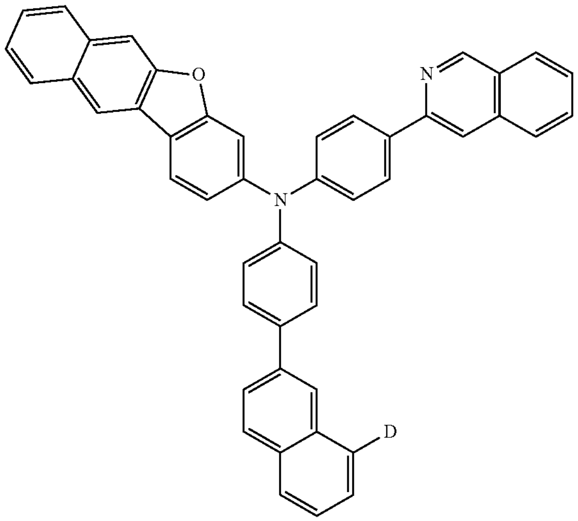
P188
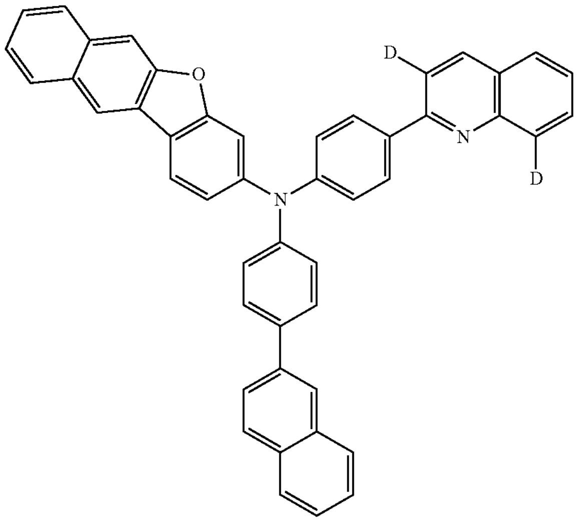
P189
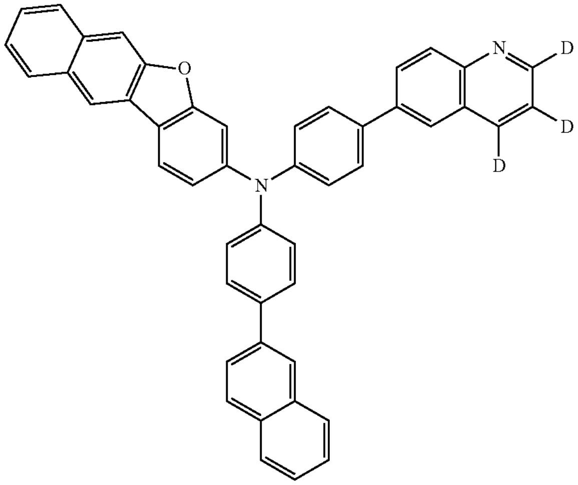

-continued
P190
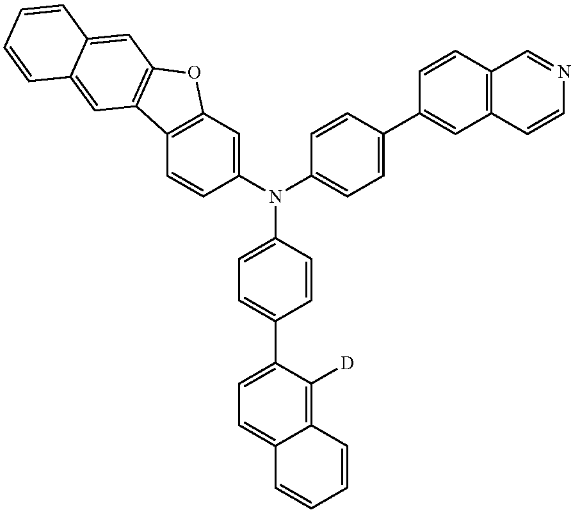
P191
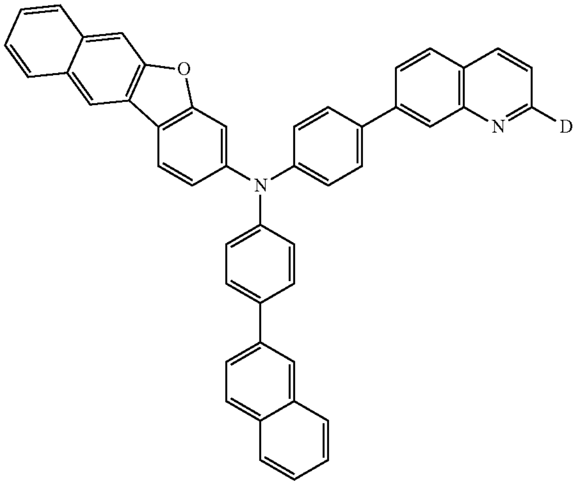
P192
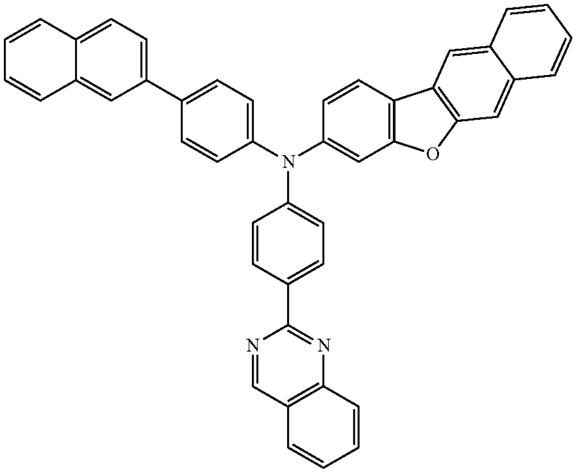
-continued
P193
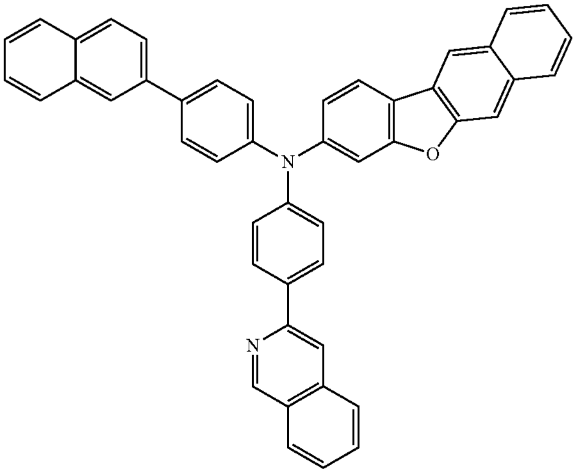
P194
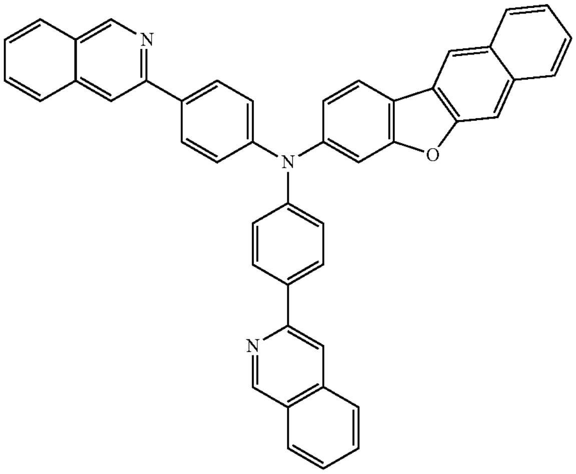
P195
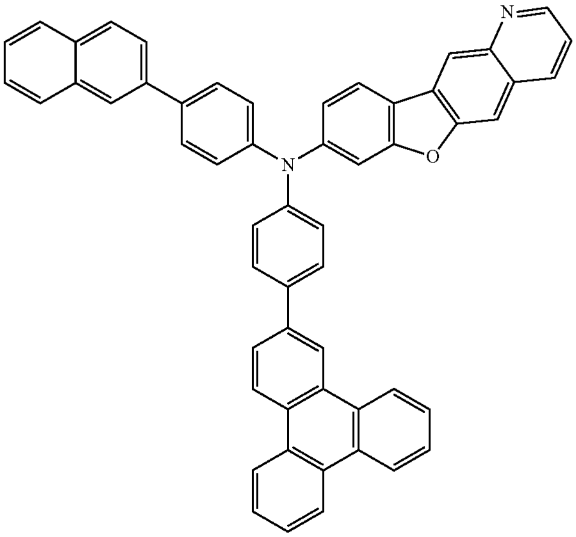

-continued
P196
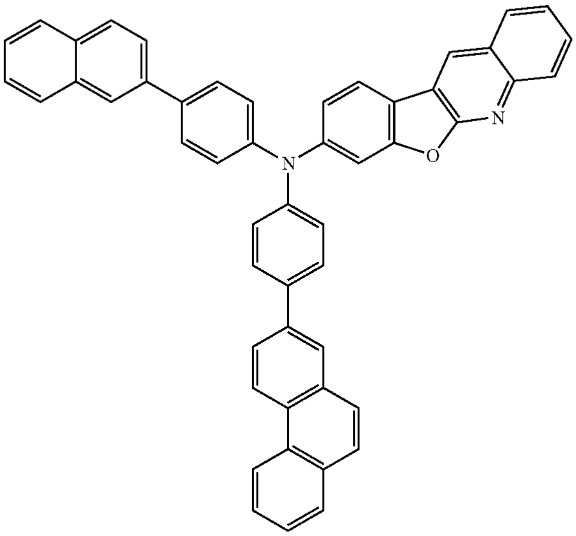
P197
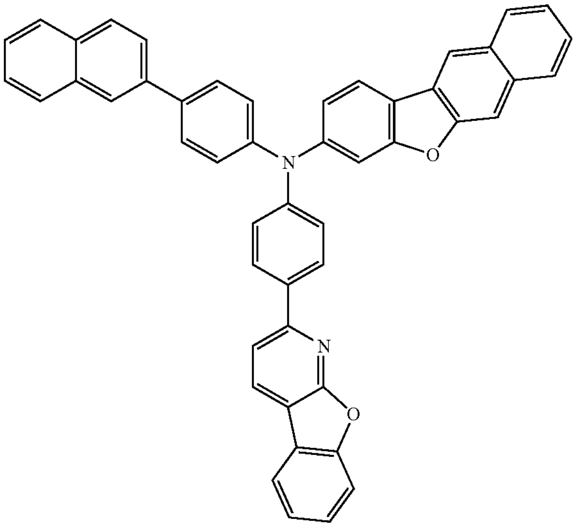
P198
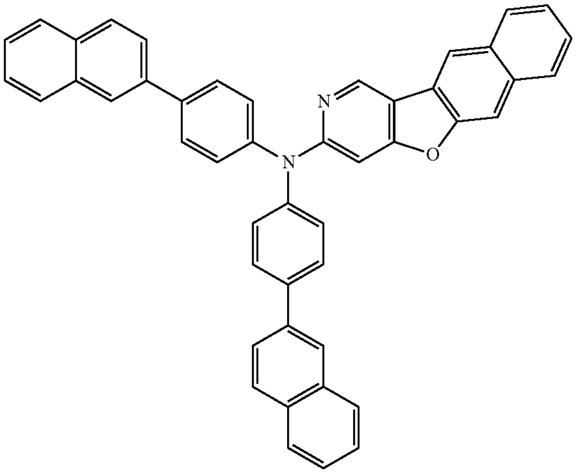
-continued
P199
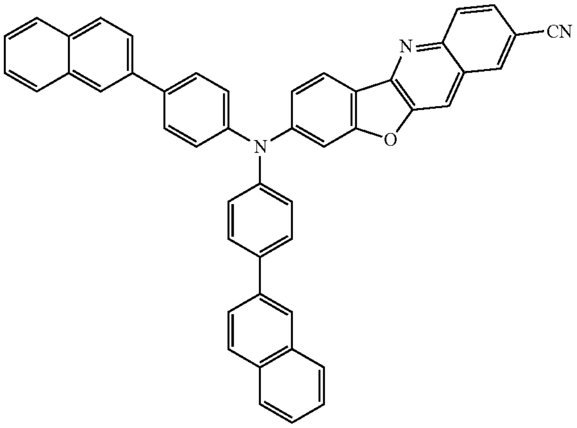
P200
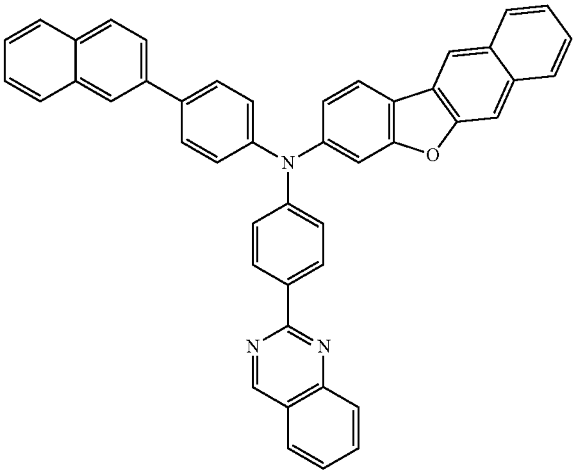
The heterocyclic arylamine compound having the structure represented by Formula I provided in the present disclosure is exemplarily prepared according to the following synthesis route:

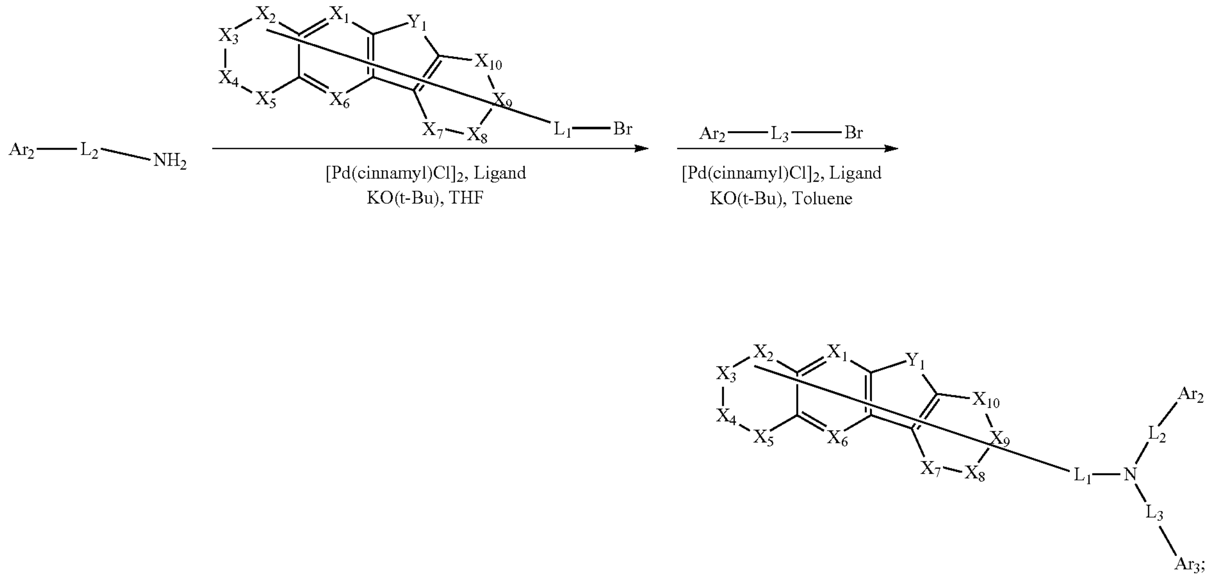

wherein, Ligand has a structural formula of

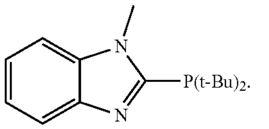

A second aspect of the present disclosure is to provide an organic electroluminescent device. The organic electroluminescent device includes an anode, an organic thin-film layer and a cathode which are stacked in sequence and a capping layer located on a side of the cathode facing away from the anode, wherein a material of the capping layer includes at least one of the heterocyclic arylamine compound according to the first aspect.

In the organic electroluminescent device of the present disclosure, a material of the anode may be a metal, a metal oxide or a conductive polymer, where the metal includes copper, gold, silver, iron, chromium, nickel, manganese, palladium, platinum or the like and alloys thereof, the metal oxide includes indium oxide, zinc oxide, indium tin oxide (ITO), indium zinc oxide (IZO) or the like, and the conductive polymer includes polyaniline, polypyrrole, poly(3-methylthiophene) or the like. In addition to the above materials that facilitate hole injection and combinations thereof, the material of the cathode further includes known materials suitable for use as the anode.

In the organic electroluminescent device, a material of the cathode may be a metal or a multilayer metal material; where the metal includes aluminum, magnesium, silver, indium, tin, titanium or the like and alloys thereof, and the multilayer metal material includes LiF/Al, $LiO_2$/Al, $BaF_2$/Al or the like. In addition to the above materials that facilitate electron injection and combinations thereof, the material of the cathode further includes known materials suitable for use as the cathode.

In the organic electroluminescent device, the organic thin-film layer includes at least one light-emitting layer (EML) and any one or a combination of at least two of a hole transport layer (HTL), a hole injection layer (HIL), an electron blocking layer (EBL), a hole blocking layer (HBL), an electron transport layer (ETL) or an electron injection layer (EIL) that are disposed on two sides of the light-emitting layer, and the capping layer (CPL) is disposed on the cathode of the OLED device (on the side of the cathode facing away from the anode).

In the present disclosure, as shown in the Figure which is a schematic diagram of the organic electroluminescent device, the organic electroluminescent device includes a substrate 1, an anode 2, a hole injection layer 3, a first hole transport layer 4, a second hole transport layer 5, an light-emitting layer 6, an electron transport layer 7, an electron injection layer 8, a cathode 9 and a capping layer 10 which are stacked in sequence.

The organic electroluminescent device is prepared according to the following method: forming the anode on a transparent or opaque smooth substrate, forming an organic thin layer on the anode, forming the cathode (magnesium-silver electrode, where a mass ratio of magnesium to silver is 1:9) on the organic thin layer and forming the capping layer on the side of the cathode facing away from the anode. The organic thin layer includes the hole injection layer, the first hole transport layer, the second hole transport layer, the light-emitting layer, the electron transport layer and the electron injection layer. The organic thin layer may be formed by a known film formation method such as deposition by means of evaporation, sputtering, spin coating, impregnation and ion plating.

A third aspect of the present disclosure is to provide a display panel. The display panel includes the organic electroluminescent device according to the second aspect.

Several examples of the heterocyclic arylamine compounds of the present disclosure are exemplarily described below.

Example 1

This example provides heterocyclic arylamine compound P001. The heterocyclic arylamine compound has the following synthesis route:

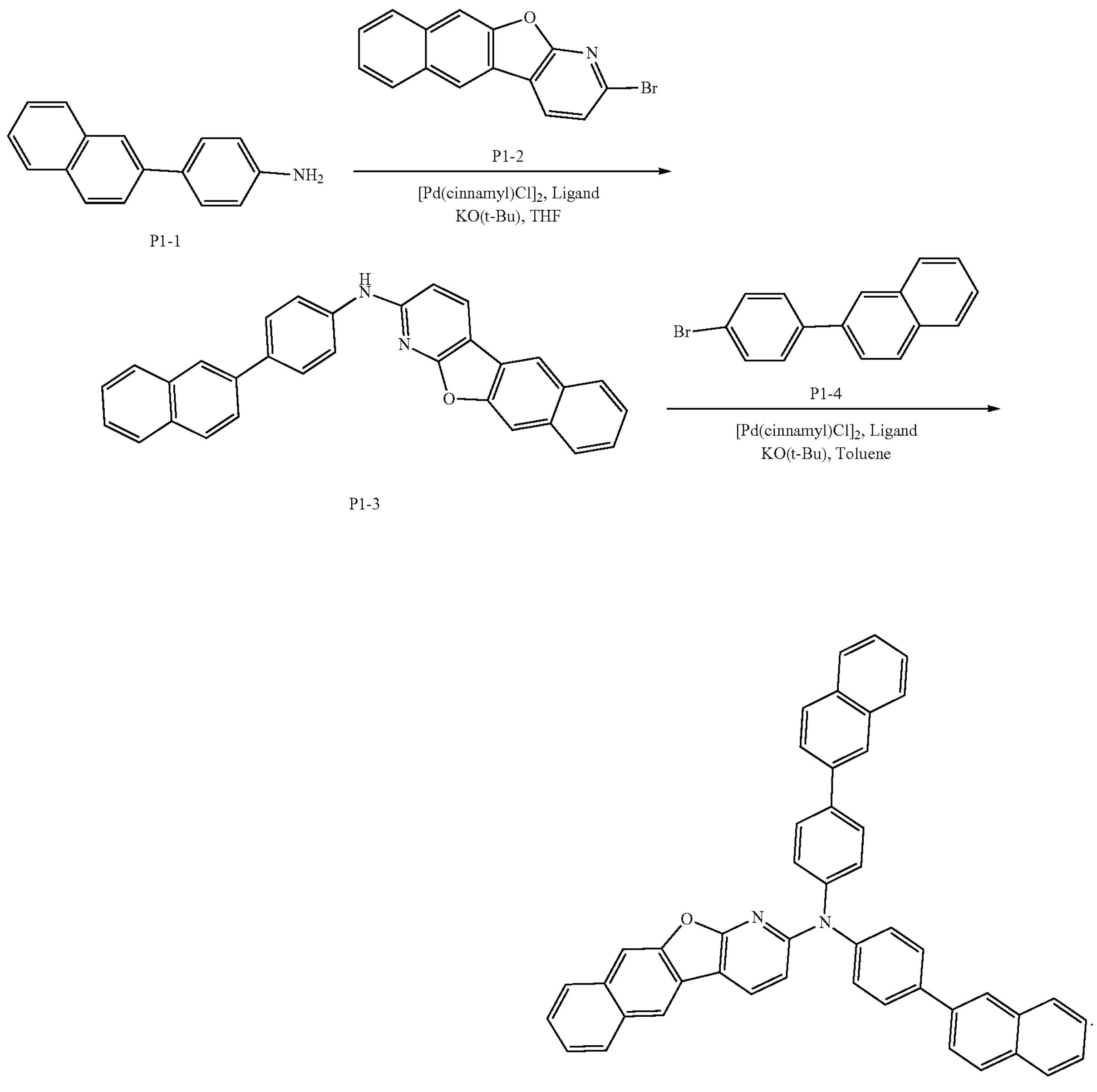

P001

A method for preparing the heterocyclic arylamine compound includes the steps below.

Compound P1-1 (0.5 mmol), compound P1-2 (0.5 mmol), KO(t-Bu) (1.0 mmol), $[Pd(cinnamyl)Cl]_2$ (0.02 mol) and Ligand (0.02 mol) were added to a solution of THF (3 mL) and mixed, placed in a 50 mL flask and reacted for 12 h at 78° C. The solution was cooled to room temperature and slowly added with a saturated aqueous solution of $MgSO_4$ and ethyl acetate to be extracted three times. Then, the organic layer passed through a rotary evaporator to remove the solvent and was subjected to column chromatography to obtain intermediate product P1-3.

Intermediate product P1-3 (0.5 mmol), compound P1-4 (0.6 mmol), KO(t-Bu) (1.0 mmol), $[Pd(cinnamyl)Cl]_2$ (0.02 mol) and Ligand (0.02 mol) were added to a solution of toluene (3 mL) and mixed, placed in a 50 mL flask and reacted for 12 h at 110° C. The solution was cooled to room temperature and slowly added with a saturated aqueous solution of $MgSO_4$ and ethyl acetate to be extracted three times. Then, the organic layer passed through a rotary evaporator to remove the solvent and was subjected to column chromatography to obtain target product P001.

The structure of target product P001 was tested through matrix-assisted laser desorption/ionization time-of-flight mass spectrometry (MALDI-TOF MS), m/z for $C_{47}H_{30}N_2O$: calcd 638.2, found 638.1.

Elemental analysis: calcd: C, 88.38; H, 4.73; N, 4.39. found: C, 88.38; H, 4.72; N, 4.39.

Example 2

This example provides heterocyclic arylamine compound P019. The heterocyclic arylamine compound has the following synthesis route:

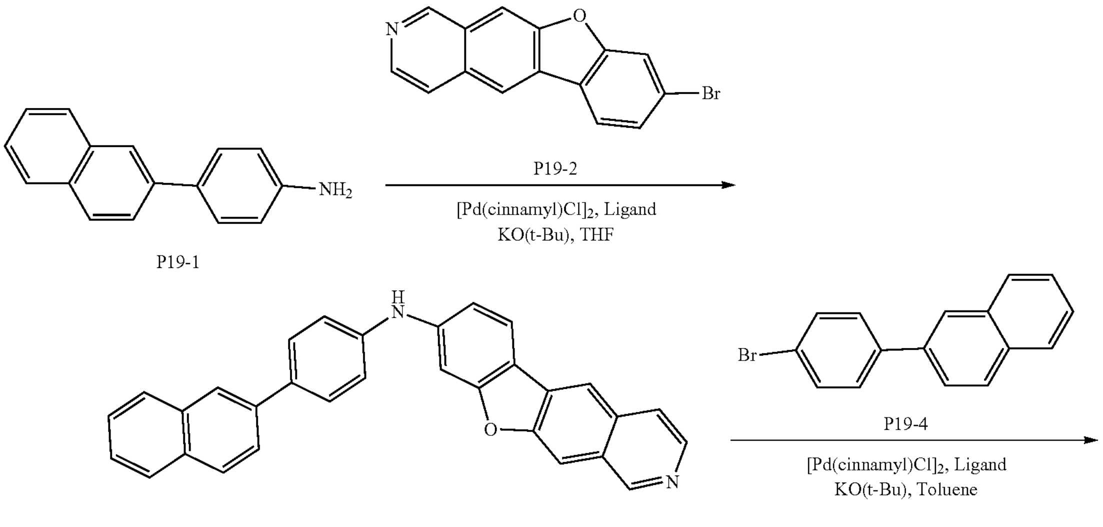

P19-1

P19-3

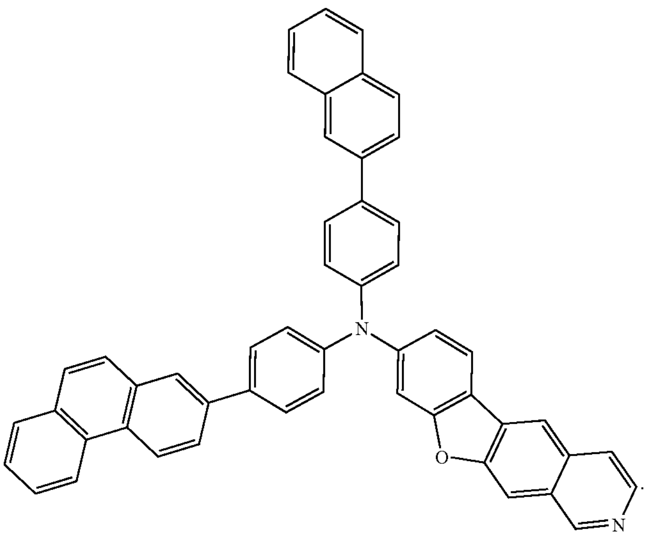

P019

A method for preparing the heterocyclic arylamine compound includes the steps below.

Compound P19-1 (0.5 mmol), compound P19-2 (0.5 mmol), KO(t-Bu) (1.0 mmol), $[Pd(cinnamyl)Cl]_2$ (0.02 mol) and Ligand (0.02 mol) were added to a solution of THF (3 mL) and mixed, placed in a 50 mL flask and reacted for 12 h at 78° C. The solution was cooled to room temperature and slowly added with a saturated aqueous solution of $MgSO_4$ and ethyl acetate to be extracted three times. Then, the organic layer passed through a rotary evaporator to remove the solvent and was subjected to column chromatography to obtain intermediate product P19-3.

Intermediate product P19-3 (0.5 mmol), compound P19-4 (0.6 mmol), KO(t-Bu) (1.0 mmol), $[Pd(cinnamyl)Cl]_2$ (0.02 mol) and Ligand (0.02 mol) were added to a solution of toluene (3 mL) and mixed, placed in a 50 mL flask and reacted for 12 h at 110° C. The solution was cooled to room temperature and slowly added with a saturated aqueous solution of $MgSO_4$ and ethyl acetate to be extracted three times. Then, the organic layer passed through a rotary evaporator to remove the solvent and was subjected to column chromatography to obtain target product P019.

The structure of target product P019 was tested through matrix-assisted laser desorption/ionization time-of-flight mass spectrometry (MALDI-TOF-MS), m/z for $C_{51}H_{32}N_2O$: calcd 688.3, found 688.1.

Elemental analysis: calcd: C, 88.93; H, 4.68; N, 4.07. found: C, 88.93; H, 4.69; N, 4.07.

Example 3

This example provides heterocyclic arylamine compound P020. The heterocyclic arylamine compound has the following synthesis route:

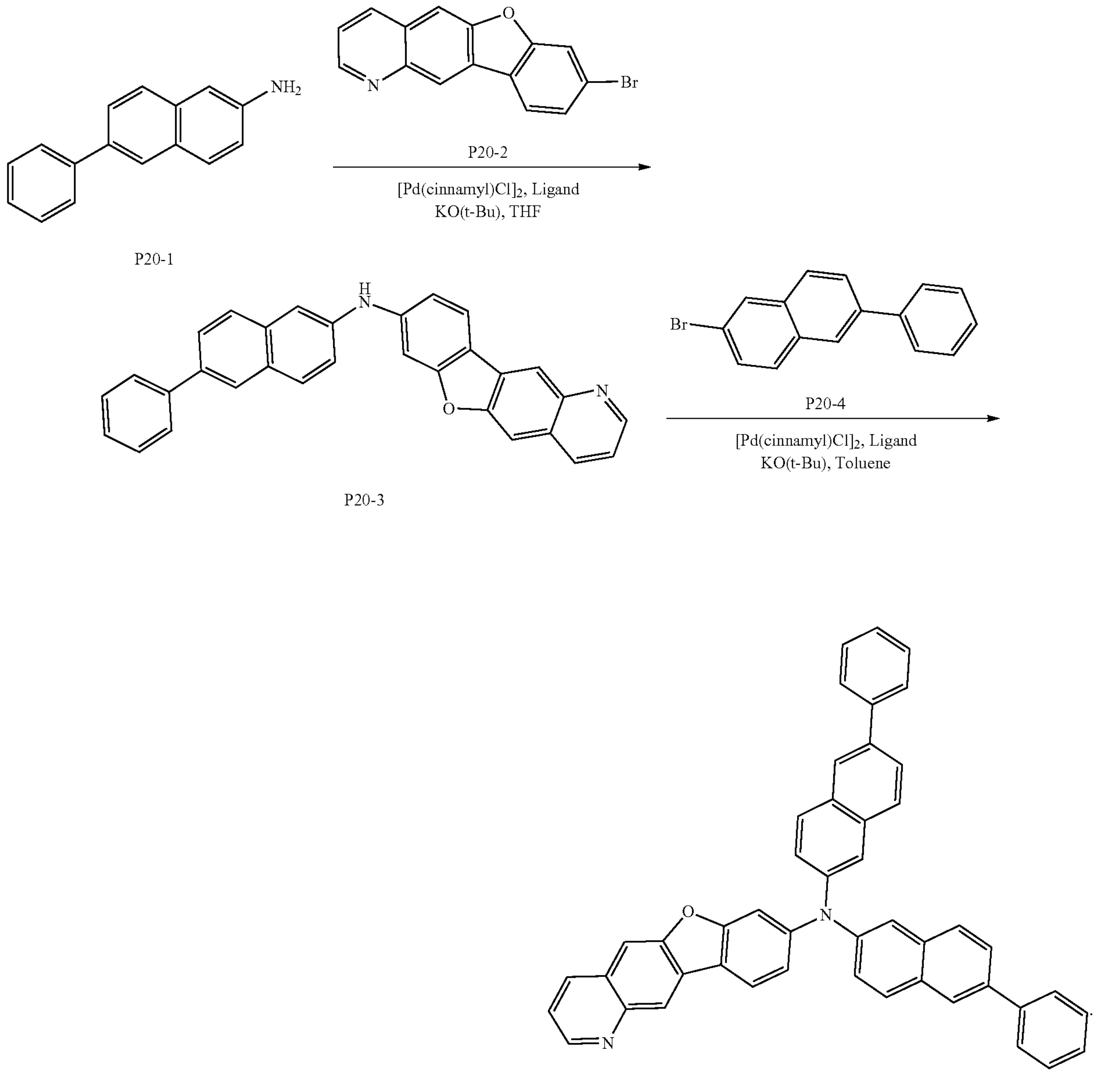

P20-1 P20-2 P20-3 P20-4 P020

A method for preparing the heterocyclic arylamine compound includes the steps below.

Compound P20-1 (0.5 mmol), compound P20-2 (0.5 mmol), KO(t-Bu) (1.0 mmol), $[Pd(cinnamyl)Cl]_2$ (0.02 mol) and Ligand (0.02 mol) were added to a solution of THF (3 mL) and mixed, placed in a 50 mL flask and reacted for 12 h at 78° C. The solution was cooled to room temperature and slowly added with a saturated aqueous solution of $MgSO_4$ and ethyl acetate to be extracted three times. Then, the organic layer passed through a rotary evaporator to remove the solvent and was subjected to column chromatography to obtain intermediate product P20-3.

Intermediate product P20-3 (0.5 mmol), compound P20-4 (0.6 mmol), KO(t-Bu) (1.0 mmol), $[Pd(cinnamyl)Cl]_2$ (0.02 mol) and Ligand (0.02 mol) were added to a solution of toluene (3 mL) and mixed, placed in a 50 mL flask and reacted for 12 h at 110° C. The solution was cooled to room temperature and slowly added with a saturated aqueous solution of $MgSO_4$ and ethyl acetate to be extracted three times. Then, the organic layer passed through a rotary evaporator to remove the solvent and was subjected to column chromatography to obtain target product P020.

The structure of target product P020 was tested through matrix-assisted laser desorption/ionization time-of-flight mass spectrometry (MALDI-TOF-MS), m/z for $C_{47}H_{30}N_2O$: calcd 638.2, found 638.1.

Elemental analysis: calcd: C, 88.38; H, 4.73; N, 4.39. found: C, 88.38; H, 4.72; N, 4.39.

Example 4

This example provides heterocyclic arylamine compound P151. The heterocyclic arylamine compound has the following synthesis route:

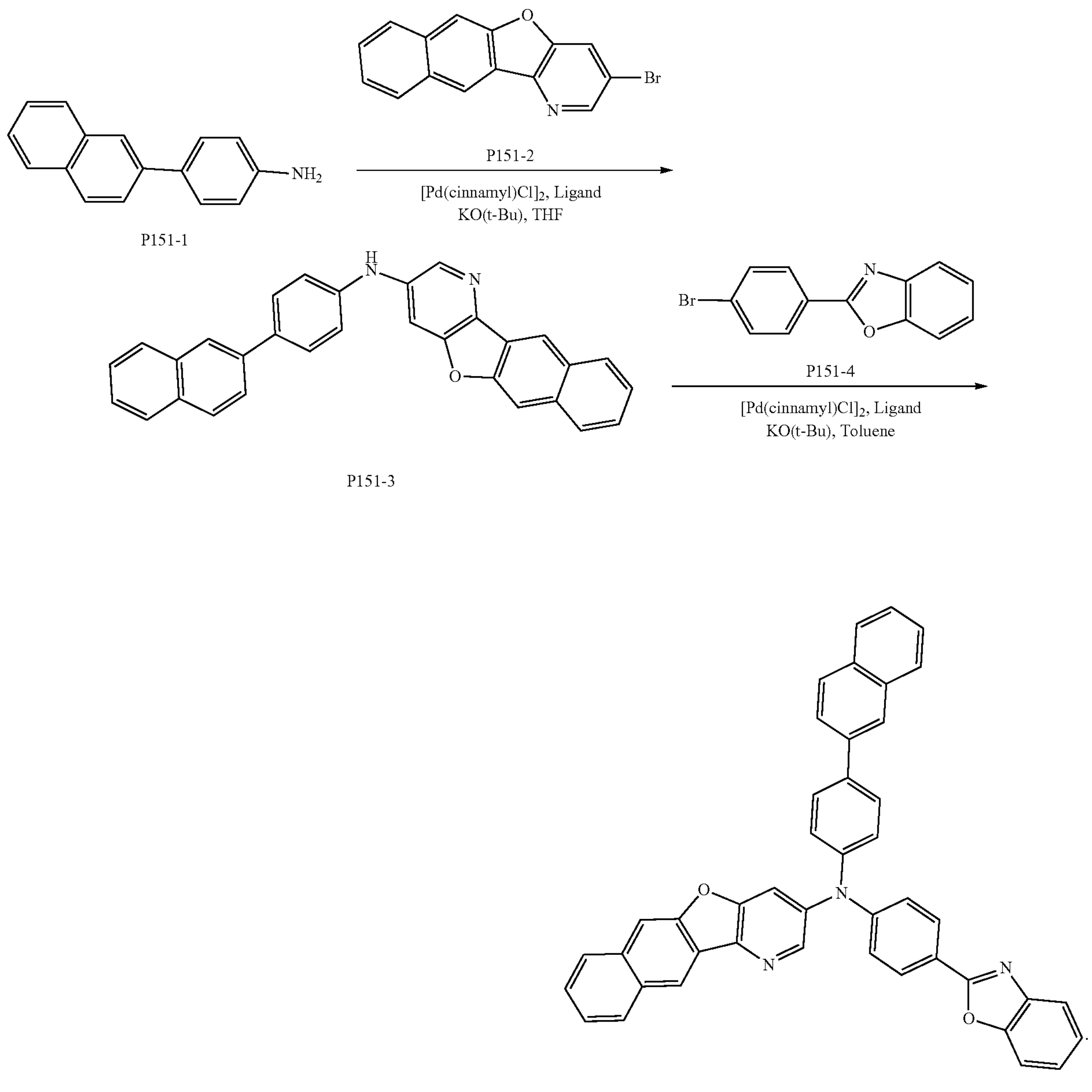

P151

A method for preparing the heterocyclic arylamine compound includes the steps below.

Compound P151-1 (0.5 mmol), compound P151-2 (0.5 mmol), KO(t-Bu) (1.0 mmol), $[Pd(cinnamyl)Cl]_2$ (0.02 mol) and Ligand (0.02 mol) were added to a solution of THF (3 mL) and mixed, placed in a 50 mL flask and reacted for 12 h at 78° C. The solution was cooled to room temperature and slowly added with a saturated aqueous solution of $MgSO_4$ and ethyl acetate to be extracted three times. Then, the organic layer passed through a rotary evaporator to remove the solvent and was subjected to column chromatography to obtain intermediate product P151-3.

Intermediate product P151-3 (0.5 mmol), compound P151-4 (0.6 mmol), KO(t-Bu) (1.0 mmol), $[Pd(cinnamyl)Cl]_2$ (0.02 mol) and Ligand (0.02 mol) were added to a solution of toluene (3 mL) and mixed, placed in a 50 mL flask and reacted for 12 h at 100° C. The solution was cooled to room temperature and slowly added with a saturated aqueous solution of $MgSO_4$ and ethyl acetate to be extracted three times. Then, the organic layer passed through a rotary evaporator to remove the solvent and was subjected to column chromatography to obtain target product P151.

The structure of target product P151 was tested through matrix-assisted laser desorption/ionization time-of-flight mass spectrometry (MALDI-TOF-MS), m/z for $C_{44}H_{27}N_3O_2$: calcd 629.2, found 629.1.

Elemental analysis: calcd: C, 83.92; H, 4.32; N, 6.67. found: C, 83.92; H, 4.32; N, 6.66.

Example 5

This example provides heterocyclic arylamine compound P156. The heterocyclic arylamine compound has the following synthesis route:

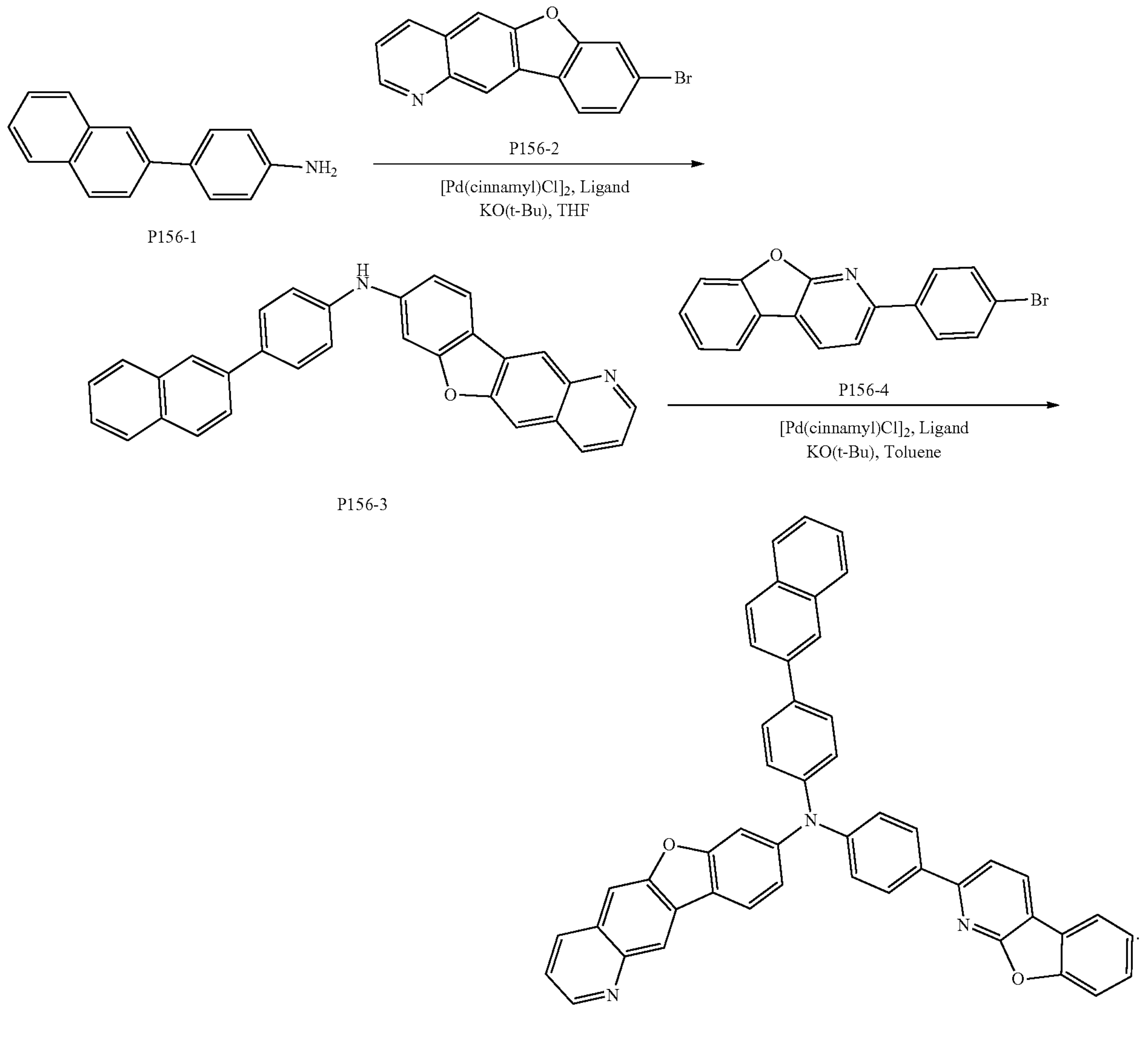

P156-1

P156-3

P156

A specific preparation method specifically includes the steps below.

Compound P156-1 (0.5 mmol), compound P156-2 (0.5 mmol), KO(t-Bu) (1.0 mmol), [Pd(cinnamyl)Cl]$_2$ (0.02 mol) and Ligand (0.02 mol) were added to a solution of THF (3 mL) and mixed, placed in a 50 mL flask and reacted for 12 h at 78° C. The solution was cooled to room temperature and slowly added with a saturated aqueous solution of $MgSO_4$ and ethyl acetate to be extracted three times. Then, the organic layer passed through a rotary evaporator to remove the solvent and was subjected to column chromatography to obtain intermediate product P156-3.

Intermediate product P156-3 (0.5 mmol), compound P156-4 (0.6 mmol), KO(t-Bu) (1.0 mmol), [Pd(cinnamyl)Cl]$_2$ (0.02 mol) and Ligand (0.02 mol) were added to a solution of toluene (3 mL) and mixed, placed in a 50 mL flask and reacted for 12 h at 110° C. The solution was cooled to room temperature and slowly added with a saturated aqueous solution of $MgSO_4$ and ethyl acetate to be extracted three times. Then, the organic layer passed through a rotary evaporator to remove the solvent and was subjected to column chromatography to obtain target product P156.

The structure of target product P156 was tested through matrix-assisted laser desorption/ionization time-of-flight mass spectrometry (MALDI-TOF-MS), m/z for $C_{44}H_{27}N_3O_2$: calcd 679.2, found 679.1.

Elemental analysis: calcd: C, 84.81; H, 4.30, N, 6.18. found: C, 84.81; H, 4.31; N, 6.17.

Methods for preparing other heterocyclic arylamine compounds are similar to the above methods and not repeated here, and only the characterization results are provided. The results of mass spectrometry and elemental analysis are shown in Table 1.

TABLE 1

| | Results of Mass Spectrometry | | Results of Elemental Analysis | |
|---|---|---|---|---|
| Compound | Calcd | Found | Calcd | Found |
| P054 | 486.2 | 486.1 | C, 86.40; H, 4.56; N, 5.76; | C, 86.40; H, 4.57; N, 5.76; |

TABLE 1-continued

| Compound | Results of Mass Spectrometry | | Results of Elemental Analysis | |
|---|---|---|---|---|
| | Calcd | Found | Calcd | Found |
| P091 | 639.2 | 639.3 | C, 86.36; H, 4.57; N, 6.57; | C, 86.36; H, 4.58; N, 6.57; |
| P123 | 639.2 | 639.1 | C, 86.36; H, 4.57; N, 6.57; | C, 86.36; H, 4.57; N, 6.58; |
| P124 | 640.2 | 640.1 | C, 84.35; H, 4.40; N, 8.74; | C, 84.35; H, 4.40; N, 8.73; |
| P137 | 688.2 | 688.1 | C, 85.45; H, 4.10; N, 8.13; | C, 85.45; H, 4.10; N, 8.12; |
| P138 | 750.4 | 750.2 | C, 87.97; H, 6.17; N, 3.73; | C, 87.97; H, 6.18;N, 3.73; |
| P139 | 674.2 | 674.1 | C, 83.66; H, 4.18; N, 4.15; | C, 83.66;H, 4.19; N, 4.15; |
| P147 | 602.2 | 602.1 | C, 85.69; H, 4.35; N, 4.65; | C, 85.69; H, 4.34; N, 4.65; |
| P148 | 603.2 | 603.3 | C, 83.56; H, 4.17; N, 6.96; | C, 83.56; H, 4.18; N, 6.96; |
| P149 | 662.2 | 662.1 | C, 88.80; H, 4.56; N, 4.23; | C, 88.80; H, 4.55; N, 4.23; |
| P150 | 553.2 | 553.1 | C, 82.44; H, 4.19; N, 7.59; | C, 82.44; H, 4.18; N, 7.59; |
| P158 | 639.2 | 639.1 | C, 86.36; H, 4.57; N, 6.57; | C, 86.36; H, 4.56; N, 6.57; |
| P180 | 704.2 | 704.1 | C, 86.90; H, 4.58; N, 3.97; | C, 86.90; H, 4.59; N, 3.97; |

The performance of the above heterocyclic arylamine compounds, Compound A, Compound B and Compound C was tested. The structural formulas of Compound A, Compound B and Compound C are as follows:

Compound A

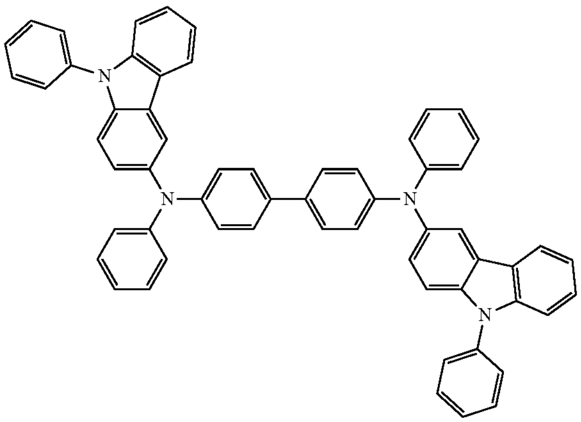

-continued

Compound B

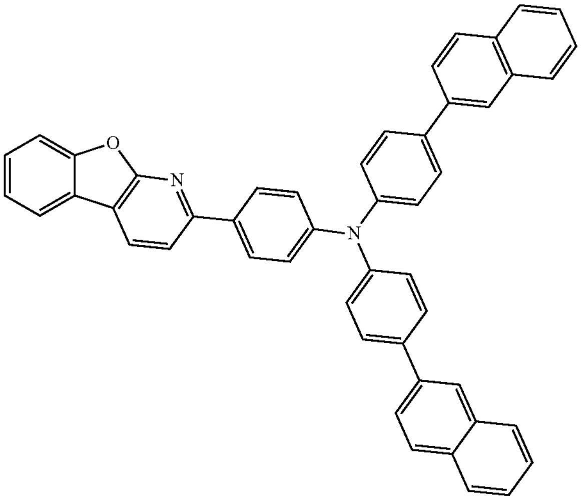

Compound C

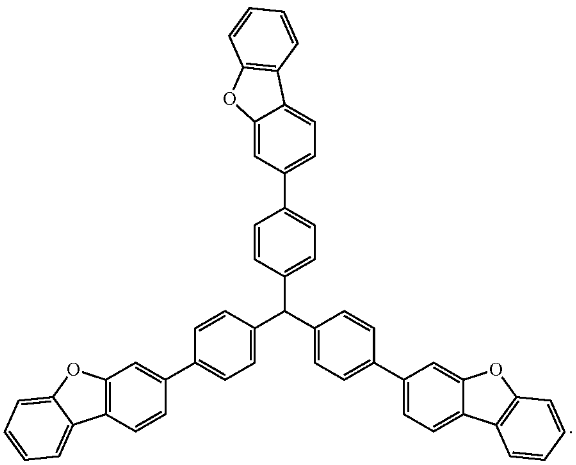

A specific test method is described below.

Refractive indexes of the above heterocyclic arylamine compounds at wavelengths of 460 nm, 530 nm and 620 nm were tested by ellipsometer. The test results are shown in Table 2 below.

TABLE 2

| Heterocyclic Arylamine | Refractive Index | | |
|---|---|---|---|
| Compound | $n_{460\ nm}$ | $n_{530\ nm}$ | $n_{620\ nm}$ |
| P001 | 2.31 | 2.15 | 2.01 |
| P019 | 2.34 | 2.14 | 2.02 |
| P020 | 2.30 | 2.13 | 2.01 |
| P054 | 2.23 | 2.12 | 2.03 |
| P091 | 2.32 | 2.13 | 2.02 |
| P123 | 2.32 | 2.11 | 2.00 |
| P124 | 2.33 | 2.13 | 2.00 |
| P137 | 2.36 | 2.17 | 2.03 |
| P138 | 2.24 | 2.08 | 2.01 |
| P139 | 2.32 | 2.13 | 2.01 |
| P147 | 2.27 | 2.16 | 2.03 |
| P148 | 2.28 | 2.18 | 2.07 |
| P149 | 2.30 | 2.17 | 2.04 |
| P150 | 2.21 | 2.13 | 2.03 |
| P151 | 2.27 | 2.17 | 2.05 |
| P156 | 2.31 | 2.12 | 2.01 |

TABLE 2-continued

| Heterocyclic Arylamine Compound | Refractive Index | | |
|---|---|---|---|
| | $n_{460\ nm}$ | $n_{530\ nm}$ | $n_{620\ nm}$ |
| P158 | 2.25 | 2.09 | 2.02 |
| P180 | 2.38 | 2.20 | 2.09 |
| Compound A | 2.03 | 1.95 | 1.90 |
| Compound B | 2.19 | 2.07 | 2.00 |
| Compound C | 2.18 | 2.08 | 2.02 |

As can be seen from the contents in Table 2, compared with Compound A, Compound B and Compound C, the heterocyclic arylamine compound provided in the present disclosure has a refractive index of not less than 2.21 at the wavelength of 460 nm, specifically 2.21 to 2.38, a refractive index of not less than 2.08 at the wavelength of 530 nm, specifically 2.08 to 2.20, and a refractive index of not less than 2.00 at the wavelength of 620 nm, specifically 2.00 to 2.09. Compared with Compound A, Compound B and Compound C, the heterocyclic arylamine compound provided in the present disclosure has a higher refractive index. The refractive index is improved by about 0.03 to 0.35 at the wavelength of 460 nm, improved by 0.25 at most at the wavelength of 530 nm and improved by 0.19 at most at the wavelength of 620 nm.

Several application examples in which the organic compounds of the present disclosure are applied to the organic electroluminescent device are described below.

Application Example 1

The present application example provides an organic electroluminescent device. Specific preparation steps are described below.

(1) A glass substrate having an indium tin oxide (ITO) anode layer (with a thickness of 15 nm) was cut into a size of 50 mm×50 mm×0.7 mm, sonicated in isopropyl alcohol and deionized water for 30 minutes separately, and then exposed to ozone for about 10 minutes for cleaning. The cleaned substrate was installed onto a vacuum deposition apparatus.

(2) A material of a hole injection layer (Compound b) and a p-type doping material (Compound a) were deposited through vacuum evaporation on the ITO anode layer at a doping ratio (mass ratio) of 3% for use as the hole injection layer with a thickness of 5 nm.

(3) A material of a hole transport layer (Compound b) was deposited through vacuum evaporation on the hole injection layer for use as a first hole transport layer with a thickness of 100 nm.

(4) A hole transport material (Compound c) was deposited through vacuum evaporation on the first hole transport layer for use as a second hole transport layer with a thickness of 5 nm.

(5) An light-emitting layer with a thickness of 30 nm was deposited through vacuum evaporation on the second hole transport layer, where Compound d was doped as a host material with Compound e as a doping material at a doping ratio (mass ratio) of 3%.

(6) An electron transport material (Compound f) was deposited through vacuum evaporation on the light-emitting layer for use as a first electron transport layer with a thickness of 30 nm.

(7) An electron transport material (Compound g) and an n-type doping material (Compound h) were deposited through vacuum evaporation on the first electron transport layer at a doping mass ratio of 1:1 for use as a second electron transport layer with a thickness of 5 nm.

(8) A magnesium-silver electrode was deposited through vacuum evaporation on the second electron transport layer at a ratio (9:1) of Mg:Ag for use as a cathode with a thickness of 10 nm.

(9) Heterocyclic arylamine compound P001 of the present disclosure was deposited through vacuum evaporation on the cathode for use as a capping layer with a thickness of 100 nm.

The compounds used in the preceding steps have the following structures:

Compound a

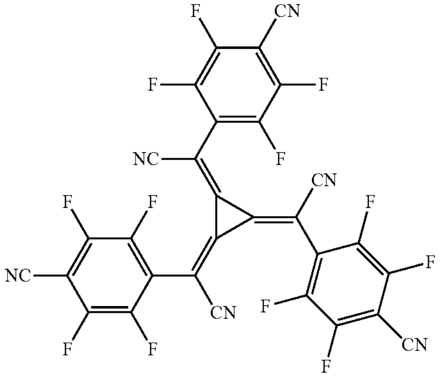

Compound b

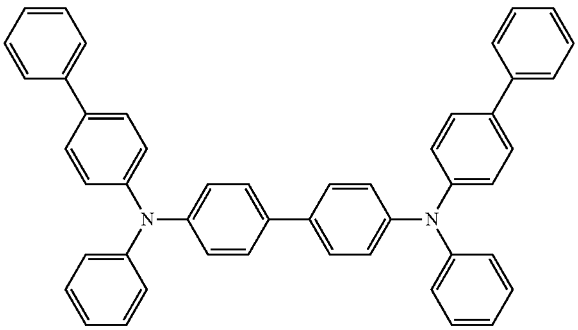

Compound c

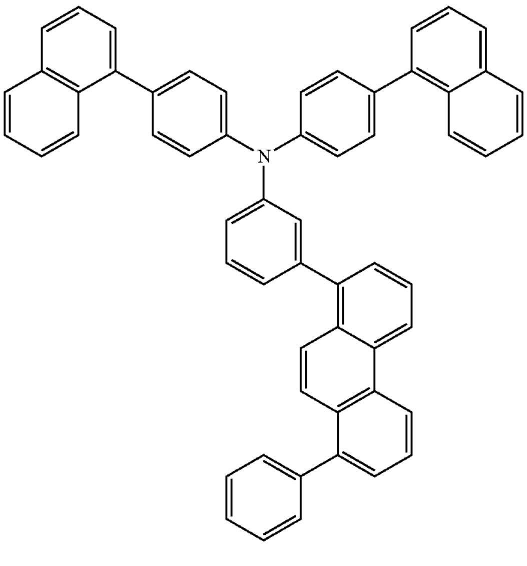

-continued

Compound d

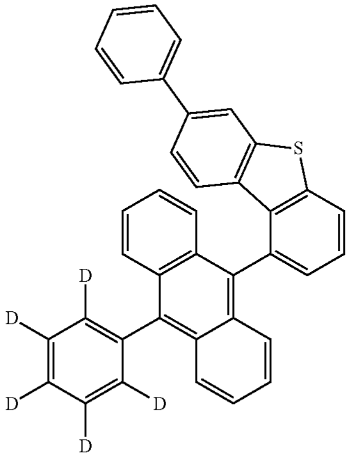

Compound e

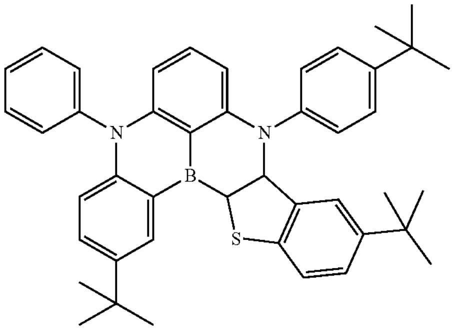

Compound f

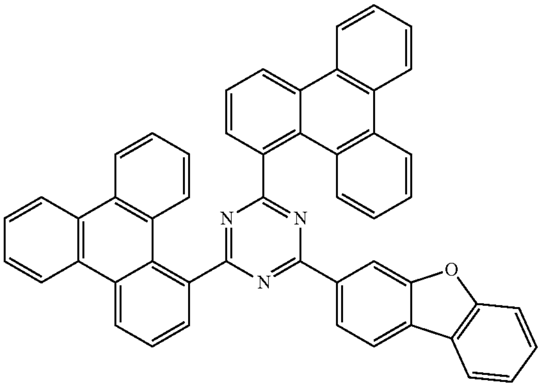

-continued

Compound g

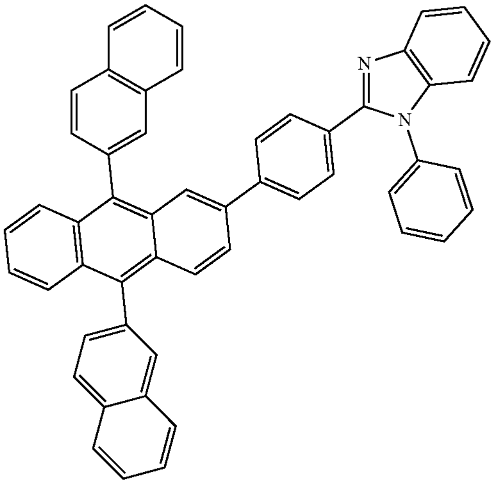

Compound h

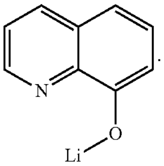

.

Application Example 2

The present application example differs from Application Example 1 only in that heterocyclic arylamine compound P001 in step (9) was replaced with another heterocyclic arylamine compound in an equivalent amount (as shown in Table 3 below), and other preparation steps were the same.

Application Comparative Example 1

The present application comparative example differs from Application Example 1 only in that heterocyclic arylamine compound P001 in step (9) was replaced with Compound A in an equivalent amount, and other preparation steps were the same.

Application Comparative Example 2

The present application comparative example differs from Application Example 1 only in that heterocyclic arylamine compound P001 in step (9) was replaced with Compound B in an equivalent amount, and other preparation steps were the same.

Application Comparative Example 3

The present application comparative example differs from Application Example 1 only in that heterocyclic arylamine compound P001 in step (9) was replaced with Compound C in an equivalent amount, and other preparation steps were the same.

Performance Evaluation of OLED Devices

A Keithley 2365A digital nanovoltmeter was used for testing currents of the OLED device at different voltages, and then the currents were divided by a luminescence area to obtain current densities of the OLED device at different voltages. A Konicaminolta CS-2000 spectroradiometer was used for testing the brightness and radiation energy flux densities of the OLED device at different voltages. According to the current densities and brightness of the OLED device at different voltages, a turn-on voltage and current efficiency (CE, cd/A) at the same current density (10 $mA/cm^2$) were obtained, where Von denotes the turn-on voltage when the brightness is 1 $cd/m^2$. A lifetime LT95 was obtained (under a testing condition of 50 $mA/cm^2$) by measuring the time taken for the OLED device to reach 95% of its initial brightness. Specific data is shown in Table 3 below.

TABLE 3

| No. | CPL Material | Current Efficiency (cd/A) | LT95 |
|---|---|---|---|
| Application Example 1 | P001 | 107% | 108% |
| Application Example 2 | P019 | 108% | 105% |
| Application Example 3 | P020 | 107% | 107% |
| Application Example 4 | P054 | 106% | 110% |
| Application Example 5 | P091 | 107% | 106% |
| Application Example 6 | P123 | 106% | 107% |
| Application Example 7 | P124 | 108% | 106% |
| Application Example 8 | P137 | 109% | 105% |
| Application Example 9 | P138 | 106% | 106% |
| Application Example 10 | P139 | 107% | 105% |
| Application Example 11 | P147 | 106% | 108% |
| Application Example 12 | P148 | 106% | 108% |
| Application Example 13 | P149 | 107% | 106% |
| Application Example 14 | P150 | 105% | 105% |
| Application Example 15 | P151 | 106% | 108% |
| Application Example 16 | P156 | 107% | 106% |
| Application Example 17 | P158 | 105% | 107% |
| Application Example 18 | P180 | 109% | 106% |
| Application Comparative Example 1 | Compound A | 100% | 100% |
| Application Comparative Example 2 | Compound B | 105% | 104% |
| Application Comparative Example 3 | Compound C | 104% | 103% |

As can be seen from the data in Table 3, compared with the OLED devices provided in Application Comparative Examples 1 to 3, the OLED device prepared by the heterocyclic arylamine compound provided in the present disclosure as the material of the capping layer has a higher current efficiency and a longer lifetime, wherein the current efficiency may be improved by 5% to 9%, and the lifetime may be improved by 5% to 10%.

The applicant has stated that although the heterocyclic arylamine compound and the organic electroluminescent device provided in the present disclosure are described through the preceding examples, the present disclosure is not limited to the processes and steps described above, which means that the implementation of the present disclosure does not necessarily depend on the processes and steps described above. It should be apparent to those skilled in the art that any improvements made to the present disclosure, equivalent replacements of raw materials selected in the present disclosure, additions of adjuvant ingredients, selections of specific methods, etc., all fall within the protection scope and the disclosure scope of the present disclosure.

What is claimed is:

1. A heterocyclic arylamine compound having a structure represented by Formula I:

Formula I

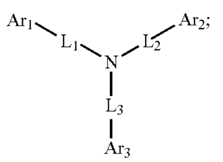

wherein $Ar_1$ has a structure represented by Formula II:

Formula II

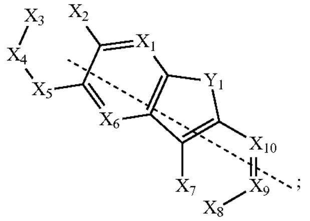

wherein $X_1$ to $X_{10}$ are each independently selected from N or C—R', wherein R' is selected from any one of H, D, halogen or cyano;

$Y_1$ is selected from O or S;

$L_1$ to $L_3$ are each independently selected from any one of a single bond, substituted or unsubstituted C6 to C18 arylene, or substituted or unsubstituted C3 to C18 heteroarylene;

substituents in substituted $L_1$ to $L_3$ are each independently selected from at least one of D, halogen or cyano;

$Ar_2$ and $Ar_3$ are each independently selected from any one of substituted or unsubstituted C6 to C30 aryl, or substituted or unsubstituted C3 to C30 heteroaryl;

substituents in substituted $Ar_2$ and $Ar_3$ are each independently selected from at least one of D, halogen, cyano or C1 to C5 alkyl;

wherein C6 to C30 aryl is selected from any one of phenyl, naphthyl, anthryl, phenanthryl, pyrenyl, perylenyl, benzophenanthryl, benzopyrenyl or benzoanthryl;

wherein C3 to C30 heteroaryl is selected from any one of furanyl, thienyl, pyrrolyl, pyridyl, pyranyl, pyrimidinyl, pyrazinyl, pyridazinyl, triazinyl, naphthyl, quinolyl, quinoxalinyl, isoquinolyl, quinazolinyl, acridinyl, carbazolyl, indolyl, benzofuranyl, benzothienyl, dibenzofuranyl, dibenzothienyl, 2-N-heterodibenzofuran or 2-N-heterodibenzothiophene; and $Ar_1$, $Ar_2$ and $Ar_3$ include at least one nitrogen atom.

2. The heterocyclic arylamine compound according to claim 1, wherein $Ar_1$ is selected from any one of the following groups, or any one of the following groups substituted with a substituent:

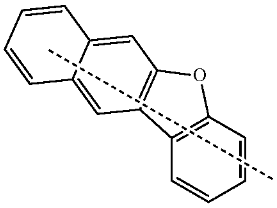,
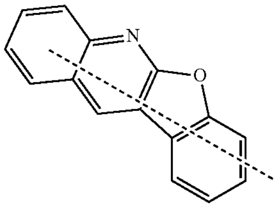,
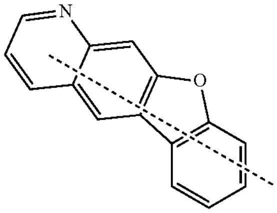,
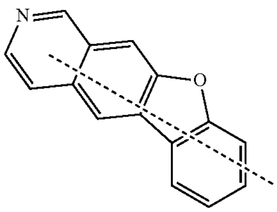,
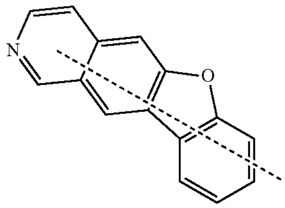,
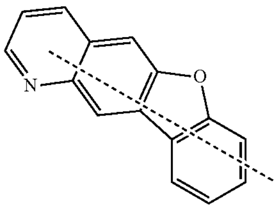,
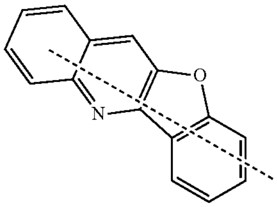,
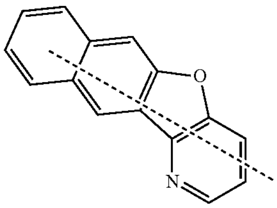,
-continued
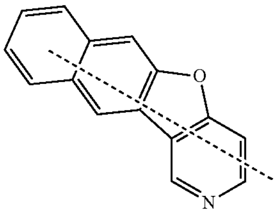, 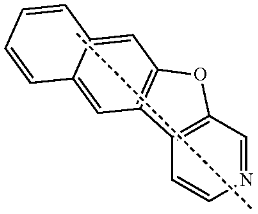,
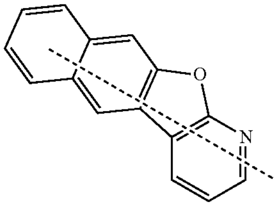,
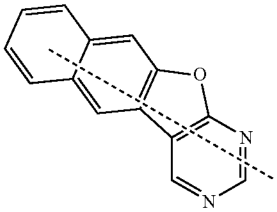,
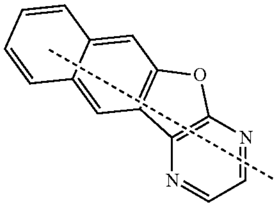,
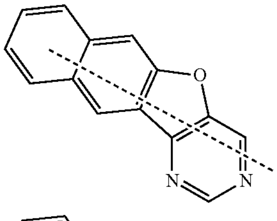,
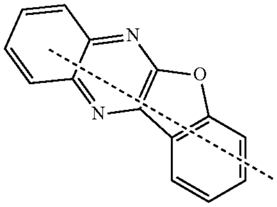,
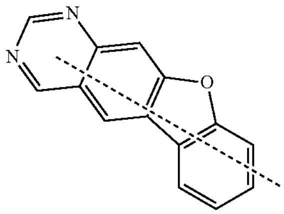,
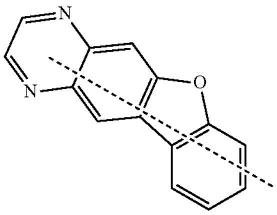, -continued
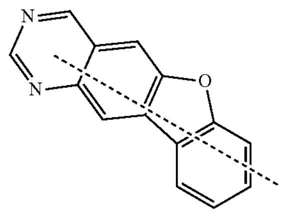
,
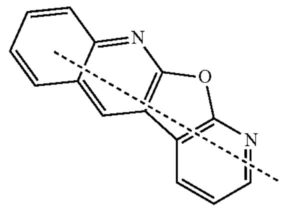
,
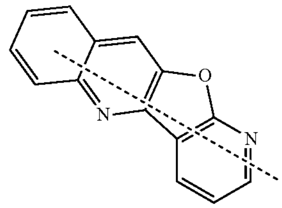
,
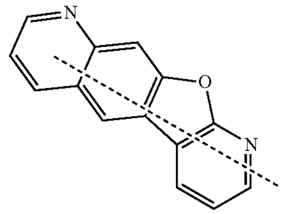
,
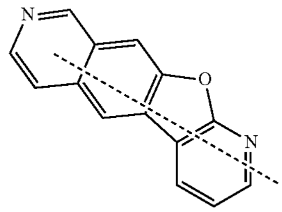
,
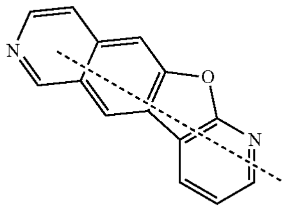
,
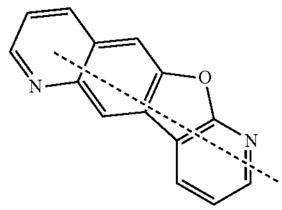
,
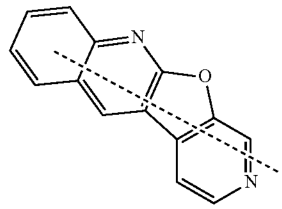
,
-continued
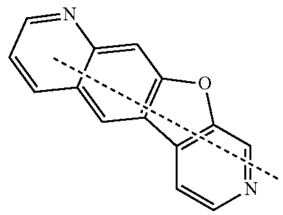
,
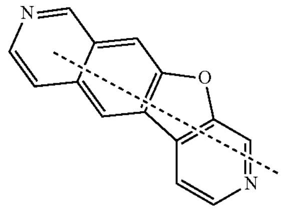
,
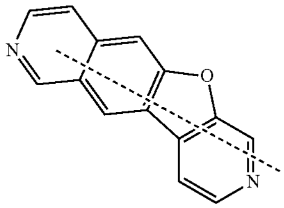
,
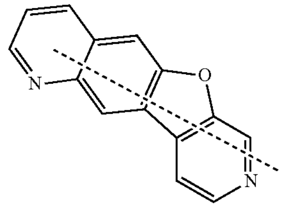
,
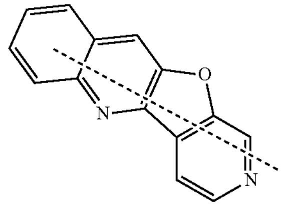
,
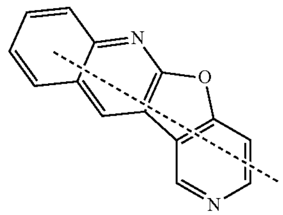
,
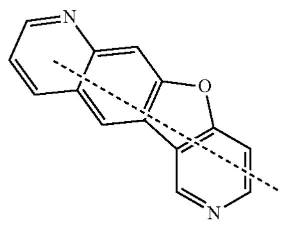
,
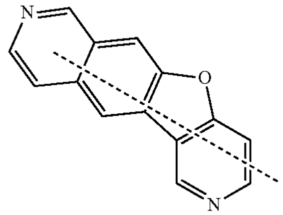
, -continued
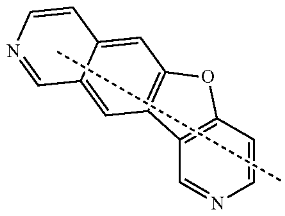
,
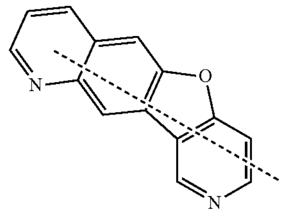
,
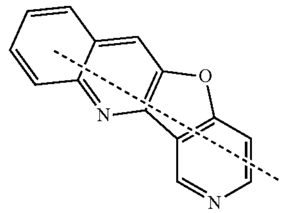
,
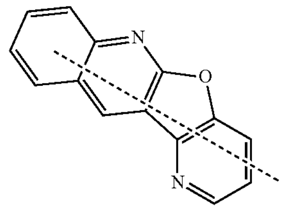
,
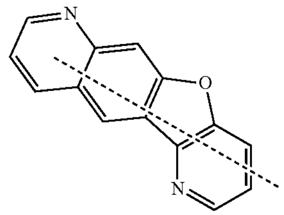
,
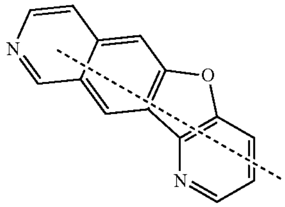
,
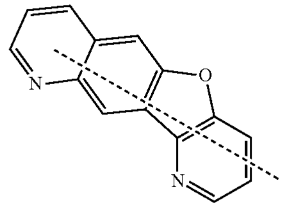
,
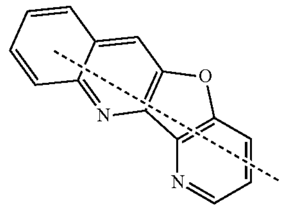
,
-continued
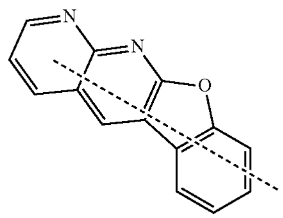
,
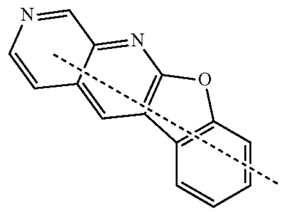
,
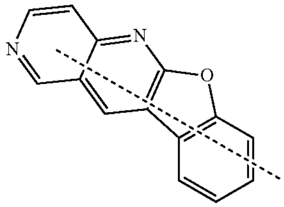
,
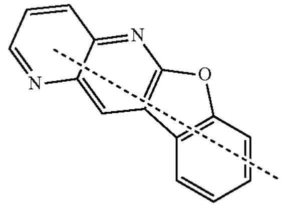
,
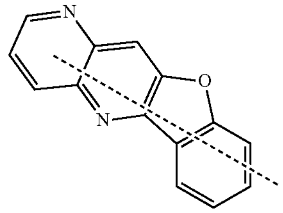
,
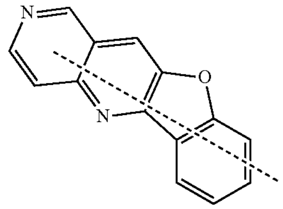
,
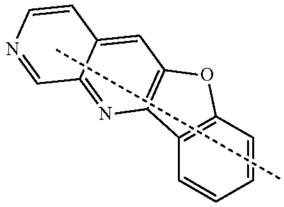
,
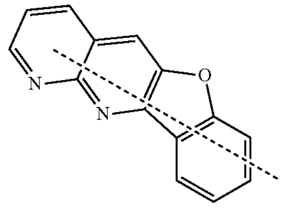

-continued
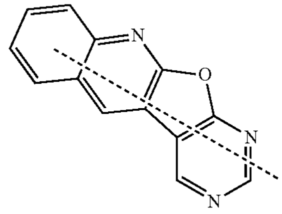
,
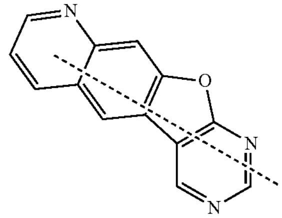
,
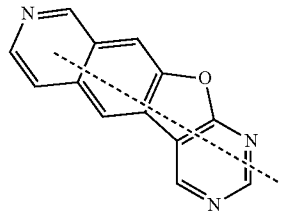
,
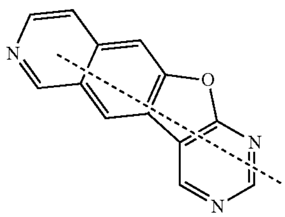
,
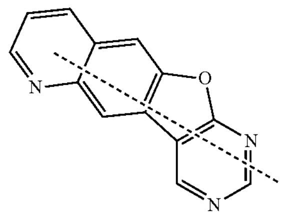
,
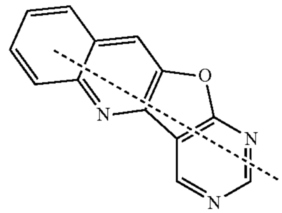
,
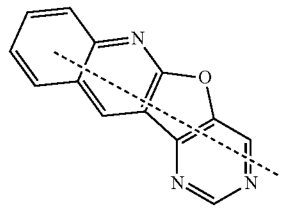
,
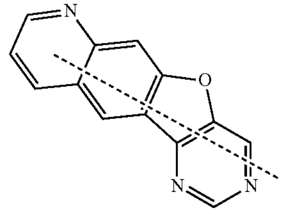
,
-continued
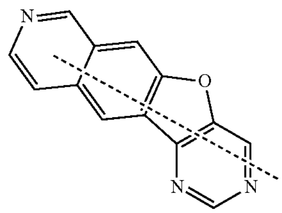
,
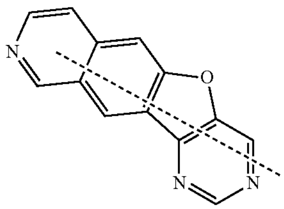
,
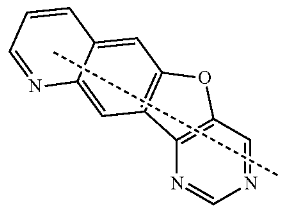
,
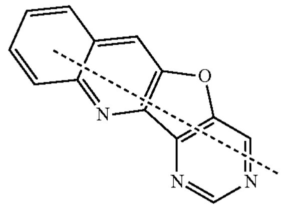
,
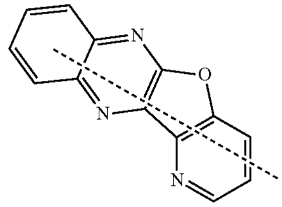
,
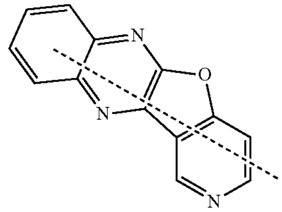
,
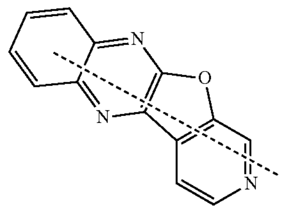
,
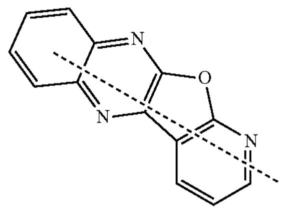
, -continued
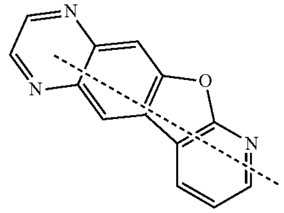,
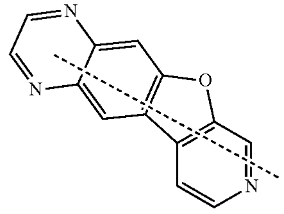,
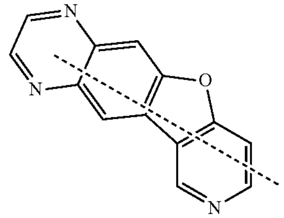,
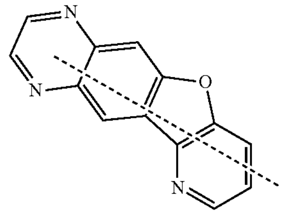,
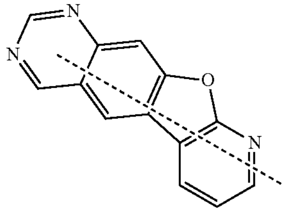,
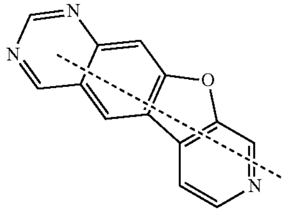,
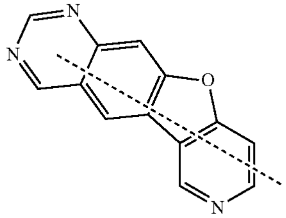,
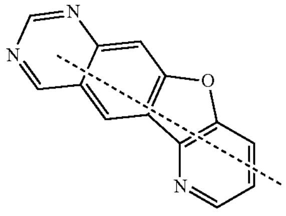,
-continued
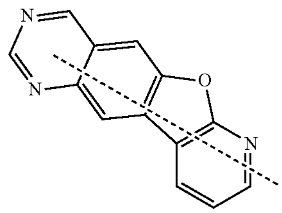,
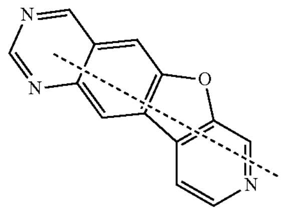,
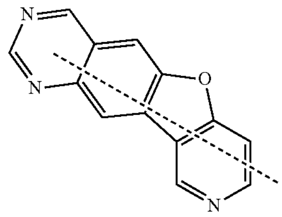,
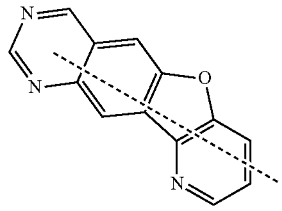,
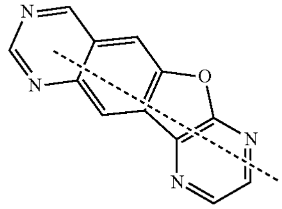,
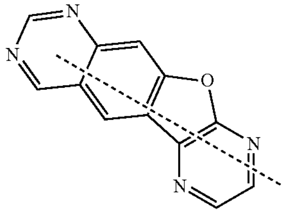,
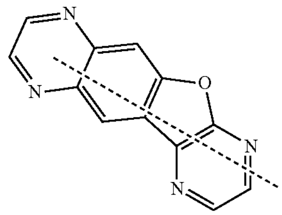,
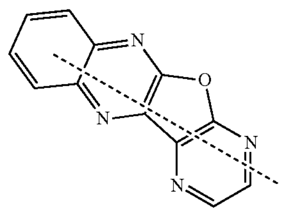, -continued
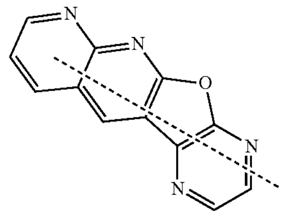
,
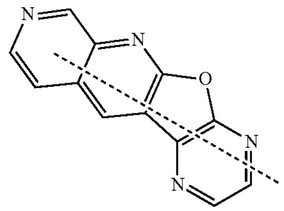
,
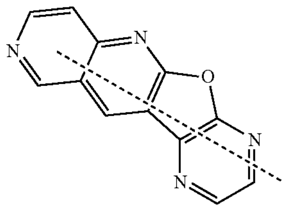
,
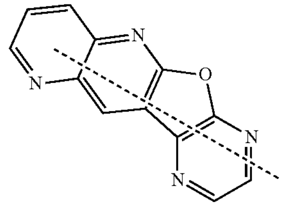
,
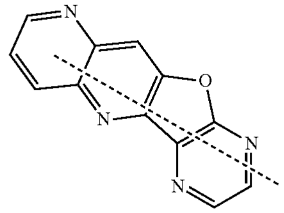
,
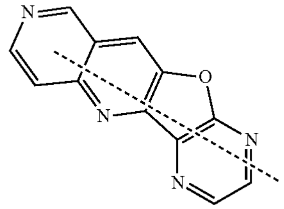
,
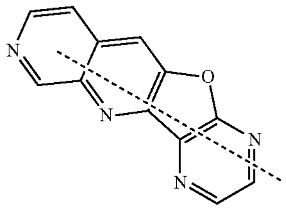
,
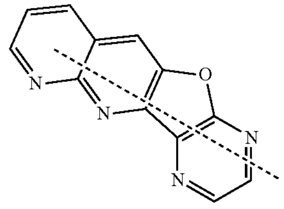
,
-continued
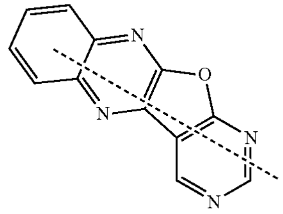
,
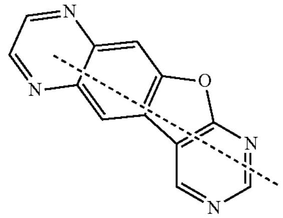
,
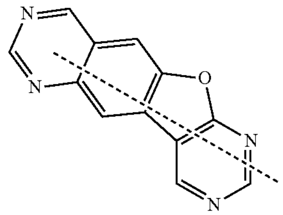
,
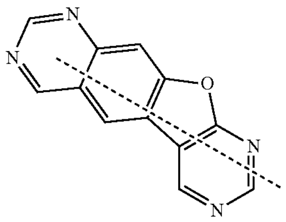
,
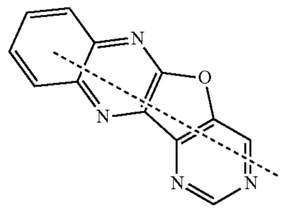
,
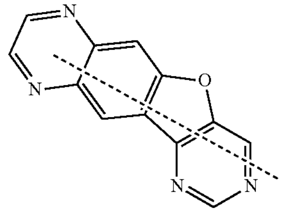
,
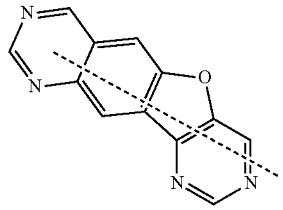
,
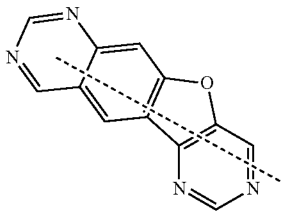
, -continued
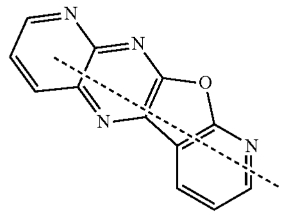
,
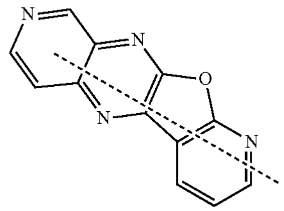
,
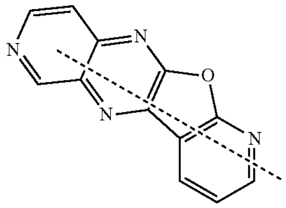
,
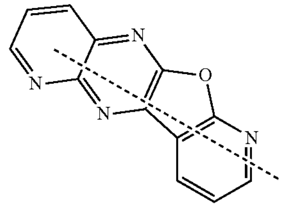
,
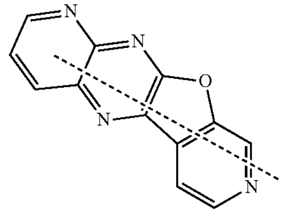
,
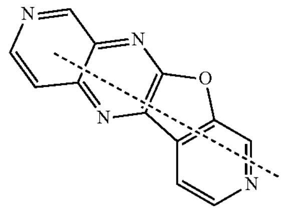
,
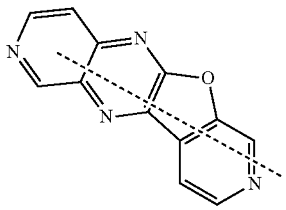
,
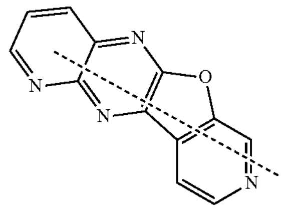
,
-continued
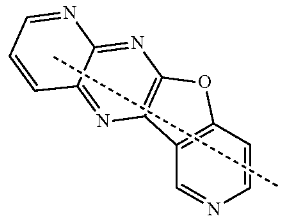
,
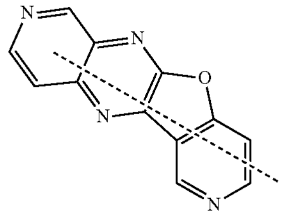
,
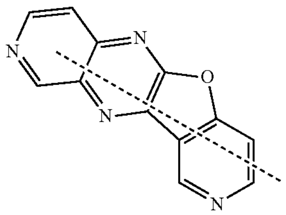
,
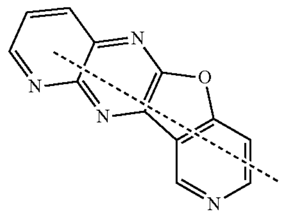
,
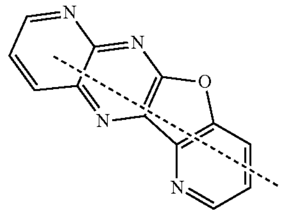
,
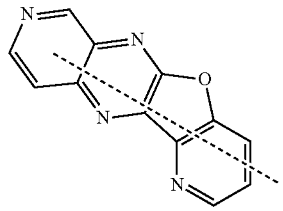
,
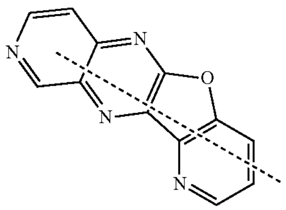
,
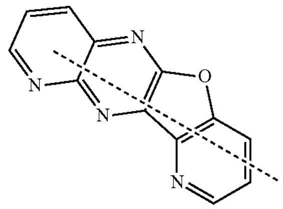
, -continued
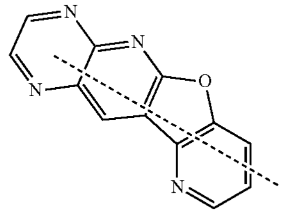
,
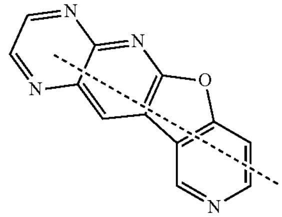
,
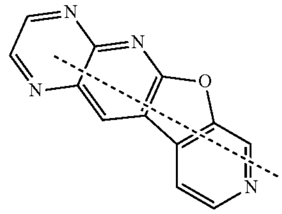
,
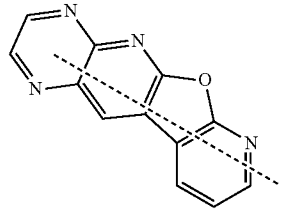
,
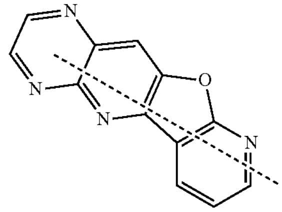
,
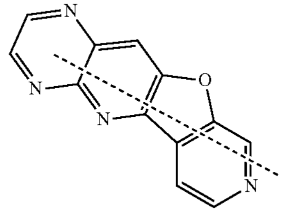
,
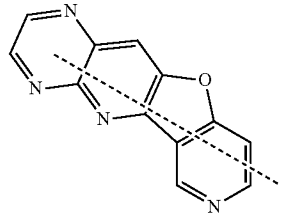
,
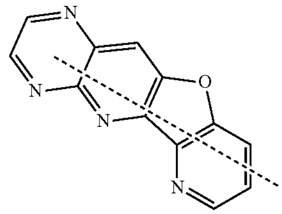
,
-continued
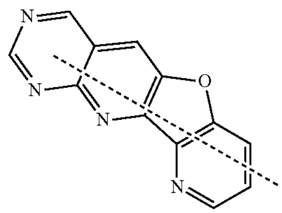
,
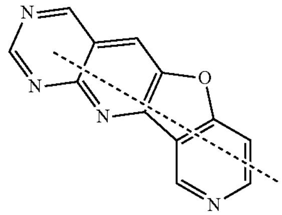
,
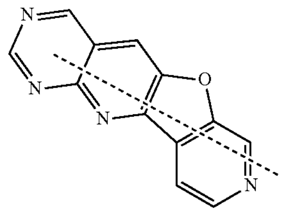
,
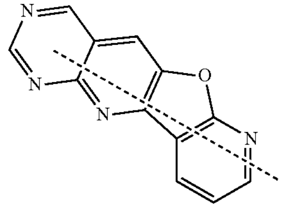
,
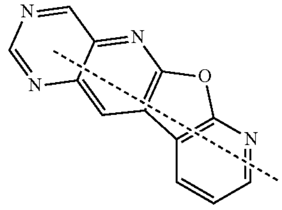
,
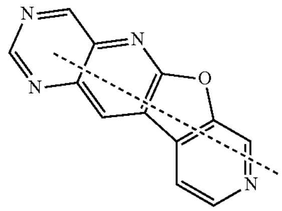
,
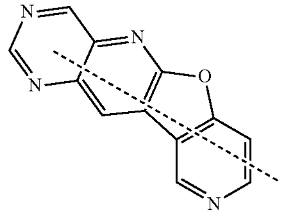
,
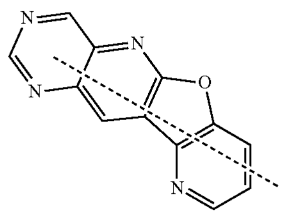
, -continued
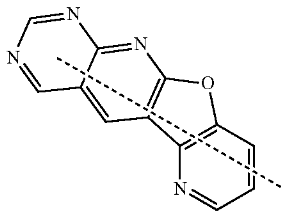
,
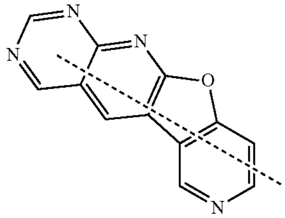
,
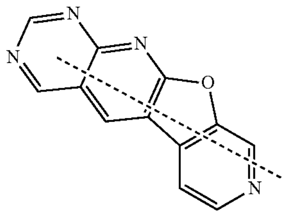
,
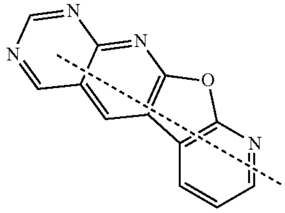
,
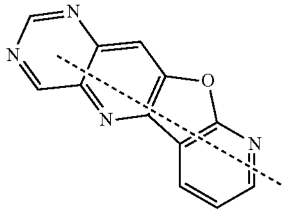
,
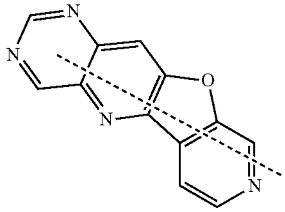
,
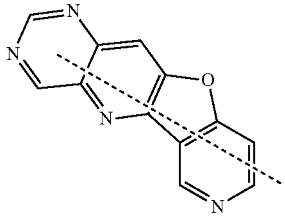
,
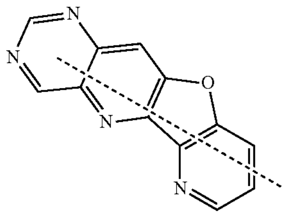
,
-continued
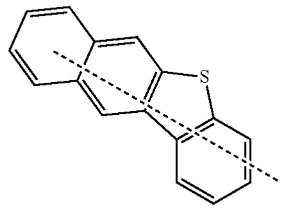
,
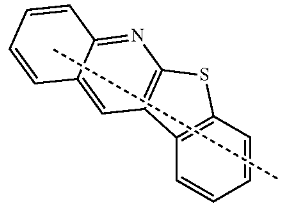
,
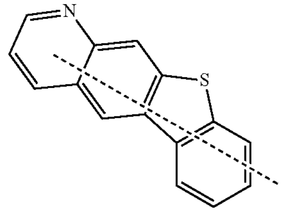
,
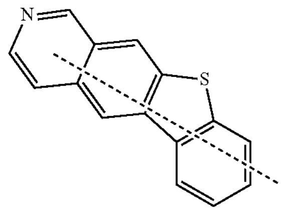
,
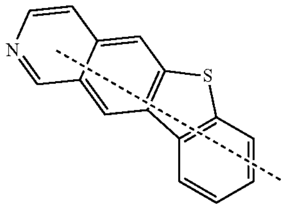
,
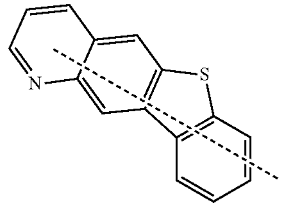
,
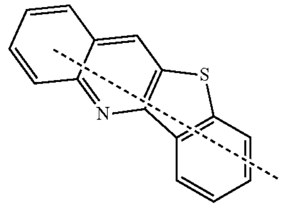
,
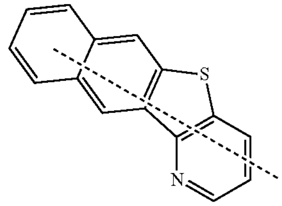
, -continued
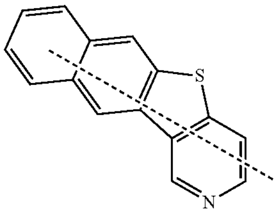
,
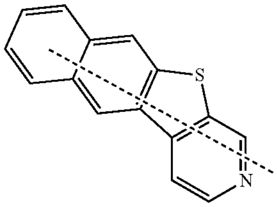
,
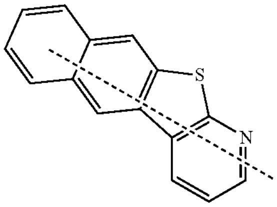
,
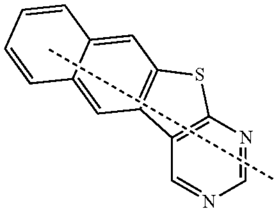
,
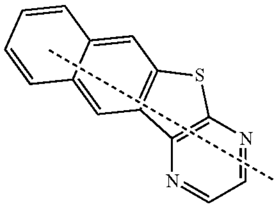
,
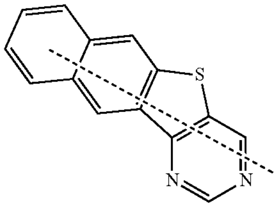
,
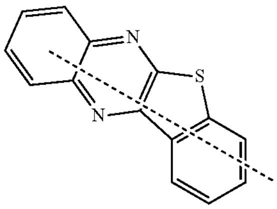
,
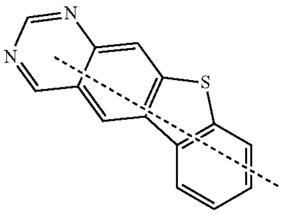
,
-continued
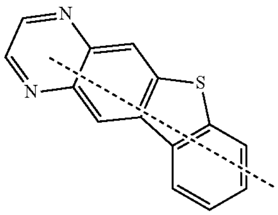
,
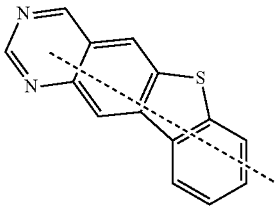
,
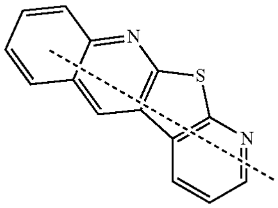
,
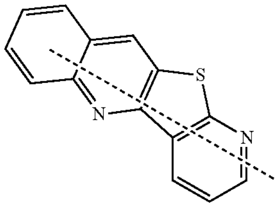
,
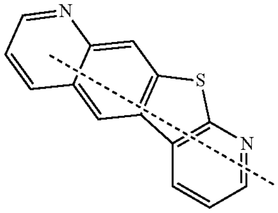
,
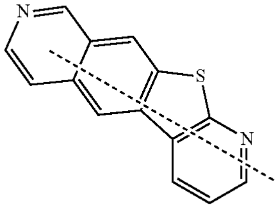
,
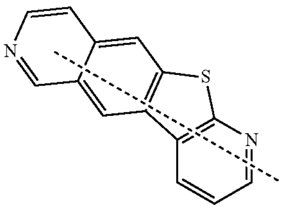
,
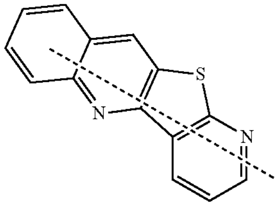
, -continued
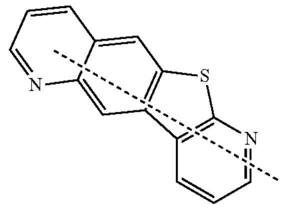
,
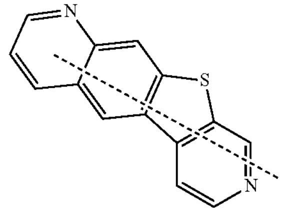
,
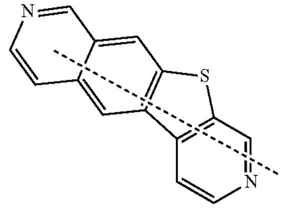
,
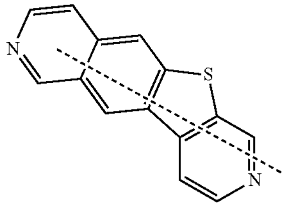
,
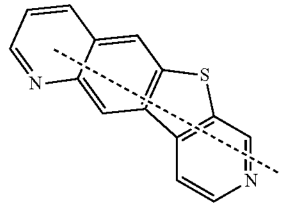
,
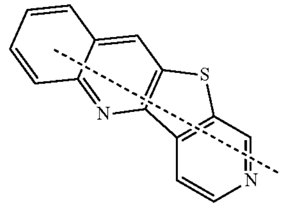
,
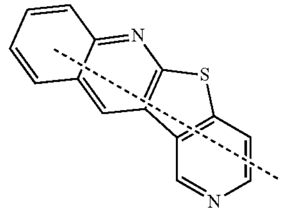
,
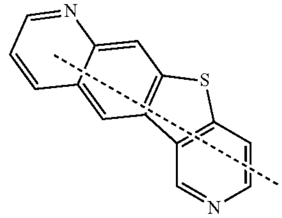
,
-continued
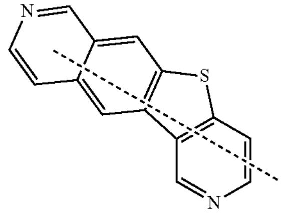
,
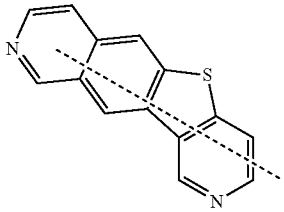
,
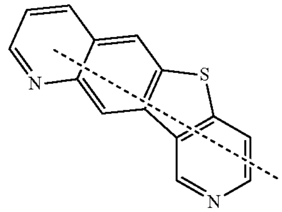
,
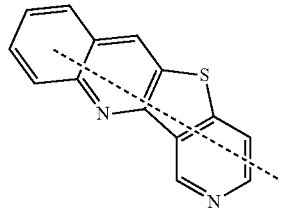
,
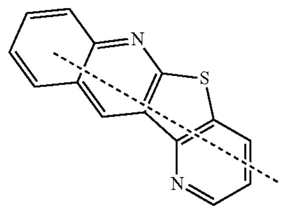
,
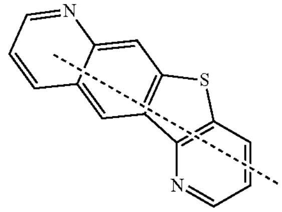
,
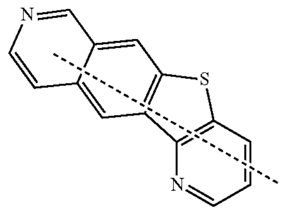
,
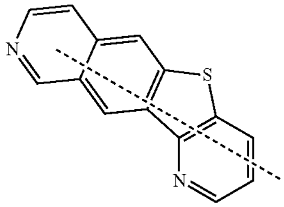
, -continued
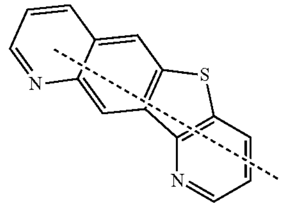,
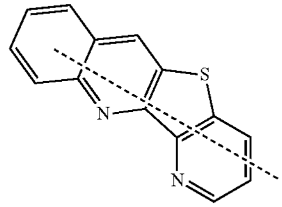,
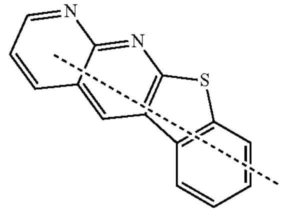,
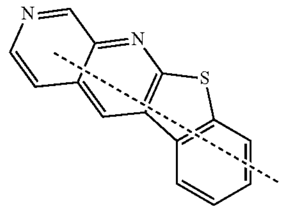,
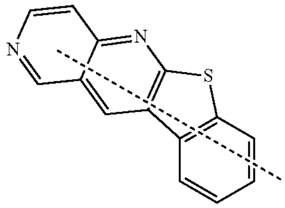,
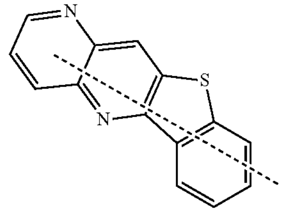,
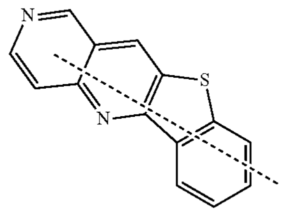,
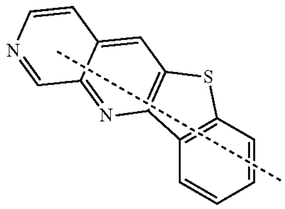,
-continued
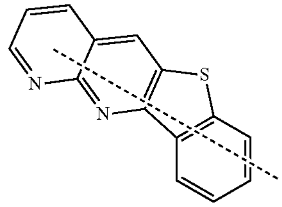,
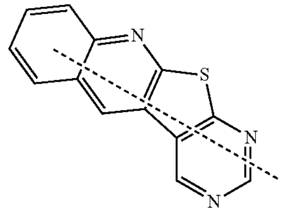,
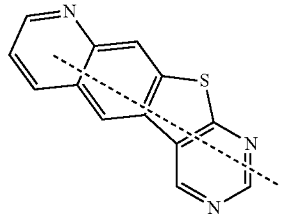,
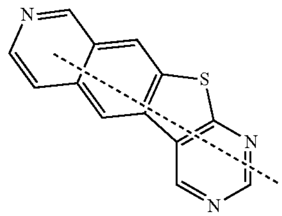,
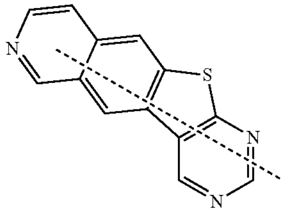,
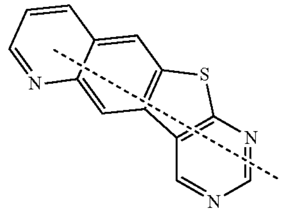,
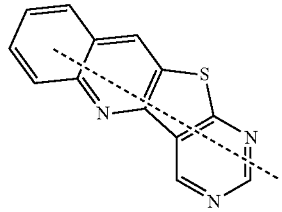,
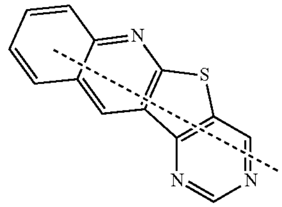, -continued
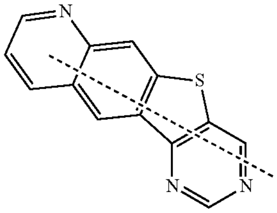
,
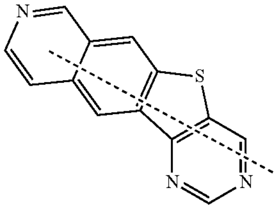
,
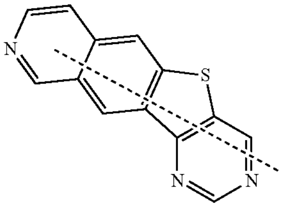
,
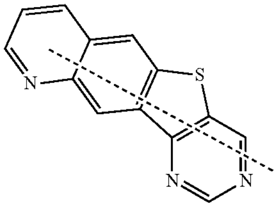
,
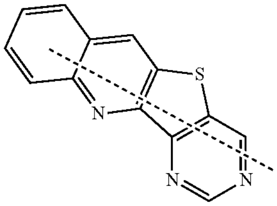
,
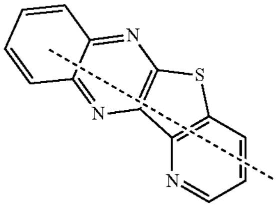
,
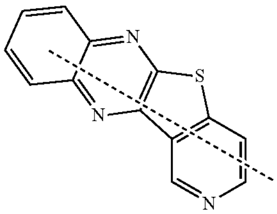
,
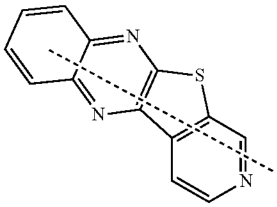
,
-continued
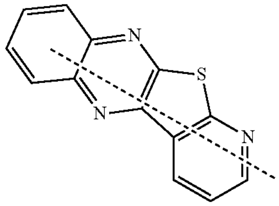
,
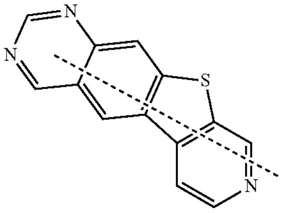
,
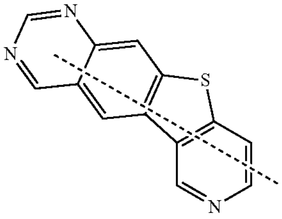
,
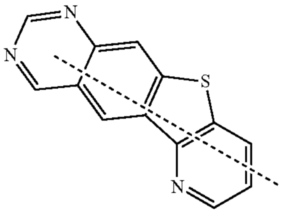
,
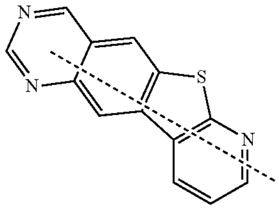
,
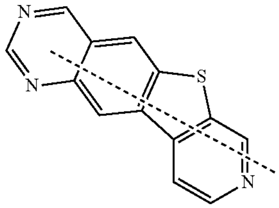
,
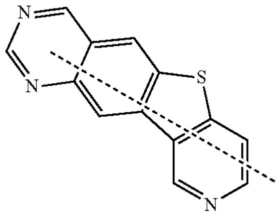
,
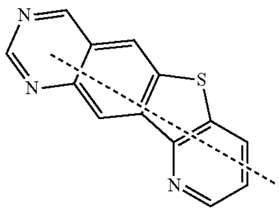
, -continued
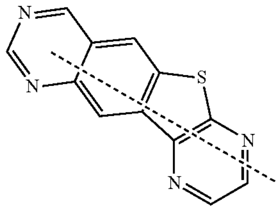
,
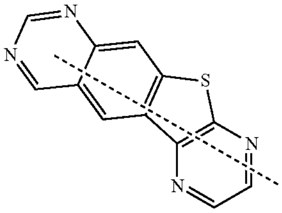
,
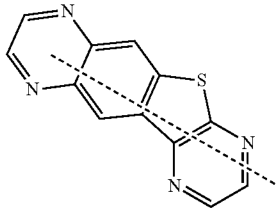
,
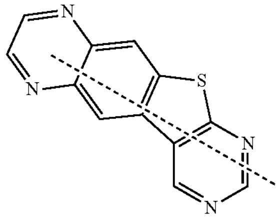
,
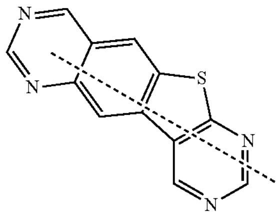
,
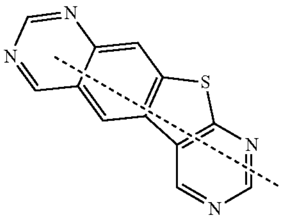
,
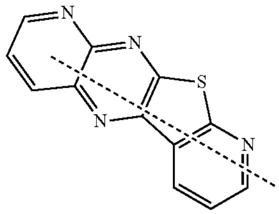
,
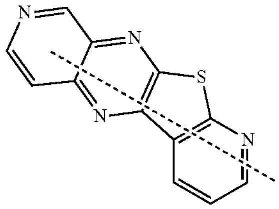
,
-continued
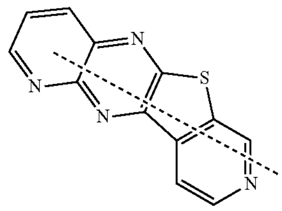
,
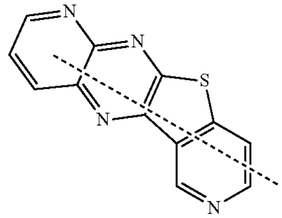
,
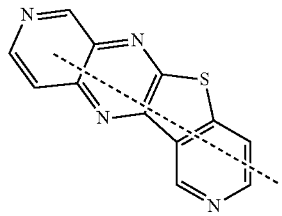
,
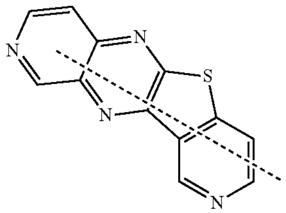
,
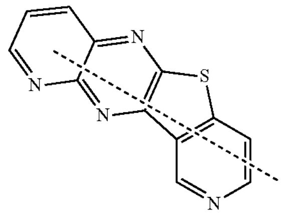
,
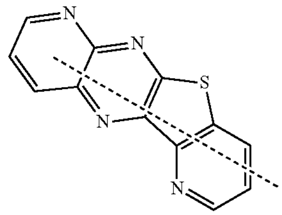
,
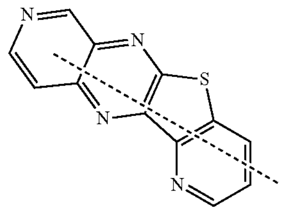
,
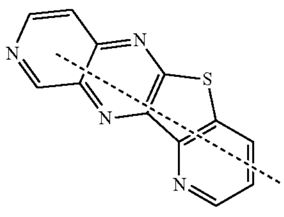
, -continued
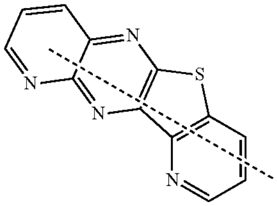
,
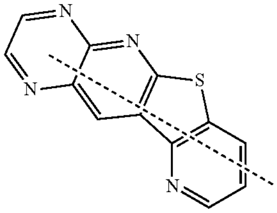
,
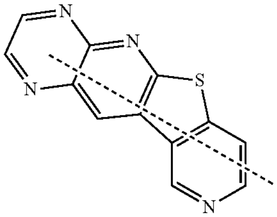
,
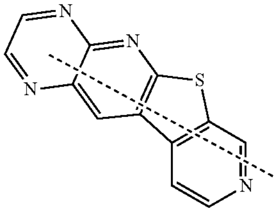
,
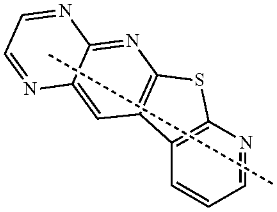
,
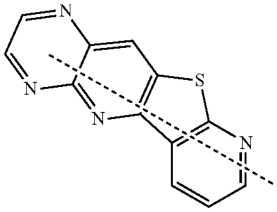
,
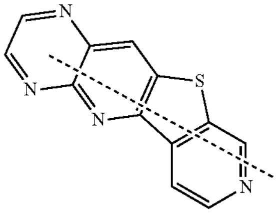
,
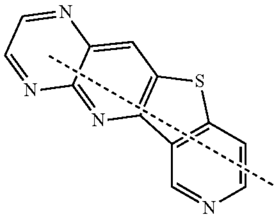
,
-continued
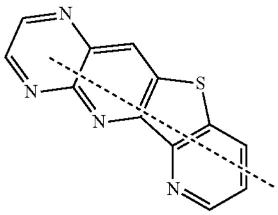
,
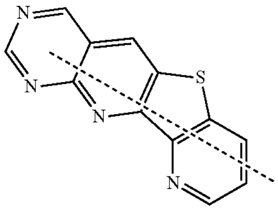
,
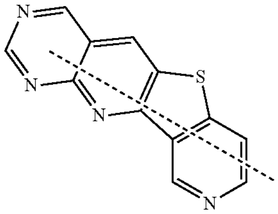
,
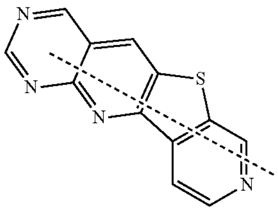
,
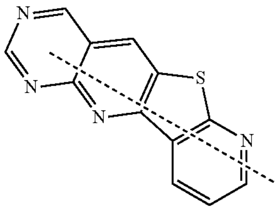
,
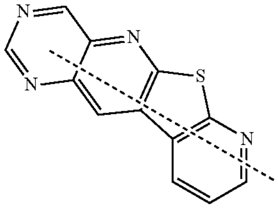
,
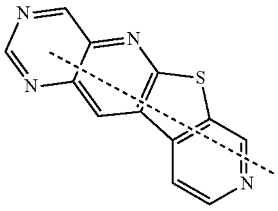
,
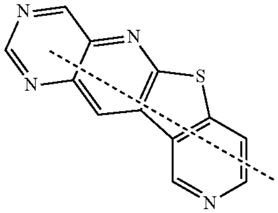

-continued
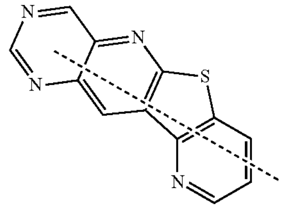
,
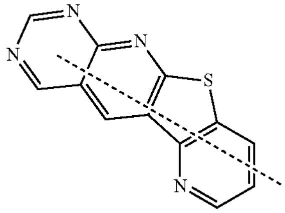
,
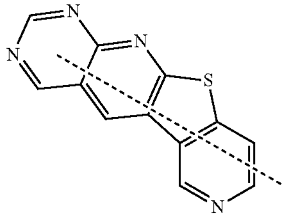
,
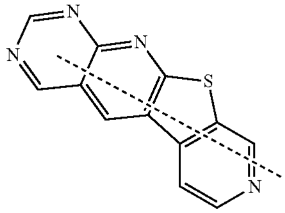
,
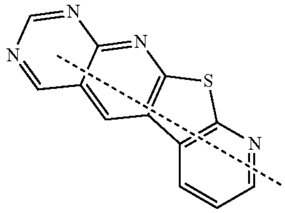
,
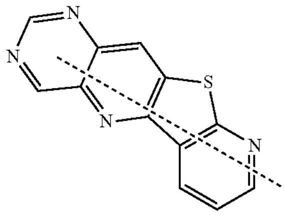
,
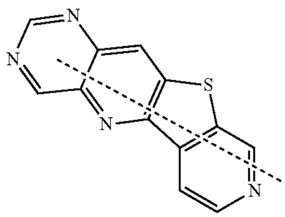
,
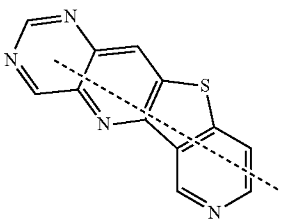
, or
-continued
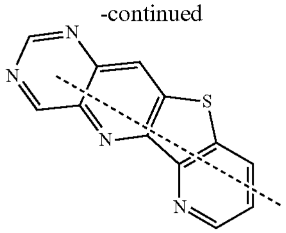
;
wherein the dashed line represents a linkage site of the group;
the substituent is selected from D, halogen or cyano.
3. The heterocyclic arylamine compound according to claim 2, wherein $Ar_1$ is selected from any one of the following groups, or any one of the following groups substituted with a substituent:
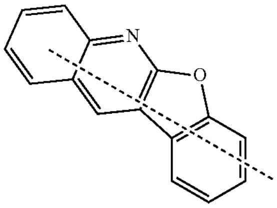
,
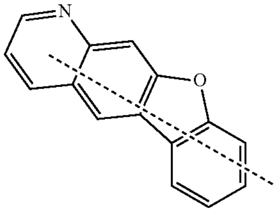
,
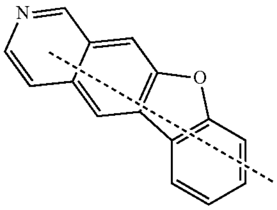
,
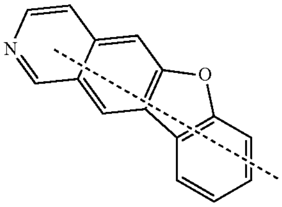
,
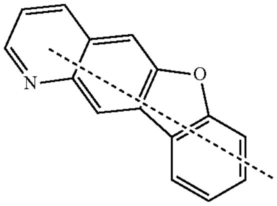
,
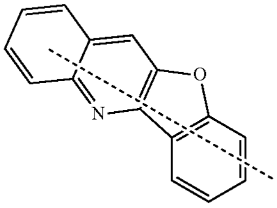
, -continued

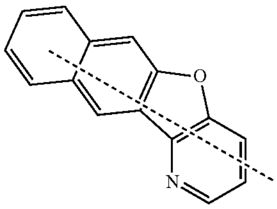
,

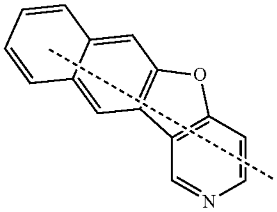
,

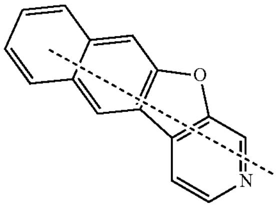
,

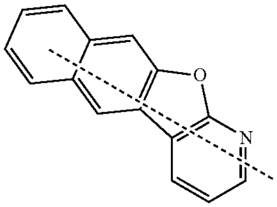
,

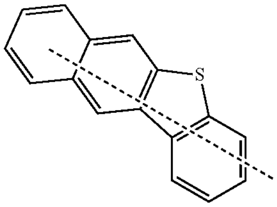
,

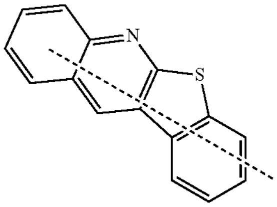
,

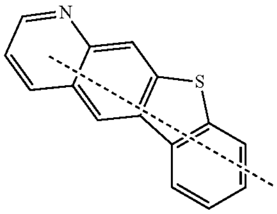
,

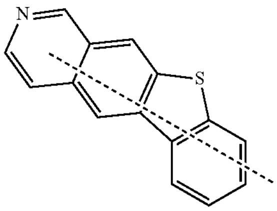
,

-continued

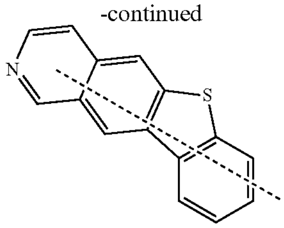
,

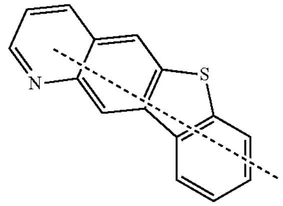
,

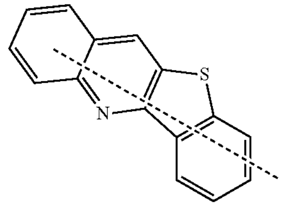
,

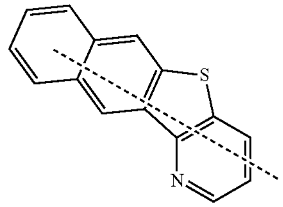
,

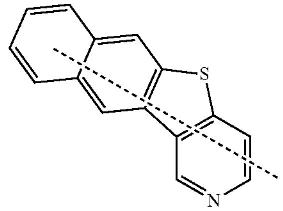
,

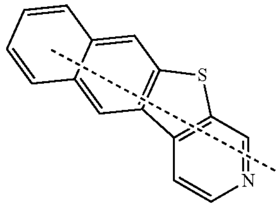
, or

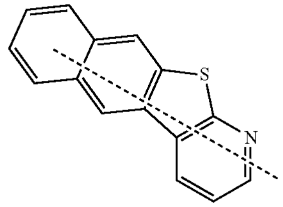
;

wherein the dashed line represents a linkage site of the group;

the substituent is selected from D, halogen or cyano.

4. The heterocyclic arylamine compound according to claim 1, wherein C6 to C18 arylene is selected from any one of phenylene, naphthylene, anthrylene or phenanthrylene.

5. The heterocyclic arylamine compound according to claim 1, wherein C3 to C18 heteroarylene is selected from any one of furanylene, thienylene, pyrrolylene, pyridylene, pyranylene, pyrimidinylene, pyrazinylene, pyridazinylene, triazinylene, naphthylene, quinolylene, quinoxalinylene, isoquinolylene or quinazolinylene.

6. The heterocyclic arylamine compound according to claim 1, wherein $L_1$ to $L_3$ are each independently selected from a single bond, substituted or unsubstituted phenylene, or substituted or unsubstituted naphthylene;

substituents in the substituted phenylene and the substituted naphthylene are each independently selected from at least one of D, halogen or cyano.

7. The heterocyclic arylamine compound according to claim 1, wherein $Ar_2$ and $Ar_3$ are each independently selected from any one of the following groups:

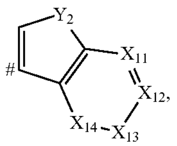
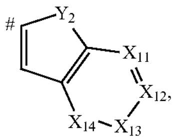
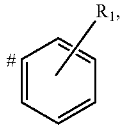
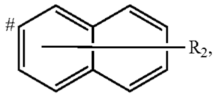
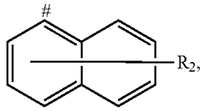
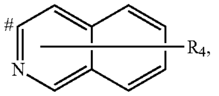
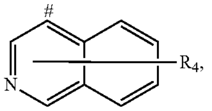
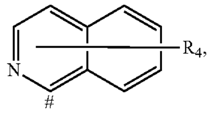
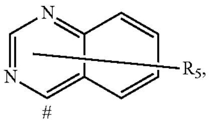
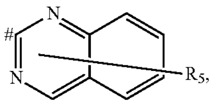
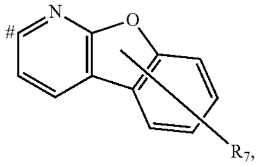
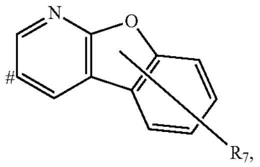
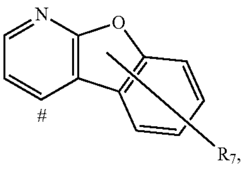
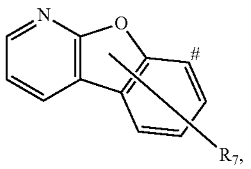
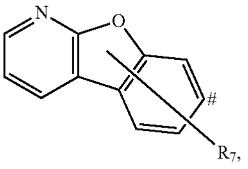
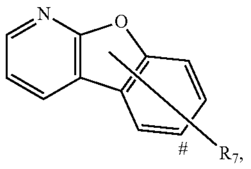

-continued

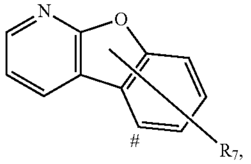
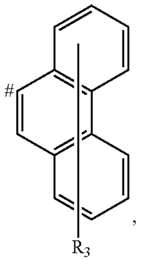
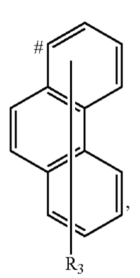
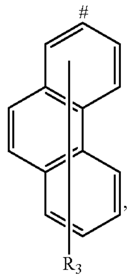
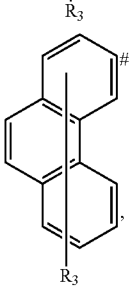
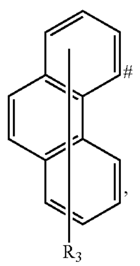
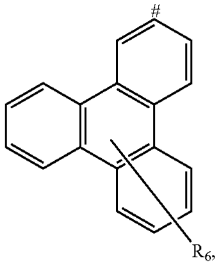
or

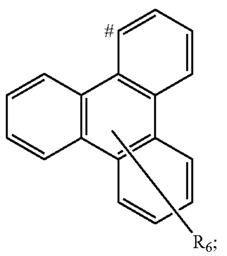

wherein "#" represents a linkage site of the group;

$X_{11}$, $X_{12}$, $X_{13}$ and $X_{14}$ are each independently selected from N or C—R;

$Y_2$ is selected from N, O or S; and

R, $R_1$, $R_2$, $R_3$, $R_4$, $R_5$, $R_6$ and $R_7$ are each independently selected from H, D, halogen or cyano.

8. The heterocyclic arylamine compound according to claim 1, wherein the heterocyclic arylamine compound is selected from any one of the following compounds:

-continued
P001
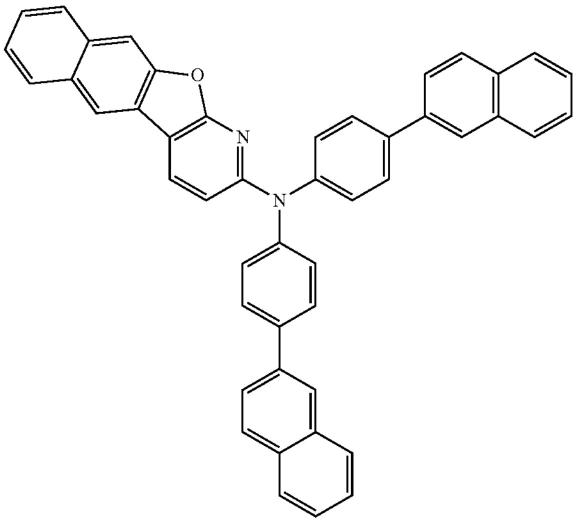
P002
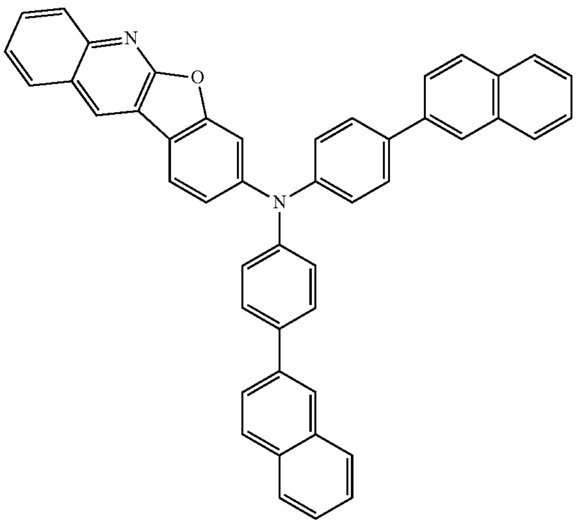
P003
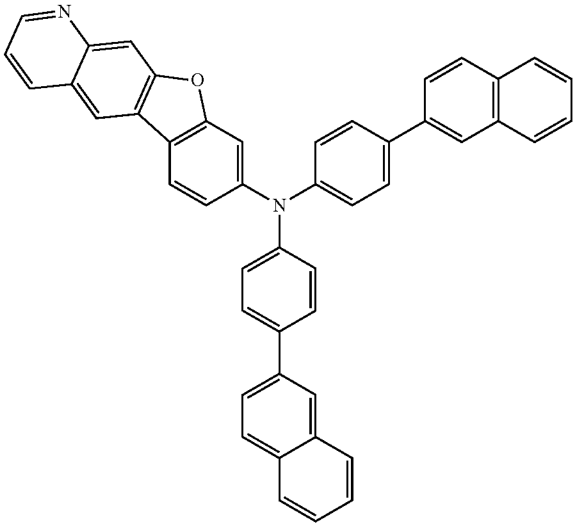
P004
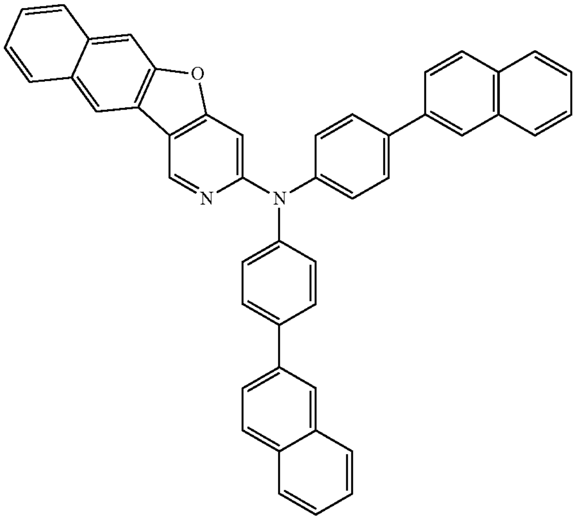
P005
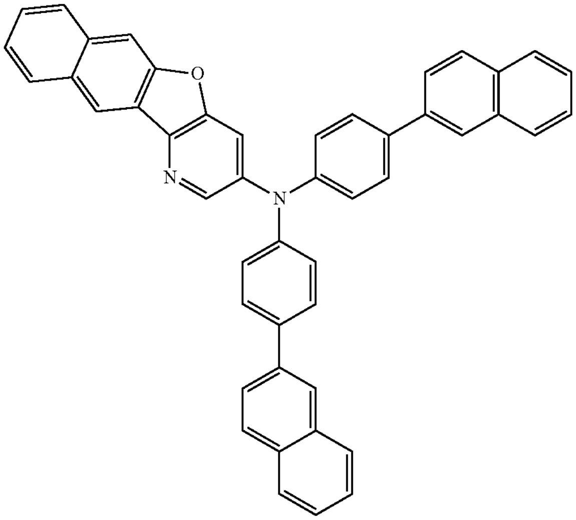
P006
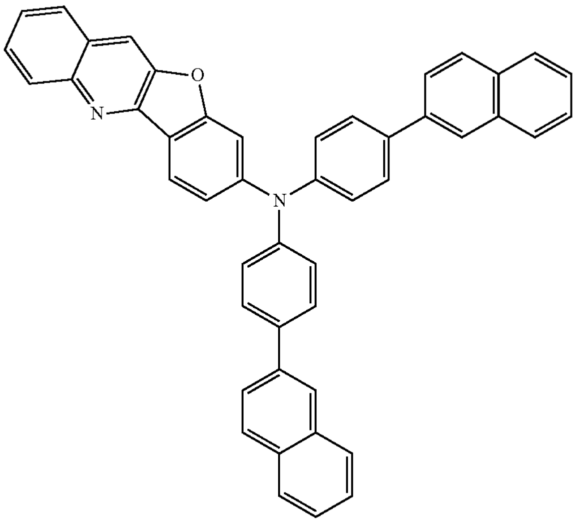

-continued
P007
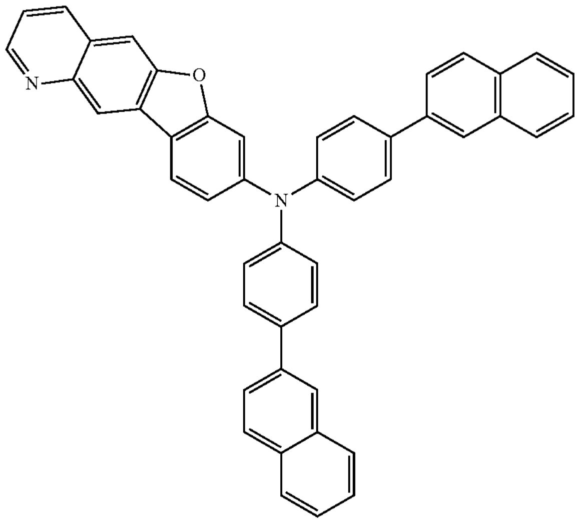
P008
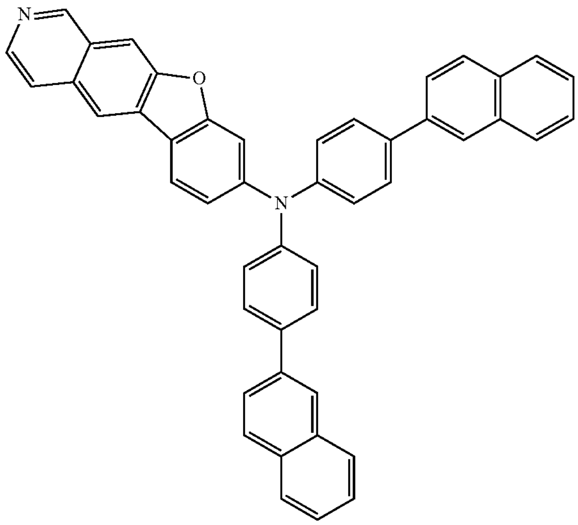
P009
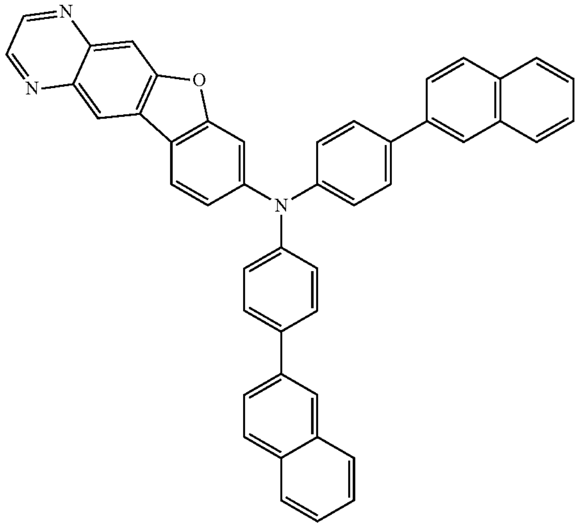
-continued
P010
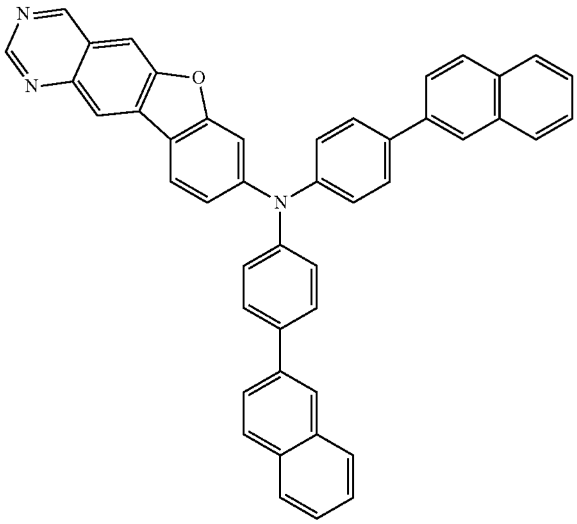
P011
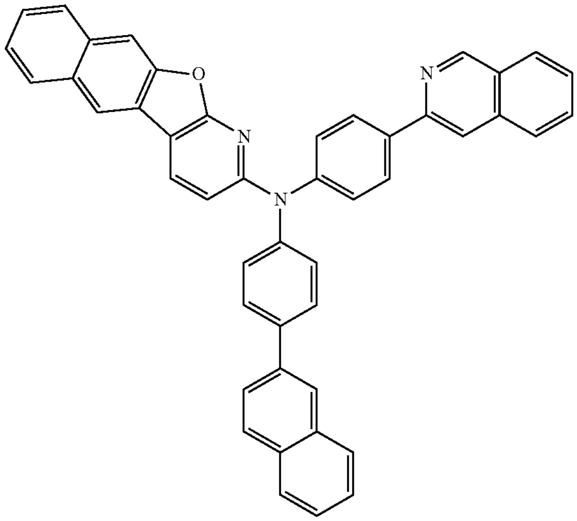
P012
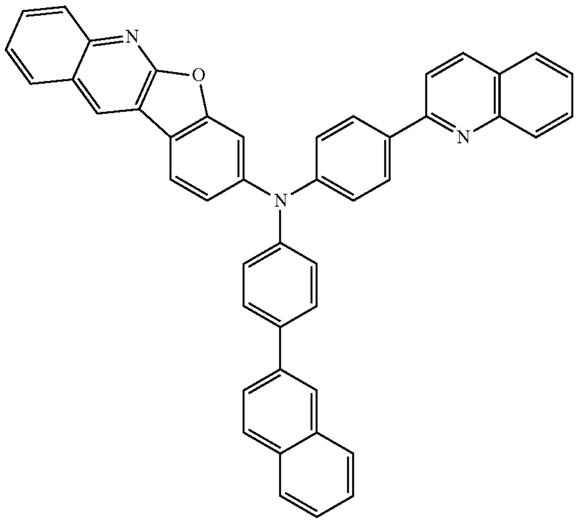

-continued
P013
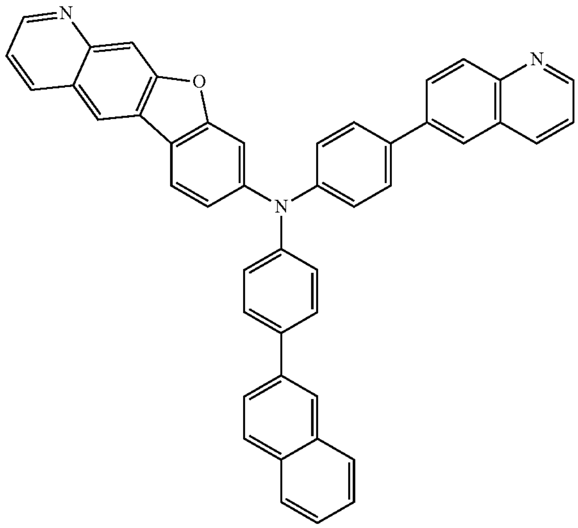
P014
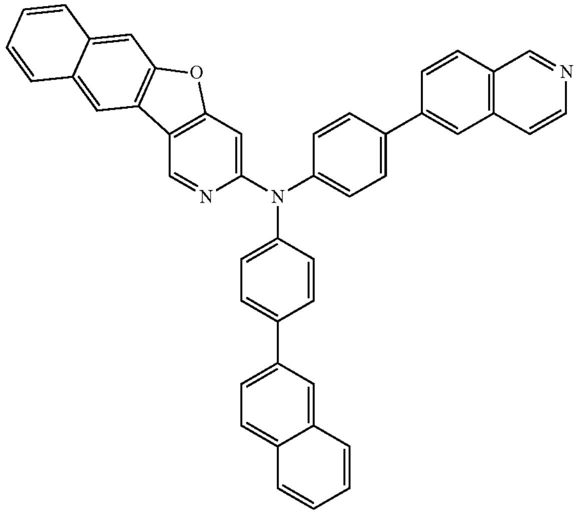
P015
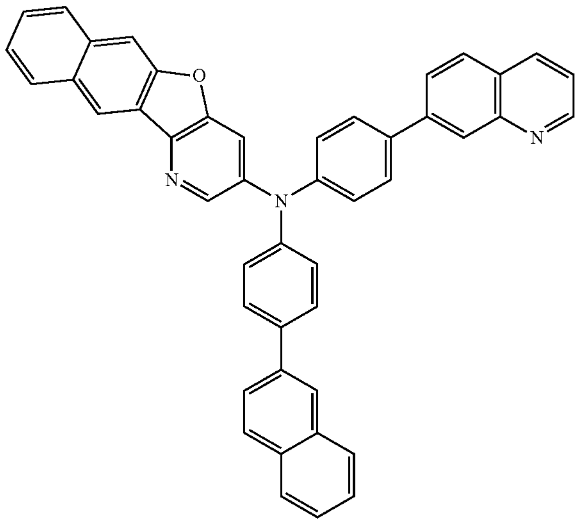
-continued
P016
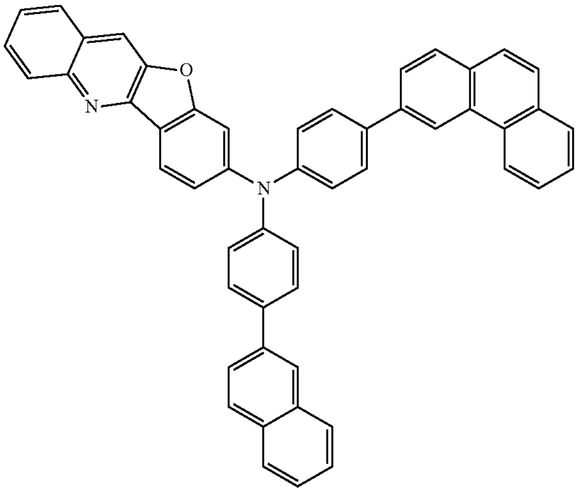
P017
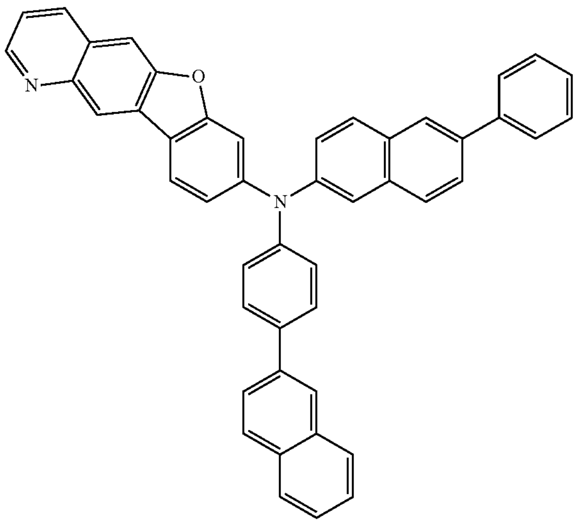
P018
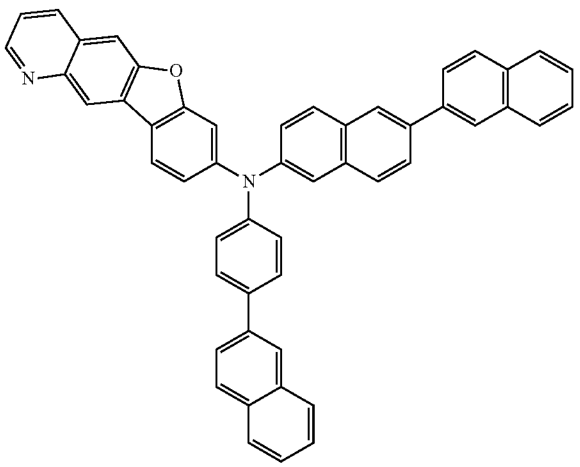

-continued
P019
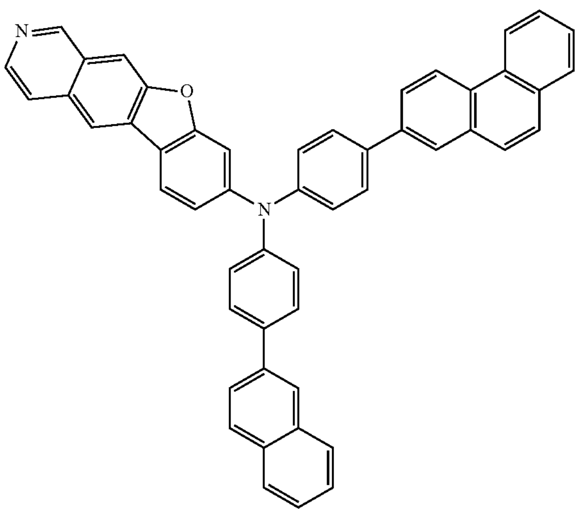
P020
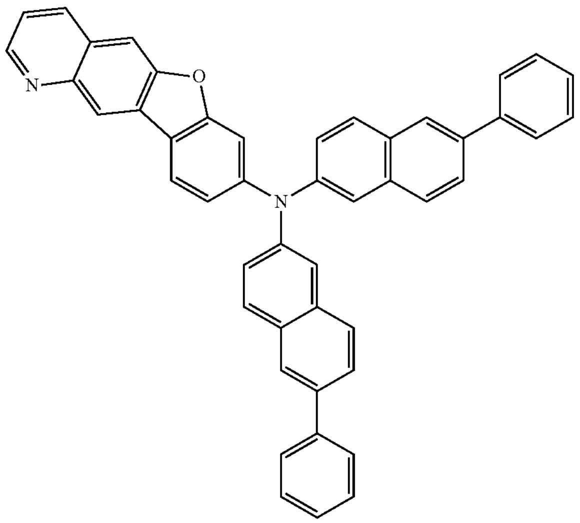
P021
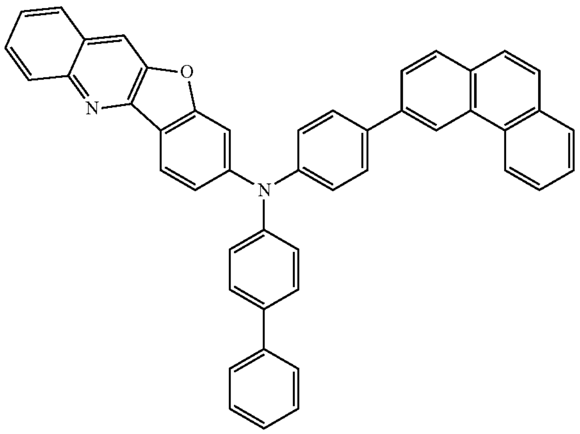
-continued
P022
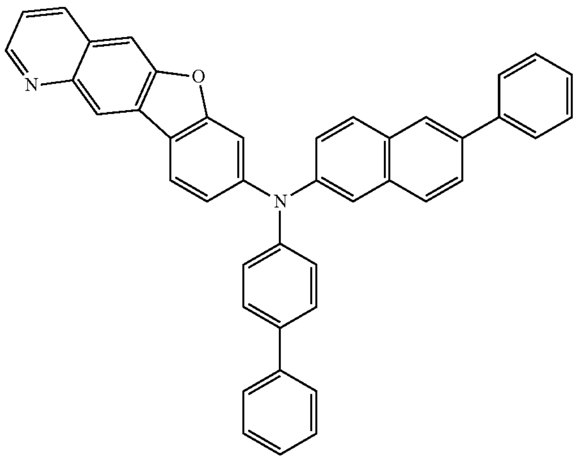
P023
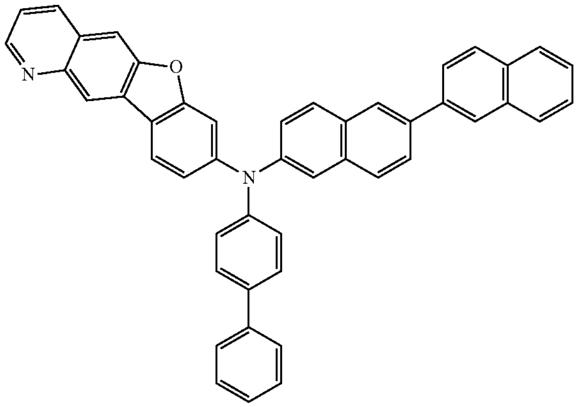
P024
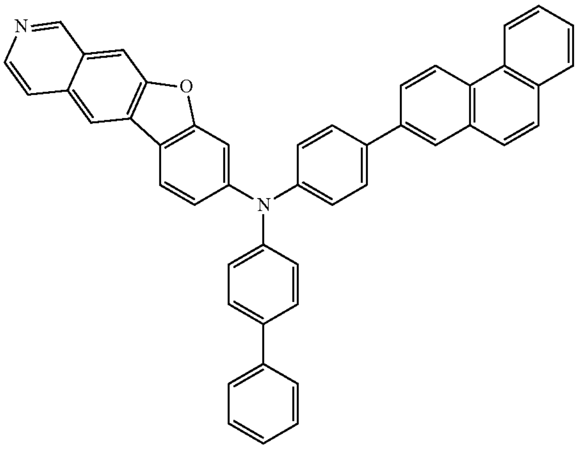

-continued
P025
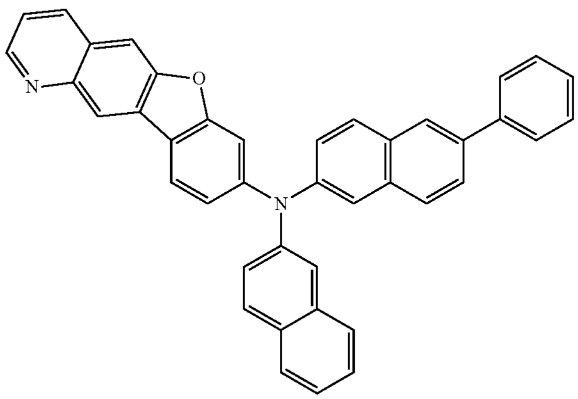
P026
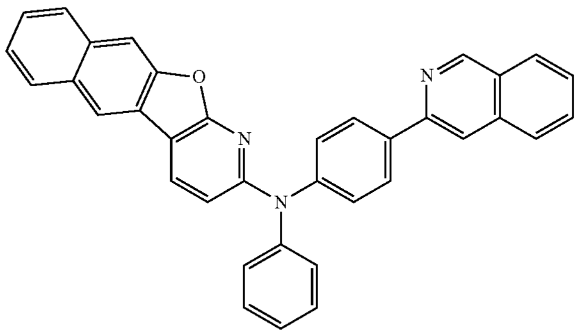
P027
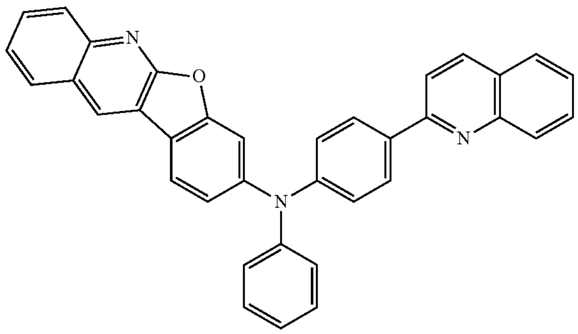
P028
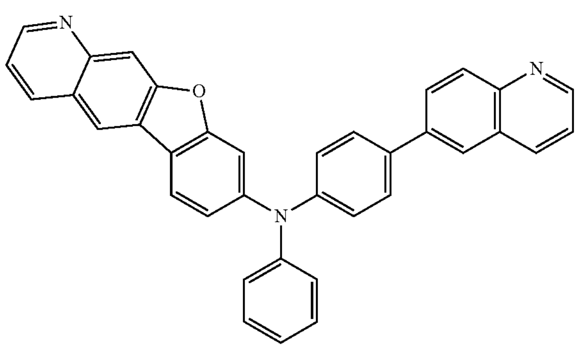
-continued
P029
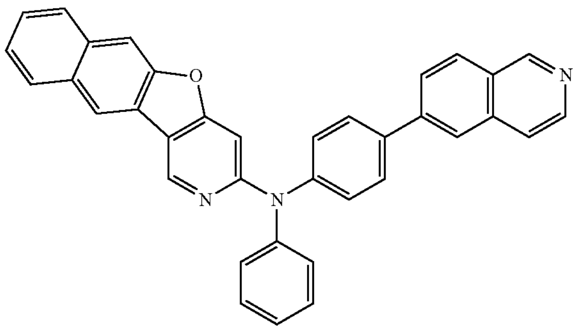
P030
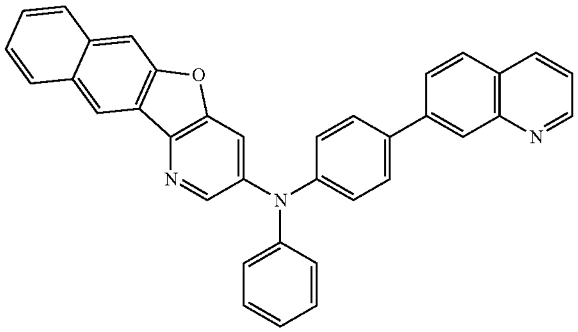
P031
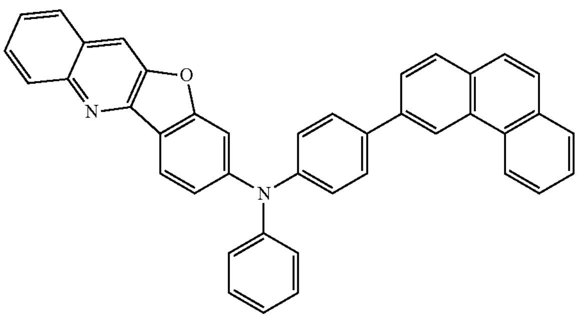
P032
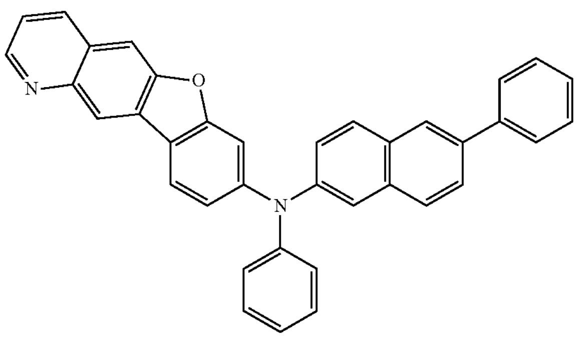

-continued
P033
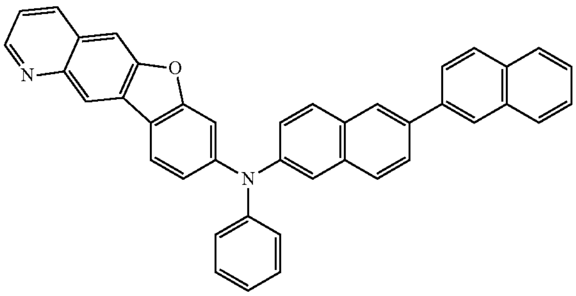
P034
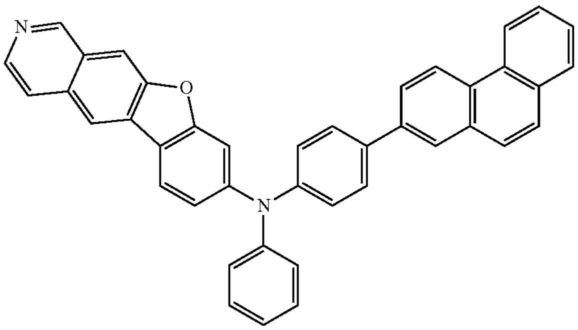
P035
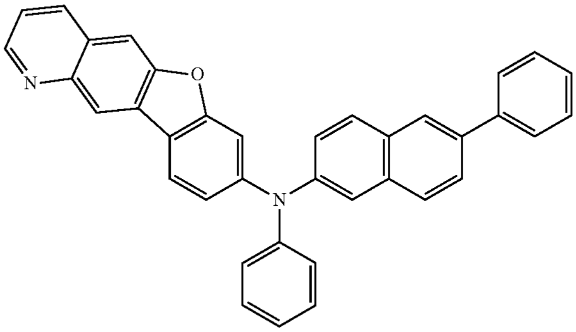
P036
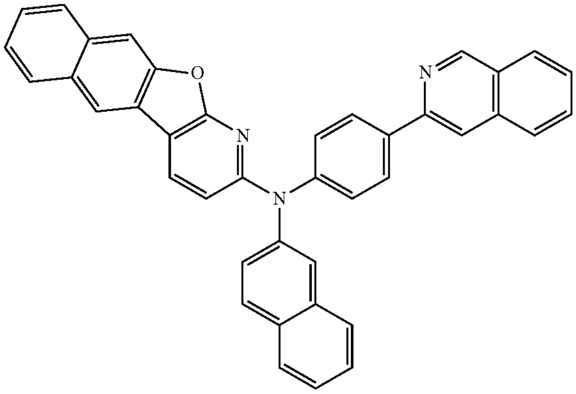
-continued
P037
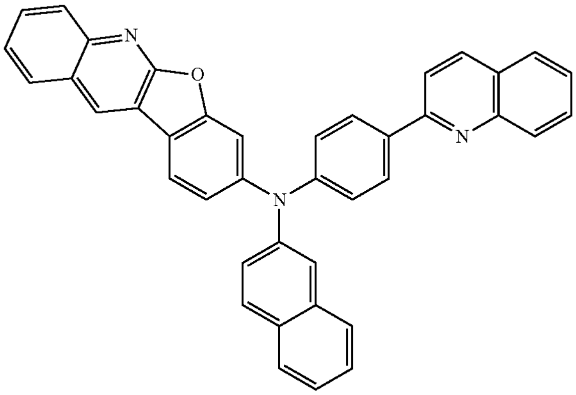
P038
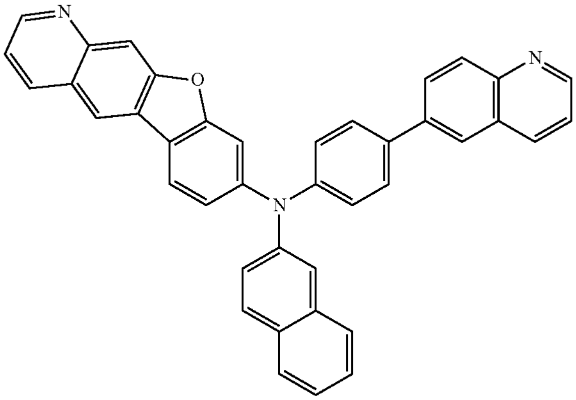
P039
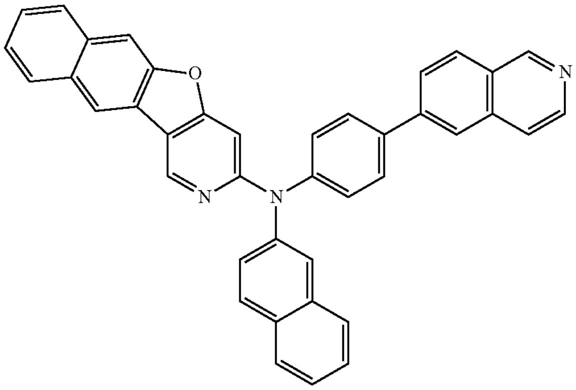

-continued
P040
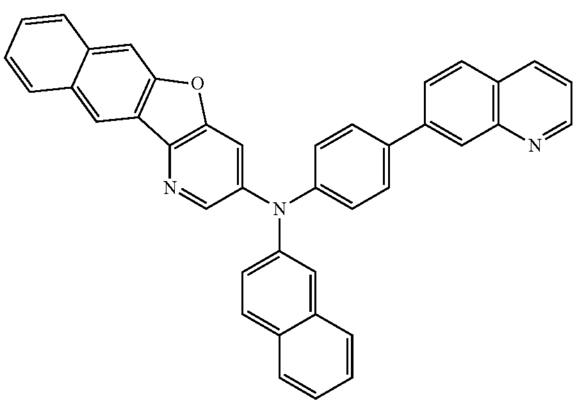
P045
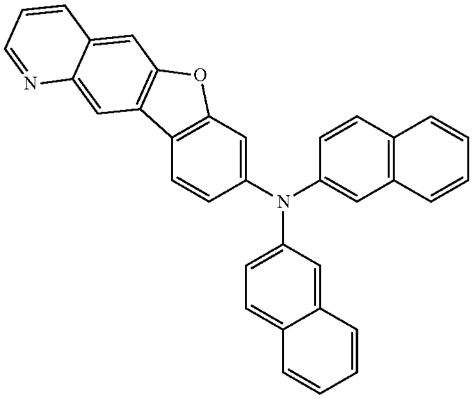
P046
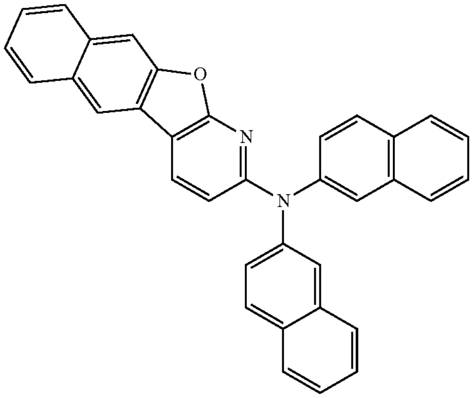
P047
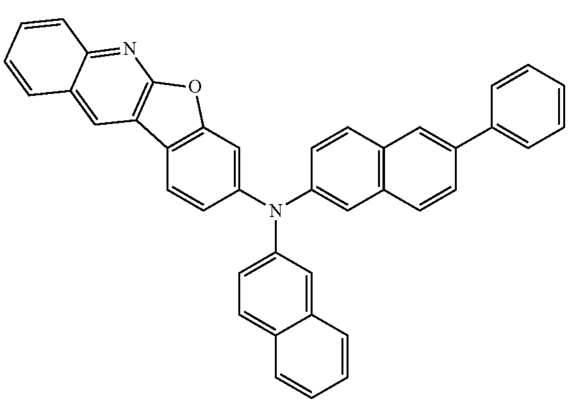
-continued
P048
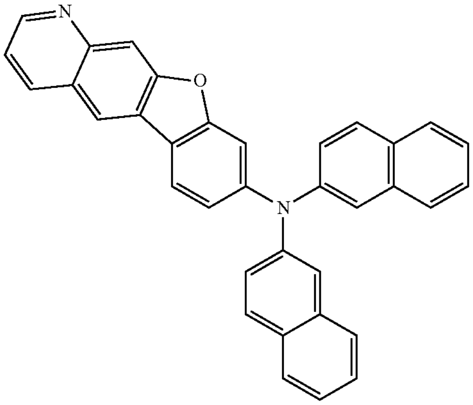
P049
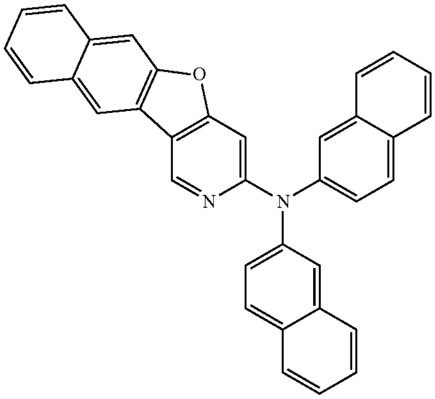
P050
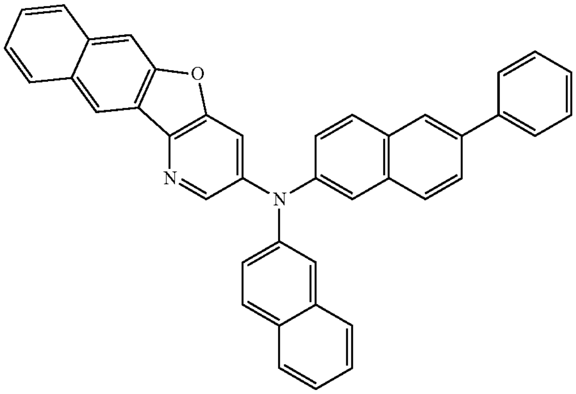
P051
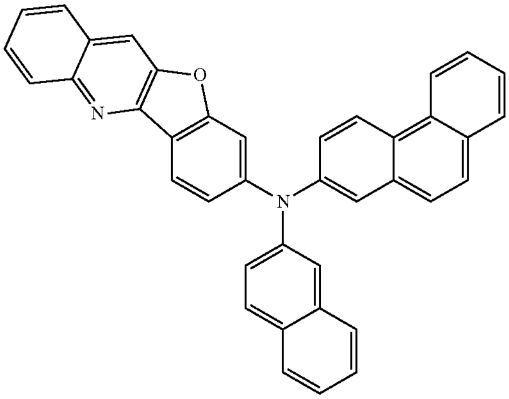

-continued
P052
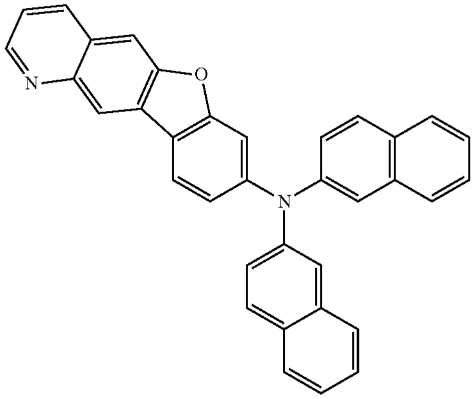
P053
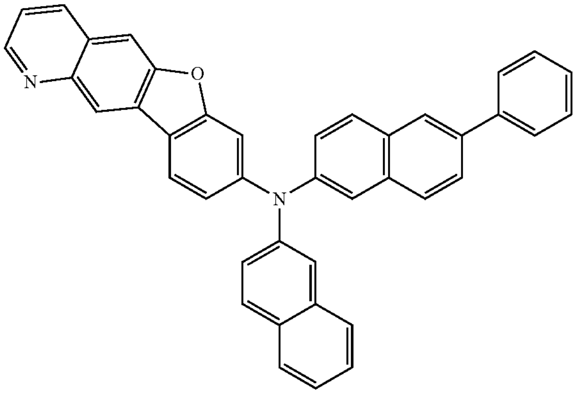
P054
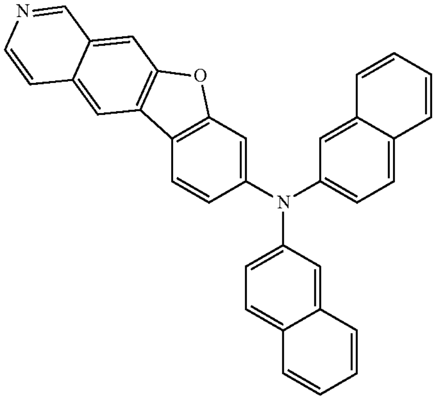
P055
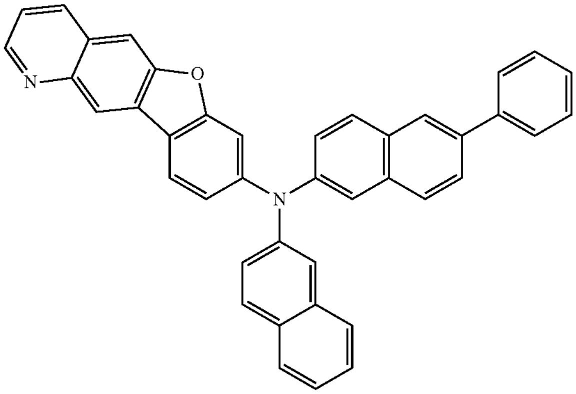
-continued
P056
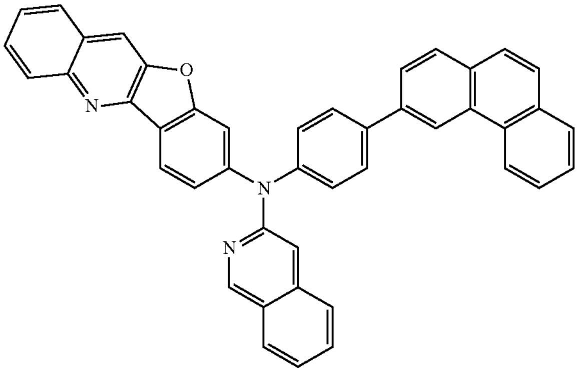
P057
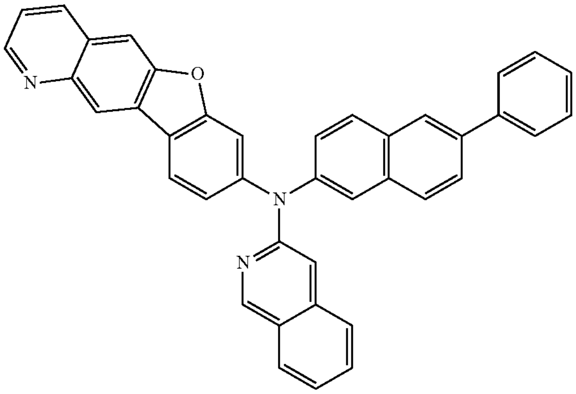
P058
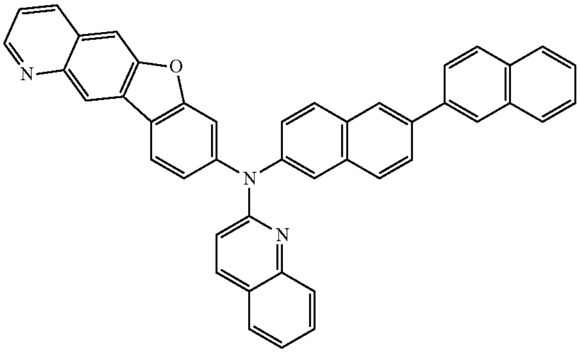
P059
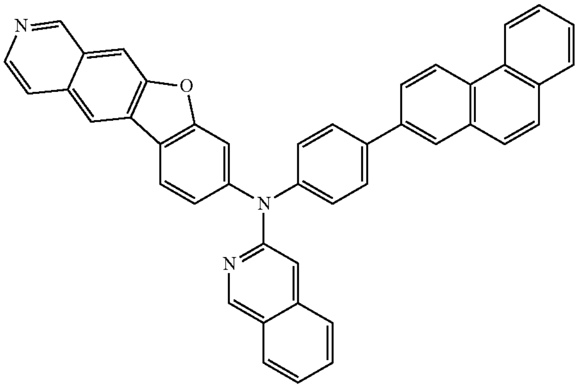

-continued
P060
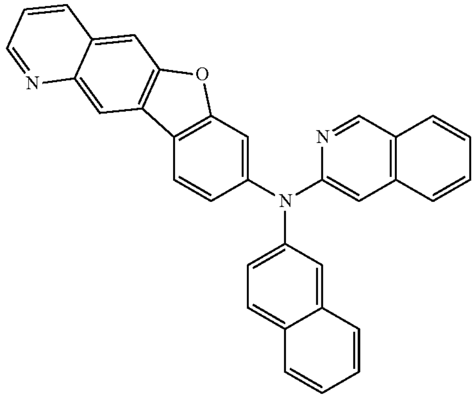
P061
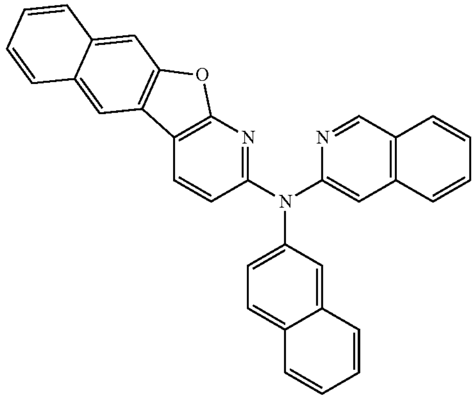
P062
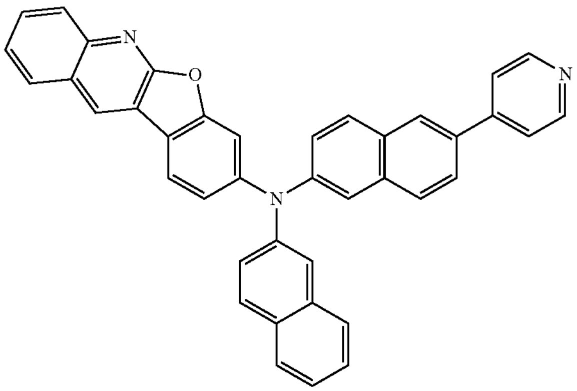
P063
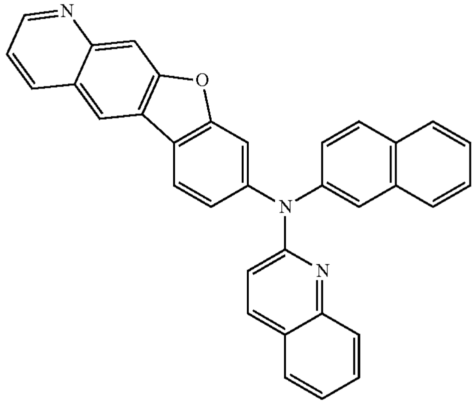
-continued
P064
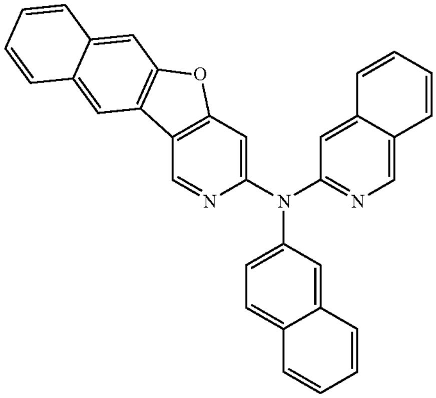
P065
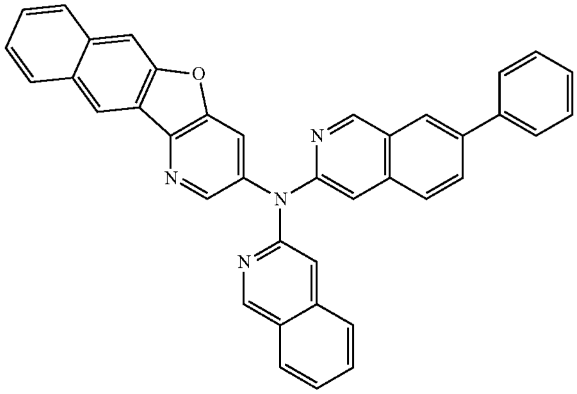
P066
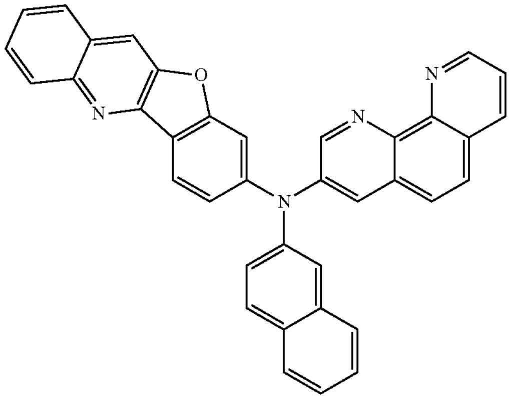
P067
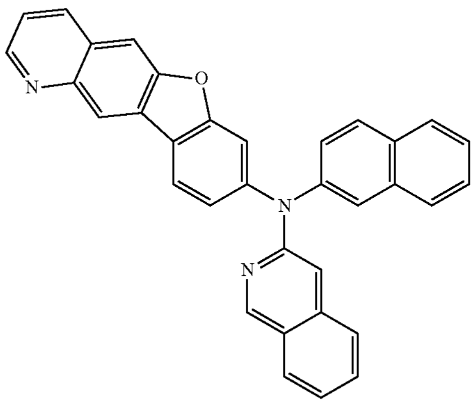

-continued
P068
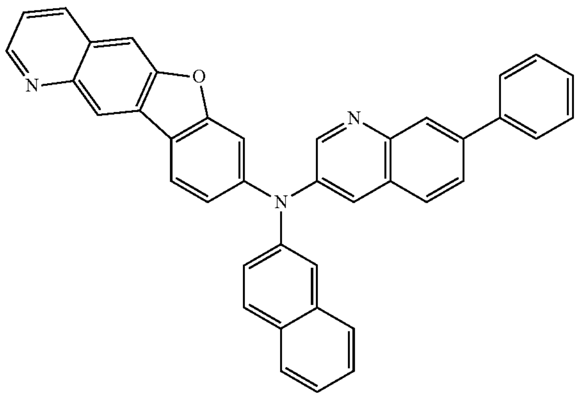
P069
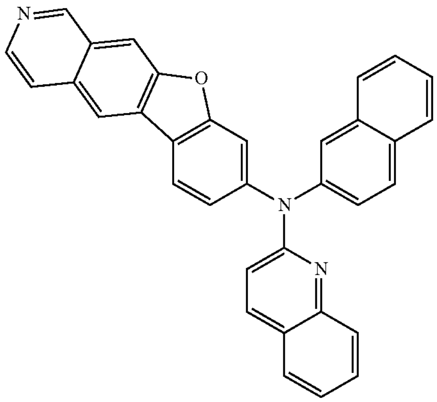
P070
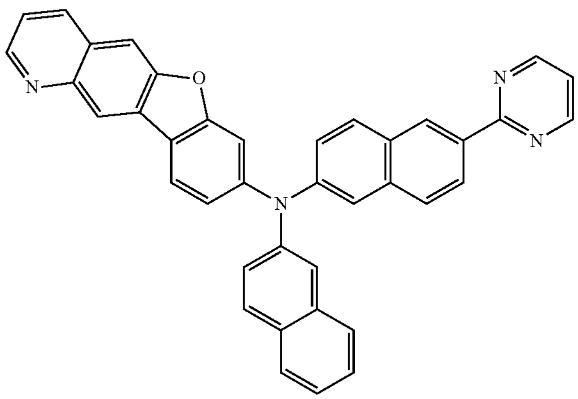
-continued
P071
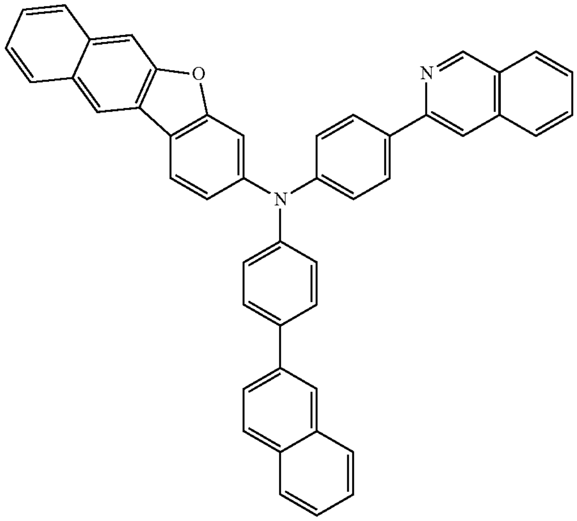
P072
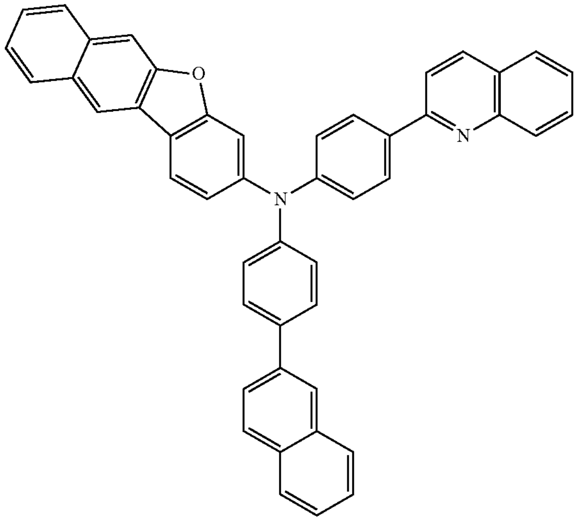
P073
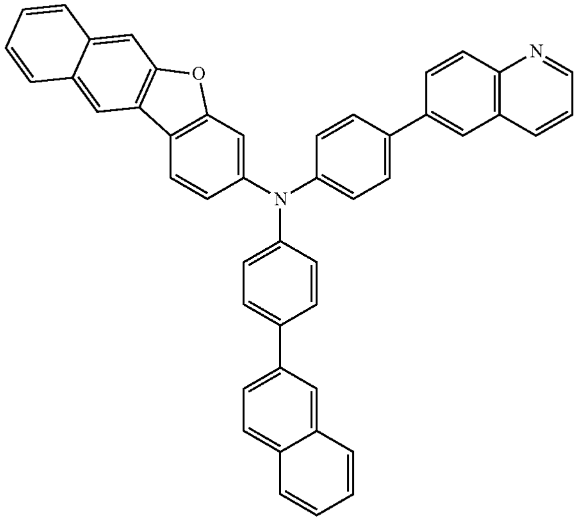

-continued
P074
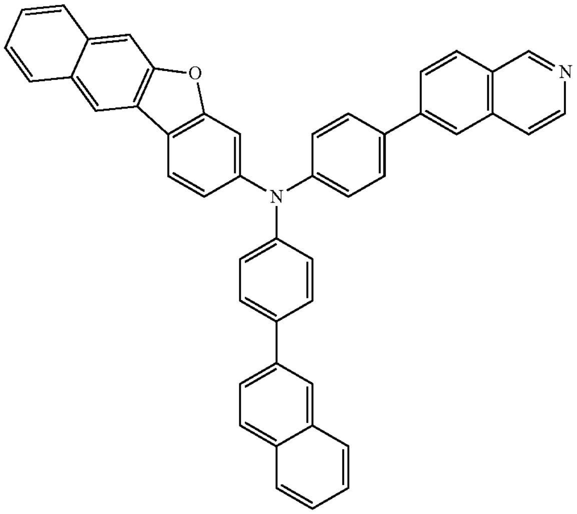
P075
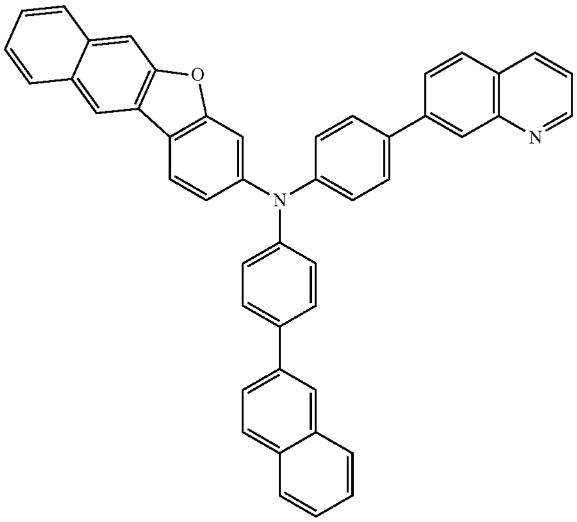
P076
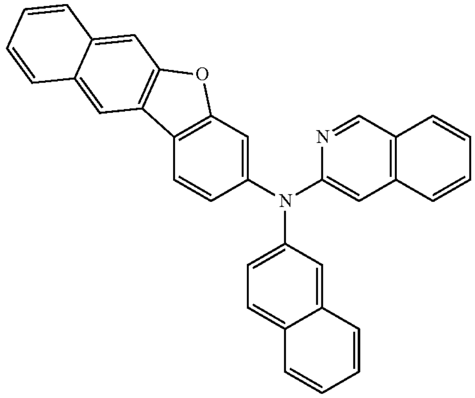
-continued
P077
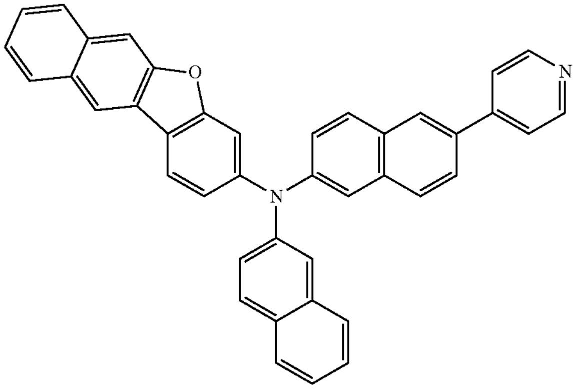
P078
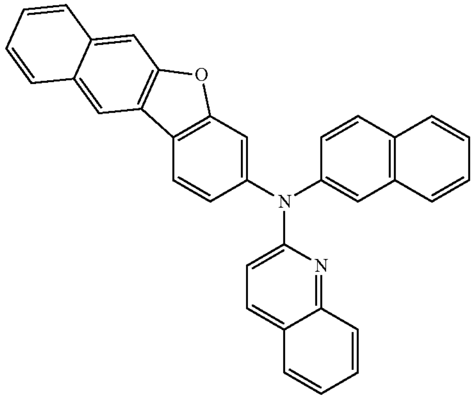
P079
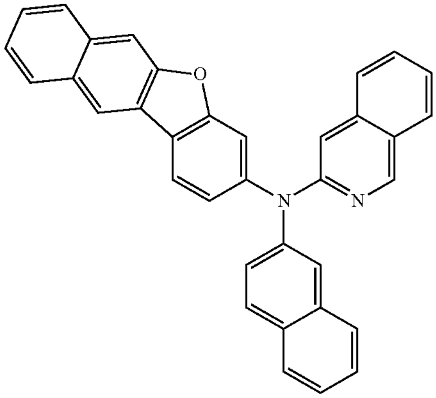
P080
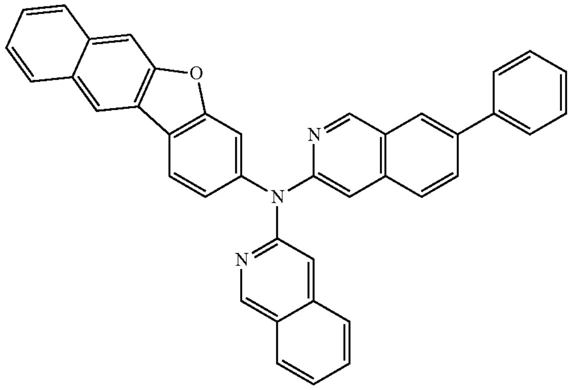

-continued
P081
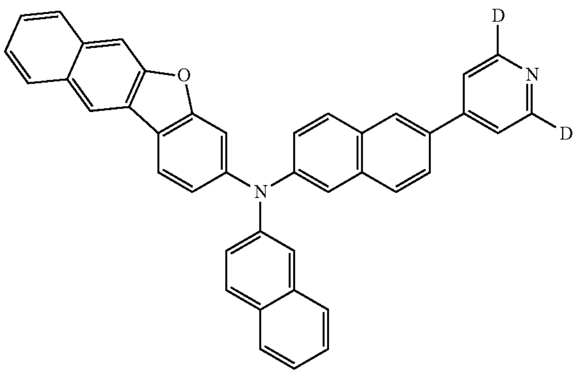
P082
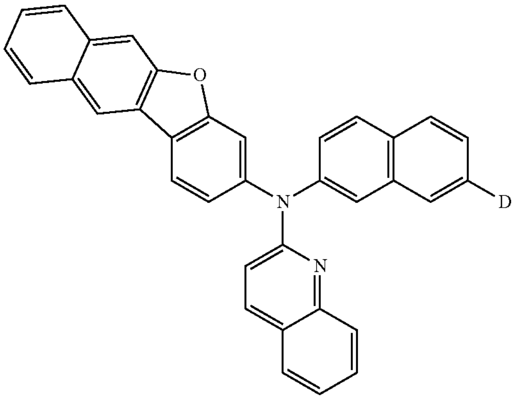
P083
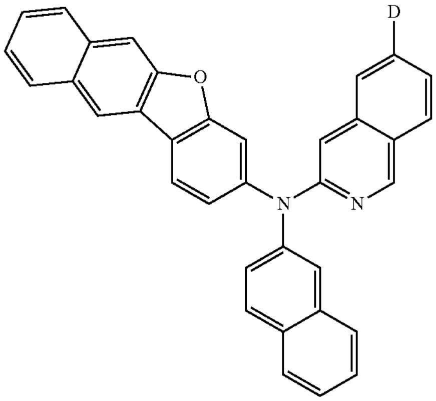
P084
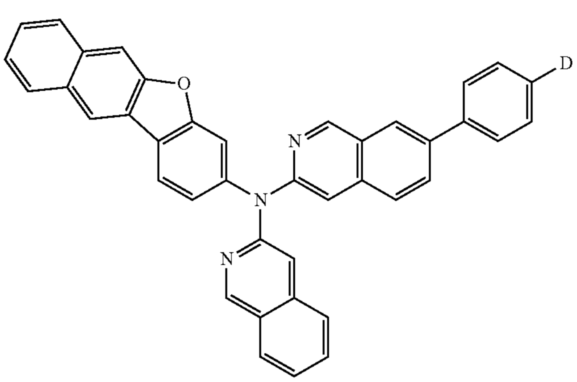
-continued
P085
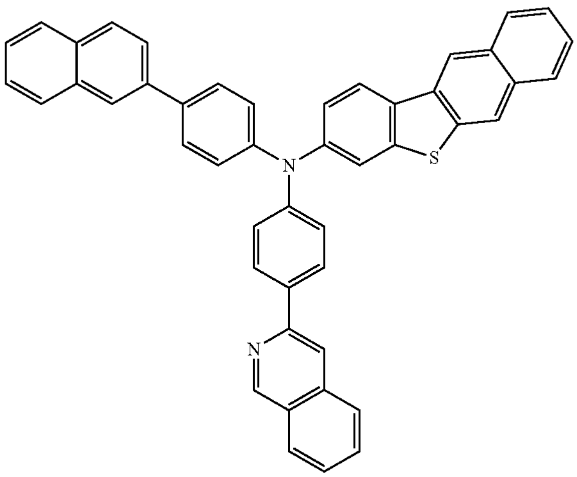
P086
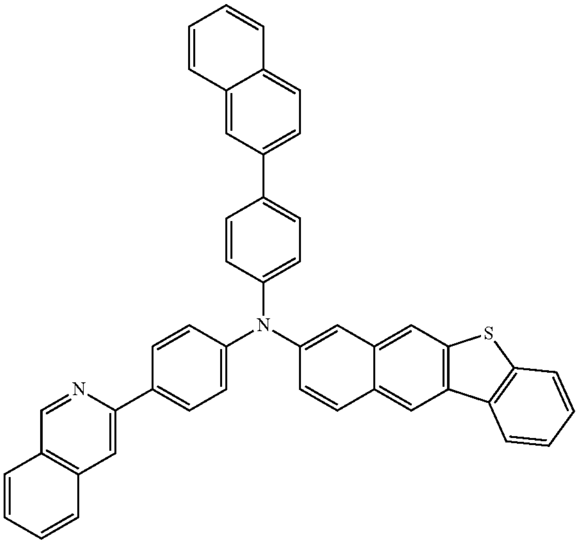
P087
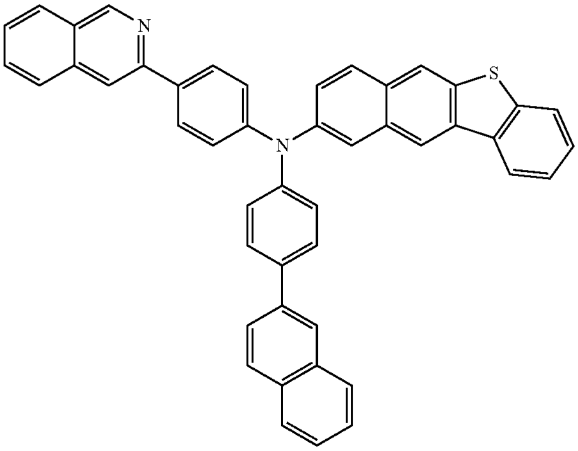

-continued
P088
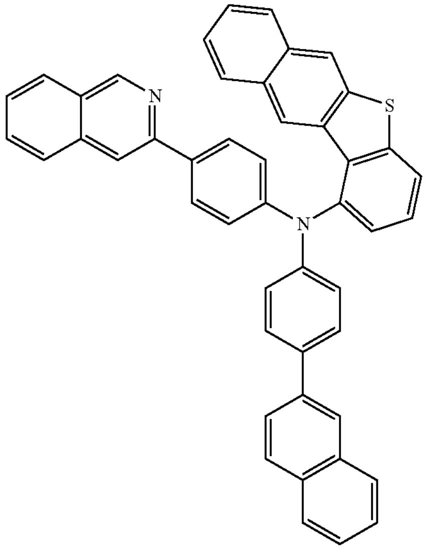
P089
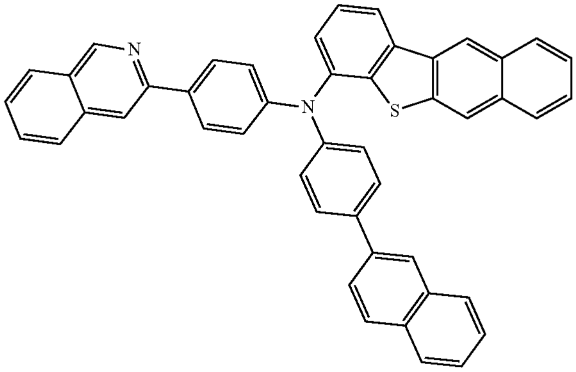
P090
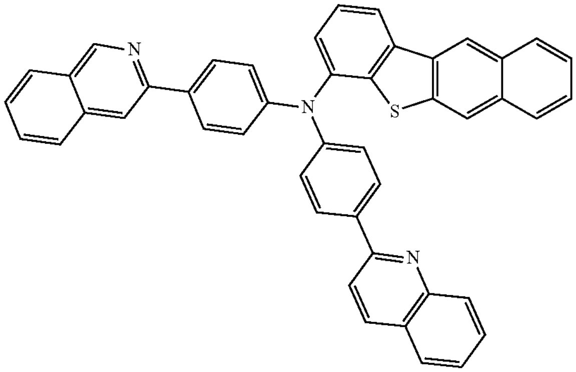
-continued
P091
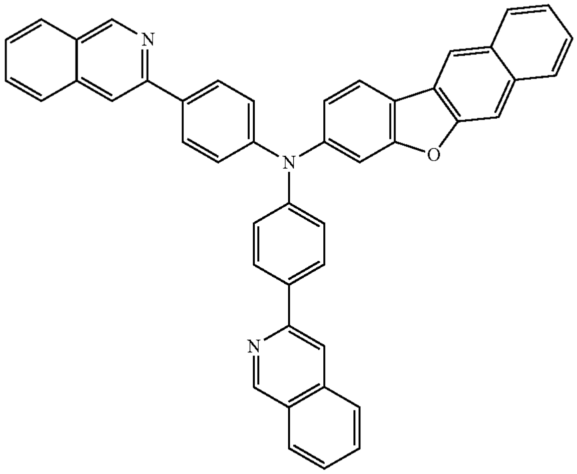
P092
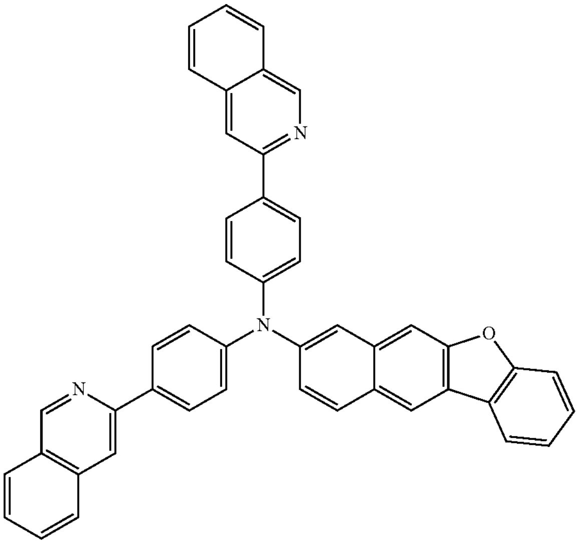
P093
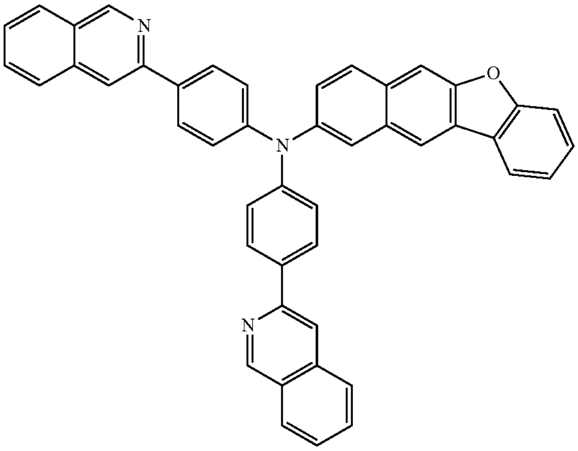

-continued
P094
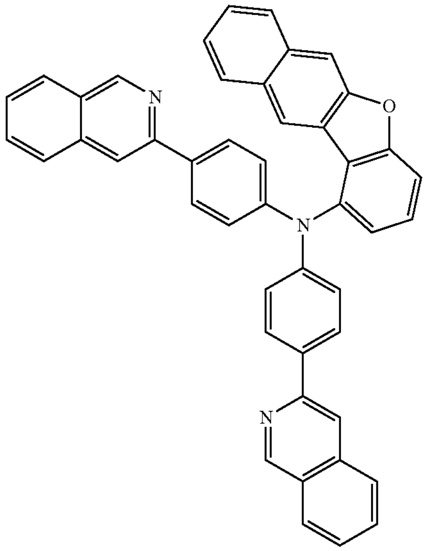
P095
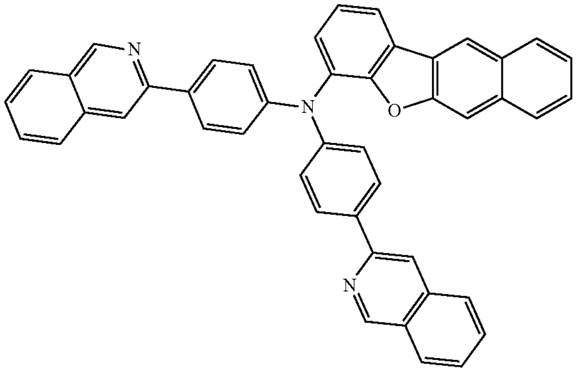
P096
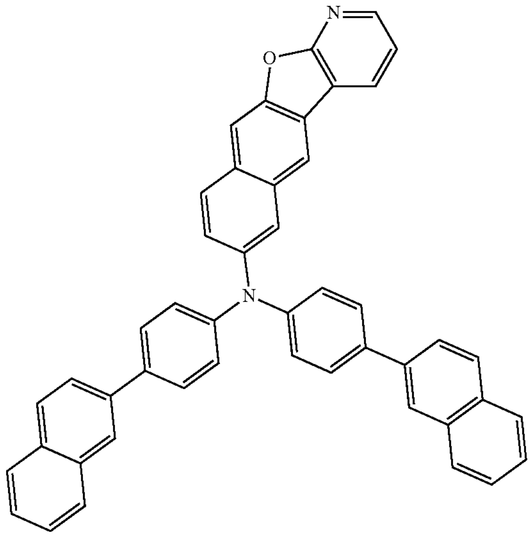
-continued
P097
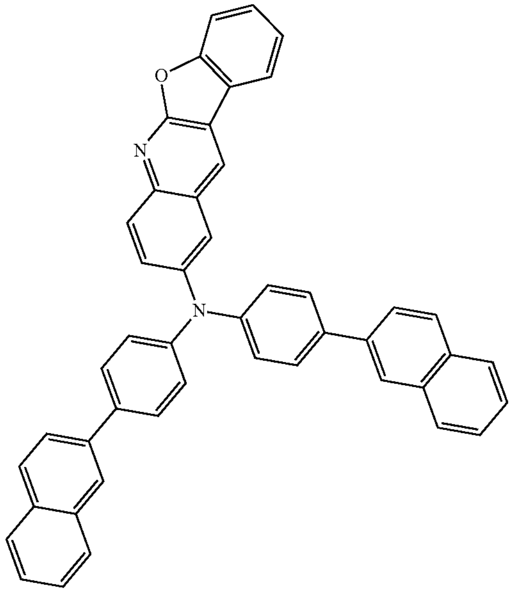
P098
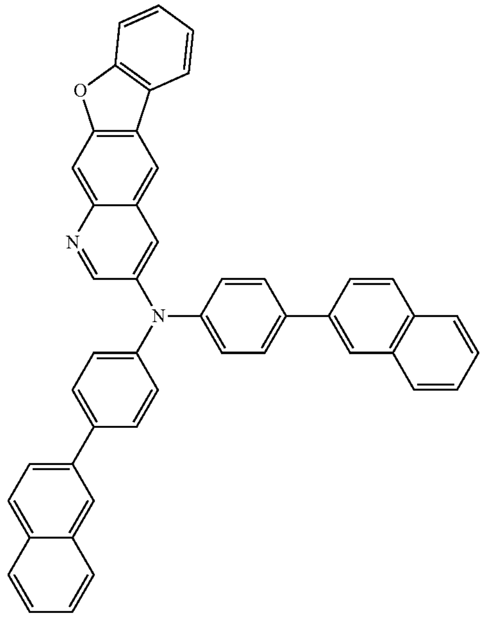

-continued
P099
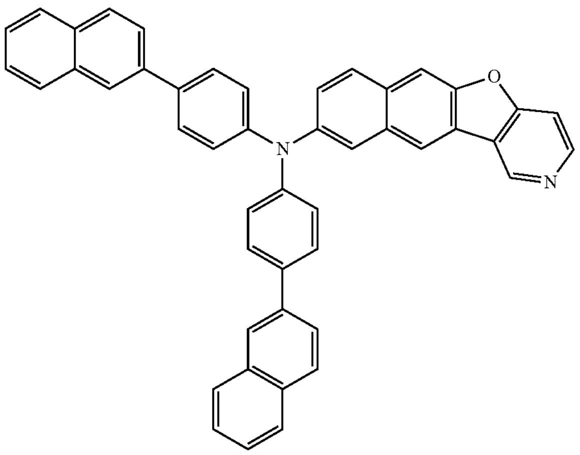
P100
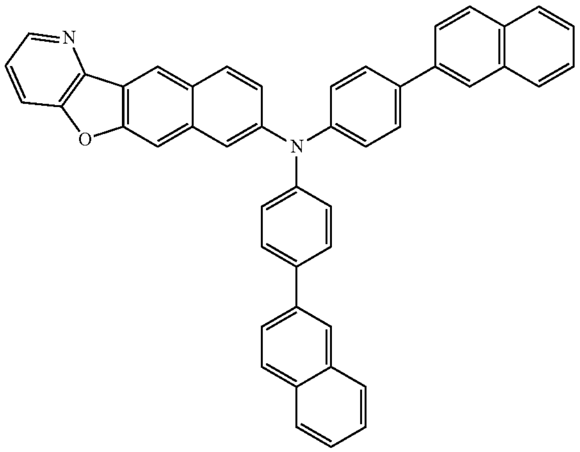
P101
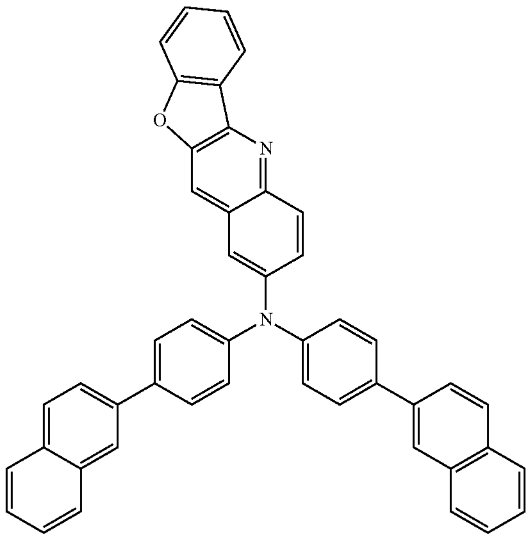
-continued
P102
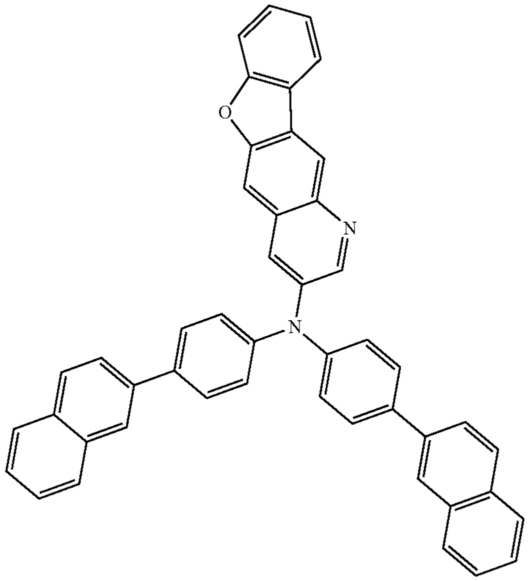
P103
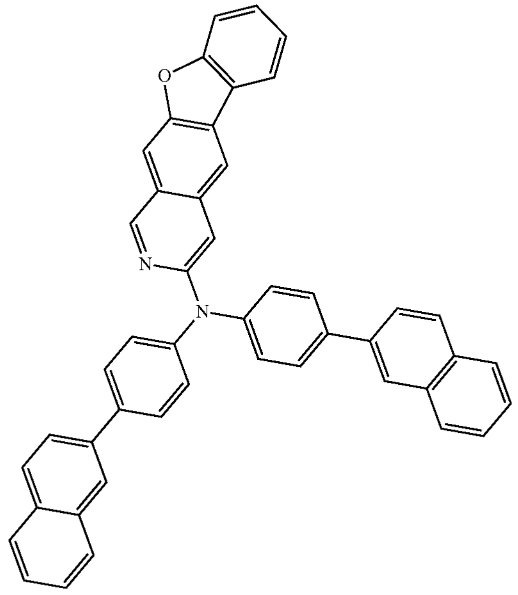

P104
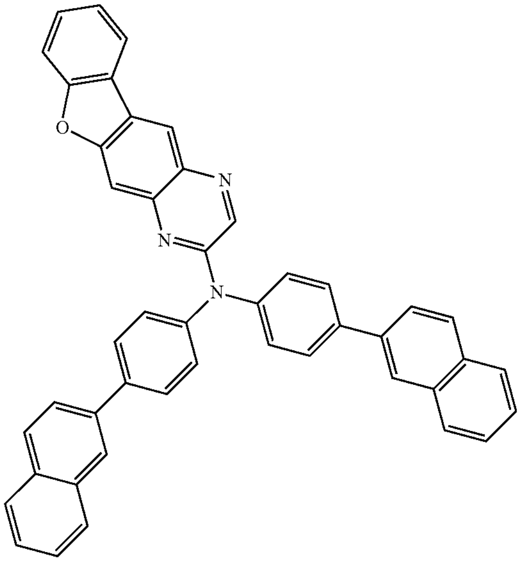
P105
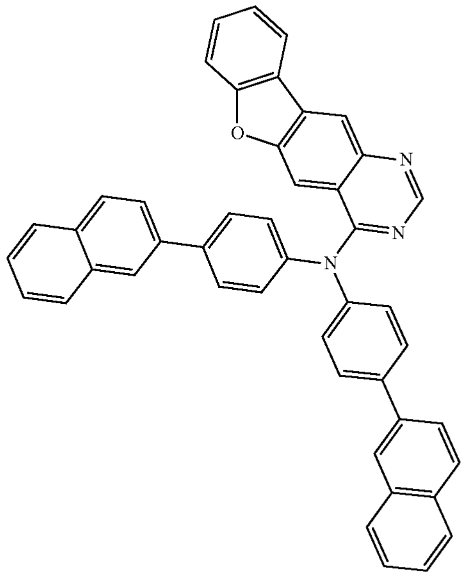
P106
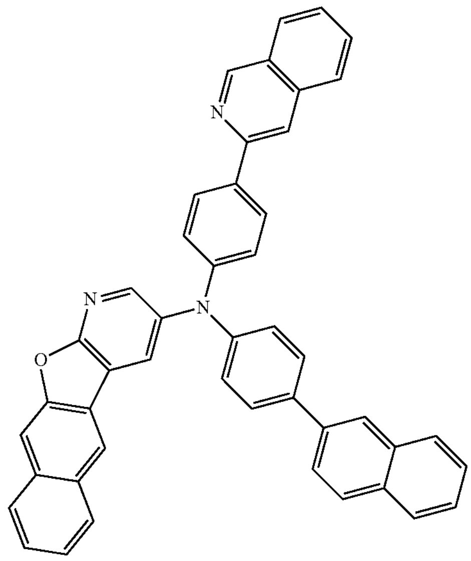
P107
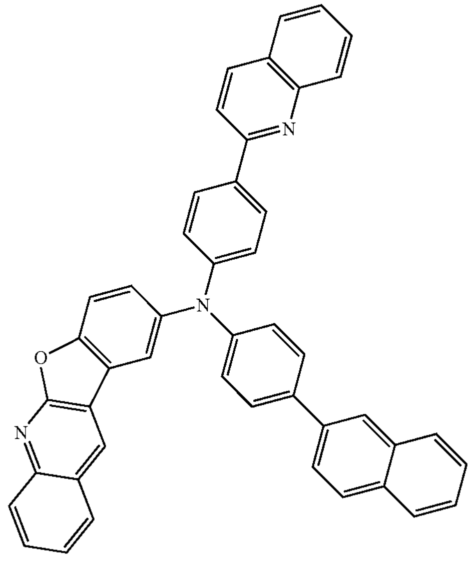

-continued
P108
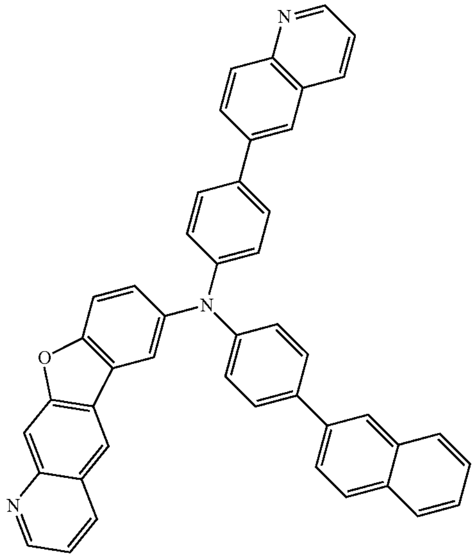
P109
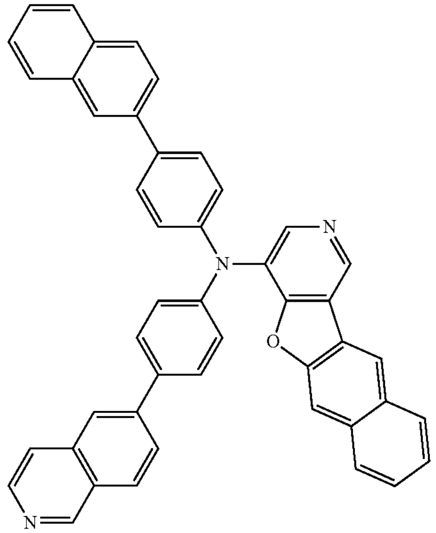
P110
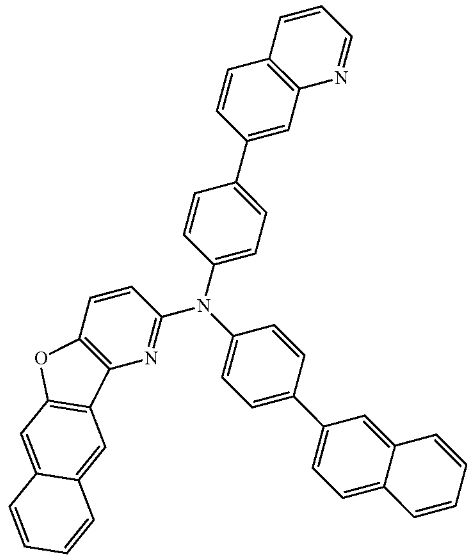
-continued
P111
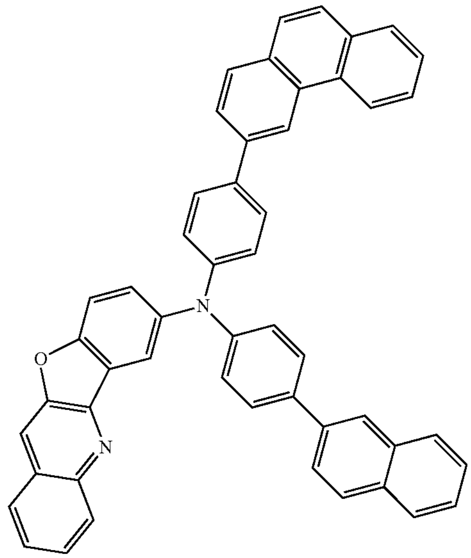
P112
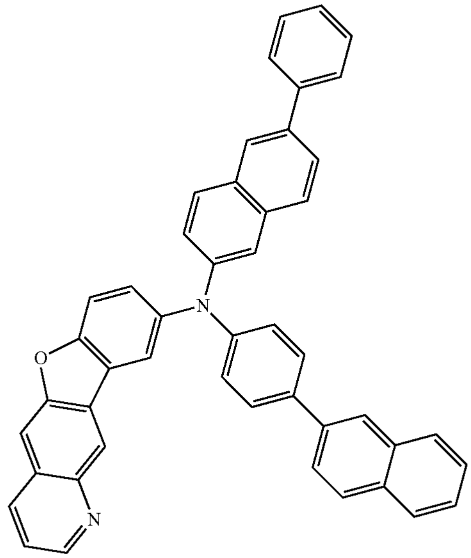

-continued
P113
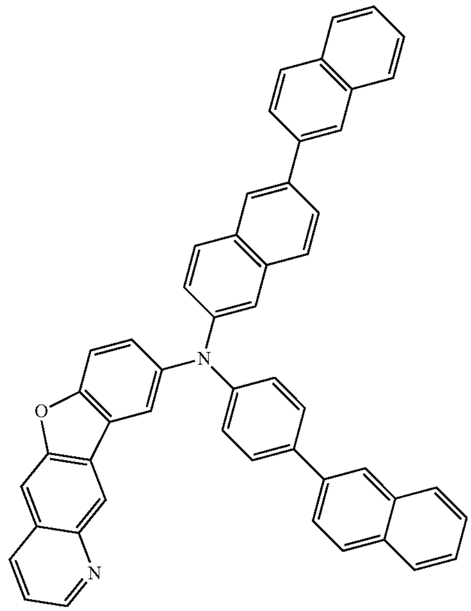
P114
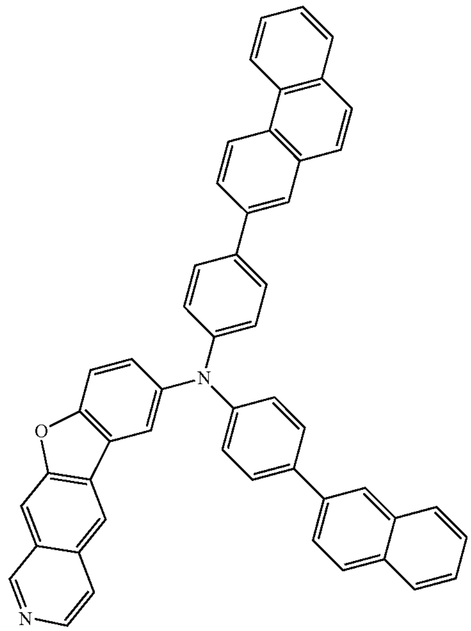
-continued
P115
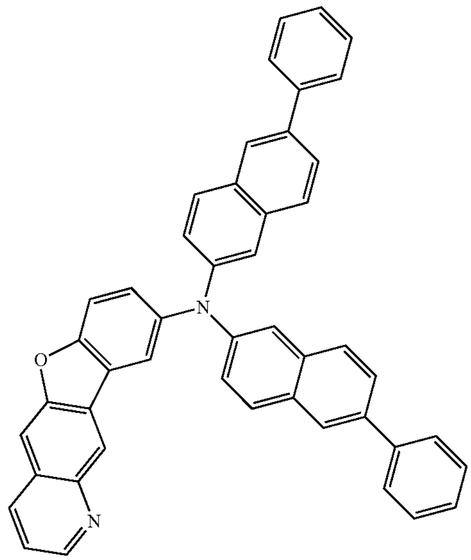
P116
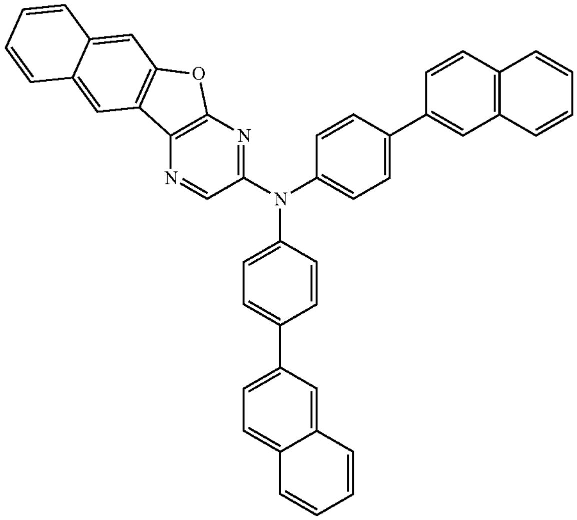
P117
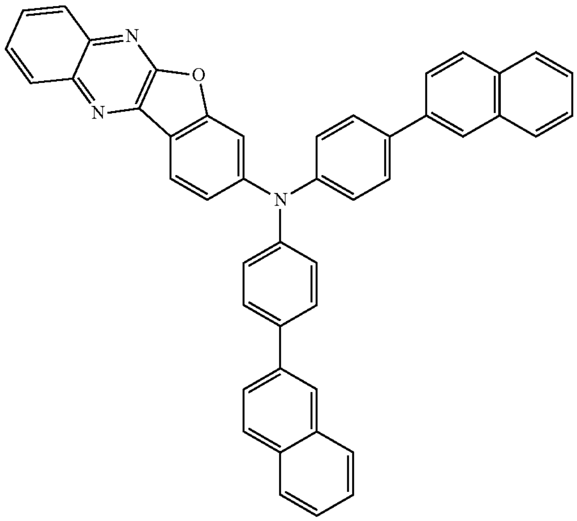

P118
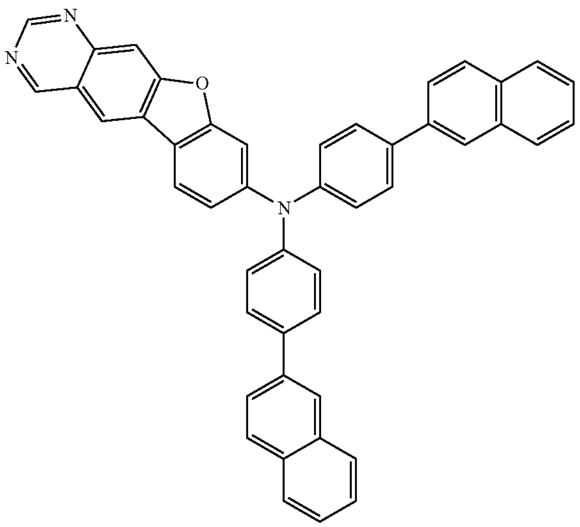
P119
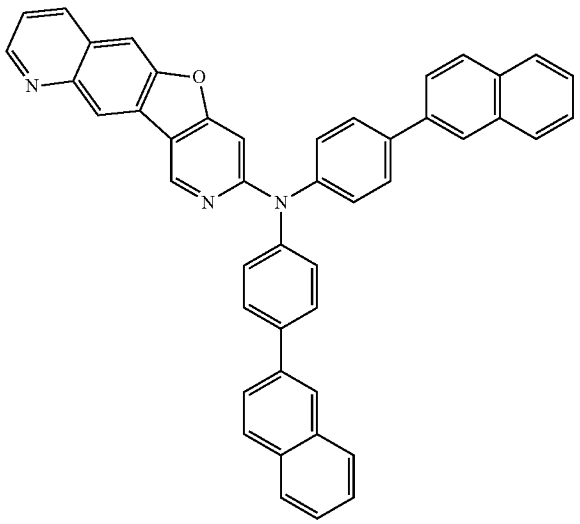
P120
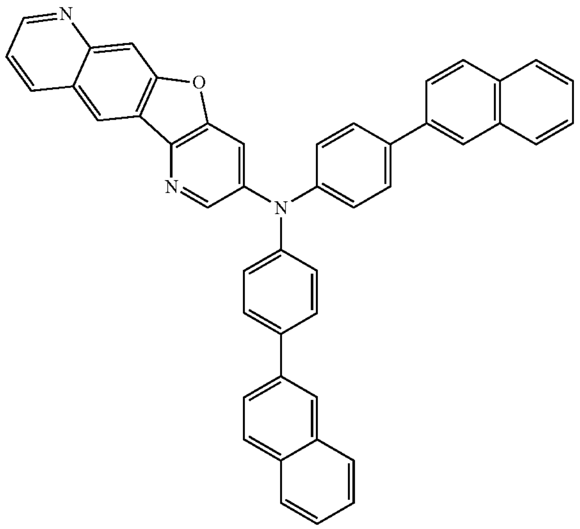
P121
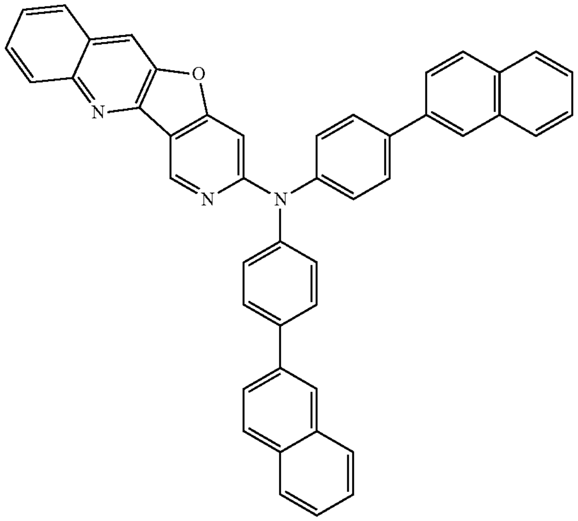
P122
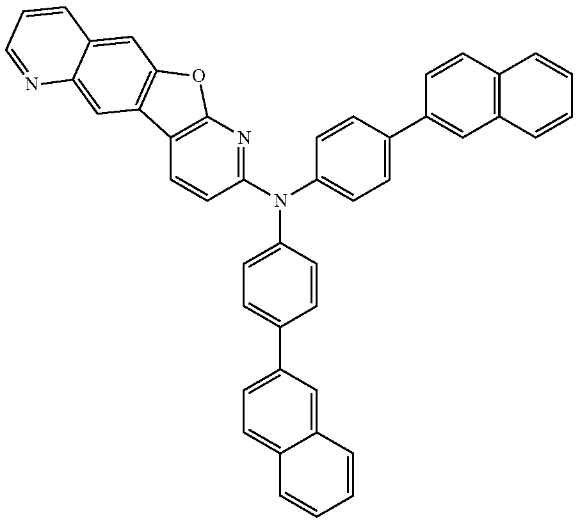
P123
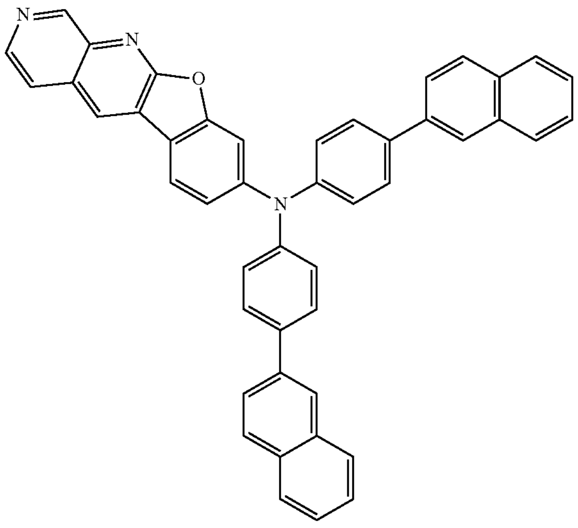

-continued
P124
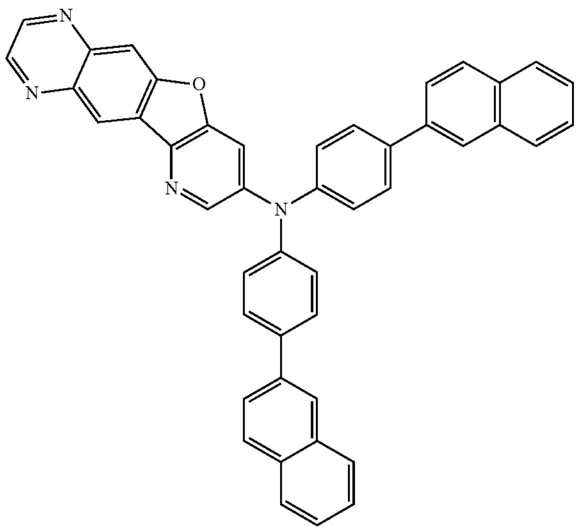
P125
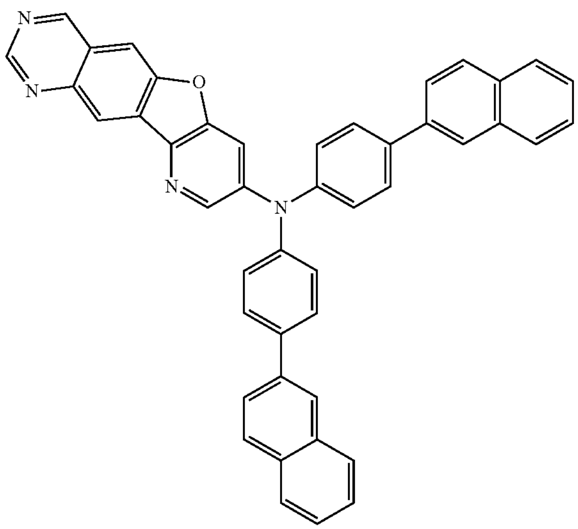
P126
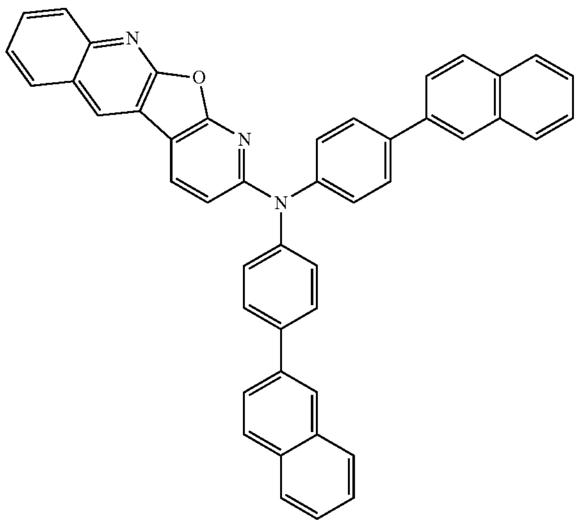
-continued
P127
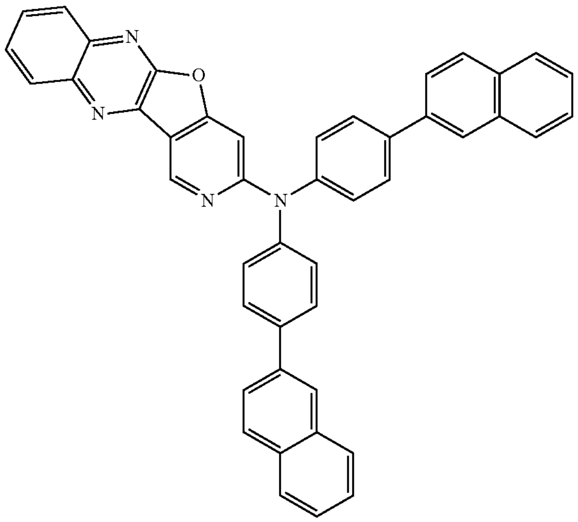
P128
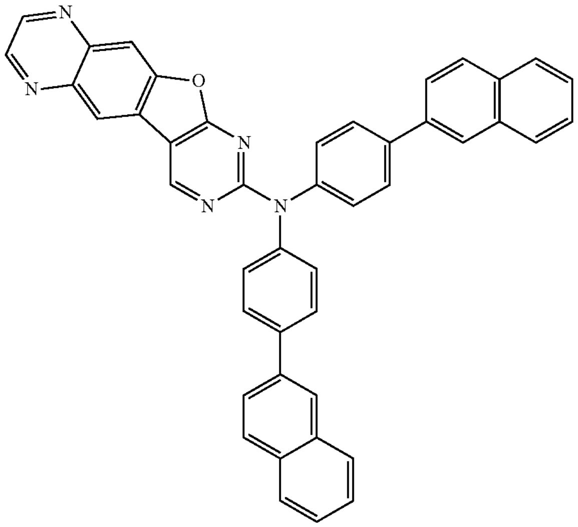
P129
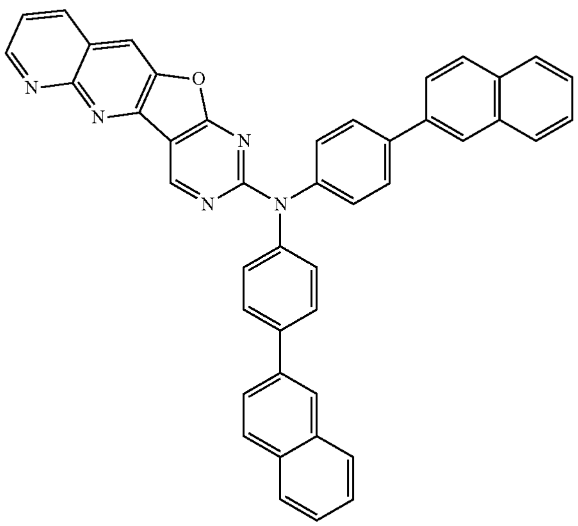

-continued
P130
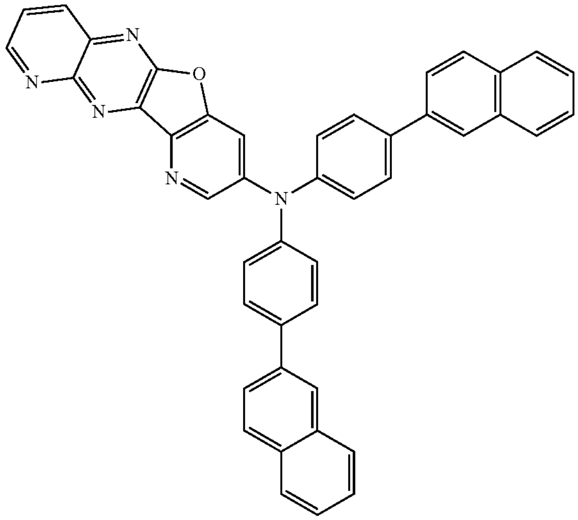
P131
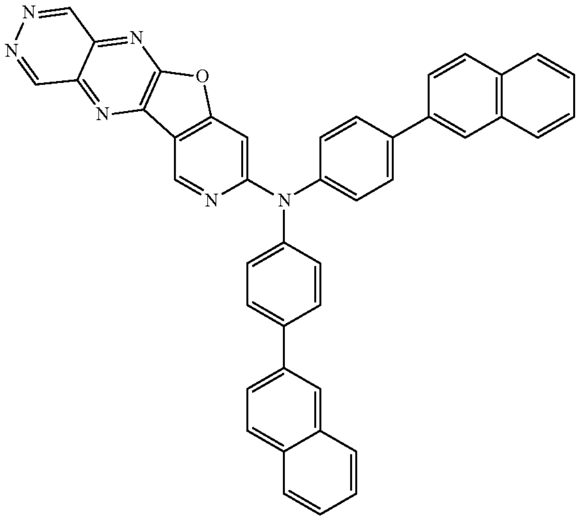
P132
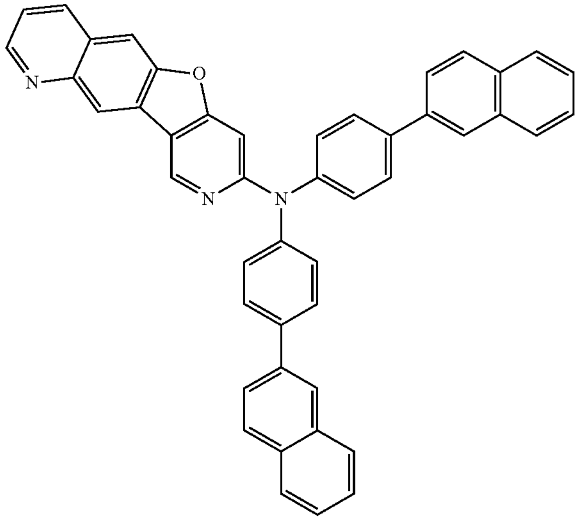
-continued
P133
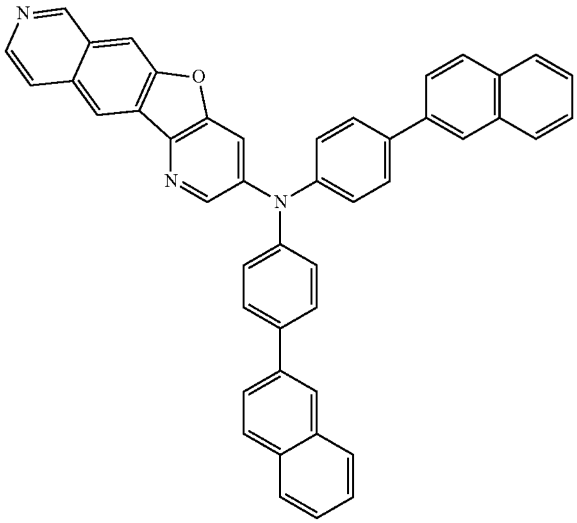
P134
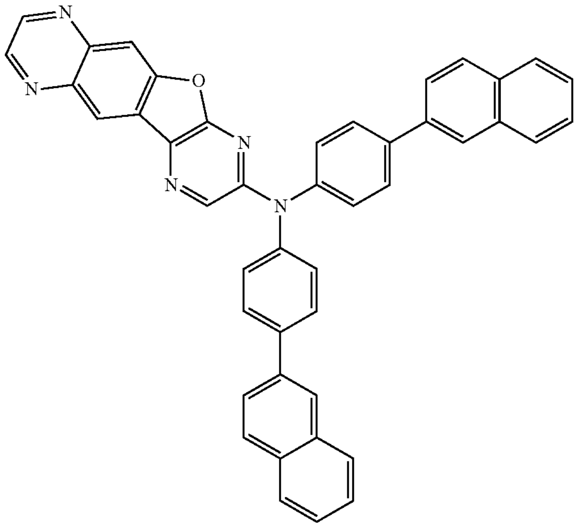
P135
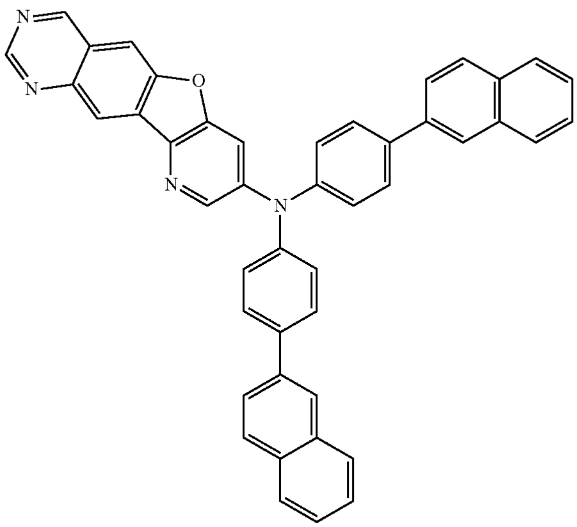

-continued
P136
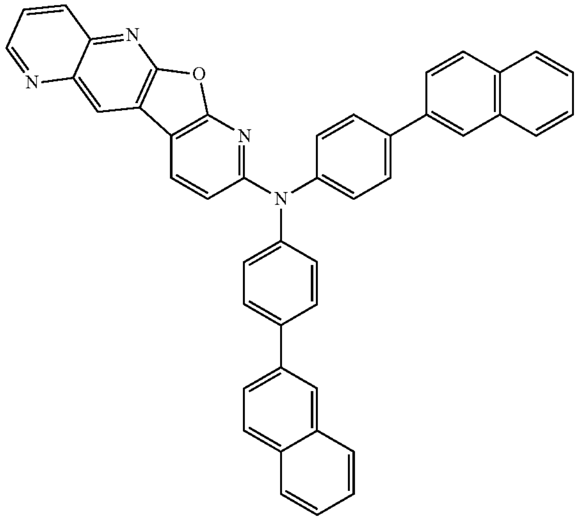
P137
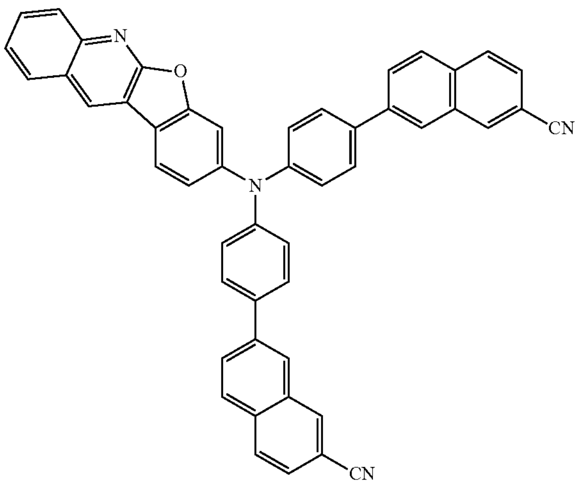
P138
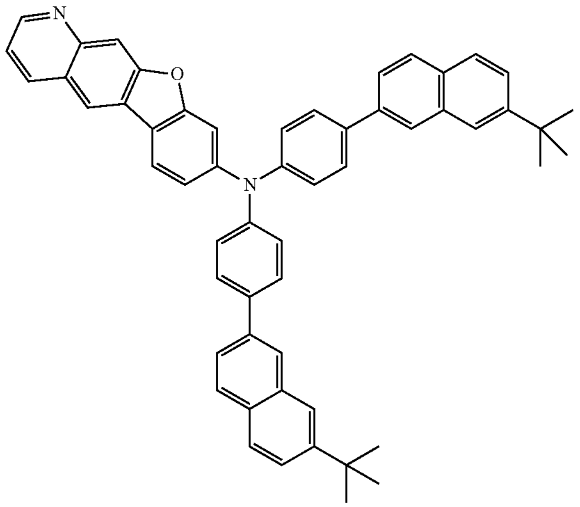
-continued
P139
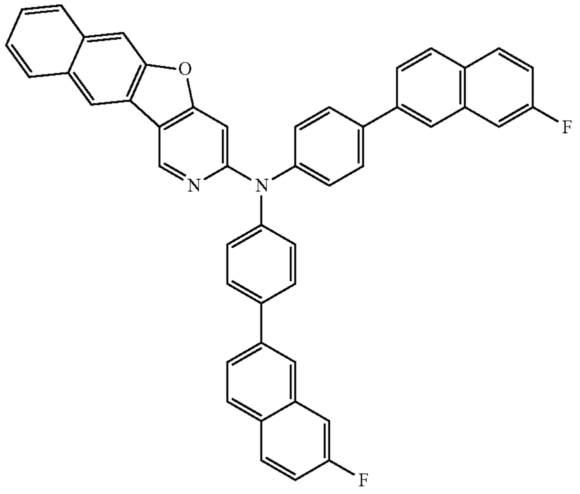
P140
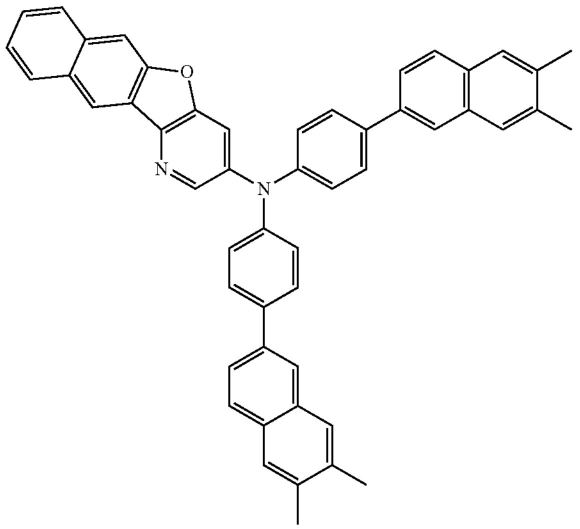
P141
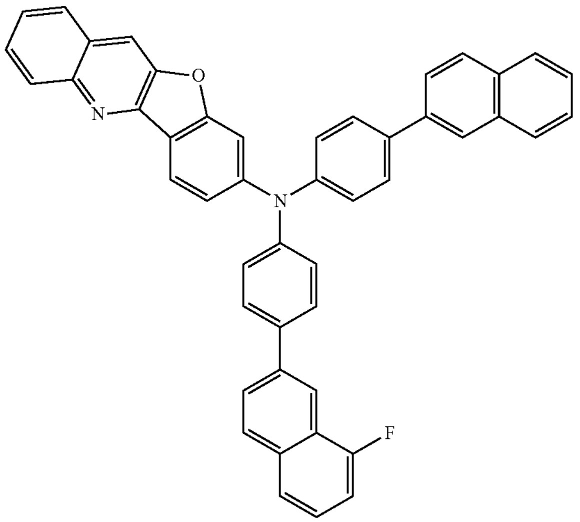

-continued
P142
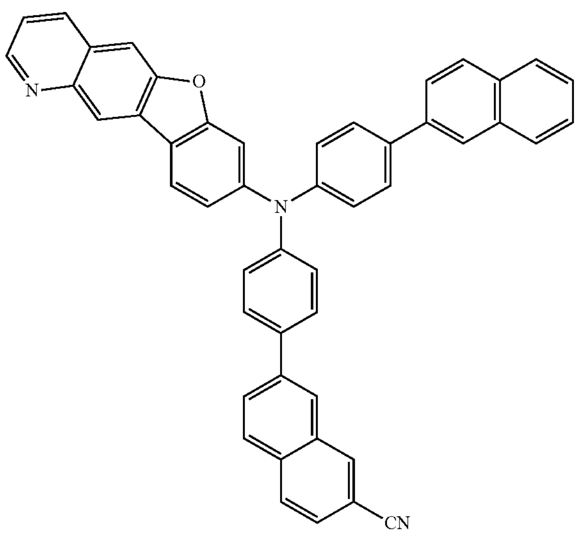
P143
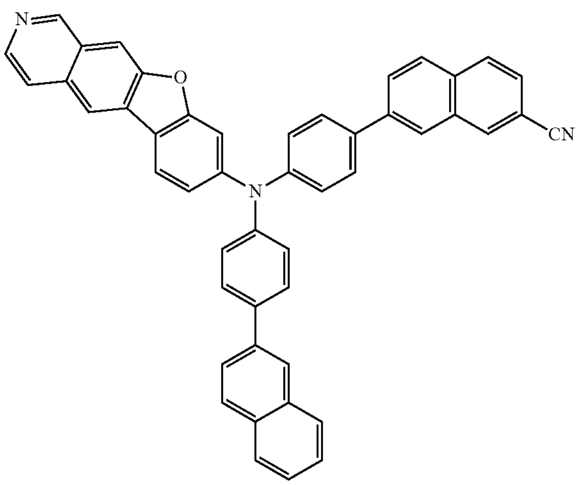
P144
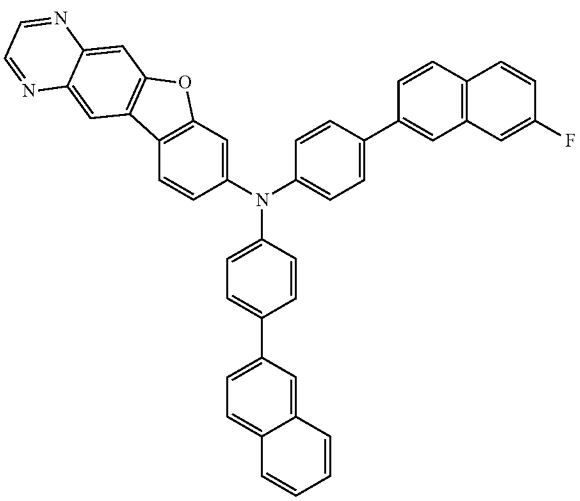
-continued
P145
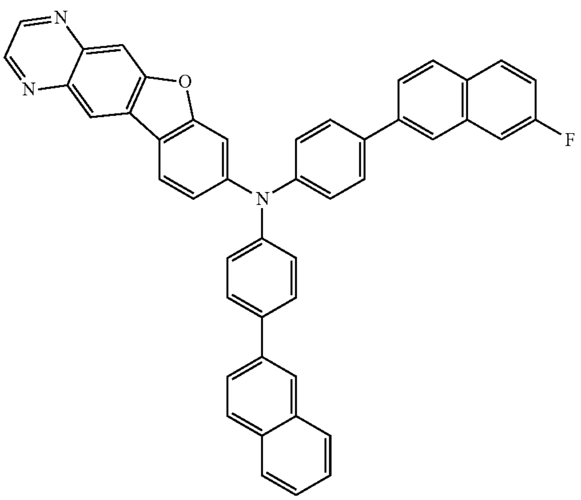
P146
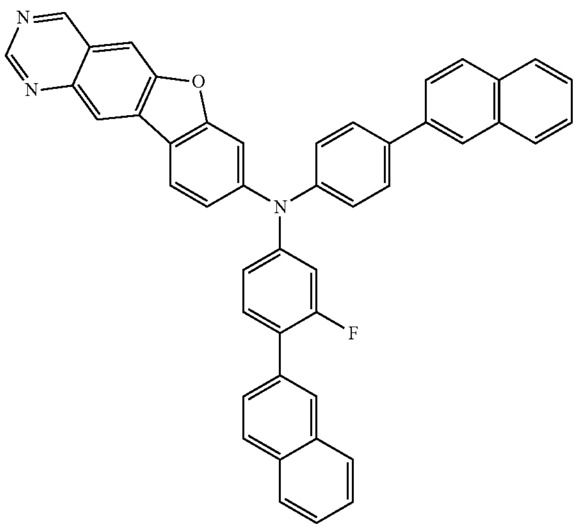
P147
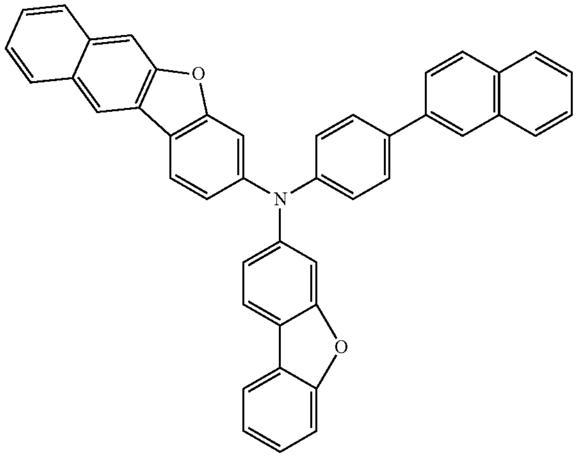

-continued
P148
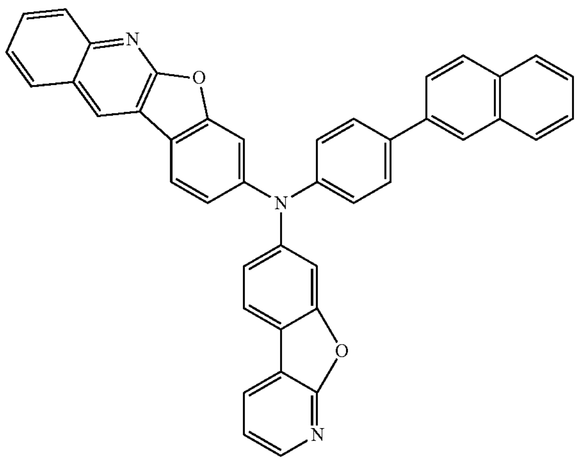
P149
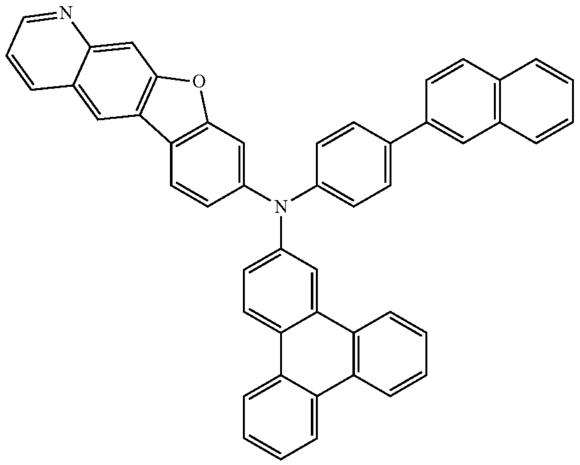
P150
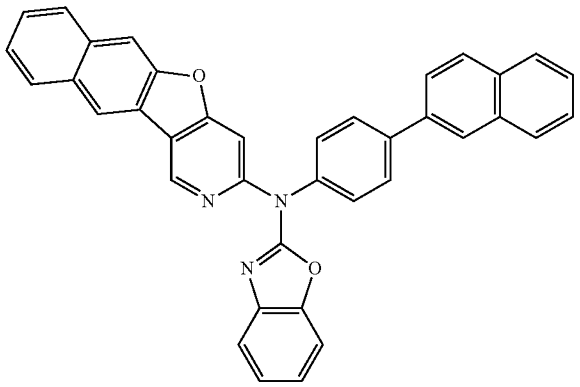
-continued
P151
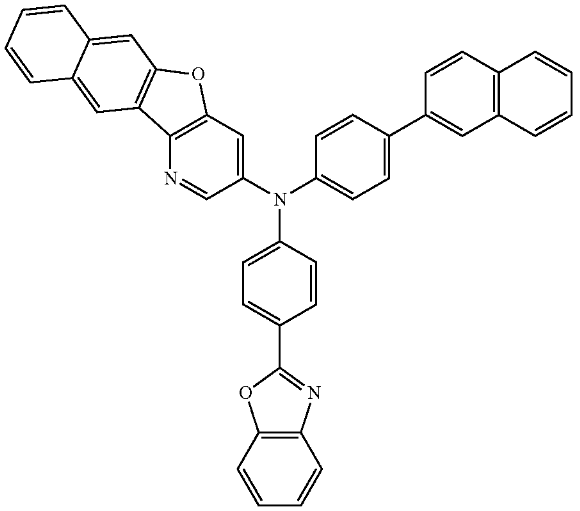
P152
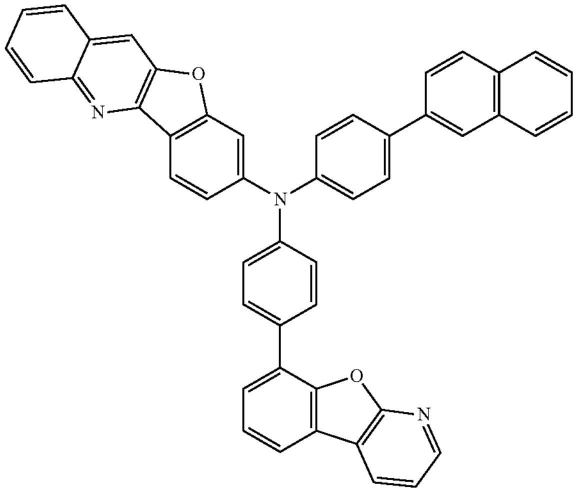
P153
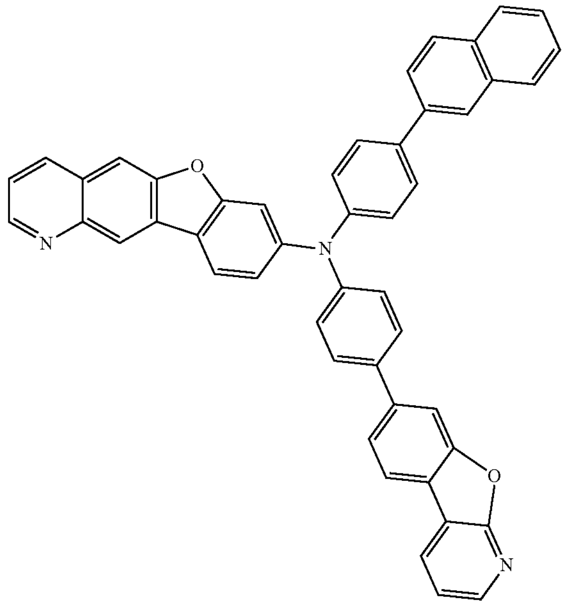

-continued
P154
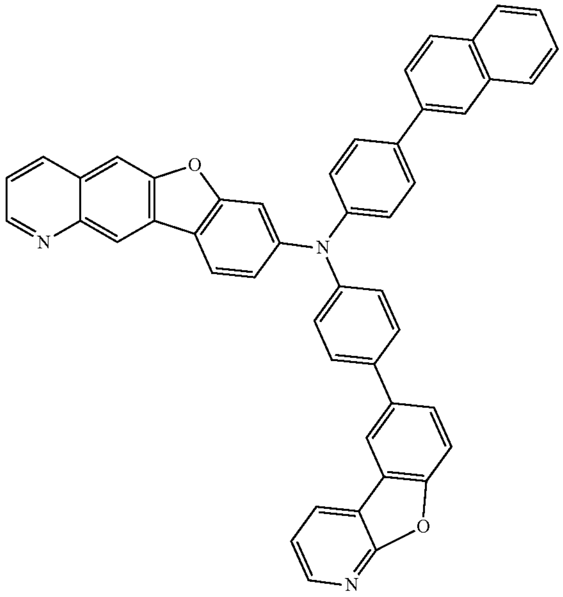
P155
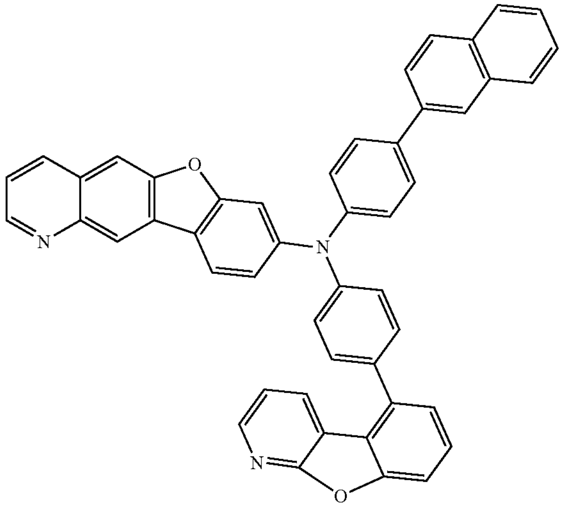
-continued
P156
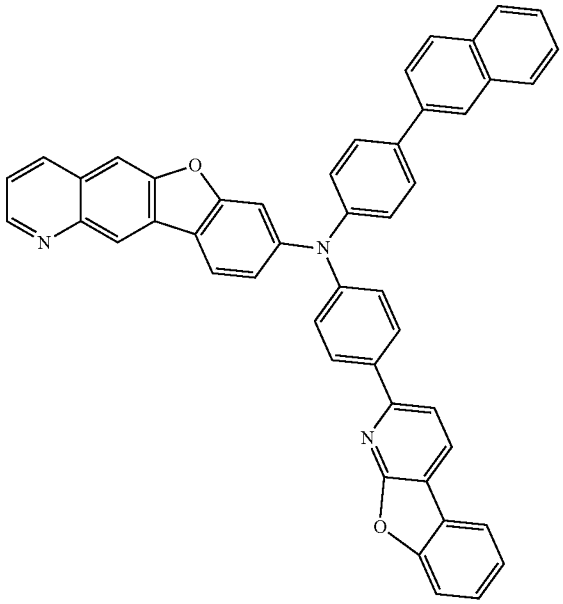
P157
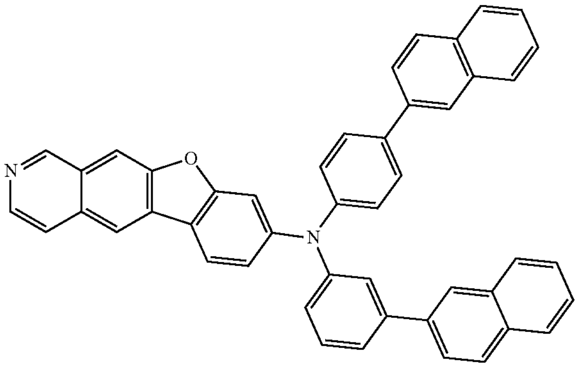
P158
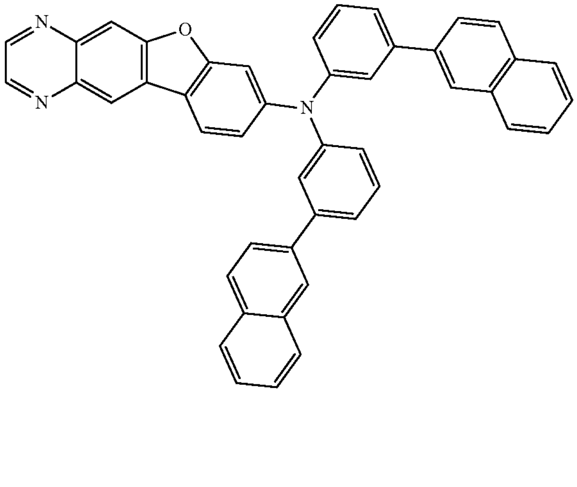

-continued
P159
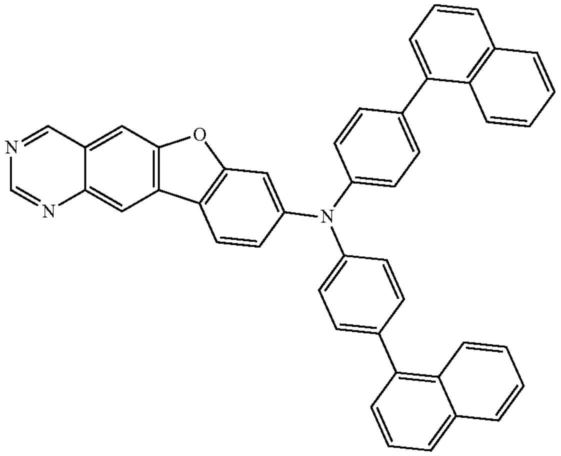
P160
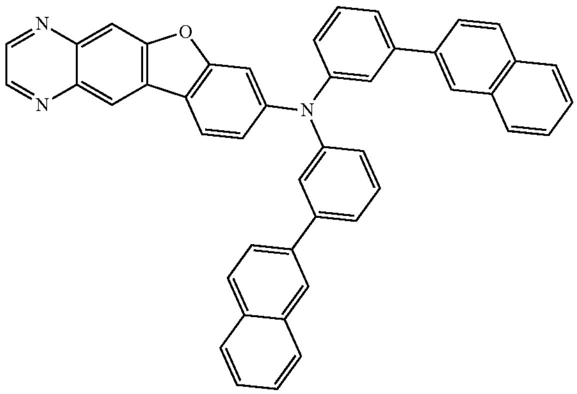
P161
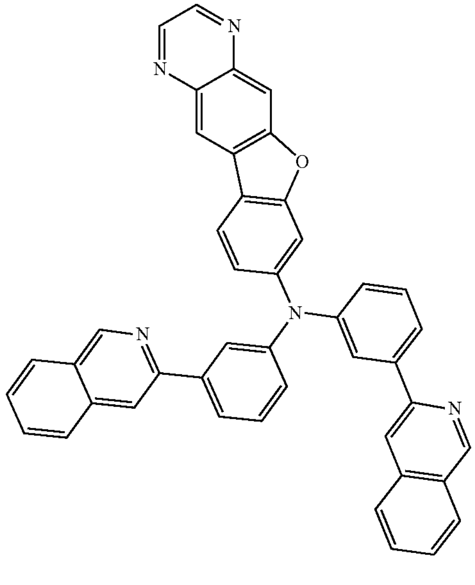
-continued
P162
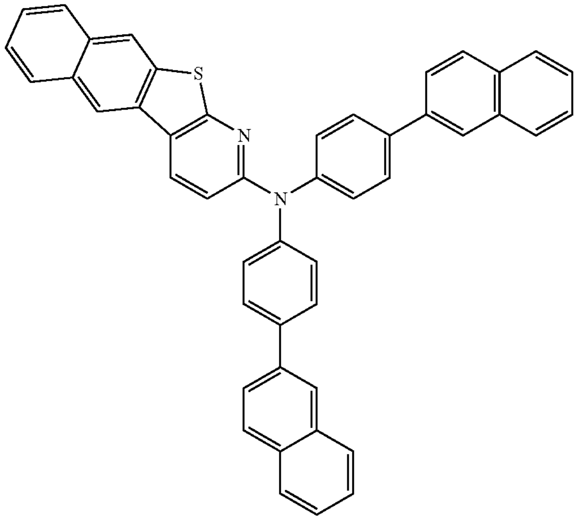
P163
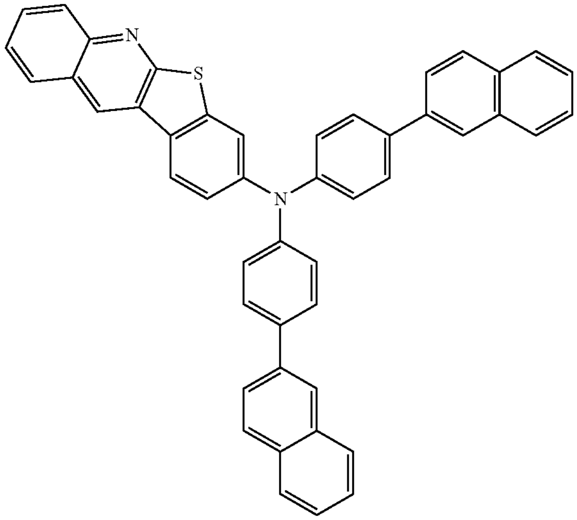
P164
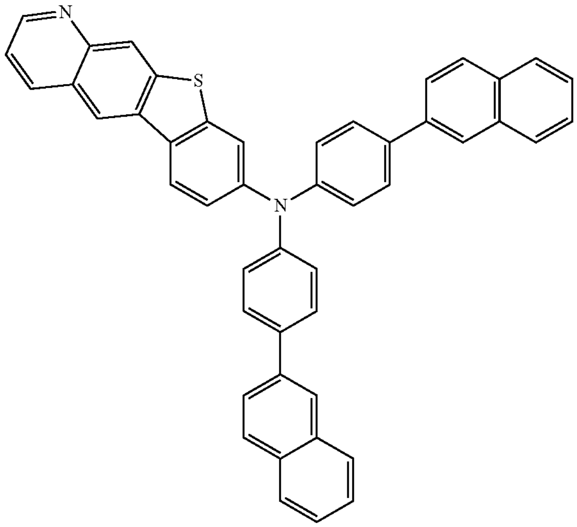

-continued
P165
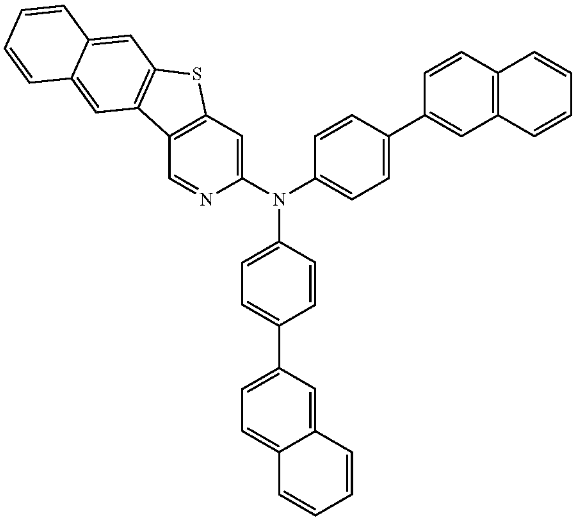
P166
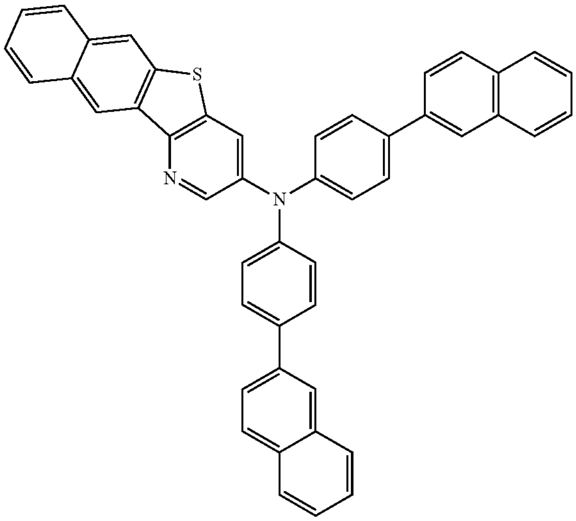
P167
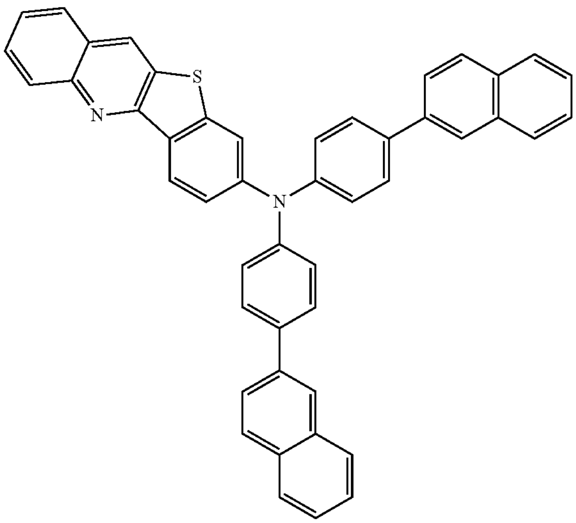
-continued
P168
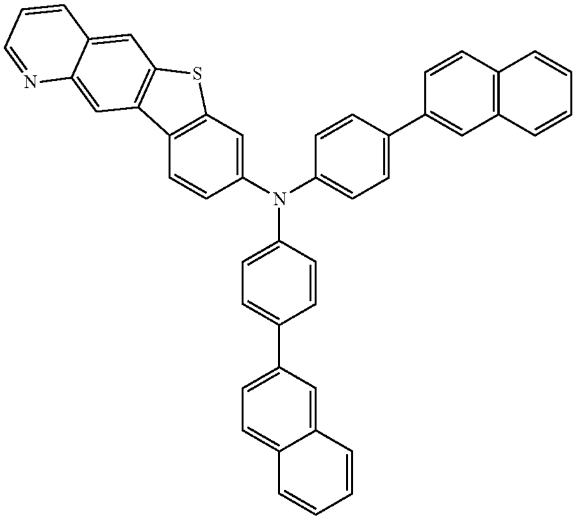
P169
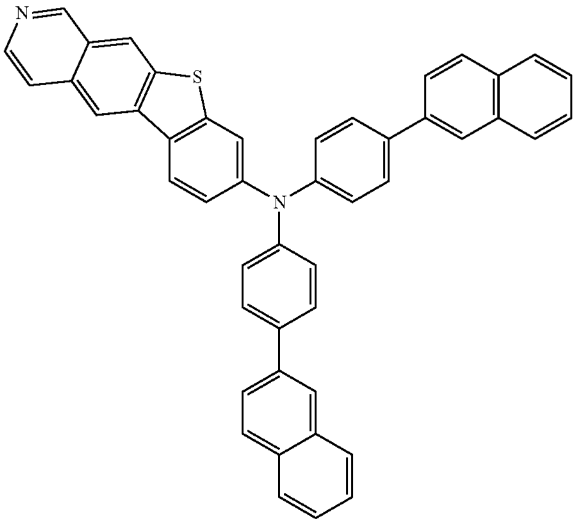
P170
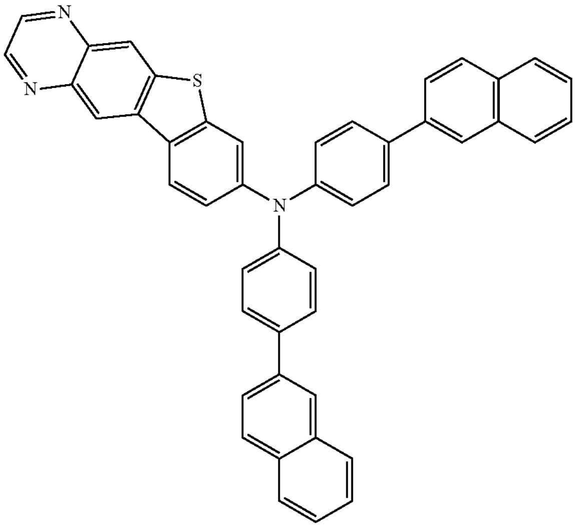

-continued
P171
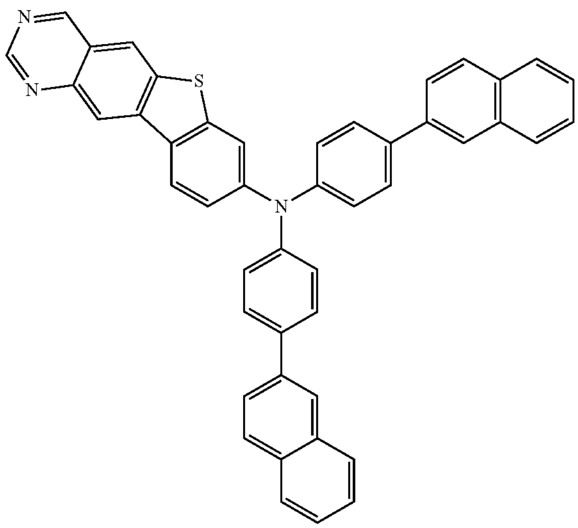
P172
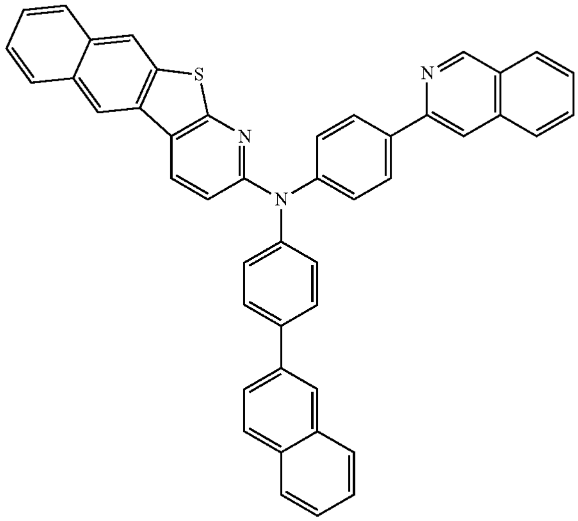
P173
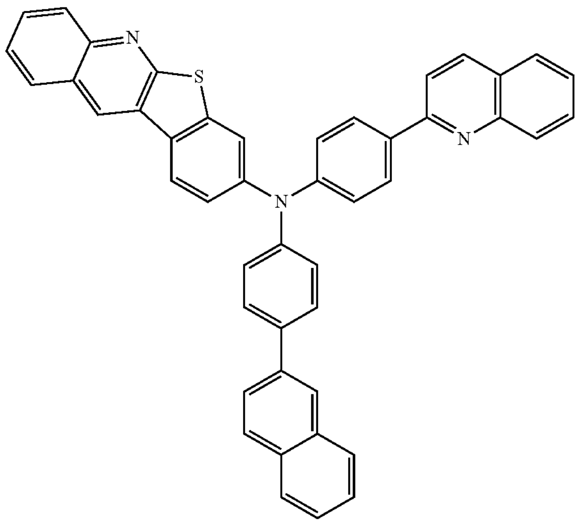
-continued
P174
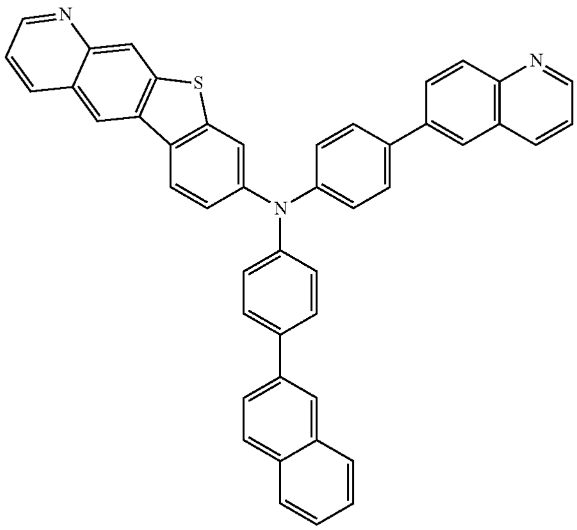
P175
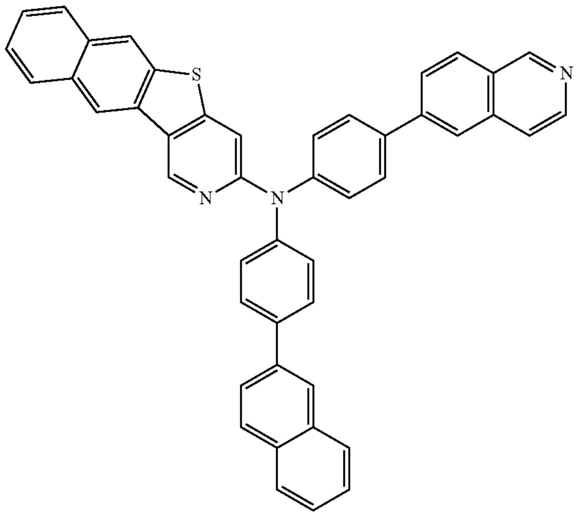
P176
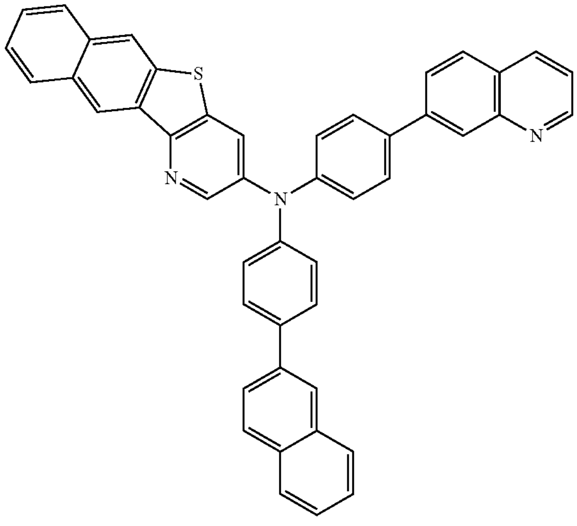

-continued
P177
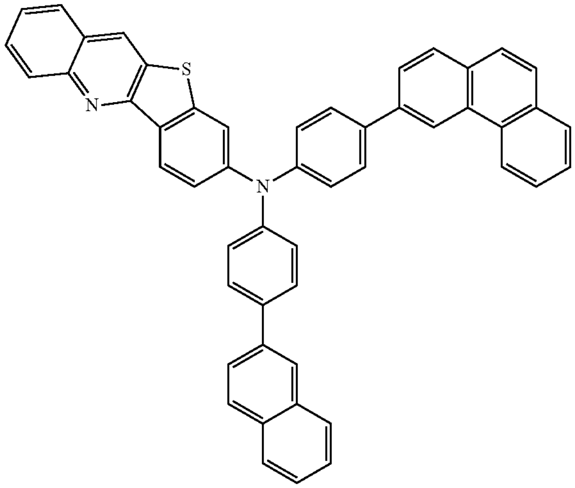
P178
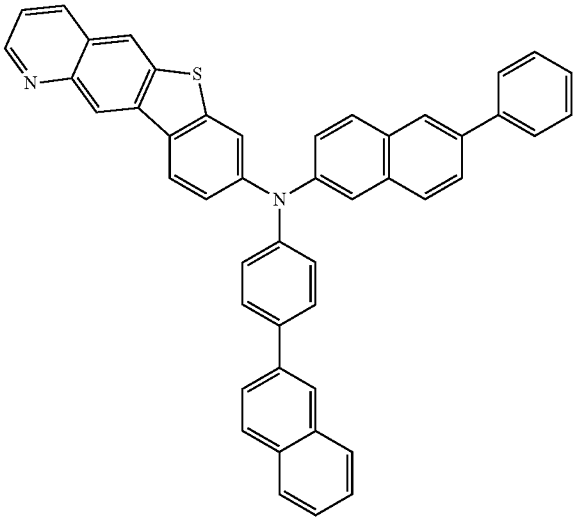
P179
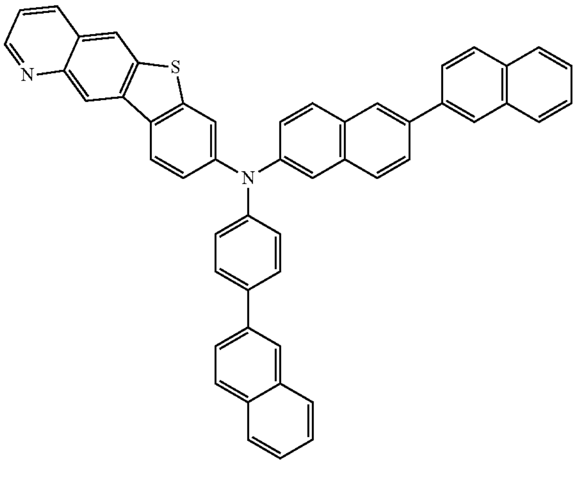
-continued
P180
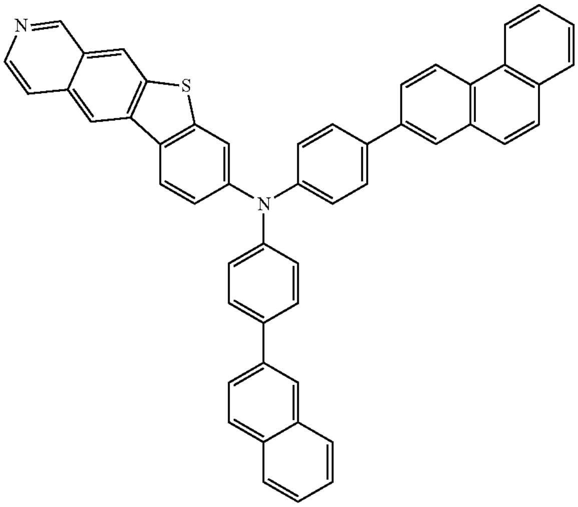
P181
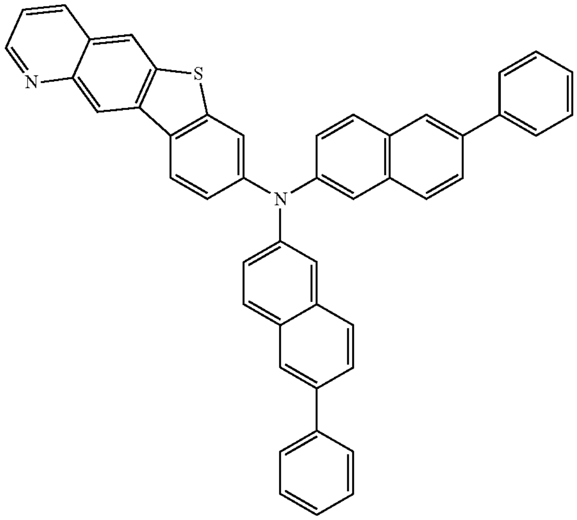
P182
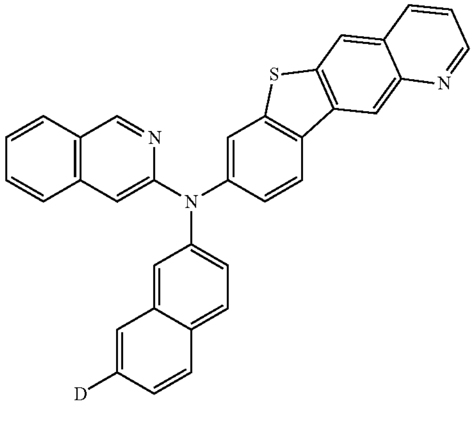

-continued
P183
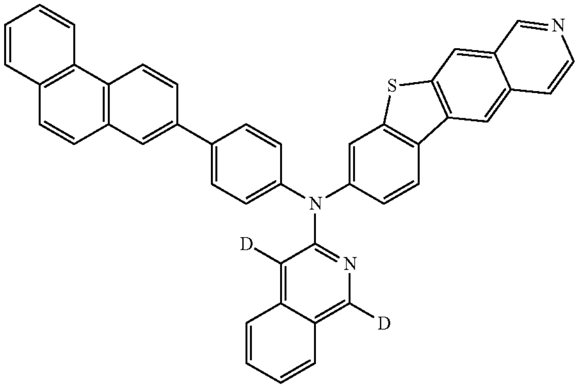
P184
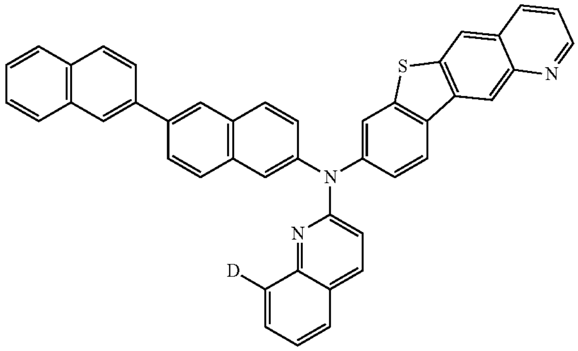
P185
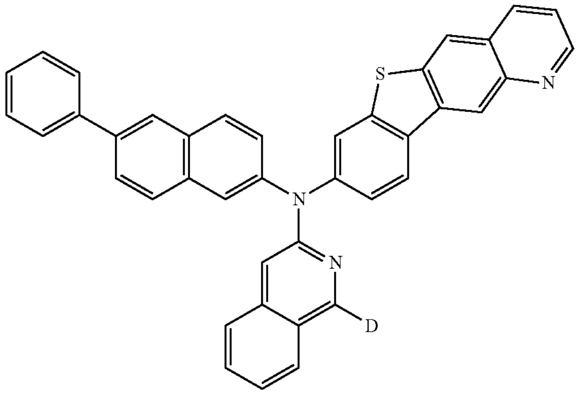
P186
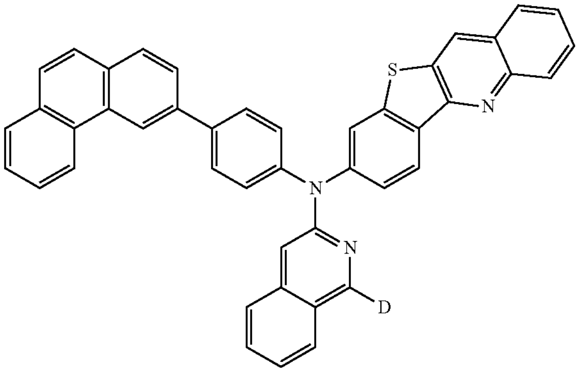
-continued
P187
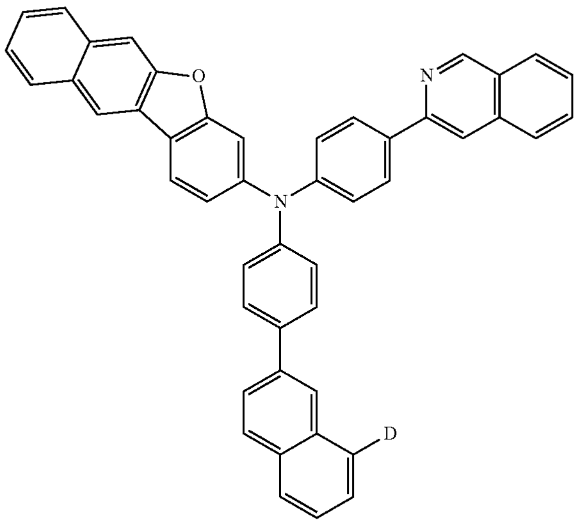
P188
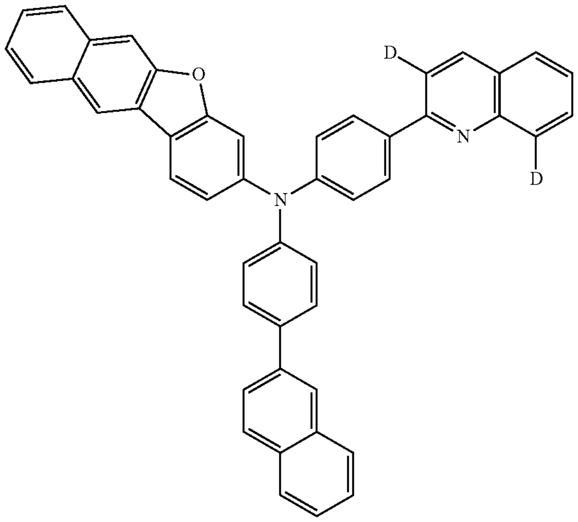
P189
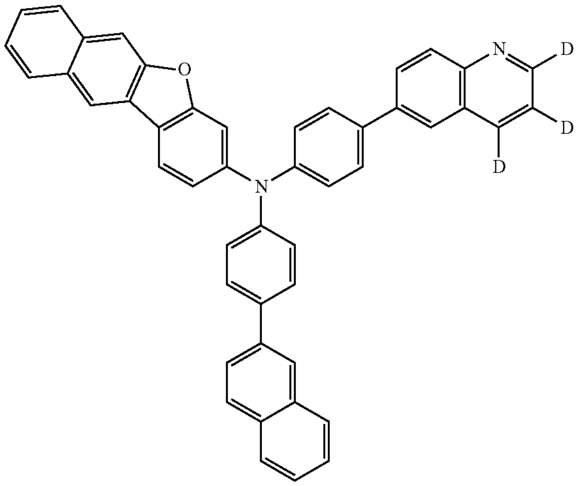

-continued
P190
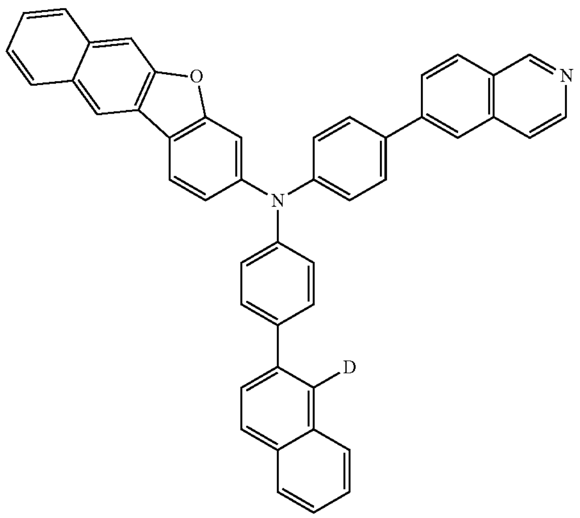
P191
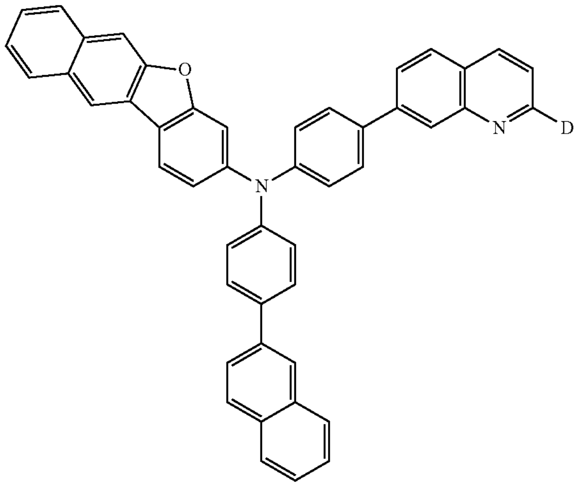
P192
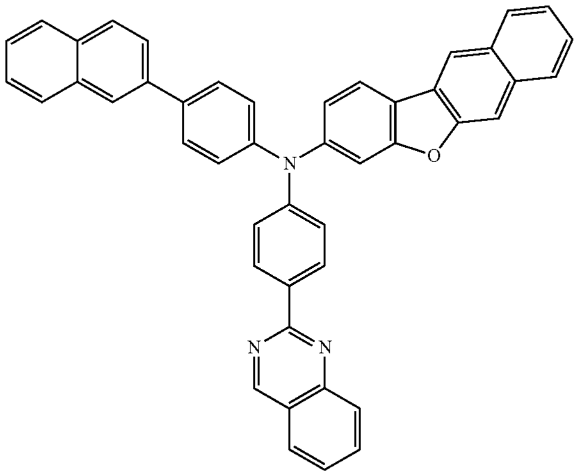
-continued
P193
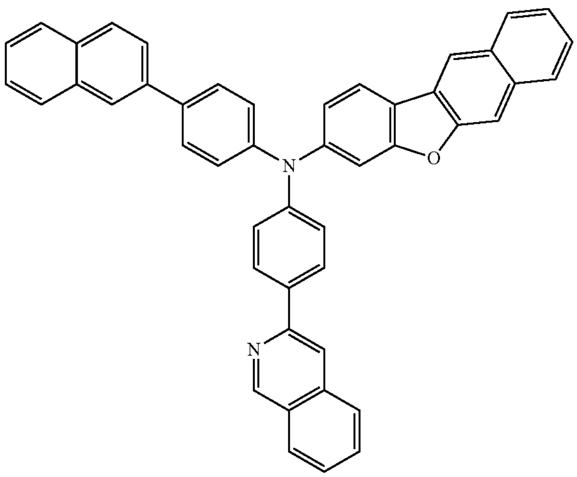
P194
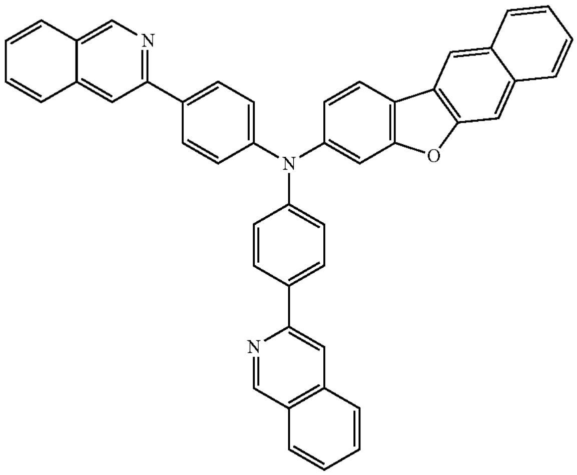
P195
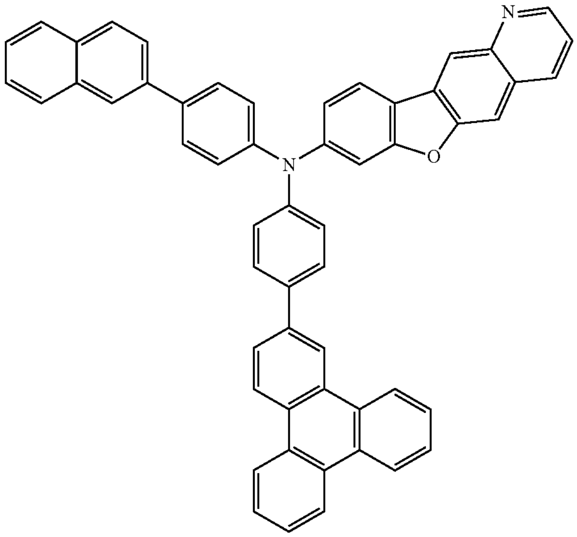

-continued

P196

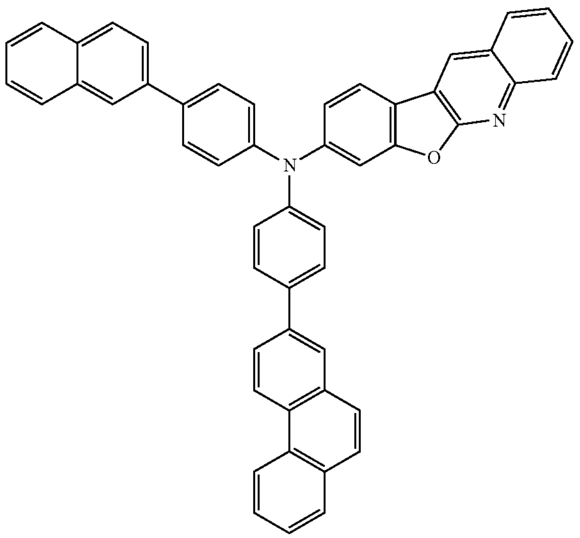

P197

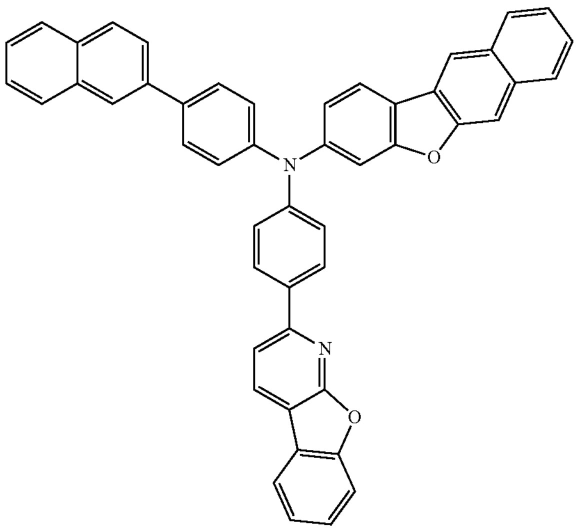

P198

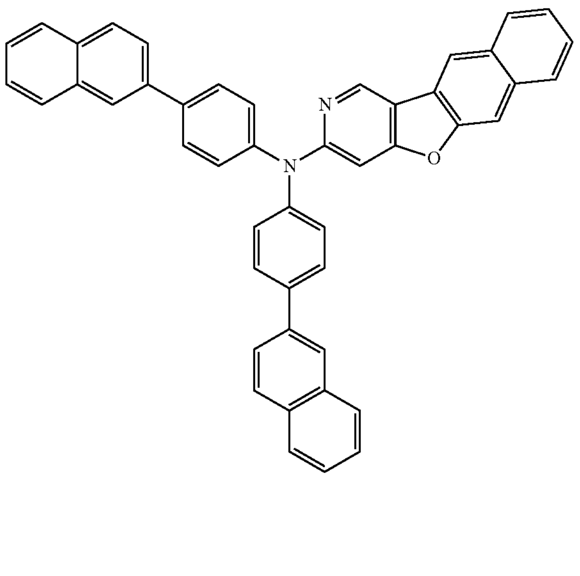

-continued

P199

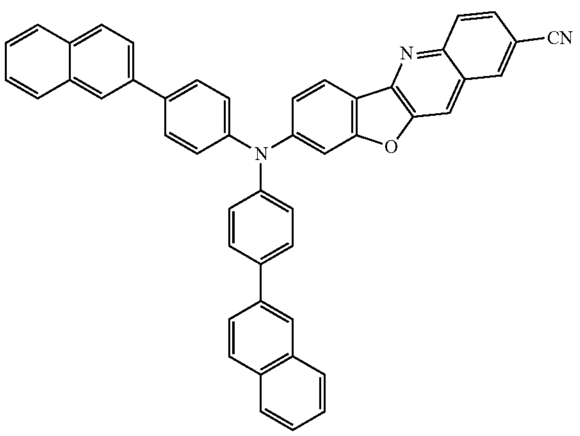

P200

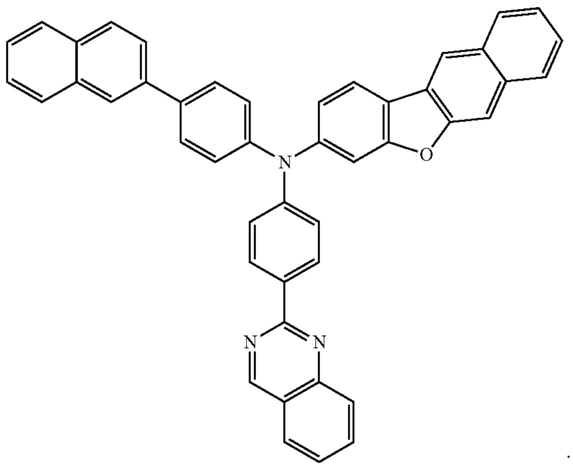

.

9. An organic electroluminescent device, comprising an anode, an organic thin-film layer and a cathode which are stacked in sequence and a capping layer located on a side of the cathode facing away from the anode;

wherein a material of the capping layer comprises the heterocyclic arylamine compound according to claim 1.

10. A display panel, comprising the organic electroluminescent device according to claim 9.

* * * * *